US012752000B2

(12) United States Patent
Kley et al.

(10) Patent No.: US 12,752,000 B2
(45) Date of Patent: Oct. 6, 2026

(54) IMMUNOSTIMULATORY ADJUVANTS

(71) Applicants: Orionis Biosciences, Inc., Waltham, MA (US); VIB VZW, Ghent (BE); Universiteit Gent, Ghent (BE)

(72) Inventors: Nikolai Kley, Waltham, MA (US); Jan Tavernier, Balegem (BE); Frank Peelman, Gentbrugge (BE); Sarah Gerlo, Ghent (BE); Bram Van Den Eeckhout, Ghent (BE)

(73) Assignees: Orionis Biosciences, Inc., Waltham, MA (US); VIB VZW, Ghent (BE); Universiteit Gent, Ghent (BE)

( * ) Notice: Subject to any disclaimer, the term of this patent is extended or adjusted under 35 U.S.C. 154(b) by 784 days.

(21) Appl. No.: 18/014,581

(22) PCT Filed: Jul. 7, 2021

(86) PCT No.: PCT/US2021/040676
§ 371 (c)(1),
(2) Date: Jan. 5, 2023

(87) PCT Pub. No.: WO2022/011005
PCT Pub. Date: Jan. 13, 2022

(65) Prior Publication Data

US 2023/0293652 A1 Sep. 21, 2023

Related U.S. Application Data

(60) Provisional application No. 63/048,789, filed on Jul. 7, 2020.

(51) Int. Cl.

| | |
|---|---|
| ***A61K 39/00*** | (2006.01) |
| ***A61K 9/00*** | (2006.01) |
| ***A61K 39/12*** | (2006.01) |
| ***A61P 31/14*** | (2006.01) |
| ***C07K 16/114*** | (2026.01) |
| ***C07K 16/28*** | (2006.01) |

(52) U.S. Cl.
CPC .... *A61K 39/001119* (2018.08); *A61K 9/0078* (2013.01); *A61K 39/12* (2013.01); *A61P 31/14* (2018.01); *C07K 16/1145* (2026.01); *C07K 16/2809* (2013.01); *C07K 16/2815* (2013.01); *A61K 2039/545* (2013.01); *A61K 2039/55527* (2013.01)

(58) Field of Classification Search
None
See application file for complete search history.

(56) References Cited

U.S. PATENT DOCUMENTS 3,536,809 A 10/1970 Applezweig
3,598,123 A 8/1971 Zaffaroni
3,845,770 A 11/1974 Theeuwes et al.
3,916,899 A 11/1975 Theeuwes et al.
4,008,719 A 2/1977 Theeuwes et al.
5,059,595 A 10/1991 Le Grazie
5,073,543 A 12/1991 Marshall et al.
5,120,548 A 6/1992 McClelland et al.
5,354,556 A 10/1994 Sparks et al.
5,475,096 A 12/1995 Gold et al.
5,591,767 A 1/1997 Mohr et al.
5,639,476 A 6/1997 Oshlack et al.
5,674,533 A 10/1997 Santus et al.
5,733,556 A 3/1998 Schrier et al.
5,831,012 A 11/1998 Nilsson et al.
5,914,254 A 6/1999 Mascarenhas et al.
6,004,746 A 12/1999 Brent et al.
6,653,104 B2 11/2003 Goldenberg
6,794,144 B1 9/2004 Saksela et al.
6,818,418 B1 11/2004 Lipovsek et al.
6,994,982 B1 2/2006 Watt et al.
7,166,697 B1 1/2007 Galanis et al.
7,186,524 B2 3/2007 Kolmar et al.
7,250,297 B1 7/2007 Beste et al.
7,417,130 B2 8/2008 Stumpp et al.
7,803,907 B2 9/2010 Stemmer et al.
7,838,629 B2 11/2010 Fielder et al.
8,980,267 B2 3/2015 Grewal et al.
9,139,634 B2 9/2015 Morrison et al.
9,932,409 B2 4/2018 Tavernier et al.
2001/0041180 A1 11/2001 Staats et al.
2004/0023334 A1 2/2004 Prior
2004/0132094 A1 7/2004 Etzerodt et al.
2004/0146938 A1 7/2004 Nguyen et al.
2004/0157209 A1 8/2004 Yilmaz et al.
(Continued)

FOREIGN PATENT DOCUMENTS

JP 2016510056 A * 4/2016 .............. A61P 37/04
WO WO 90/14837 A1 12/1990
(Continued)

OTHER PUBLICATIONS

Lin et al. Clin Infect Dis. Dec. 1995; 21(6):1439-49.*
Acres, et al., "Fusokine Interleukin-2/Interleukin-18, a Novel Potent Innate and Adaptive Immune Stimulator with Decreased Toxicity," Cancer Res., vol. 65, No. 20, pp. 9536-9546, 2005.
Allen, et al., "The NLRP3 Inflammasome Mediates In Vivo Innate Immunity to Influenza A Virus through Recognition of Viral RNA," Immunity 30, pp. 556-565, 2009.
Baba, et al., "Identification of CCR6, the Specific Receptor for a Novel Lymphocyte-directed CC Chemokine LARC," The Journal of Biological Chemistry, vol. 272, No. 23, pp. 14893-14898, 1997.
Ben-Sasson, et al., "IL-1 acts directly on CD4 T cells to enhance their antigen-driven expansion and differentiation," Proc. Natl Acad. Sci. USA 106, pp. 7119-7124, 2009.
(Continued)

*Primary Examiner* — Oluwatosin A Ogunbiyi
(74) *Attorney, Agent, or Firm* — Morgan, Lewis & Bockius LLP

(57) ABSTRACT

The present invention relates, in part, to vaccine compositions, adjuvants, chimeric proteins, or chimeric protein complexes and their use as vaccines or therapeutic agents. The present invention further relates to methods of vaccination or treatment of various diseases.

19 Claims, 75 Drawing Sheets

Specification includes a Sequence Listing.

(56) References Cited

U.S. PATENT DOCUMENTS

| | | | | |
|---|---|---|---|---|
| 2004/0209243 | A1 | 10/2004 | Nixon et al. | |
| 2004/0253208 | A1 | 12/2004 | Dondero et al. | |
| 2010/0119446 | A1 | 5/2010 | Grabulovski et al. | |
| 2010/0172868 | A1 | 7/2010 | Morrison et al. | |
| 2010/0239633 | A1 | 9/2010 | Strome et al. | |
| 2010/0297076 | A1 | 11/2010 | Morrison et al. | |
| 2011/0104112 | A1 | 5/2011 | Morrison et al. | |
| 2011/0274658 | A1 | 11/2011 | Silver et al. | |
| 2013/0058962 | A1 | 3/2013 | Shoemaker et al. | |
| 2013/0183298 | A1 | 7/2013 | Le et al. | |
| 2014/0271462 | A1 | 9/2014 | Ho et al. | |
| 2015/0139951 | A1 | 5/2015 | Grewal et al. | |
| 2019/0144553 | A1* | 5/2019 | Kley | C07K 14/525 424/136.1 |
| 2019/0202934 | A1* | 7/2019 | Tavernier | A61P 35/00 |

FOREIGN PATENT DOCUMENTS

| | | | |
|---|---|---|---|
| WO | WO 91/02754 | A1 | 3/1991 |
| WO | WO 99/37681 | A2 | 7/1999 |
| WO | WO 00/43507 | A1 | 7/2000 |
| WO | WO 01/90190 | A2 | 11/2001 |
| WO | WO 02/085945 | A2 | 10/2002 |
| WO | WO 03/025020 | A1 | 3/2003 |
| WO | WO 03/035694 | A2 | 5/2003 |
| WO | WO 2004/005350 | A2 | 1/2004 |
| WO | WO 2004/049794 | A2 | 6/2004 |
| WO | WO 2004/060965 | A2 | 7/2004 |
| WO | WO 2004/083247 | A1 | 9/2004 |
| WO | WO 2006/053883 | A1 | 5/2006 |
| WO | WO 2006/115800 | A2 | 11/2006 |
| WO | WO 2008/014612 | A1 | 2/2008 |
| WO | WO 2008/124086 | A2 | 10/2008 |
| WO | WO 2008/134046 | A1 | 11/2008 |
| WO | WO 2009/003145 | A1 | 12/2008 |
| WO | WO 2009/012944 | A1 | 1/2009 |
| WO | WO 2009/039409 | A1 | 3/2009 |
| WO | WO 2009/053368 | A1 | 4/2009 |
| WO | WO 2010/036918 | A2 | 4/2010 |
| WO | WO 2010/066740 | A1 | 6/2010 |
| WO | WO 2011/020783 | A2 | 2/2011 |
| WO | WO 2011/029870 | A1 | 3/2011 |
| WO | WO 2012/145238 | A2 | 10/2012 |
| WO | WO 2012/170072 | A1 | 12/2012 |
| WO | WO 2013/059885 | A2 | 5/2013 |
| WO | WO 2013/107791 | A1 | 7/2013 |
| WO | WO 2013/134138 | A1 | 9/2013 |
| WO | WO 2014/100139 | A1 | 6/2014 |
| WO | WO 2014/164553 | A1 | 10/2014 |
| WO | WO 2015/007520 | A1 | 1/2015 |
| WO | WO 2015/007536 | A2 | 1/2015 |
| WO | WO 2015/007542 | A1 | 1/2015 |
| WO | WO 2015/007903 | A1 | 1/2015 |
| WO | WO 2015/184203 | A1 | 12/2015 |
| WO | WO 2016/113555 | A1 | 7/2016 |
| WO | WO 2016/113557 | A1 | 7/2016 |
| WO | WO 2016/156570 | A1 | 10/2016 |
| WO | 2017134305 | A1 | 8/2017 |
| WO | WO 2018/170096 | A1 | 9/2018 |
| WO | WO 2019/023148 | A1 | 1/2019 |
| WO | WO 2019/033043 | A2 | 2/2019 |
| WO | WO 2019/191519 | A1 | 10/2019 |
| WO | WO 2020/082045 | A1 | 4/2020 |

OTHER PUBLICATIONS

Ben-Sasson, et al., "IL-1 enhances expansion, effector function, tissue localization, and memory response of antigen-specific CD8 T cells," J. Exp. Med. 210, pp. 491-502, 2013.

Camacho, et al., "Structure of an Interleukin-1β Mutant with Reduced Bioactivity Shows Multiple Subtle Changes in Conformation That Affect Protein-Protein Recognition," Biochemistry, vol. 32, No. 34, pp. 8749-8757, 1993.

Chen, et al., "Fusion Protein Linkers: Property, Design and Functionality," Adv Drug Deliv Rev., vol. 65, No. 10, pp. 1357-1369, 2013.

Chichili, et al., "Linkers in the structural biology of protein-protein interactions," Protein Science, vol. 22, pp. 153-167, 2013.

Coulstock, et al., "Liver-Targeting of Interferon-Alpha with Tissue-Specific Domain Antibodies," PLOS One, vol. 8, No. 2, pp. 1-11, 2013.

Crasto, et al., "Linker: a program to generate linker sequences for fusion proteins," Protein Engineering, vol. 13, No. 5, pp. 309-312, 2000.

Deffar, et al., "Nanobodies—the new concept in antibody engineering," African Journal of Biotechnology, vol. 8, No. 12, pp. 2645-2652, 2009.

De Bruyn, et al., "Antibody-based fusion proteins to target death receptors in cancer," Cancer Letters, vol. 332, pp. 175-183, 2013.

Dijkmans, et al., "Murine Interferon-γ/Interleukin-1 Fusion Proteins Used as Antigens for the Generation of Hybridomas Producing Monoclonal Anti-Interleukin-1 Antibodies," Cytokine, vol. 3, No. 2, pp. 134-140, 1991.

Dimitrov, et al., "Engineered CH2 Domains (Nanoantibodies)," mAbs, vol. 1, No. 1, pp. 26-28, 2009.

Edelman, et al., "The Covalent Structure of an Entire γg Immunoglobulin Molecule," PNAS, vol. 63, No. 1, pp. 78-85, 1969.

Frey, et al., "Antibody-Based Targeting of Interferon-Alpha to the Tumor Neovasculature: A Critical Evaluation," Integrative Biology, vol. 3, pp. 468-478, 2011.

Garcin, et al., "High Efficiency Cell-Specific Targeting of Cytokine Activity," Nature Communications, 9 pages, 2014.

Gardella, et al., "Secretion of bioactive interleukin-13 by dendritic cells is modulated by interaction with antigen specific T cells," Blood 95, pp. 3809-3815, 2000.

Garlanda, et al., "The Interleukin-1 Family: Back to the Future," Immunity, vol. 39, No. 6, pp. 1003-1018, 2013.

Holler, et al., "Two adjacent Trimeric Fas Ligands are Required for Fas Signaling and Formation of a Death-Inducing Signaling Complex," Molecular and Cellular Biology, vol. 23, No. 4, pp. 1428-1440, 2003.

Huang, et al., "A Trimeric Anti-HER2/neu ScFv and Tumor Necrosis Factor-α Fusion Protein Induces HER2/neu Signaling and Facilitates Repair of Injured Epithelia," The Journal of Pharmacology and Experimental Therapeutics, vol. 316, No. 3, pp. 983-991, 2006.

Ichinohe, et al., "Inflammasome recognition of influenza virus is essential for adaptive immune responses," J. Exp. Med. 206, pp. 79-87, 2009.

International Search Report & Written Opinion for PCT/EP2013/050787, dated Jun. 14, 2013.

International Search Report & Written Opinion for PCT/EP2014/063976, dated Oct. 26, 2014.

International Search Report & Written Opinion for PCT/EP2014/064227, dated Feb. 5, 2015.

International Search Report & Written Opinion for PCT/EP2014/064283, dated Oct. 1, 2014.

International Search Report & Written Opinion for PCT/EP2014/065554, dated Oct. 30, 2014.

Jain, et al., "T cell-intrinsic IL-1R signaling licenses effector cytokine production by memory CD4 T cells," Nat. Commun. 9, 3185, 13 pages, 2018.

Kaneko, et al., "The role of interleukin-1 in general pathology," Regen. 39, pp. 1-16, 2019.

Krippner-Heidenreich, et al., "Single-Chain TNF, a TNF Derivative with Enhanced Stability and Antitumoral Activity," The Journal of Immunology, vol. 180, pp. 8176-8183, 2008.

Lapuente, et al., "IL-1β as mucosal vaccine adjuvant: the specific induction of tissue-resident memory T cells improves the heterosubtypic immunity against influenza A viruses," Mucosal Immunol. 11, pp. 1265-1278, 2018.

Lo, et al., "High level expression and secretion of Fc-X fusion proteins in mammalian cells," Protein Engineering, vol. 11, No. 6, pp. 495-500, 1998.

Masci, et al., "New and Modified Inteferon alfas: Preclinical and Clinical Data," Current Oncology Reports, vol. 5, pp. 108-113, 2003.

(56) References Cited

OTHER PUBLICATIONS

Pan, et al., "Mutation of the IFNAR-1 Receptor Binding Site of Human IFN-α2 Generates Type I IFN Competitive Antagonists," Biochemistry, vol. 47, pp. 12018-12027, 2008.
Pang, et al., "IL-1R signaling in dendritic cells replaces pattern recognition receptors to promote CD8+ T cell responses to influenza A virus," Nat. Immunol. 14, pp. 246-253, 2013.
Patris, et al., "Nanoimmunoassay onto a screen printed electrode for HER2 breast cancer biomarker determination," Talanta, vol. 130, pp. 1647-170, 2014.
Penafuerte, et al., "The Human Ortholog of Granulocyte Macrophage Colony-Stimulating Factor and Interleukin-2 Fusion Protein Induces Potent Ex Vivo Natural Killer Cell Activation and Maturation," Cancer Res., vol. 69, No. 23, pp. 9020-9028, 2009.
Rafei, et al., "A MCPI Fusokine with CCR2-Specific Tumoricidal Activity," Molecular Cancer, vol. 10, No. 121, pp. 1-11, 2011.
Rafei, et al., "An engineered GM-CSF-CCL2 Fusokine Is a Potent Inhibitor of CCR2-Driven Inflammation as Demonstrated in a Murine Model of Inflammatory Arthritis," The Journal of Immunology, vol. 183, pp. 1759-1766, 2009.
Roisman, et al., "Structure of the Interferon-Receptor Complex Determined by Distant Constraints from Double Mutant Cycles and Flexible Docking," PNAS, vol. 98, No. 23, pp. 13231-13236, 2001.
Rovero, et al., "Insertion of the DNA for the 163-171 peptide of IL1β enables a DNA vaccine encoding p185$^{neu}$ to inhibit mammary carcinogenesis in Her-2/neu transgenic BALB/c mice," Gene Therapy, vol. 8, pp. 447-452, 2001.
Sarkar, et al., "Programming of CD8 T Cell Quantity and Polyfunctionality by Direct IL-1 Signals," J. Immunol. 201, pp. 3641-3650, 2018.
Sayers, et al., "Vaxjo: A Web-Based Vaccine Adjuvant Database and Its Application for Analysis of Vaccine Adjuvants and Their Uses in Vaccine Development," J Biomed Biotechnol. 2012; 831486, 13 pages.
Schutyser, et al., "The CC Chemokine CCL20 and its Receptor CCR6," Cytokine & Growth Factor Reviews, vol. 14, pp. 409-426, 2003.
Song, et al., "Salient type 1 interleukin 1 receptor expression in peripheral non-immune cells," Sci. Rep. 8, 723, 14 pages, 2018.
Storz, "Intellectual property protection," mAbs, vol. 3, No. 3, pp. 310-317, May/Jun. 2011.
Tate, et al., "Reassessing the role of the NLRP3 inflammasome during pathogenic influenza A virus infection via temporal inhibition," Sci. Rep. 6, 27912, 8 pages, 2016.
Vaneycken, et al., "Preclinical screening of anti-HER2 nanobodies for molecular imaging of breast cancer," The FASEB Journal, vol. 5, pp. 2433-2446, 2011.
Veltri, et al., "Interleukin 1 Trials in Cancer Patients: A Review of the Toxicity, Antitumor and Hematopoietic Effects," Oncologist 1, pp. 190-200, 1996.
Weber, et al., "Single Amino Acid Changes that Render Human IFN-α2 biologically active on mouse cells," The EMBO Journal, vol. 6, No. 3, pp. 591-598, 1987.
Wesolowski, et al., "Single domain antibodies: promising experimental and therapeutics tools in infections and immunity," Med. Microbiol. Immunol., vol. 198, pp. 157-174, 2009.
Wu, et al., "A new coronavirus associated with human respiratory disease in China," Nature, vol. 579, 20 pages, 2020.
Wüthrich, et al., "Interleukin 1 Enhances Vaccine-Induced Antifungal T-Helper 17 Cells and Resistance Against Blastomyces dermatitidis Infection," J. Infect. Dis. 208, pp. 1175-1182, 2013.
Yang, et al., "Tailoring structure±function and pharmacokinetic properties of single-chain Fv proteins by site-specific PEGylation," Protein Engineering, vol. 16, No. 10, pp. 761-770, 2003.
Ben-Sasson, et al., "IL-1 acts on T cells to enhance the magnitude of in vivo immune responses," Cytokine, vol. 56, No. 1, pp. 122-125, 2011.
Davidson, et al., "Lactobacillus GG as an immune adjuvant for live-attenuated influenza vaccine in healthy adults: a randomized double-bline placebo-controlled trial," European Journal of Clinical Nutrition, vol. 65, pp. 501-507, 2011.
International Search Repot & Written Opinion, PCT Application No. PCT/US21/40676, dated Oct. 28, 2021, 14 pages.
Van Den Eeckhout, et al., "Specific targeting of IL-1β activity to CD8+ T cells allows for safe use as a vaccine adjuvant," NPJ Vaccines, vol. 5, No. 64, pp. 1-17, 2020.
Kayamuro, Hiroyuki et al. "Interleukin-1 family cytokines as mucosal vaccine adjuvants for induction of protective immunity against influenza virus." Journal of virology vol. 84,24 (2010).

* cited by examiner

Fig. 2E
Fig. 2F
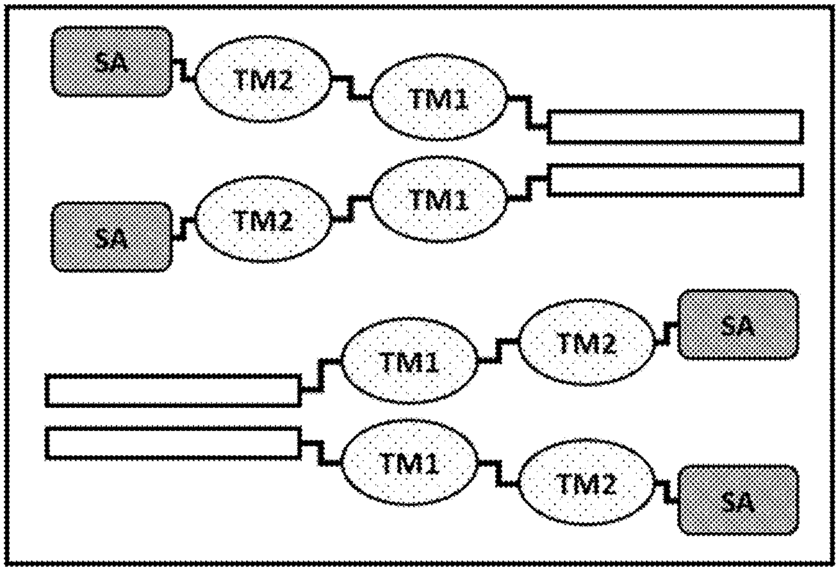
Fig. 2G
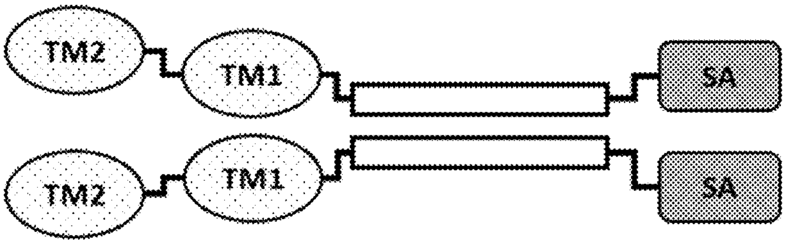
Fig. 2H
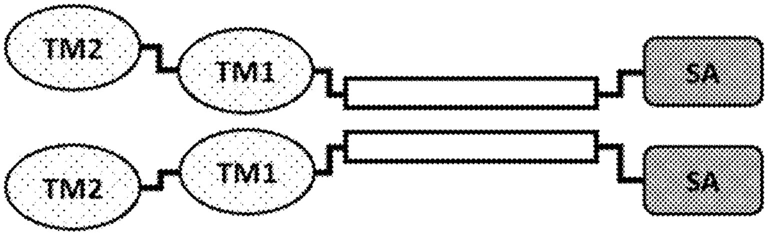

FIG. 22
H
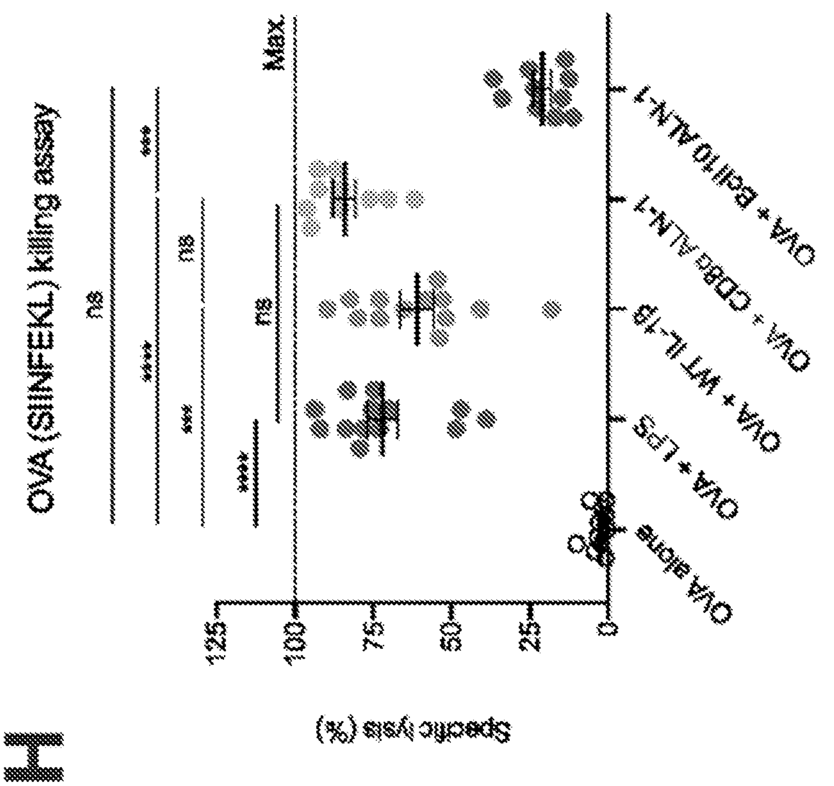
I
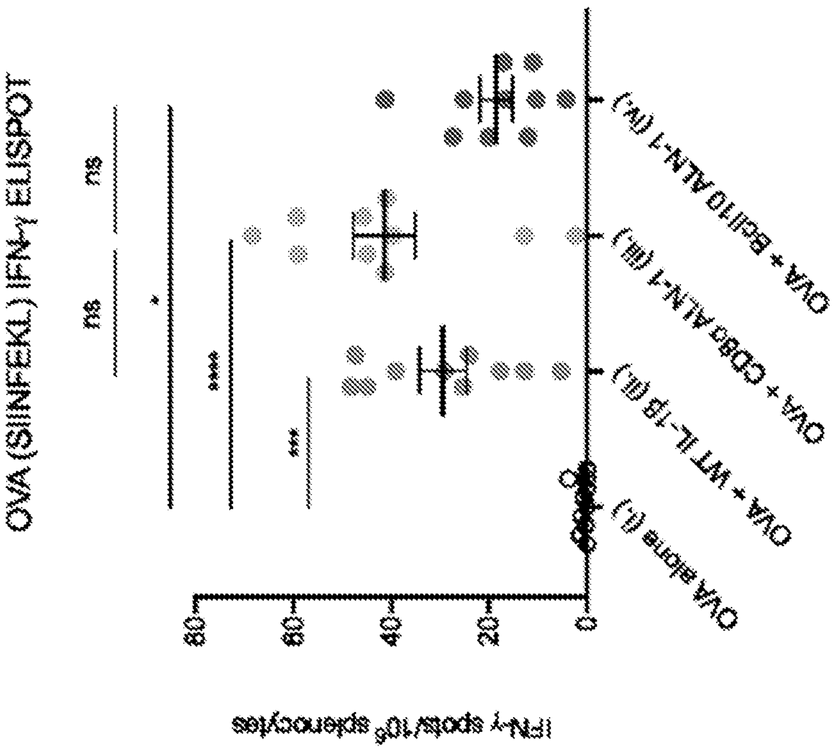

J

A

E

C

IMMUNOSTIMULATORY ADJUVANTS

CROSS-REFERENCE TO RELATED APPLICATIONS

This application is a National Stage Entry of PCT/US2021/040676, filed on Jul. 7, 2021, which claims the benefit of U.S. Provisional Application No. 63/048,789, filed on Jul. 7, 2020, the entire contents of which are incorporated herein.

FIELD

The present invention relates, in part, to new vaccine compositions and methods for vaccination and their use in the treatment of infectious diseases including, e.g., influenza and severe acute respiratory syndrome.

SEQUENCE LISTING

The contents of the text file submitted electronically herewith are incorporated herein by reference in their entirety. A computer readable format copy of the Sequence Listing (filename: ORN-074 ST25.text, date created: Jan. 5, 2023; file size: 220,680 bytes).

BACKGROUND

Vaccination is one of the most effective preventative health tools available against infectious diseases. A vaccine helps the body's immune system to recognize and fight pathogens like viruses or bacteria, which then provides safety from the diseases they cause. Vaccination aims to generate a strong immune response to an administrated antigen and provide long-term protection against the disease. Often, however, an antigen alone is insufficient to stimulate protective immunity in a vaccine and needs an adjuvant.

Vaccine adjuvants are compounds that enhance the specific immune responses against a desired antigen. Currently, several hundred natural and synthetic compounds are known to have adjuvant activity but only alum salts and AS04 are licensed for use in humans in the United States. Vaccine adjuvants based on alum are low in cost and potent in raising neutralizing antibodies. Unfortunately, alum-supplemented vaccines score poorly in inducing antigen-specific $CD8^+$ T cell responses. In contrast to alum, agonists of pattern-recognition receptors (PRRs), such as monophosphoryl lipid A (MPLA), can potently promote cellular immunity, which is desirable. One of the PRRs that plays an essential role in connecting innate and adaptive immunity is the NLRP3 inflammasome. NLRP3 inflammasome assembly can be triggered by a variety of pathogen- and damage-associated molecular patterns, leading to the activation of the cysteine protease caspase-1 and the subsequent cleavage of immature pro-IL-1β to active IL-1β, which can ultimately be released by different innate immune cells. The NLRP3 inflammasome and its product interleukin-1β (IL-1β) are pivotal mediators of cellular immune responses, yet, overactivation of these systems leads to side effects, which hamper clinical applications.

Accordingly, there remains a need for safe and effective vaccine compositions and adjuvants that can effectively stimulate a subject's immune response and exhibit minimal toxicity.

SUMMARY

One aspect of the present application is related to a vaccine composition comprising: (a) an adjuvant, and (b) an antigen that is suitable for inducing an immune response. The adjuvant comprises a chimeric protein or chimeric protein complex comprising: (i) a wild type or mutant IL-1β (which is an example of a signaling agent as described herein), (ii) one or more targeting moieties, said targeting moieties comprising recognition domains which specifically bind to an antigen or receptor of interest; and (iii) a connector between (i) and (ii).

The connector comprises: (1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii); and/or (2) a flexible linker that connects (i) and (ii), wherein the mutant IL-1β is characterized by low affinity or activity at the IL-1 receptor.

In some embodiments, the adjuvants, the chimeric proteins, or the chimeric protein complexes described herein comprise IL-1β mutants (which is an example of a cytokine/signaling agent that may also be used in the present invention) with reduced biological activity that is coupled to one or more targeting moieties. In some embodiments, the adjuvants, chimeric proteins, or chimeric protein complexes of the present invention include AcTakines (Activity-on-Target cytokines) that have one or more mutated cytokines that remain inactive en route through the body and only reveal their full agonistic activity upon target cell binding. In some embodiments, the adjuvants, chimeric proteins, or chimeric protein complexes target a mutant IL-1β to $CD8^+$ T cells (sometimes referred to as CD8α AcTaleukin-1/ALN-1). In vivo, this CD8α ALN-1 can act as an adjuvant that potently promotes the $CD8^+$ T cell response to antigens, with a significantly reduced toxicity profile compared to wild-type (WT) IL-1β.

In some embodiments, the present vaccine adjuvants as described herein have the capacity to safely promote activation, expansion and memory differentiation of $CD8^+$ cells.

The present disclosure also concerns, in part, to the finding that adjuvants, chimeric proteins, or chimeric protein complexes comprising wild type IL-1β, or variants thereof, exhibit substantially reduced IL-1β activity compared to wild type IL-1β. This reduced IL-1β-activation signaling activity, however, can be induced and/or restored at a target cell when directed to such a cell through a targeting moiety, which binds to an antigen or receptor of interest. Surprisingly, the induced IL-1β activity at a target cell, achieved through targeting of adjuvants, chimeric proteins, or chimeric protein complexes comprising IL-1β, or variants thereof, may be similar or greater at the target cell than that of wild type IL-1β.

Importantly, the adjuvants, chimeric proteins, and chimeric protein complexes comprising mutant IL-1β described herein, exhibit substantial and surprising selectivity for target cells versus non-target cells, and substantially more than, for example, achieved with targeted wild type IL-1β chimeric protein(s). In summary, a unique combination of highly potent and highly cell target-selective signaling activation can be achieved with the adjuvants, chimeric proteins, or chimeric protein complexes described herein.

In some embodiments, the loss in affinity and/or activity of wild type IL-1β for its receptor, e.g., IL-1 receptor, can be induced and restored upon directing or targeting of the adjuvant, the chimeric protein, or the chimeric protein complex comprising IL-1β to a target cell through a targeting moiety. In some embodiments, the induction and restoration of IL-1-mediated activation at a target cell may reach a level that is similar to or higher than activation achieved with wild type (non-chimeric) IL-1β.

In some embodiments, the IL-1β is modified, i.e., it is a variant and comprises one or more mutations in IL-1β. In some embodiments, the one or more mutations reduce the biological activity of the IL-1β (sometimes referred to as "attenuated by mutation"). For example, the one or more mutations may reduce the affinity and/or activity of the IL-1β for IL-1 receptor. In an embodiment, the IL-1 receptors comprise the IL-1R1 and IL-1RACP.

In an embodiment, the modified IL-1β comprises one or more mutations that reduce its affinity and/or activity for IL-1R1. In another embodiment, the modified IL-1β comprises one or more mutations that reduce its affinity and/or activity for IL-1R2. In an embodiment, the modified IL-1β comprises one or more mutations that reduce its affinity and/or activity for IL-1R1 and comprises one or more mutations that reduce its affinity and/or activity for IL-1R2. In some embodiments, the loss in affinity and/or activity of the modified IL-1β ("attenuated by mutation") for a receptor, e.g., IL-1R1, IL-1R2, can be induced and restored upon directing or targeting of the adjuvant, the chimeric protein, or the chimeric protein complex comprising the modified IL-1β to a target cell through a targeting moiety.

In some embodiments, the adjuvant, the chimeric protein, and the chimeric protein complex, including Fc-based chimeric protein complex, comprises one or more additional signaling agents or cytokines, e.g., without limitation, an interferon, an interleukin, and a tumor necrosis factor, that may be modified. In various embodiments, the adjuvant, the chimeric protein, or chimeric protein complex, including Fc-based chimeric protein complex, of the invention provides improved safety and/or therapeutic activity and/or pharmacokinetic profiles (e.g., increased serum half-life) compared to an untargeted and/or unmodified IL-1β or an unmodified, wild type IL-1β.

In various embodiments, the adjuvants, the chimeric proteins, or the chimeric protein complexes, including Fc-based chimeric protein complexes, comprise one or more targeting moieties which have recognition domains (e.g. antigen recognition domains, including without limitation various antibody formats, inclusive of single-domain antibodies) which specifically bind to a target (e.g. antigen, receptor) of interest. In various embodiments, the targeting moieties have recognition domains that specifically bind to a target (e.g. antigen, receptor) of interest, including those found on one or more immune cells, which can include, without limitation, T cells, cytotoxic T lymphocytes, T helper cells, T regulatory cells (Tregs), natural killer (NK) cells, natural killer T (NKT) cells, macrophages (e.g. M1 and M2 macrophages), B cells, B regulatory (Breg) cells, neutrophils, monocytes, myeloid derived cells, and dendritic cells. In various embodiments, the targeting moieties have recognition domains that specifically bind to a target (e.g. antigen, receptor) of interest, including those found on one or more endothelial cells, epithelial cells, mesenchymal cells, stromal cells or other cell types that are characteristic of and/or unique for specific organs and/or tissues, including those specifically associated with disease. In some embodiments, the recognition domains specifically bind to a target (e.g. antigen, receptor) of interest and effectively recruit one or more immune cells.

In some embodiments, the adjuvants, the chimeric proteins, or the chimeric protein complexes, including Fc-based chimeric protein complexes, may recruit an immune cell, e.g., an immune cell that can cause an anti-infective effect, or modulate other immune cells, to a site of action. In some embodiments, the adjuvants, the chimeric proteins, or the chimeric protein complexes, including Fc-based chimeric protein complexes, may modulate an immune cell at a site of action, or recruit an immune cell to a site of action.

In one aspect, the present invention is related to a method for vaccinating a subject against an infectious disease, comprising administering: (a) an adjuvant comprising a chimeric protein or chimeric protein complex, comprising: (i) a wild type or mutant IL-1β (which is an example of a signaling agent as described herein), (ii) one or more targeting moieties, said targeting moieties comprising recognition domains which specifically bind to an antigen or receptor of interest; and (iii) a connector between (i) and (ii), the connector being: (1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii) and/or (2) a flexible linker that connects (i) and (ii); wherein the mutant IL-1β is characterized by low affinity or activity at the IL-1 receptor; and (b) an antigen which is suitable for inducing an immune response.

Another aspect of the invention is related to a method for vaccinating a subject against an influenza infection, comprising administering: (a) an adjuvant comprising a chimeric protein or chimeric protein complex, comprising: (i) a wild type or mutant IL-1β (which is an example of a signaling agent as described herein), (ii) one or more targeting moieties, said targeting moieties comprising recognition domains which specifically bind to an antigen or receptor of interest; and (iii) a connector between (i) and (ii), the connector being: (1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii) and/or (2) a flexible linker that connects (i) and (ii); wherein the mutant IL-1β is characterized by low affinity or activity at the IL-1 receptor; and (b) an influenza antigen which is suitable for inducing an immune response.

Yet another aspect of the invention is related to a method for vaccinating a subject against a severe acute respiratory syndrome coronavirus 2 (SARS-CoV-2) infection comprising administering(a) an adjuvant comprising a chimeric protein or chimeric protein complex, comprising: (i) a wild type or mutant IL-1β, (ii) one or more targeting moieties, said targeting moieties comprising recognition domains which specifically bind to an antigen or receptor of interest; and (iii) a connector between (i) and (ii), the connector being(1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii) and/or (2) a flexible linker that connects (i) and (ii); wherein the mutant IL-1β is characterized by low affinity or activity at the IL-1 receptor; and (b) a SARS-CoV-2 antigen which is suitable for inducing an immune response.

Another aspect of the invention is related to a method for treating a subject afflicted with an infectious disease, comprising administering a chimeric protein or chimeric protein complex, comprising: (i) a wild type or mutant IL-1β IL-1β, (ii) one or more targeting moieties, said targeting moieties comprising recognition domains which specifically bind to an antigen or receptor of interest; and (iii) a connector between (i) and (ii), the connector being: (1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii) and/or (2) a flexible linker that connects (i) and (ii); wherein the mutant IL-1β is characterized by low affinity or activity at the IL-1 receptor.

In various embodiments, the adjuvants, the chimeric proteins, and the chimeric protein complexes find use in the vaccination against or treatment of various diseases or disorders, such as infections. The present invention encompasses various methods of treatment or various methods of vaccination against such diseases or disorders.

BRIEF DESCRIPTION OF THE DRAWINGS

FIGS. 1A-F, 2A-H, 3A-H, 4A-D, 5A-F, 6A-J, 7A-D, 8A-F, 9A-J, 10A-F, 11A-L, 12A-L, 13A-F, 14A-L, 15A-L, 16A-J, 17A-J, 18A-F, and 19A-F show various non-limiting illustrative schematics of the Fc-based chimeric protein complexes of the present invention. In embodiments, each schematic is a composition of the present invention. Where applicable in the figures, “TM” refers to a “targeting moiety” as described herein, “SA” refers to a “signaling agent” as described herein, “ ” is an optional “linker” as described herein, the two long parallel rectangles are human Fc domains, e.g. from IgG1, from IgG2, or from IgG4, as described herein and optionally with effector knock-out and/or stabilization mutations as also described herein, and the two long parallel rectangles with one having a protrusion and the other having an indentation are human Fc domains, e.g. from IgG1, from IgG2, or from IgG4 as described herein, with knob-in-hole and/or ionic pair (a/k/a charged pairs, ionic bond, or charged residue pair) mutations as described herein and optionally with effector knock-out and/or stabilization mutations as also described herein.

FIGS. 1A-F show illustrative homodimeric 2-chain complexes. These figures show illustrative configurations for the homodimeric 2-chain complexes.

FIGS. 2A-H show illustrative homodimeric 2-chain complexes with two targeting moieties TM (as described herein, more targeting moieties may be present in some embodiments). In embodiments, the position of TM1 and TM2 are interchangeable. In embodiments, the constructs shown in the box (i.e., FIGS. 2G and 2H) have signaling agent (SA) between TM1 and TM2 or between TM1 and Fc.

FIGS. 3A-H show illustrative homodimeric 2-chain complexes with two signaling agents (as described herein, more signaling agents may be present in some embodiments). In embodiments, the position of SA1 and SA2 are interchangeable. In embodiments, the constructs shown in the box (i.e., FIGS. 3G and 3H) have TM between SA1 and SA2 or TM at N- or C-terminus.

FIGS. 4A-D show illustrative heterodimeric 2-chain complexes with split TM and SA chains, namely the TM on the knob chain of the Fc and the SA on hole chain of the Fc.

FIGS. 5A-F show illustrative heterodimeric 2-chain complexes with split TM and SA chains, namely with both TMs on the knob chain of the Fc and with SA on hole chain of the Fc, with two targeting moieties (as described herein, more targeting moieties may be present in some embodiments). In embodiments, the position of TM1 and TM2 are interchangeable. In some embodiments, TM1 and TM2 can be identical.

FIGS. 6A-J show illustrative heterodimeric 2-chain complexes with split TM and SA chains, namely with TM on the knob chain of the Fc and with a SA on the hole chain of the Fc, with two signaling agents (as described herein, more signaling agents may be present in some embodiments). In these orientations and/or configurations, one SA is on the knob chain and one SA is on the hole chain. In embodiments, the position of SA1 and SA2 are interchangeable.

FIGS. 7A-D show illustrative heterodimeric 2-chain complexes with split TM and SA chains, namely the SA on the knob chain of the Fc and the TM on hole chain of the Fc.

FIGS. 8A-F show illustrative heterodimeric 2-chain complexes with split TM and SA chains, namely with SA on the knob chain of the Fc and both TMs on hole chain of the Fc, with two targeting moieties (as described herein, more targeting moieties may be present in some embodiments). In embodiments, the position of TM1 and TM2 are interchangeable. In some embodiments, TM1 and TM2 can be identical.

FIGS. 9A-J show illustrative heterodimeric 2-chain complexes with split TM and SA chains, namely with SA on the knob chain of the Fc and TM on hole chain of the Fc, with two signaling agents (as described herein, more signaling agents may be present in some embodiments). In these orientations and/or configurations, one SA is on the knob chain and one SA is on the hole chain. In embodiments, the position of SA1 and SA2 are interchangeable.

FIGS. 10A-F show illustrative heterodimeric 2-chain complexes with TM and SA on the same chain, namely the SA and TM both on the knob chain of the Fc.

FIGS. 11A-L show illustrative heterodimeric 2-chain complexes with a TM and a SA on the same chain, namely with SA and with TM both on the knob chain of the Fc, with two targeting moieties (as described herein, more targeting moieties may be present in some embodiments). In embodiments, the position of TM1 and TM2 are interchangeable. In some embodiments, TM1 and TM2 can be identical.

FIGS. 12A-L show illustrative heterodimeric 2-chain complexes with a TM and a SA on the same chain, namely with SA and with TM both on the knob chain of the Fc, with two signaling agents (as described herein, more signaling agents may be present in some embodiments). In embodiments, the position of SA1 and SA2 are interchangeable.

FIGS. 13A-F show illustrative heterodimeric 2-chain complexes with TM and SA on the same chain, namely the SA and TM both on the hole chain of the Fc.

FIGS. 14A-L show illustrative heterodimeric 2-chain complexes with a TM and a SA on the same chain, namely with SA and with TM both on the hole chain of the Fc, with two targeting moieties (as described herein, more targeting moieties are present in some embodiments). In embodiments, the position of TM1 and TM2 are interchangeable. In embodiments, TM1 and TM2 can be identical.

FIGS. 15A-L show illustrative heterodimeric 2-chain complexes with a TM and a SA on the same chain, namely with SA and with TM both on the hole chain of the Fc, with two signaling agents (as described herein, more signaling agents may be present in some embodiments). In embodiments, the position of SA1 and SA2 are interchangeable.

FIGS. 16A-J show illustrative heterodimeric 2-chain complexes with two targeting moieties (as described herein, more targeting moieties may be present in some embodiments) and with SA on knob Fc and TM on each chain. In embodiments, TM1 and TM2 can be identical.

FIGS. 17A-J show illustrative heterodimeric 2-chain complexes with two targeting moieties (as described herein, more targeting moieties may be present in some embodiments) and with SA on hole Fc and TM on each chain. In embodiments, TM1 and TM2 can be identical.

FIGS. 18A-F show illustrative heterodimeric 2-chain complexes with two signaling agents (as described herein, more signaling agents may be present in some embodiments) and with split SA and TM chains: SA on knob and TM on hole Fc.

FIGS. 19A-F show illustrative heterodimeric 2-chain complexes with two signaling agents (as described herein, more signaling agents may be present in some embodiments) and with split SA and TM chains: TM on knob and SA on hole Fc.

CD25 upregulation was evaluated in the proliferated OT-I subset. Panel B shows OT-I proliferation induced by treatment with CD8α ALN-1 in the absence (left) and presence (right) of SIINFEKL on BM-DCs. Bars represent mean±s.e.m of three independent experiments. **, $p<0.01$ by unpaired Student's t-test (two-tailed). Panel C shows flow cytometry analysis of OT-I proliferation (CFSE dilution, left) and activation (CD25 upregulation, right) in in vitro OT-I co-cultures with $IL\text{-}1R1^{-/-}$ BM-DCs. OT-I cells were defined as $CD3^+CD4$-$CFSE^{labeled}$ cells. Each bar represents the mean fold induction of treatment vs. vehicle±s.e.m. of two independent experiments. Panel D shows ELISA detection of IFN-γ and TNF in the conditioned supernatant of OT-I cocultures with WT BM-DCs. Each bar represents the mean fold induction of treatment vs. vehicle±s.e.m. of at least two independent experiments. Treatments with vehicle, inhibitory antibody and WT IL-1β are included as controls. In each set of histograms, the bars represent, from left to right: Vehicle; Inhibitory antibody; WT IL-1β; and CD8α ALN-1.

FIGS. 30A-F. Panel A shows the gating strategy for the detection of OT-1 activation and proliferation after transfer in C57BL/6 recipient mice. Staining of splenocytes with CD19, CD3, CD4, CD62L, CD44 and CD45.1 antibodies and OVA-pentamer. Panels B-E show the treatment with OVA and CD8α ALN-1 promotes OT-1 proliferation and increases the amount of OT-1 cells in lymphoid and peripheral organs compared with OVA treatment alone. Experiment performed according to Panel A with two treatment groups: OVA (100 g) alone or combined with CD8α ALN-1 (10 g). Staining with LIVE/DEAD, CD19, CD3, CD4, CD8 and CD45.1. OT-1 cells were detected in the single cell population (based on FSC/SSC) as LIVE/DEAD-$CD19^-$ $CD3^+CD4^-CD8^+$ $CD45.1^+$cells. Displayed are the relative (% in the $CD8^+$ T cell population) and absolute (counts in the $CD8^+$ T cell population) amounts of OT-1 cells in LNs (Panel B), spleen (Panel C), lungs (Panel D) and liver (Panel E). Data points represent individual mice±s.e.m. of one experiment with n=5 mice/group. ns, $p>0.05$; *, $p<0.05$ by unpaired Mann-Whitney U test (two-tailed). Panel F. Representative dot plots illustrating simultaneous upregulation of CD44 and downregulation of CD62L on CTLs induced by CD8α ALN-1 treatment. In each set of histograms, the left bar represents OVA alone and the right bar represents OVA+CD8α ALN-1.

Figure 31:
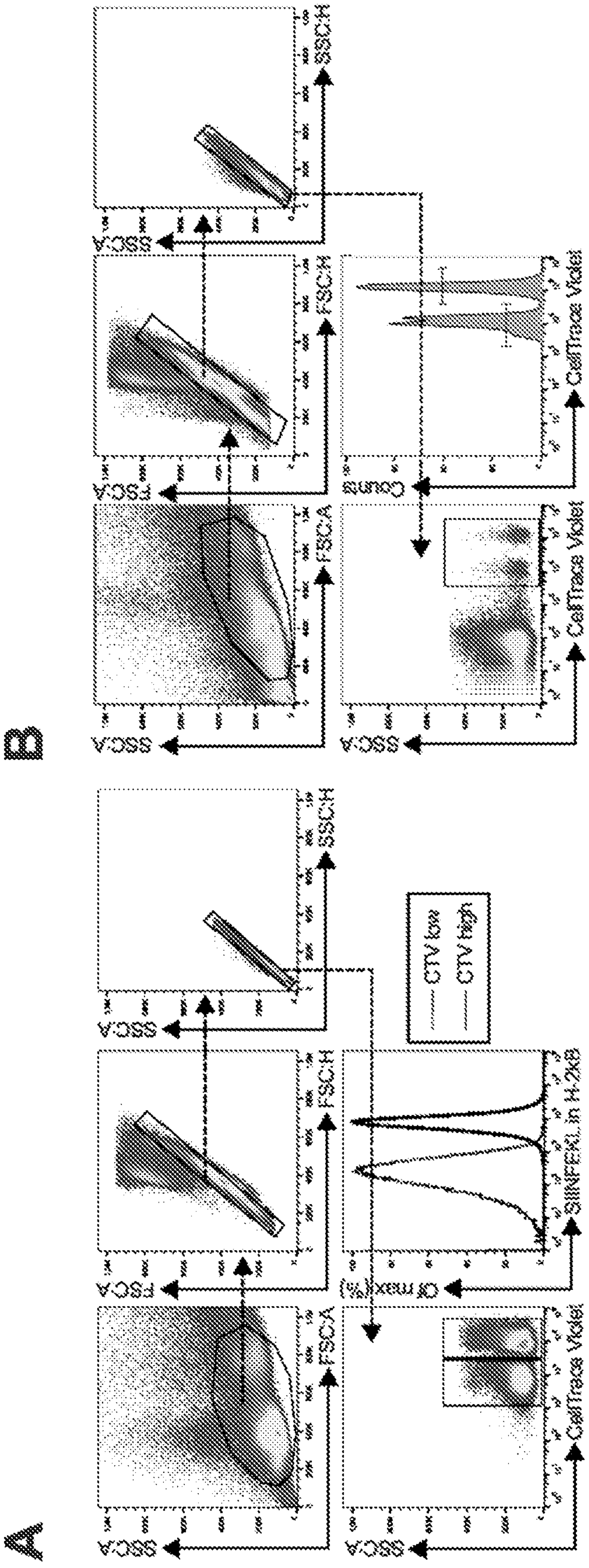

FIGS. 31A-B. Panel A shows splenocyte labeling for the in vivo killing assay experiment. Cells were labeled with a high or low intensity of CTV and loaded with SIINFEKL ($CTV^{high}$) or left unloaded ($CTV^{low}$). Peptide presentation is detected with a SIINFEKL in H-2 kB antibody. Panel B shows gating strategy for the detection of adoptively transferred target cells in the spleens of acceptor mice and measurement of SIINFEL-directed cytotoxicity.

Figure 32:
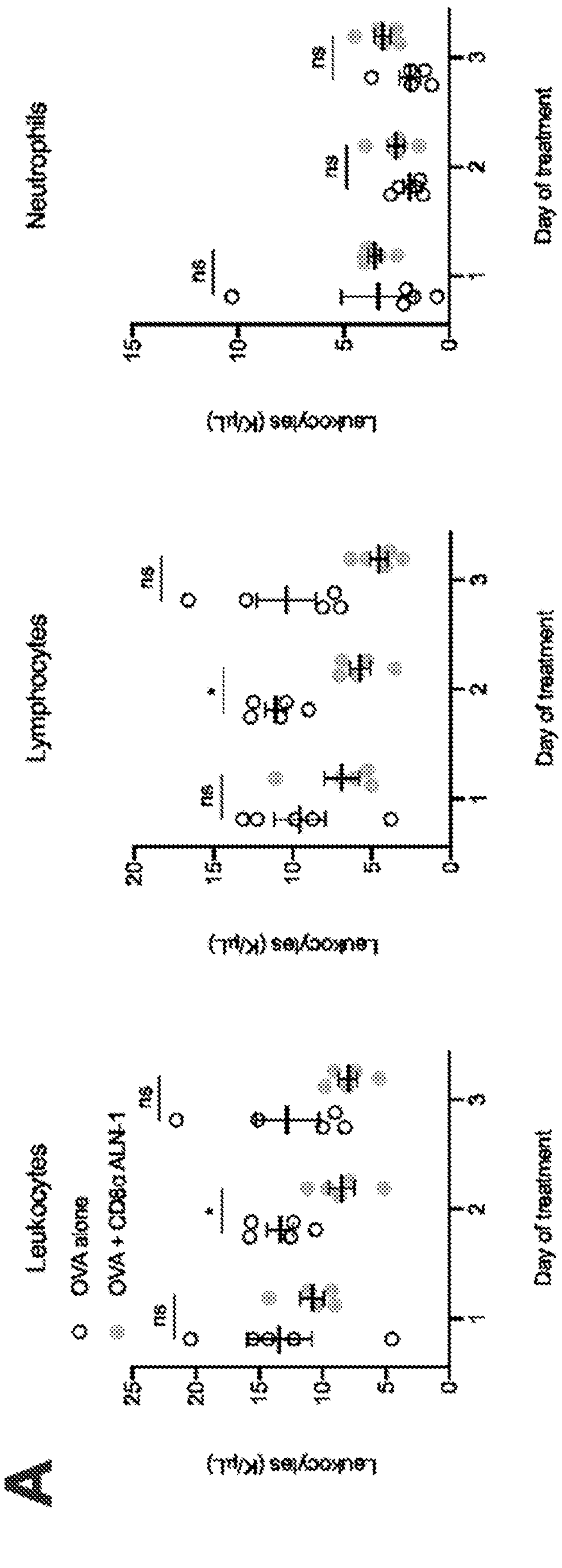
Figure 32:
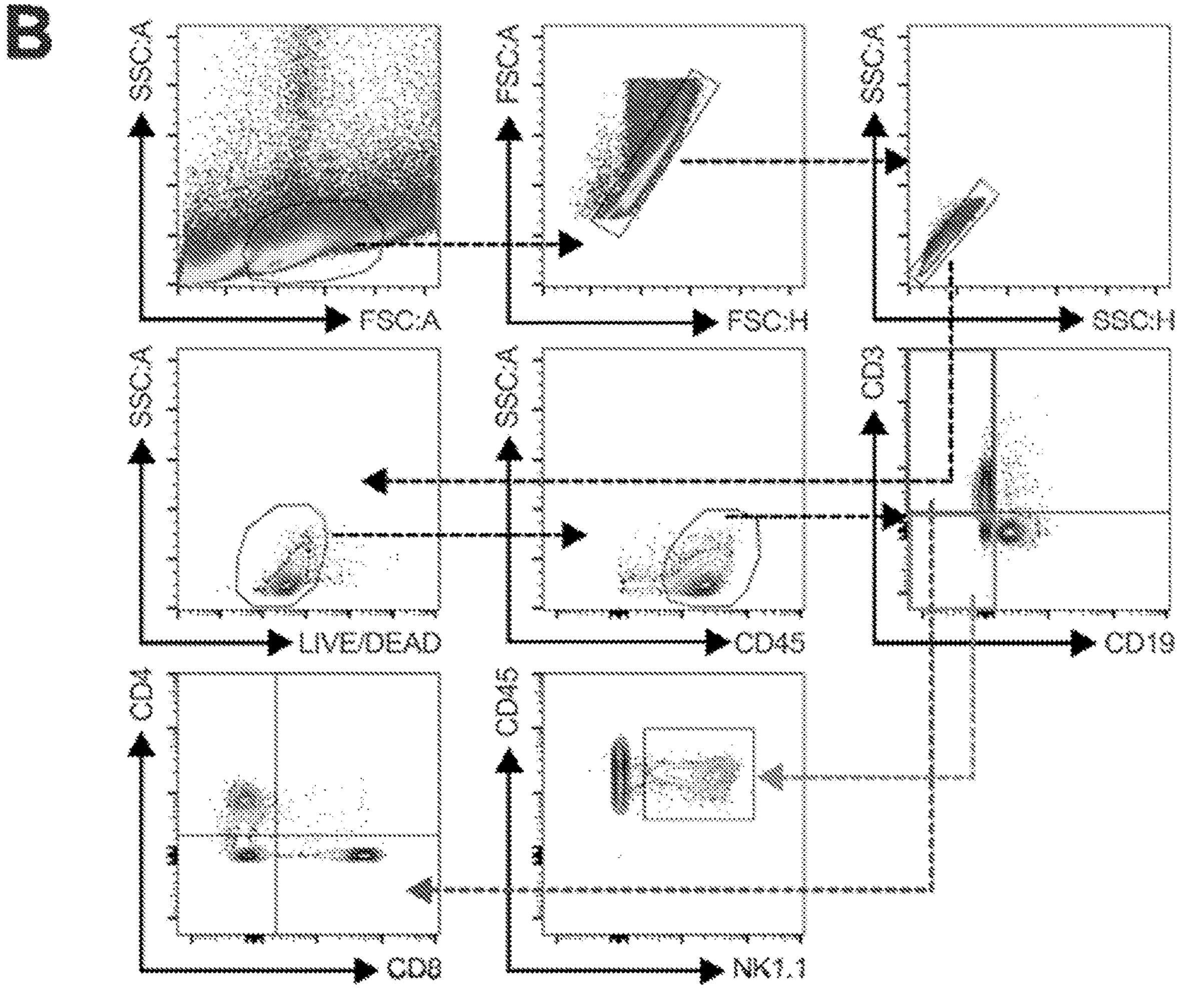
Figure 32:
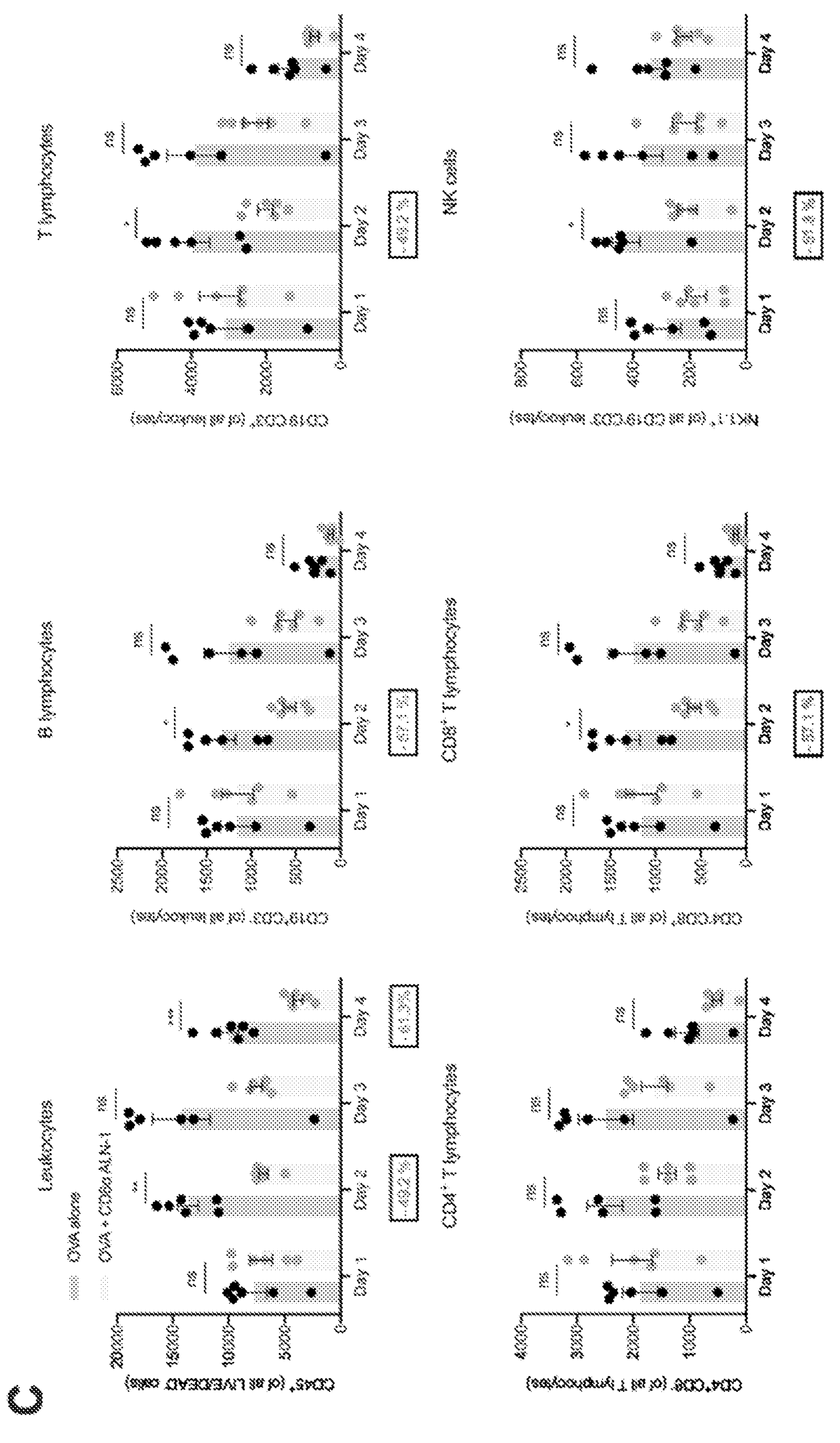

FIGS. 32A-C. Panel A shows white blood cell counts in C57BL/6 mice treated i.p. with OVA (100 g), either alone or combined with CD8α ALN-1 (daily i.p. treatment with 10 g for three consecutive days). Tail vein blood was sampled 6 h after every administration and analyzed on the Hemavet 950FS system. Panel B shows the gating strategy for the detection of different lymphocyte populations in mouse peripheral blood. Staining with LIVE/DEAD and CD45, CD19, CD3, CD4, CD8 and NK1.1 antibodies. Panel C shows flow cytometry analysis for measurement of absolute cells counts in mouse peripheral blood, sampled at the indicated timepoints as described in (Panel A). Day 4 means sampling 24 h after the last treatment. In the single (based on FSC/SSC) living (LIVE/DEAD-) cell population, we identified leukocytes ($CD45^+$), B cells ($CD45^+CD19^+CD3^-$), T cells ($CD45^+CD19^-CD3^+$), $CD4^+$ T cells ($CD45^+CD19^-CD3^+CD4^+CD8^-$), $CD8^+$ T cells ($CD45^+CD19^-CD3^+CD4^-CD8^+$) and NK cells ($CD45^+CD19^-CD3^-NK1.1^+$). Data points represent individual mice±s.e.m. of one experiment with n=5 mice/group in (Panel A) or n=6 mice/group in (Panel C). *, $p<0.001$; , $p<0.01$; *, $p<0.05$; ns, $p\geq 0.05$ by two-way repeated measures ANOVA with Sidak's multiple comparisons test. In each set of histograms, the left bar represents OVA alone and the right bar represents OVA+CD8α ALN-1.

Figure 33:
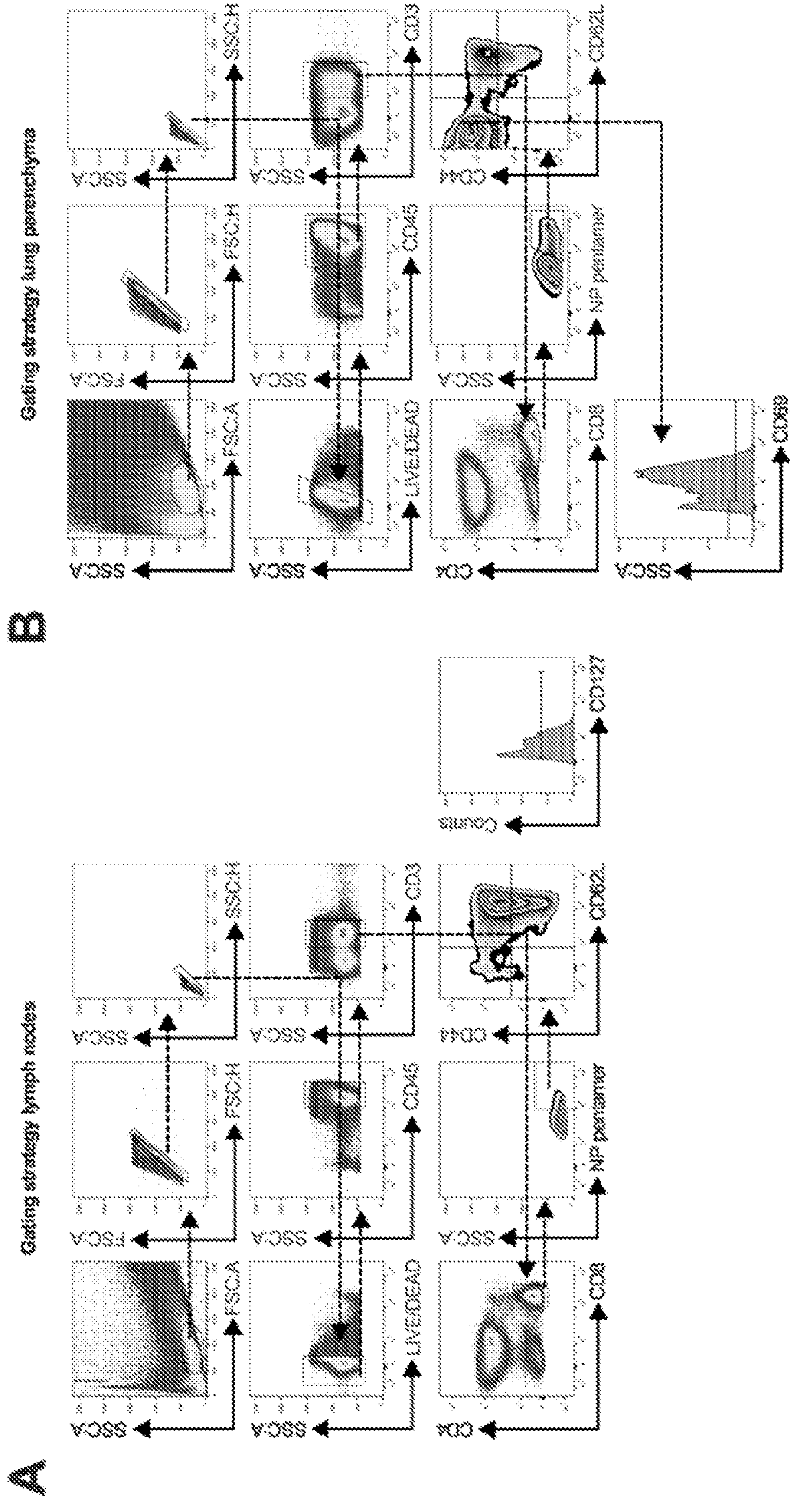
Figure 33:
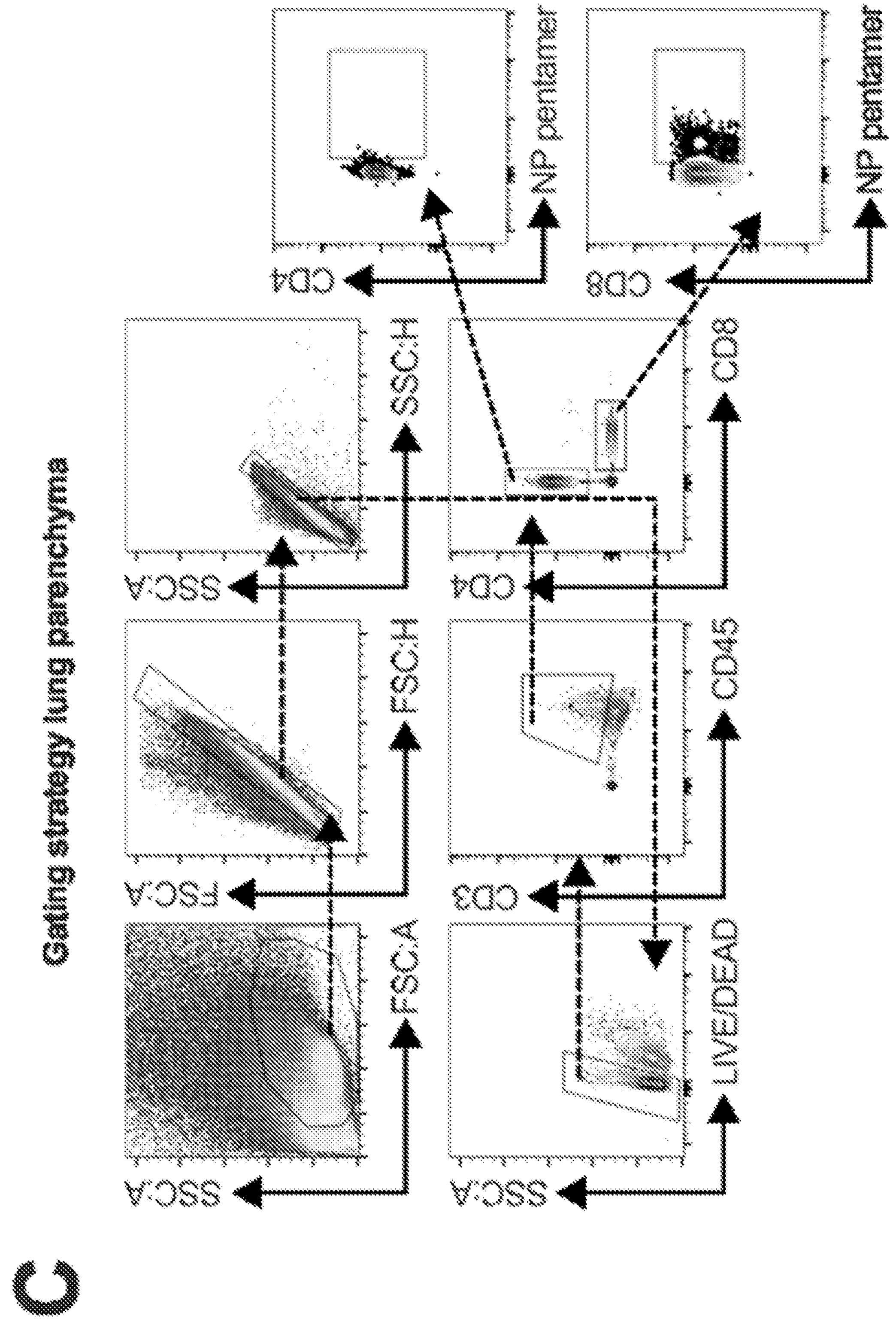

FIGS. 33A-C. Panels A and B show the gating strategy for the detection of NP-specific CTLs in lung-draining mediastinal LNs (Panel A) or lung parenchyma (Panel B) one week post-influenza infection. Staining with LIVE/DEAD, CD45, CD3, CD4, CD8, CD44, CD62L, CD127 and CD69 antibodies and NP-pentamer. Panel C. Gating strategy for the detection of long-lasting NP-specific CTLs in lung parenchyma 50 days post-influenza infection. Staining with LIVE/DEAD, CD45, CD3, CD4 and CD8 antibodies and NP-pentamer. Panels on the right indicate the cleanliness of the NP pentamer staining, which is shown to be selective for $CD8^+$ T cells.

Figure 34:
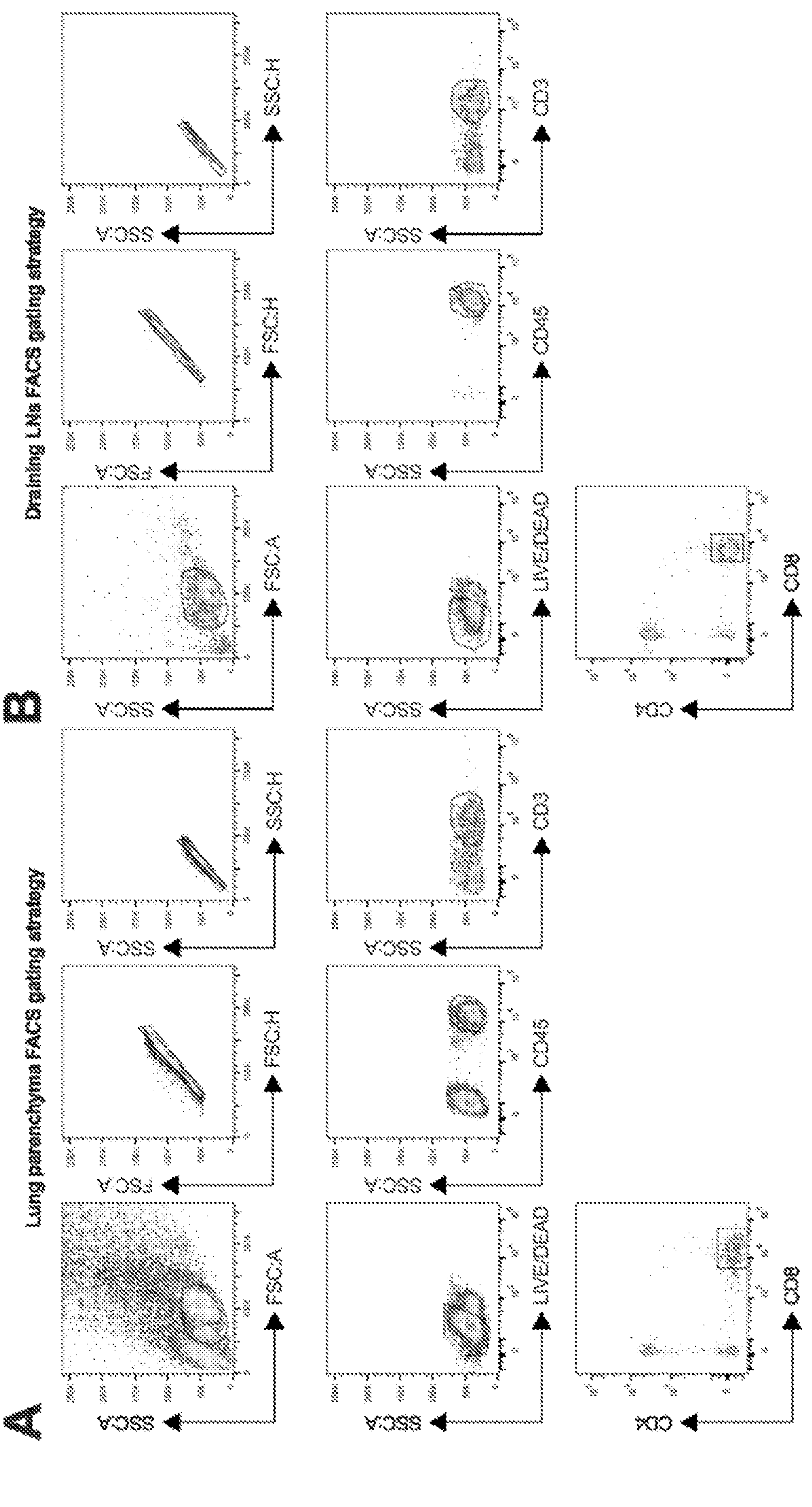
Figure 34:
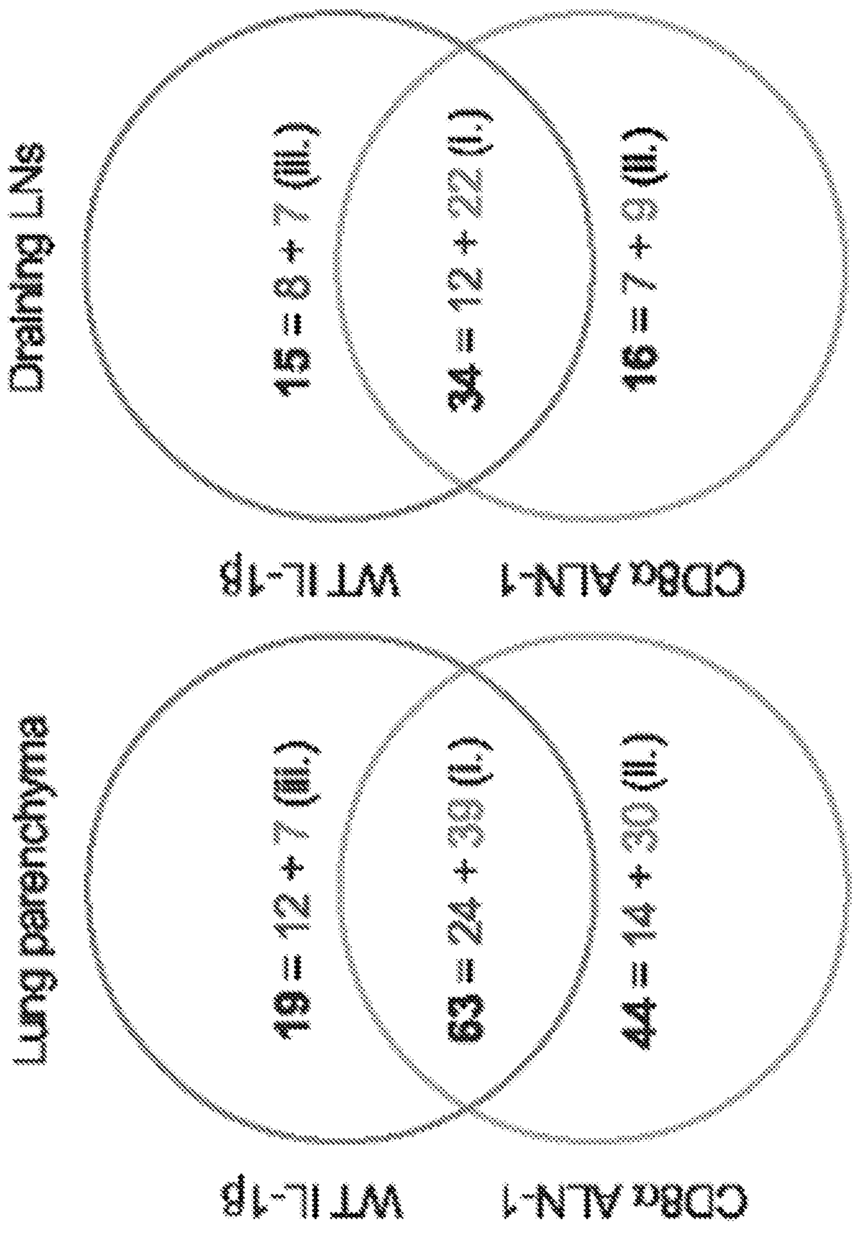

FIGS. 34A-C. Panels A-C show the gating strategy for sorting $CD8^+$ T lymphocytes from the lung parenchyma (Panel A) and lung-draining LNs (Panel B) of influenza-infected mice one week post-influenza A virus challenge. Staining with LIVE/DEAD, CD45, CD3, CD4 and CD8 antibodies. Panel C shows venn diagrams representing the numbers of DEGs shared between (i.) or unique for treatment with WT IL-1β (iii.) and/or CD8α ALN-1 (ii.). Upregulated genes are printed in blue, whereas downregulated genes are printed in red. In $CD8^+$ T cells isolated from lung, 63 differentially expressed genes (DEGs) (24 up- and 39 downregulated) were shared between WT IL-1β and CD8α ALN-1-vaccinated mice. Both WT IL-1β and CD8α ALN-1 had non-redundant effects on gene modulation in lung, as evidenced by 19 DEGs (12 up- and 7 downregulated) unique to WT IL-1β and 44 DEGs (14 up- and 30 downregulated) unique to CD8α ALN-1 treatment. In $CD8^+$ T cells sorted from draining LNs, 34 DEGs (12 up- and 22 downregulated) were shared between mice that received WT IL-1β or CD8α ALN-1 as adjuvant. Here, we identified 15 DEGs (8 up- and 7 downregulated) modulated by WT IL-1β only and 16 DEGs (7 up- and 9 downregulated) uniquely regulated upon CD8α ALN-1-treatment.

DETAILED DESCRIPTION

One aspect of the present application is related to a vaccine composition comprising: (a) an adjuvant, and (b) an antigen that is suitable for inducing an immune response. The adjuvant comprises a chimeric protein or chimeric protein complex comprising: (i) a wild type or mutant IL-1β (which is an example of a signaling agent as described herein), (ii) one or more targeting moieties, said targeting moieties comprising recognition domains, which specifically bind to an antigen or receptor of interest; and (iii) a connector between (i) and (ii).

In embodiments, the connector comprises: (1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii); and/or (2) a flexible linker that connects (i) and (ii), wherein the mutant IL-1β is characterized by low affinity or activity at the IL-1 receptor.

In embodiments, the adjuvant is a nucleic acid, which encodes the chimeric protein or chimeric protein complex. In embodiments, the nucleic acid is an mRNA, optionally comprising one or more non-canonical nucleotides, optionally selected from pseudouridine and 5-methoxyuridine. In embodiments, the nucleic acid is DNA, optionally selected from linear DNA, DNA fragments, or DNA plasmids.

In some embodiments, the vaccine composition of the present invention further comprises an aluminum gel or salt. In embodiments, the aluminum gel or salt is selected from aluminum hydroxide, aluminum phosphate, and aluminum sulfate. In some embodiments, the adjuvant is a nucleic acid encoding the chimeric protein or chimeric protein complex as described herein.

In some embodiments, the additional adjuvant is selected from, oil-in-water emulsion formulations, saponin adjuvants, ovalbumin, toll like receptors ligands, Freunds Adjuvant, cytokines, and chitosans. Illustrative additional adjuvants include, but are not limited to: (1) ovalbumin (e.g. ENDOFIT), which is often used for biochemical studies; (2) oil-in-water emulsion formulations (with or without other specific immunostimulating agents such as muramyl peptides or bacterial cell wall components), such as for example (a) MF59 (PCT Publ. No. WO 90/14837), containing 5% Squalene, 0.5% Tween 80, and 0.5% Span 85 (optionally containing various amounts of MTP-PE) formulated into submicron particles using a microfluidizer such as, for example, Model HOy microfluidizer (Microfluidics, Newton, Mass.), (b) SAF, containing 10% Squalane, 0.4% Tween 80, 5% pluronic-blocked polymer L121, and thr-MDP either microfluidized into a submicron emulsion or vortexed to generate a larger particle size emulsion, (c) RIBI adjuvant system (RAS), (RIBI IMMUNOCHEM, Hamilton, MO.) containing 2% Squalene, 0.2% Tween 80, and, optionally, one or more bacterial cell wall components from the group of monophosphorylipid A (MPL), trehalose dimycolate (TDM), and cell wall skeleton (CWS), including MPL+CWS (DETOX™); and (d) ADDAVAX (Invitrogen); (3) saponin adjuvants, such as STIMULON (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (by way of non-limiting example, IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) chitosans and other derivatives of chitin or poly-N-acetyl-D-glucosamine in which the greater proportion of the N-acetyl groups have been removed through hydrolysis (see, e.g., European Patent Application 460 020, which is hereby incorporated by reference in its entirety, disclosing pharmaceutical formulations including chitosans as mucosal absorption enhancers; and (7) other substances that act as immunostimulating agents to enhance the effectiveness of the composition, e.g., monophosphoryl lipid A. In other embodiments, the additional adjuvant is one or more of an aluminum salt or gel, a pattern recognition receptors (PRR) agonist, CpG ODNs and imidazoquinolines. In some embodiments, the additional adjuvant is one or more of cyclic [G(3',5')pA(3',5')p](e.g. 3'3'-cGAMP VACCIGRADE); cyclic [G(2',5')pA(3',5')p] 2'3' (e.g. 2'3' cGAMP VACCIGRADE); cyclic [G(2',5')pA (2',5')p](e.g. 2'2'-cGAMP VACCIGRADE), cyclic diadenylate monophosphate (e.g. c-di-AMP VACCIGRADE);

cyclic diguanylate monophosphate (e.g. c-di-GMP VACCIGRADE); TLR7 agonist-imidazoquinolines compound (e.g. TLR7 agonists, such as, for example, Gardiquimod VACCIGRADE, Imiquimod VACCIGRADE, R848 VACCIGRADE); lipopolysaccharides (e.g. TLR4 agonists), such as that from *E. coli* 0111:B4 strain (e.g. LPS-EB VACCIGRADE); monophosphoryl lipid A (e.g. MPLA-SM VACCIGRADE and MPLA Synthetic VACCIGRADE); N-glycolylated muramyldipeptide (e.g. N-Glycolyl-MDP VACCIGRADE); CpG ODN, class A and/or CpG ODN, class B and/or CpG ODN, class C (e.g. ODN 1585 VACCIGRADE, ODN 1826 VACCIGRADE, ODN 2006 VACCIGRADE, ODN 2395 VACCIGRADE), a triacylated lipoprotein (e.g. Pam3CSK4 VACCIGRADE); Polyinosine-polycytidylic acid (e.g. Poly(I:C) (HMW) VACCIGRADE); and cord factor (i.e. mycobacterial cell wall component trehalose 6,6' dimycolate (TDM,)) or an analog thereof (e.g. TDB VACCIGRADE, TDB-HS15 VACCIGRADE). In some embodiments, the additional adjuvant is a TLR agonist (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13), a nucleotide-binding oligomerization domain (NOD) agonist, a stimulator of interferon genes (STING) ligand, or related agent. In some embodiments, the adjuvant is a ligand for toll like receptors (TLR) including endotoxin derived compounds, CpG, and flagellin.

In some embodiments, the additional adjuvant is one or more of a mineral adjuvant, gel-based adjuvant, tensoactive agent, bacterial product, oil emulsion, particulated adjuvant, fusion protein, and lipopeptide. Other mineral salt adjuvants, besides the aluminum adjuvants described elsewhere, include salts of calcium (e.g. calcium phosphate), iron and zirconium. Other gel-based adjuvants, besides the aluminum gel-based adjuvants described elsewhere, include Acemannan. Tensoactive agents include Quil A, saponin derived from an aqueous extract from the bark of *Quillaja saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gram-negative bacteria (e.g. from *Mycobacterium* spp., *Corynebacterium parvum, C. granulosum, Bordetella pertussis* and *Neisseria meningitidis*), N-acetyl muramyl-L-alanyl-D-isoglutamine (MDP), different compounds derived from MDP (e.g. threonyl-MDP), lipopolysaccharides (LPS) (e.g. from the cell wall of Gram-negative bacteria), trehalose dimycolate (TDM), and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide) microspheres have been extensively studied and find use herein.

Further, in some embodiments, cytokines are an adjuvant of the present invention (e.g. IFN-γ and granulocyte-macrophage colony stimulating factor (GM-CSF)). Also carbohydrate adjuvants (e.g. inulin-derived adjuvants, such as, gamma inulin, algammulin (a combination of γ-inulin and aluminum hydroxide), and polysaccharides based on glucose and mannose, such as glucans, dextrans, lentinans, glucomannans and galactomannans) find use in the present invention. In some embodiments, adjuvant formulations are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol.

In some embodiments, the additional adjuvants are described in Jennings et al. Adjuvants and Delivery Systems for Viral Vaccines-Mechanisms and Potential. In: Brown F, Haaheim L R, (eds). Modulation of the Immune Response to Vaccine Antigens. Dev. Biol. Stand, Vol. 92. Basel: Karger 1998; 19-28 and/or Sayers et al. J Biomed Biotechnol. 2012; 2012: 831486, and/or Petrovsky and Aguilar, Immunology and Cell Biology (2004) 82, 488-496 the contents of which are hereby incorporated by reference in their entireties.

In various embodiments, the present adjuvants may be part of live and attenuated, or killed or inactivated, or toxoid, or subunit or conjugate vaccines.

In some embodiments, the vaccine or vaccine composition of the present invention causes an improvement in adjuvant properties relative to a vaccine comprising the antigen and the aluminum gel or salt alone. In various embodiments, the vaccine and/or adjuvant described herein causes a broader, more diverse, more robust and longer lasting immunostimulatory effect than the vaccine comprising the antigen and the aluminum gel or salt alone and/or the adjuvant comprising the aluminum gel or salt alone.

In some embodiments, the described vaccine, vaccine composition, and/or described adjuvant causes immunostimulation of one or more of $T_{H1}$ and $T_{H2}$-mediated immune response. In some embodiments, the described vaccine, vaccine composition, and/or described adjuvant causes immunostimulation of both of $T_{H1}$ and $T_{H2}$-mediated immune response. In some embodiments, the described vaccine, vaccine composition, and/or described adjuvant causes immunostimulation of $T_{H1}$-mediated immune response at levels greater than a vaccine comprising the antigen and the aluminum gel or salt alone or an adjuvant comprising the aluminum gel or salt alone.

In various embodiments, the present vaccine composition is part of the following vaccines (e.g. the antigens of these vaccines may be used as the antigen of the present vaccines): DTP (diphtheria-tetanus-pertussis vaccine), DTaP (diphtheria-tetanus-acellular pertussis vaccine), Hib (*Haemophilus influenzae* type b) conjugate vaccines, Pneumococcal conjugate vaccine, Hepatitis A vaccines, Poliomyelitis vaccines, Yellow fever vaccines, Hepatitis B vaccines, combination DTaP, Tdap, Hib, Human Papillomavirus (HPV) vaccine, Anthrax vaccine, and Rabies vaccine.

In some embodiments, the adjuvant or vaccine composition as described herein has (a) low toxicity; (b) an ability to stimulate a long-lasting immune response against the antigen; (c) substantial stability; (d) an ability to elicit a humoral immune response and/or a cell-mediated immunity to the antigen; (e) a capability of selectively interacting with populations of antigen presenting cells; (f) an ability to specifically elicit $T_{H1}$ and/or $T_{H2}$ cell-specific immune responses to the antigen; and/or (g) an ability to selectively increase appropriate antibody isotype levels against antigens, the isotype optionally being IgA, when administered to a patient.

$T_{H1}$-mediated immune response (or "Type 1 response") largely involves interaction with macrophages and CD8+ T cells and may be linked to interferon-γ, TNF-p, interleukin-2, and interleukin-10 production. The $T_{H1}$-mediated immune response promotes cellular immune system and maximizes the killing efficacy of the macrophages and the proliferation of cytotoxic $CD8^+$ T cells. The $T_{H1}$-mediated immune response also promotes the production of opsonizing antibodies (e.g. IgG, IgM and IgA). The Type 1 cytokine IFN-γ increases the production of interleukin-12 by dendritic cells and macrophages, and via positive feedback, IL-12 stimulates the production of IFN-γ in helper T cells, thereby promoting the $T_{H1}$ profile. Interferon-γ also inhibits the production of cytokines such as interleukin-4, a cytokine associated with the Type 2 response, and thus it also acts to preserve its own response. $T_{H2}$-mediated immune response (or "Type 2 response") largely involves interaction with B-cells, eosinophils, and mast cells and may be linked to interleukin-4, interleukin-5, interleukin-6, interleukin-9, interleukin-10, and interleukin-13. $T_{H2}$-mediated immune response promotes humoral immune system and may stimulate B-cells into proliferation, induce B-cell antibody class switching, and increase neutralizing antibody production (e.g. IgG, IgM and IgA as well as IgE antibodies). Other functions of the Type 2 response include promoting its own profile using two different cytokines. Interleukin-4 acts on helper T cells to promote the production of $T_{H2}$ cytokines, while interleukin-10 (IL-10) inhibits a variety of cytokines including interleukin-2 and IFN-γ in helper T cells and IL-12 in dendritic cells and macrophages.

In some embodiments, the adjuvant or vaccine composition stimulates a $CD8^+$ T cell response to the antigen, when administered to a patient. In embodiments, the adjuvant or vaccine composition does not substantially cause one or more of fever, neutrophilia and the release of acute phase proteins when administered to a patient. In some embodiments, the adjuvant or vaccine composition stimulates activation of the IL-1R, when administered to a patient.

In some embodiments, the methods described herein are where the adjuvant or vaccine composition stimulates activation of the IL-1R, when administered to a patient.

In some embodiments, the present invention is related to a vaccine composition comprising a wild type IL-1β, e.g. with an amino acid sequence of SEQ ID NO: 1, or a variant having at least about 95%, or at least about 97%, or at least about 99% identity thereto, and a targeting moiety that comprises a recognition domain that recognizes and/or binds CD8.

In some embodiments, the present invention is related to a vaccine composition comprising a mutant IL-1β that comprises Q148G, with respect to the amino acid sequence of SEQ ID NO: 1, or a variant having at least about 95%, or at least about 97%, or at least about 99% identity thereto, and a targeting moiety that comprises a recognition domain that recognizes and/or binds CD8.

In some embodiments, the antigen of the present invention is a protein or an antigenic fragment of a protein. In some embodiments, the antigen is a nucleic acid encoding a protein or an antigenic fragment of a protein. In embodiments, the nucleic acid which is an antigen or which encodes a protein or an antigenic fragment of a protein can be an mRNA, optionally comprising one or more non-canonical nucleotides, optionally selected from pseudouridine and 5-methoxyuridine. In embodiments, the nucleic acid is DNA, optionally selected from linear DNA, DNA fragments, or DNA plasmids.

Interleukin-1R or a Mutant Thereof

In one aspect, the present invention provides a vaccine composition comprising a chimeric protein or a chimeric protein complex that includes a wild type or engineered/mutant interleukin-1β. IL-1β is a proinflammatory cytokine and an important immune system regulator. It is a potent activator of CD4 T cell responses, increases proportion of Th17 cells and expansion of IFNγ and IL-4 producing cells. IL-1β is also a potent regulator of $CD8^+$ T cells, enhancing antigen-specific $CD8^+$ T cell expansion, differentiation, migration to periphery and memory. IL-1 receptors comprise IL-1R1 and IL-1RACP. Binding to and signaling through the IL-1R1 constitutes the mechanism whereby IL-1β mediates many of its biological (and pathological) activities. IL1-R2 can function as a decoy receptor, thereby reducing IL-1β availability for interaction and signaling through the IL-1R1.

In various embodiments, the present invention provides a vaccine composition that comprises a chimeric protein or chimeric protein complexes, such as Fc-based chimeric protein complexes, that include the mutant IL-1β fused to one or more targeting moieties. In some embodiments, the mutant IL-1β is human IL-1β. In some embodiments, the mutant IL-1β has low affinity and/or activity for IL-1 receptor. In some embodiments, the mutant IL-1β has substantially reduced or ablated affinity and/or activity for IL-1 receptor. In some embodiments, the low affinity or activity of mutant IL-1β at the IL-1 receptor is restorable by attachment to one or more targeting moieties or upon inclusion in the chimeric protein complex.

In an embodiment, the wild type IL-1β has the amino acid sequence of:

```
IL-1 beta (mature form, wild type)
                                        (SEQ ID NO: 1)
APVRSLNCTLRDSQQKSLVMSGPYELKALHLQGQDMEQQVVFSMSFVQG

EESNDKIPVALGLKEKNLYLSCVLKDDKPTLQLESVDPKNYPKKKMEKR

FVFNKIEINNKLEFESAQFPNWYISTSQAENMPVFLGGTKGGQDITDFT

MQFVSS
```

In some embodiments, the mutant human IL-1β has an amino acid sequence of at least 95%, or 97% or 98% identity to SEQ ID NO: 1. In some embodiments, the mutant IL-1β has a deletion of amino acids at positions 52-54 which produces a modified human IL-1β with reduced binding affinity for type I IL-1R and reduced biological activity. See, for example, WO 1994/000491, the entire contents of which are hereby incorporated by reference. In some embodiments, the mutant IL-1β has one or more substitution mutations selected from A117G/P118G, R120X, L122A, T125G/L126G, R127G, Q130X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, 1172A, V174A, K208E, K209X, K209A/K210A, K219X, E221X, E221 S/N224A, N224S/K225S, E244K, N245Q (where X can be any change in amino acid, e.g., a non-conservative change), which exhibit reduced binding to IL-1R, as described, for example, in WO2015/007542 and WO/2015/007536, the entire contents of which is hereby incorporated by reference (numbering base on the human IL-1β sequence, Genbank accession number NP_000567, version NP-000567.1, GI: 10835145). In some embodiments, the modified human IL-1β may have one or more mutations selected from R120A, R120G, Q130A, Q130W, H146A, H146G, H146E, H146N, H146R, Q148E, Q148G, Q148L, K209A, K209D, K219S, K219Q, E221S and E221K. In an embodiment, the modified human IL-1β comprises the mutations Q131G and Q148G. In an embodiment, the modified human IL-1β comprises the mutations Q148G and K208E. In an embodiment, the modified human IL-1β comprises the mutations R120G and Q131G. In an embodiment, the modified human IL-1β comprises the mutations R120G and H146A. In an embodiment, the modified human IL-1β comprises the mutations R120G and H146N. In an embodiment, the modified human IL-1β comprises the mutations R120G and H146R. In an embodiment, the modified human IL-1β comprises the mutations R120G and H146E. In an embodiment, the modified human IL-1β comprises the mutations R120G and H146G. In an embodiment, the modified human IL-1β comprises the mutations R120G and K208E. In an embodiment, the modified human IL-1β comprises the mutations R120G, F162A, and Q164E.

In one embodiment, the mutant IL-1β comprises Q148G, with respect to the amino acid sequence of SEQ ID NO: 1.

In various embodiments, the mutations allow for IL-1β to have one or more of attenuated activity such as one or more of reduced binding affinity, reduced endogenous activity, and reduced specific bioactivity relative to unmodified or unmutated, i.e., the wild type form of IL-1β (e.g. comparing IL-1β in a wild type form versus a modified (e.g. mutant) form). In some embodiments, the mutations that attenuate or reduce binding or affinity include those mutations that substantially reduce or ablate binding or activity. In some embodiments, the mutations that attenuate or reduce binding or affinity are different than those mutations which substantially reduce or ablate binding or activity. Consequentially, in various embodiments, the mutations allow for IL-1β to have improved safety, e.g. have reduced systemic toxicity, reduced side effects, and reduced off-target effects relative to unmutated, i.e. wild type, IL-1β (e.g. comparing IL-1β in a wild type form versus a modified (e.g. mutant) form).

In various embodiments, IL-1β is modified to have one or more mutations that reduce its binding affinity or activity for one or more of its receptors. In some embodiments, IL-1β is modified to have one or more mutations that substantially reduce or ablate binding affinity or activity for the receptors. In some embodiments, the activity provided by the wild type IL-1β is agonism at the receptor (e.g. activation of a cellular effect at a site of therapy). For example, the wild type IL-1β may activate its receptor. In such embodiments, the mutations result in the modified IL-1β to have reduced or ablated activating activity at the receptor. For example, the mutations may result in the modified IL-1β to deliver a reduced activating signal to a target cell or the activating signal could be ablated.

In some embodiments, the reduced affinity or activity of IL-1β at the receptor is restorable by attachment with one or more of the targeting moieties. In other embodiments, the reduced affinity or activity of IL-1β at the receptor is not substantially restorable by the activity of one or more of the targeting moieties.

In various embodiments, the chimeric proteins of the present invention reduce off-target effects because the IL-1β has mutations that weaken or ablate binding affinity or activity at a receptor. In various embodiments, this reduction in side effects is observed relative with, for example, the wild type IL-1β. In various embodiments, the IL-1β is active on target cells because the targeting moiety(ies) compensates for the missing/insufficient binding (e.g., without limitation and/or avidity) required for substantial activation. In various embodiments, the modified IL-1β is substantially inactive en route to the site of therapeutic activity and has its effect substantially on specifically targeted cell types that greatly reduces undesired side effects.

In various embodiments, substantially reducing or ablating binding or activity at the receptor causes the therapeutic effect of IL-1β to improve as there is a reduced or eliminated sequestration of the therapeutic chimeric proteins away from the site of therapeutic action. For instance, in some embodiments, this obviates the need of high doses of the present vaccine compositions that compensate for loss at the other receptor. Such ability to reduce dose further provides a lower likelihood of side effects.

In various embodiments, the modified IL-1β comprises one or more mutations that cause IL-1β to have reduced, substantially reduced, or ablated affinity, e.g. binding (e.g. $K_D$) and/or activation. In various embodiments, the reduced affinity at IL-1β's receptor allows for attenuation of activity (inclusive of agonism or antagonism). In such embodiments, the modified IL-1β has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor relative to the wild type IL-1β. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type IL-1β.

In various embodiments, the modified IL-1β comprises one or more mutations that reduce the endogenous activity of IL-1β to about 75%, or about 70%, or about 60%, or about 50%, or about 40%, or about 30%, or about 25%, or about 20%, or about 10%, or about 5%, or about 3%, or about 1%, e.g., relative to the wild type IL-1β. In some embodiments, the modified IL-1β comprises one or more mutations that cause IL-1β to have reduced affinity for its receptor that is lower than the binding affinity of the targeting moiety(ies) for its(their) receptor(s). In some embodiments, this binding affinity differential is between IL-1β/receptor and targeting moiety/receptor on the same cell. In some embodiments, this binding affinity differential allows for mutant IL-1β to have localized, on-target effects and to minimize off-target effects that underlie side effects that are observed with wild type IL-1β. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold.

Receptor binding activity may be measured using methods known in the art. For example, affinity and/or binding activity may be assessed by Scatchard plot analysis and computer-fitting of binding data (e.g. Scatchard, 1949) or by reflectometric interference spectroscopy under flow through conditions, as described by Brecht et al. (1993), the entire contents of all of which are hereby incorporated by reference.

In various embodiments the modified IL-1β comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known wild type IL-1β (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments the modified IL-1β comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any of amino acid sequences of the wildtype IL-1β disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the modified IL-1β comprises an amino acid sequence having one or more amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt a-helices.

As used herein, "non-conservative substitutions" are defined as exchanges of an amino acid by another amino acid listed in a different group of the six standard amino acid groups (1) to (6) shown above. In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as p methyl amino acids, C α-methyl amino acids, N α-methyl amino acids, and amino acid analogs in general).

In some embodiments, the reduced affinity or activity of the modified IL-1β at the therapeutic receptor is inducible or restorable by attachment to a targeting moiety or upon inclusion of a targeting moiety in a chimeric protein or a chimeric protein complex, e.g., a Fc-based chimeric protein complex as disclosed herein. In some embodiments, the activity of IL-1β is reduced or attenuated by virtue of its fusion with another protein, including, in some instances, by fusion with targeting moieties as described herein. In other embodiments, the activity of IL-1β is reduced or attenuated by modifying the IL-1β, e.g., by introducing mutations as described herein. In some embodiments, attenuation of the activity can be restored by attaching the IL-1β to a targeting moiety or by the action of the attached targeting moiety. In embodiments, the targeting moiety-by virtue of its attachment or by its activity-induces IL-1β's activity. In some embodiments, the reduced affinity or activity at the receptor is inducible or restorable by attachment with one or more of the targeting moieties as described herein or upon inclusion in the chimeric protein complexes, such as Fc-based chimeric protein complex disclosed herein.

Targeting Moiety

In various embodiments, the adjuvants, chimeric proteins, or chimeric protein complexes, such as Fc-based chimeric protein complexes of the present invention comprise one or more targeting moieties having recognition domains which specifically bind to a target (e.g. antigen or receptor of interest). In some embodiments, the adjuvants, chimeric proteins, or chimeric protein complexes, may comprise two, three, four, five, six, seven, eight, nine, ten or more targeting moieties. In illustrative embodiments, the adjuvants, chimeric proteins, or chimeric protein complexes comprise two or more targeting moieties. In such embodiments, the adjuvants, chimeric proteins, or chimeric protein complexes can target two different cells (e.g. to make a synapse) or the same cell (e.g. to get a more concentrated signaling agent effect).

In various embodiments, the target (e.g. antigen, receptor) of interest can be found on one or more immune cells, which can include, without limitation, T cells, cytotoxic T lymphocytes, T helper cells, natural killer (NK) cells, natural killer T (NKT) cells, macrophages (e.g. M1 or M2 macrophages), B cells, Breg cells, dendritic cells, or subsets thereof. In some embodiments, the recognition domains specifically bind to a target (e.g. antigen, receptor) of interest and effectively, directly or indirectly, recruit one of more immune cells. In some embodiments, the adjuvants, chimeric proteins, or chimeric protein complexes may directly or indirectly recruit an immune cell, e.g., in some embodiments, to a therapeutic site (e.g. a locus with one or more disease cell or cell to be modulated for a therapeutic effect). In some embodiments, the adjuvants, chimeric proteins, or chimeric protein complexes may directly or indirectly recruit an immune cell, e.g. an immune cell that can kill an infectious agent and/or suppress an infection, to a site of action.

In various embodiments, the adjuvants, chimeric proteins, or chimeric protein complexes such as Fc-based chimeric protein complexes have targeting moieties having recognition domains which specifically bind to a target (e.g. antigen, receptor) which is part of a non-cellular structure. In some embodiments, the antigen or receptor is not an integral component of an intact cell or cellular structure. In some embodiments, the antigen or receptor is an extracellular antigen or receptor. In some embodiments, the target is a non-proteinaceous, non-cellular marker, including, without limitation, nucleic acids, inclusive of DNA or RNA, such as, for example, DNA released from necrotic cells or extracellular deposits such as cholesterol.

In some embodiments, the target (e.g. antigen, receptor) of interest is part of the non-cellular component of the stroma or the extracellular matrix (ECM) or the markers associated therewith. As used herein, stroma refers to the connective and supportive framework of a tissue or organ. Stroma may include a compilation of cells such as fibroblasts/myofibroblasts, glial, epithelia, fat, immune, vascular, smooth muscle, and immune cells along with the extracellular matrix (ECM) and extracellular molecules. In various embodiments, the target (e.g. antigen, receptor) of interest is part of the non-cellular component of the stroma such as the extracellular matrix and extracellular molecules.

As used herein, the ECM refers to the non-cellular components present within all tissues and organs. The ECM is composed of a large collection of biochemically distinct components including, without limitation, proteins, glycoproteins, proteoglycans, and polysaccharides. These components of the ECM are usually produced by adjacent cells and secreted into the ECM via exocytosis. Once secreted, the ECM components often aggregate to form a complex network of macromolecules. In various embodiments, the adjuvants, chimeric proteins, or chimeric protein complexes of the invention comprises a targeting moiety that recognizes a target (e.g., an antigen or receptor or non-proteinaceous molecule) located on any component of the ECM. Illustrative components of the ECM include, without limitation, the proteoglycans, the non-proteoglycan polysaccharides, fibers, and other ECM proteins or ECM non-proteins, e.g. polysaccharides and/or lipids, or ECM associated molecules (e.g. proteins or non-proteins, e.g. polysaccharides, nucleic acids and/or lipids).

In some embodiments, the targeting moiety recognizes one or more ECM proteins including, but not limited to, a tenascin, a fibronectin, a fibrin, a laminin, or a nidogen/entactin.

In various embodiments, the targeting moiety may bind to the full-length and/or mature forms and/or isoforms and/or splice variants and/or fragments and/or any other naturally occurring or synthetic analogs, variants, or mutants of any of the targets described herein. In various embodiments, the targeting moiety may bind to any forms of the proteins described herein, including monomeric, dimeric, trimeric, tetrameric, heterodimeric, multimeric and associated forms.

In various embodiments, the targeting moiety may bind to any post-translationally modified forms of the proteins described herein, such as glycosylated and/or phosphorylated forms.

In various embodiments, the targeting moiety comprises an antigen recognition domain that recognizes extracellular molecules such as DNA. In some embodiments, the targeting moiety comprises an antigen recognition domain that recognizes DNA. In an embodiment, the DNA is shed into the extracellular space from necrotic or apoptotic cells or other diseased cells.

In some embodiments, the adjuvants, chimeric proteins or chimeric protein complexes such as Fc-based chimeric protein complexes of the invention may have two or more targeting moieties that bind to non-cellular structures. In some embodiments, there are two targeting moieties and one targets a cell while the other targets a non-cellular structure. In various embodiments, the targeting moieties can directly or indirectly recruit cells, such as disease cells and/or effector cells. In some embodiments, the adjuvants, chimeric proteins, or chimeric protein complexes are capable of, or find use in methods involving, shifting the balance of immune cells in favor of immune attack of an infection. For instance, the adjuvants, chimeric proteins, or chimeric protein complexes can shift the ratio of immune cells at a site of clinical importance in favor of cells that can kill and infectious agent and/or suppress an infection (e.g. T cells, cytotoxic T lymphocytes, T helper cells, natural killer (NK) cells, natural killer T (NKT) cells, macrophages (e.g. M1 macrophages), B cells, dendritic cells, or subsets thereof) and in opposition to cells that reduce immunity (e.g. myeloid-derived suppressor cells (MDSCs), regulatory T cells (Tregs); tumor associated neutrophils (TANs), M2 macrophages, tumor associated macrophages (TAMs), or subsets thereof). In some embodiments, the adjuvants, chimeric proteins, or chimeric protein complexes are capable of increasing a ratio of effector T cells to regulatory T cells.

For example, in some embodiments, the recognition domains specifically bind to a target (e.g. antigen, receptor) associated with T cells. In some embodiments, the recognition domains directly or indirectly recruit T cells. In an embodiment, the recognition domains specifically bind to effector T cells. In some embodiments, the recognition domain directly or indirectly recruits effector T cells, e.g., in some embodiments, to a therapeutic site (e.g. a locus with one or more disease cell or cell to be modulated for a therapeutic effect). Illustrative effector T cells include cytotoxic T cells (e.g. αβ TCR, $CD3^+$, $CD8^+$, $CD45RO^+$); $CD4^+$effector T cells (e.g. ap TCR, $CD3^+$, $CD4^+$, $CCR7^+$, CD62Lhi, IL-7R/$CD127^+$); $CD8^+$ effector T cells (e.g. ap TCR, $CD3^+$, $CD8^+$, $CCR7^+$, CD62Lhi, IL-7R/$CD127^+$); effector memory T cells (e.g. $CD62L^{low}$, $CD44^+$, TCR, $CD3^+$, IL-7R/$CD127^+$, IL-$15R^+$, $CCR7^{low}$); central memory T cells (e.g. $CCR7^+$, $CD62L^+$, $CD27^+$; or CCR7hi, $CD44^+$, CD62Lhi, TCR, $CD3^+$, IL-7R/$CD127^+$, IL-$15R^+$); $CD62L^+$ effector T cells; $CD8^+$ effector memory T cells (TEM) including early effector memory T cells ($CD27^+CD62L^-$) and late effector memory T cells ($CD27^-CD62L^-$) (TemE and TemL, respectively); CD127(+)CD25(low/−) effector T cells; CD127(−)CD25(−) effector T cells; $CD8^+$ stem cell memory effector cells (TSCM) (e.g. CD44(low)CD62L (high)CD122(high)sca(+)); TH1 effector T-cells (e.g. $CXCR3^+$, $CXCR6^+$and $CCR5^+$; or ap TCR, $CD3^+$, $CD4^+$, IL-$12R^+$, $IFN\gamma R^+$, $CXCR3^+$), TH2 effector T cells (e.g. $CCR3^+$, $CCR4^+$and $CCR8^+$; or αβ TCR, $CD3^+$, $CD4^+$, IL-$4R^+$, IL-$33R^+$, $CCR4^+$, IL-$17RB^+$, $CRTH2^+$); TH9 effector T cells (e.g. ap TCR, $CD3^+$, $CD4^+$); TH17 effector T cells (e.g. ap TCR, $CD3^+$, $CD4^+$, IL-$23R^+$, $CCR6^+$, IL-$1R^+$); $CD4^+CD45RO^+CCR7^+$effector T cells, $ICOS^+$ effector T cells; $CD4^+CD45RO^+$CCR7(−) effector T cells; and effector T cells secreting IL-2, IL-4 and/or IFN-γ.

Illustrative T cell antigens of interest include, for example (and inclusive of the extracellular domains, where applicable): CD8, CD3, SLAMF4, IL-2Ra, 4-1BB/TNFRSF9, IL-2R β, ALCAM, B7-1, IL-4R, B7-H3, BLAME/SLAMFS, CEACAM1, IL-6R, CCR3, IL-7 Rα, CCR4, CXCR1/IL-S RA, CCR5, CCR6, IL-10R α, CCR 7, IL-10R p, CCRS, IL-12R β, CCR9, IL-12R β 2, CD2, IL-1β R a 1, IL-1β, CD3, CD4, ILT2/CDS5a, ILT3/CDS5k, ILT4/CDS5d, ILT5/CDS5a, lutegrin α 4/CD49d, CDS, Integrin a E/CD103, CD6, Integrin a M/CD 11 b, CDS, Integrin a X/CD11c, Integrin β 2/CDIS, KIR/CD15S, CD27/TNFRSF7, KIR2DL1, CD2S, KIR2DL3, CD30/TNFRSF6, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common y Chain/IL-2R γ, Osteopontin, CRACC/SLAMF7, PD-1, CRTAM, PSGL-1, CTLA-4, RANK/TNFRSF11A, CX3CR1, CX3CL1, L-Selectin, CXCR3, SIRP 1 1, CXCR4, SLAM, CXCR6, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD102, TRAILR3/TNFRSF10C, IFN-γR1, TRAILR4/TNFRSF10D, IFN-γ R2, TSLP, IL-1 R1 and TSLP R. In various embodiments, a targeting moiety of the adjuvants, chimeric proteins, or chimeric protein complexes binds one or more of these illustrative T cell antigens.

By way of non-limiting example, in various embodiments, the adjuvants, chimeric proteins, or chimeric protein complexes have a targeting moiety directed against a checkpoint marker expressed on a T cell, e.g. one or more of PD-1, CD28, CTLA4, ICOS, BTLA, KIR, LAG3, CD137, OX40, CD27, CD40L, TIM3, and A2aR.

For example, in some embodiments, the recognition domains specifically bind to a target (e.g. antigen, receptor) associated with B cells. In some embodiments, the recognition domains directly or indirectly recruit B cells, e.g., in some embodiments, to a therapeutic site (e.g. a locus with one or more disease cell or cell to be modulated for a therapeutic effect). Illustrative B cell antigens of interest include, for example, CD10, CD19, CD20, CD21, CD22, CD23, CD24, CD37, CD38, CD39, CD40, CD70, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138, CDw150, CS1, and B-cell maturation antigen (BCMA). In various embodiments, a targeting moiety of the adjuvants, chimeric proteins, or chimeric protein complexes binds one or more of these illustrative B cell antigens.

By way of further example, in some embodiments, the recognition domains specifically bind to a target (e.g. antigen, receptor) associated with Natural Killer cells. In some embodiments, the recognition domains directly or indirectly recruit Natural Killer cells, e.g., in some embodiments, to a therapeutic site (e.g. a locus with one or more disease cell or cell to be modulated for a therapeutic effect). Illustrative Natural Killer cell antigens of interest include, for example TIGIT, 2B4/SLAMF4, KIR2DS4, CD155/PVR, KIR3DL1, CD94, LMIR1/CD300A, CD69, LMIR2/CD300c, CRACC/SLAMF7, LMIR3/CD300LF, DNAM-1, LMIR5/CD300LB, Fc-epsilon RII, LMIR6/CD300LE, Fc-γ RI/CD64, MICA, Fc-γ RIIB/CD32b, MICB, Fc-γ RIIC/CD32c, MULT-1, Fc-γ RIIA/CD32a, Nectin-2/CD112, Fc-γ RIII/CD16, NKG2A, FcRH1/IRTA5, NKG2C, FcRH2/IRTA4, NKG2D, FcRH4/IRTA1, NKp30, FcRH5/IRTA2, NKp44, Fc-Receptor-like 3/CD16-2, NKp46/NCR1, NKp80/KLRF1, NTB-A/SLAMF6, Rae-1, Rae-1 a, Rae-1 p, Rae-1 delta, H60, Rae-1 epsilon, ILT2/CD85j, Rae-1γ, ILT3/CD85k, TREM-1, ILT4/CD85d, TREM-2, ILT5/CD85a, TREM-3, KIR/CD158, TREML1/TLT-1, KIR2DL1, ULBP-1, KIR2DL3, ULBP-2, KIR2DL4/CD158d and ULBP-3. In various embodiments, a targeting moiety of the adjuvants, chimeric proteins, or chimeric protein complexes binds one or more of these illustrative NK cell antigens.

Also, in some embodiments, the recognition domains specifically bind to a target (e.g. antigen, receptor) associated with macrophages/monocytes. In some embodiments, the recognition domains directly or indirectly recruit macrophages/monocytes, e.g., in some embodiments, to a therapeutic site (e.g. a locus with one or more disease cell or cell to be modulated for a therapeutic effect). Illustrative macrophages/monocyte antigens of interest include, for example SIRP1a, B7-1/CD80, ILT4/CD85d, B7-H1, ILT5/CD85a, Common p Chain, Integrin a 4/CD49d, BLAME/SLAMF8, Integrin a X/CDIIc, CCL6/C10, Integrin β 2/CD18, CD155/PVR, Integrin 1 3/CD61, CD31/PECAM-1, Latexin, CD36/SR-B3, Leukotriene B4 R1, CD40/TNFRSF5, LIMPIIISR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc-γ RI/CD64, Osteopontin, Fc-γ RIIB/CD32b, PD-L2, Fc-γ RIIC/CD32c, Siglec-3/CD33, Fc-γ RIIA/CD32a, SIGNR1/CD209, Fc-γ RIII/CD16, SLAM, GM-CSF R a, TCCR/WSX-1, ICAM-2/CD102, TLR3, IFN-γ RI, TLR4, IFN-γ R2, TREM-I, IL-I RII, TREM-2, ILT2/CD85j, TREM-3, ILT3/CD85k, TREML1/TLT-1, 2B4/SLAMF 4, IL-10R α, ALCAM, IL-10R p, AminopeptidaseN/ANPEP, ILT2/CD85j, Common p Chain, ILT3/CD85k, C1q R1/CD93, ILT4/CD85d, CCR1, ILT5/CD85a, CCR2, Integrin a 4/CD49d, CCR5, Integrin a M/CDII b, CCR8, Integrin a X/CDIIc, CD155/PVR, Integrin β 2/CD18, CD14, Integrin β 3/CD61, CD36/SR-B3, LAIR1, CD43, LAIR2, CD45, Leukotriene B4-R1, CD68, LIMPIIISR-B2, CD84/SLAMF5, LMIR1/CD300A, CD97, LMIR2/CD300c, LMIR3/CD300LF, Coagulation Factor Ill/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc-γ RI/CD64, PSGL-1, Fc-γ RIIICD16, RP105, G-CSF R, L-Selectin, GM-CSF R a, Siglec-3/CD33, HVEM/TNFRSF14, SLAM, ICAM-1/CD54, TCCR/WSX-1, ICAM-2/CD102, TREM-I, IL-6R, TREM-2, CXCR1/IL-8 RA, TREM-3 and TREMLI/TLT-1. In various embodiments, a targeting moiety of the adjuvants, chimeric proteins, or chimeric protein complexes binds one or more of these illustrative macrophage/monocyte antigens.

Also, in some embodiments, the recognition domains specifically bind to a target (e.g. antigen, receptor) associated with dendritic cells. In some embodiments, the recognition domains directly or indirectly recruit dendritic cells, e.g., in some embodiments, to a therapeutic site (e.g. a locus with one or more disease cell or cell to be modulated for a therapeutic effect). Illustrative dendritic cell antigens of interest include, for example, CLEC9A, XCR1, RANK, CD36/SRB3, LOX-1/SR-E1, CD68, MARCO, CD163, SR-A1/MSR, CD5L, SREC-1, CL-PI/COLEC12, SREC-II, LIMPIIISRB2, RP105, TLR4, TLR1, TLR5, TLR2, TLR6, TLR3, TLR9, 4-IBB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, lutegrin a 4/CD49d, Aag, Integrin β 2/CD18, AMICA, Langerin, B7-2/CD86, Leukotriene B4 RI, B7-H3, LMIR1/CD300A, BLAME/SLAMF8, LMIR2/CD300c, C1q R1/CD93, LMIR3/CD300LF, CCR6, LMIR5/CD300LB CCR7, LMIR6/CD300LE, CD40/TNFRSF5, MAG/Siglec-4-a, CD43, MCAM, CD45, MD-1, CD68, MD-2, CD83, MDL-1/CLEC5A, CD84/SLAMF5, MMR, CD97, NCAMLI, CD2F-10/SLAMF9, Osteoactivin GPNMB, Chern 23, PD-L2, CLEC-1, RP105, CLEC-2, CLEC-8, Siglec-2/CD22, CRACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC/CLEC4C, SLAM, EMMPRIN/CD147, TCCR/WSX-1, Fc-γ R1/CD64, TLR3, Fc-γ RIIB/CD32b, TREM-1, Fc-γ RIIC/CD32c, TREM-2, Fc-γ RIIA/CD32a, TREM-3, Fc-γ RIII/CD16, TREML1/TLT-1, ICAM-2/CD102 and Vanilloid R1. In various embodiments, a targeting moiety of the adjuvants, chimeric proteins, or chimeric protein complexes binds one or more of these illustrative DC antigens.

In some embodiments, the recognition domains specifically bind to a target (e.g. antigen, receptor) on immune cells selected from, but not limited to, megakaryocytes, thrombocytes, erythrocytes, mast cells, basophils, neutrophils, myeloid cells, monocytes, eosinophils, or subsets thereof. In some embodiments, the recognition domains directly or indirectly recruit megakaryocytes, thrombocytes, erythrocytes, mast cells, basophils, neutrophils, myeloid cells, monocytes, eosinophils, or subsets thereof, e.g., in some embodiments, to a therapeutic site (e.g. a locus with one or more disease cell or cell to be modulated for a therapeutic effect). In some embodiments, the immune cell is selected from a T cell, a B cell, a dendritic cell, a macrophage, a neutrophil, a mast cell, a monocyte, a red blood cell, myeloid cell, myeloid derived suppressor cell, a NKT cell, and a NK cell, or derivatives thereof.

In some embodiments, the recognition domains specifically bind to a target (e.g. antigen, receptor) associated with megakaryocytes and/or thrombocytes. Illustrative megakaryocyte and/or thrombocyte antigens of interest include, for example, GP IIb/IIIa, GPIb, vWF, PF4, and TSP. In various embodiments, a targeting moiety of the adjuvants, chimeric proteins, or chimeric protein complexes binds one or more of these illustrative megakaryocyte and/or thrombocyte antigens.

In some embodiments, the recognition domains specifically bind to a target (e.g. antigen, receptor) associated with erythrocytes. Illustrative erythrocyte antigens of interest include, for example, CD34, CD36, CD38, CD41a (platelet glycoprotein IIb/IIIa), CD41b (GPIIb), CD71 (transferrin receptor), CD105, glycophorin A, glycophorin C, c-kit, HLA-DR, H2 (MHC-II), and Rhesus antigens. In various embodiments, a targeting moiety of the adjuvants, chimeric proteins, or chimeric protein complexes binds one or more of these illustrative erythrocyte antigens.

In some embodiments, the recognition domains specifically bind to a target (e.g. antigen, receptor) associated with mast cells. Illustrative mast cells antigens of interest include, for example, SCFR/CD117, $Fc_{\varepsilon}RI$, CD2, CD25, CD35, CD88, CD203c, C5R1, CMAI, FCERIA, FCER2, TPSABI. In various embodiments, a targeting moiety of the adjuvants, chimeric proteins, or chimeric protein complexes binds one or more of these mast cell antigens.

In some embodiments, the recognition domains specifically bind to a target (e.g. antigen, receptor) associated with basophils. Illustrative basophils antigens of interest include, for example, $Fc_{\varepsilon}RI$, CD203c, CD123, CD13, CD107a, CD107b, and CD164. In various embodiments, a targeting moiety of the adjuvants, chimeric proteins, or chimeric protein complexes binds one or more of these basophil antigens.

In some embodiments, the recognition domains specifically bind to a target (e.g. antigen, receptor) associated with neutrophils. Illustrative neutrophils antigens of interest include, for example, 7D5, CD10/CALLA, CD13, CD16 (FcRIII), CD18 proteins (LFA-1, CR3, and p150, 95), CD45, CD67, and CD177. In various embodiments, a targeting moiety of the adjuvants, chimeric proteins, or chimeric protein complexes binds one or more of these neutrophil antigens.

In some embodiments, the recognition domains specifically bind to a target (e.g. antigen, receptor) associated with eosinophils. Illustrative eosinophils antigens of interest include, for example, CD35, CD44 and CD69. In various embodiments, a targeting moiety of the adjuvants, chimeric proteins, or chimeric protein complexes binds one or more of these eosinophil antigens.

In various embodiments, the recognition domain may bind to any appropriate target, antigen, receptor, or cell surface markers known by the skilled artisan. In some embodiments, the antigen or cell surface marker is a tissue-specific marker. Illustrative tissue-specific markers include, but are not limited to, endothelial cell surface markers such as ACE, CD14, CD34, CDH5, ENG, ICAM2, MCAM, NOS3, PECAMI, PROCR, SELE, SELP, TEK, THBD, VCAMI, VWF; smooth muscle cell surface markers such as ACTA2, MYHIO, MYHI 1, MYH9, MYOCD; fibroblast (stromal) cell surface markers such as ALCAM, CD34, COLIAI, COL1A2, COL3A1, FAP, PH-4; epithelial cell surface markers such as CDID, K6IRS2, KRTIO, KRT13, KRT17, KRT18, KRT19, KRT4, KRT5, KRT8, MUCI, TACSTDI; neovasculature markers such as CD13, TFNA, Alpha-v beta-3 ($\alpha_v\beta_3$), E-selectin; and adipocyte surface markers such as ADIPOQ, FABP4, and RETN. In various embodiments, a targeting moiety of the adjuvants, chimeric proteins, or chimeric protein complexes binds one or more of these antigens. In various embodiments, a targeting moiety of the adjuvants, chimeric proteins, or chimeric protein complexes binds one or more of cells having these antigens.

By way of non-limiting example, in various embodiments, the adjuvants, chimeric proteins, or chimeric protein complexes have (i) a targeting moiety directed against a T cell, for example, mediated by targeting to CD8, SLAMF4, IL-2R α, 4-1BB/TNFRSF9, IL-2R β, ALCAM, B7-1, IL-4R, B7-H3, BLAME/SLAMFS, CEACAM1, IL-6R, CCR3, IL-7Rα, CCR4, CXCR1/IL-S RA, CCR5, CCR6, IL-10R α, CCR 7, IL-10R p, CCRS, IL-12R β 1, CCR9, IL-12R β 2, CD2, IL-1β R a 1, IL-1β, CD3, CD4, ILT2/CDS5j, ILT3/CDS5k, ILT4/CDS5d, ILT5/CDS5a, lutegrin a 4/CD49d, CDS, Integrin a E/CD103, CD6, Integrin a M/CD 11 b, CDS, Integrin a X/CD11c, Integrin β 2/CDIS, KIR/CD15S, CD27/TNFRSF7, KIR2DL1, CD2S, KIR2DL3, CD30/TNFRSF6, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common y Chain/IL-2R γ, Osteopontin, CRACC/SLAMF7, PD-1, CRTAM, PSGL-1, CTLA-4, RANK/TNFRSF11A, CX3CR1, CX3CL1, L-Selectin, CXCR3, SIRP 1 1, CXCR4, SLAM, CXCR6, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD102, TRAILR3/TNFRSF10C, IFN-γR1, TRAILR4/TNFRSF10D, IFN-γ R2, TSLP, IL-1 R1, or TSLP R.

By way of non-limiting example, in various embodiments, the adjuvants, chimeric proteins, or chimeric protein complexes have (i) a targeting moiety directed against a dendritic cell, for example, mediated by targeting to CLEC-9A, XCR1, RANK, CD36/SRB3, LOX-1/SR-E1, CD68, MARCO, CD163, SR-A1/MSR, CD5L, SREC-1, CL-PI/COLEC12, SREC-II, LIMPIIISRB2, RP105, TLR4, TLR1, TLR5, TLR2, TLR6, TLR3, TLR9, 4-IBB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, lutegrin a 4/CD49d, Aag, Integrin β 2/CD18, AMICA, Langerin, B7-2/CD86, Leukotriene B4 RI, B7-H3, LMIR1/CD300A, BLAME/SLAMF8, LMIR2/CD300c, C1q R1/CD93, LMIR3/CD300LF, CCR6, LMIR5/CD300LB CCR7, LMIR6/CD300LE, CD40/TNFRSF5, MAG/Siglec-4-a, CD43, MCAM, CD45, MD-1, CD68, MD-2, CD83, MDL-1/CLEC5A, CD84/SLAMF5, MMR, CD97, NCAMLI, CD2F-10/SLAMF9, Osteoactivin GPNMB, Chern 23, PD-L2, CLEC-1, RP105, CLEC-2, Siglec-2/CD22, CRACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD147, TCCR/WSX-1, Fc-γ R1/CD64, TLR3, Fc-γ RIIB/CD32b, TREM-1, Fc-γ RIIC/CD32c, TREM-2, Fc-γ RIIA/CD32a, TREM-3, Fc-γ RIII/CD16, TREML1/TLT-1, ICAM-2/CD102, or Vanilloid R1.

By way of non-limiting example, in various embodiments, the adjuvants, chimeric proteins, or chimeric protein complexes have (i) a targeting moiety directed against a monocyte/macrophage, for example, mediated by targeting to SIRP1a, B7-1/CD80, ILT4/CD85d, B7-H1, ILT5/CD85a, Common p Chain, Integrin a 4/CD49d, BLAME/SLAMF8, Integrin a X/CDIIc, CCL6/C10, Integrin β 2/CD18, CD155/PVR, Integrin β 3/CD61, CD31/PECAM-1, Latexin, CD36/SR-B3, Leukotriene B4 R1, CD40/TNFRSF5, LIMPIIISR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc-γ RI/CD64, Osteopontin, Fc-γ RIIB/CD32b, PD-L2, Fc-γ RIIC/CD32c, Siglec-3/CD33, Fc-γ RIIA/CD32a, SIGNR1/CD209, Fc-γ RIII/CD16, SLAM, GM-CSF R a, TCCR/WSX-1, ICAM-2/CD102, TLR3, IFN-γ RI, TLR4, IFN-γ R2, TREM-I, IL-I RII, TREM-2, ILT2/CD85j, TREM-3, ILT3/CD85k, TREML1/TLT-1, 2B4/SLAMF 4, IL-10R α, ALCAM, IL-10R p, AminopeptidaseN/ANPEP, ILT2/CD85j, Common p Chain, ILT3/CD85k, C1q R1/CD93, ILT4/CD85d, CCR1, ILT5/CD85a, CCR2, CD206, Integrin a 4/CD49d, CCR5, Integrin a M/CDII b, CCR8, Integrin a X/CDIIc, CD155/PVR, Integrin 1 2/CD18, CD14, Integrin β 3/CD61, CD36/SR-B3, LAIR1, CD43, LAIR2, CD45, Leukotriene B4-R1, CD68, LIMPIIISR-B2, CD84/SLAMF5, LMIR1/CD300A, CD97, LMIR2/CD300c, CD163, LMIR3/CD300LF, Coagulation Factor Ill/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc-γ RI/CD64, PSGL-1, Fc-γ RIIICD16, RP105, G-CSF R, L-Selectin, GM-CSF R a, Siglec-3/CD33, HVEM/TNFRSF14, SLAM, ICAM-1/CD54, TCCR/WSX-1, ICAM-2/CD102, TREM-I, IL-6R, TREM-2, CXCR1/IL-8 RA, TREM-3, or TREMLI/TLT-1.

In one embodiment, the present adjuvants, chimeric proteins or chimeric protein complexes such as Fc-based chimeric protein complex comprises one or more targeting moieties directed against a T cell and one or more targeting moieties directed against the same or another T cell. In one embodiment, the present adjuvants, chimeric proteins or chimeric protein complexes such as Fc-based chimeric protein complex comprises one or more targeting moieties directed against a T cell and one or more targeting moieties directed against a B cell. In one embodiment, the present adjuvants, chimeric proteins or chimeric protein complexes such as Fc-based chimeric protein complex comprises one or more targeting moieties directed against a T cell and one or more targeting moieties directed against a dendritic cell. In one embodiment, the present adjuvants, chimeric proteins or chimeric protein complexes such as Fc-based chimeric protein complex comprises one or more targeting moieties against a T cell and one or more targeting moieties directed against a macrophage. In one embodiment, the present adjuvants, chimeric proteins or chimeric protein complexes such as Fc-based chimeric protein complex comprises one or more targeting moieties against a T cell and one or more targeting moieties directed against a NK cell.

In one embodiment, the present adjuvants, chimeric proteins or chimeric protein complexes such as Fc-based chimeric protein complex comprises one or more targeting moieties directed against a B cell and one or more targeting moieties directed against the same or another B cell. In one embodiment, the present adjuvants, chimeric proteins or chimeric protein complexes such as Fc-based chimeric protein complex comprises one or more targeting moieties directed against a B cell and one or more targeting moieties directed against a T cell. In one embodiment, the present adjuvants, chimeric proteins or chimeric protein complexes such as Fc-based chimeric protein complex comprises one or more targeting moieties directed against a B cell and one or more targeting moieties directed against a dendritic cell. In one embodiment, the present adjuvants, chimeric proteins or chimeric protein complexes such as Fc-based chimeric protein complex comprises one or more targeting moieties against a B cell and one or more targeting moieties directed against a macrophage. In one embodiment, the present adjuvants, chimeric proteins or chimeric protein complexes such as Fc-based chimeric protein complex comprises one or more targeting moieties against a B cell and one or more targeting moieties directed against a NK cell.

In one embodiment, the present adjuvants, chimeric proteins or chimeric protein complexes such as Fc-based chimeric protein complex comprises one or more targeting moieties directed against a dendritic cell and one or more targeting moieties directed against the same or another dendritic cell. In one embodiment, the present adjuvants, chimeric proteins or chimeric protein complexes such as Fc-based chimeric protein complex comprises one or more targeting moieties directed against a dendritic cell and one or more targeting moieties directed against a T cell. In one embodiment, the present adjuvants, chimeric proteins or chimeric protein complexes such as Fc-based chimeric protein complex comprises one or more targeting moieties directed against a dendritic cell and one or more targeting moieties directed against a B cell. In one embodiment, the present adjuvants, chimeric proteins or chimeric protein complexes such as Fc-based chimeric protein complex comprises one or more targeting moieties against a dendritic cell and one or more targeting moieties directed against a macrophage. In one embodiment, the present adjuvants, chimeric proteins or chimeric protein complexes such as Fc-based chimeric protein complex comprises one or more targeting moieties against a dendritic cell and one or more targeting moieties directed against a NK cell.

In one embodiment, the present adjuvants, chimeric proteins or chimeric protein complexes such as Fc-based chimeric protein complex comprises one or more targeting moieties directed against a macrophage and one or more targeting moieties directed against the same or another macrophage. In one embodiment, the present adjuvants, chimeric proteins or chimeric protein complexes such as Fc-based chimeric protein complex comprises one or more targeting moieties directed against a macrophage and one or more targeting moieties directed against a T cell. In one embodiment, the present adjuvants, chimeric proteins or chimeric protein complexes such as Fc-based chimeric protein complex comprises one or more targeting moieties directed against a macrophage and one or more targeting moieties directed against a B cell. In one embodiment, the present adjuvants, chimeric proteins or chimeric protein complexes such as Fc-based chimeric protein complex comprises one or more targeting moieties against a macrophage and one or more targeting moieties directed against a dendritic cell. In one embodiment, the present adjuvants, chimeric proteins or chimeric protein complexes such as Fc-based chimeric protein complex comprises one or more targeting moieties against a macrophage and one or more targeting moieties directed against a NK cell.

In one embodiment, the present adjuvants, chimeric proteins or chimeric protein complexes such as Fc-based chimeric protein complex comprises one or more targeting moieties directed against an NK cell and one or more targeting moieties directed against the same or another NK cell. In one embodiment, the present adjuvants, chimeric proteins or chimeric protein complexes such as Fc-based chimeric protein complex comprises one or more targeting moieties directed against an NK cell and one or more targeting moieties directed against a T cell. In one embodiment, the present adjuvants, chimeric proteins or chimeric protein complexes such as Fc-based chimeric protein complex comprises one or more targeting moieties directed against an NK cell and one or more targeting moieties directed against a B cell. In one embodiment, the present adjuvants, chimeric proteins or chimeric protein complexes such as Fc-based chimeric protein complex comprises one or more targeting moieties against an NK cell and one or more targeting moieties directed against a macrophage. In one embodiment, the present adjuvants, chimeric proteins or chimeric protein complexes such as Fc-based chimeric protein complex comprises one or more targeting moieties against an NK cell and one or more targeting moieties directed against a dendritic cell.

In some embodiments, the adjuvants, chimeric proteins or chimeric protein complexes such as Fc-based chimeric protein complex of the invention comprises one or more targeting moieties having recognition domains that bind to a target (e.g. antigen, receptor) of interest including those found on one or more cells selected from adipocytes (e.g., white fat cell, brown fat cell), liver lipocytes, hepatic cells, kidney cells (e.g., kidney parietal cell, kidney salivary gland, mammary gland, etc.), duct cells (of seminal vesicle, prostate gland, etc.), intestinal brush border cells (with microvilli), exocrine gland striated duct cells, gall bladder epithelial cells, ductulus efferens nonciliated cells, epididymal principal cells, epididymal basal cells, endothelial cells, ameloblast epithelial cells (tooth enamel secretion), planum semilunatum epithelial cells of vestibular system of ear (proteoglycan secretion), organ of *Corti* interdental epithelial cells (secreting tectorial membrane covering hair cells), loose connective tissue fibroblasts, corneal fibroblasts (corneal keratocytes), tendon fibroblasts, bone marrow reticular tissue fibroblasts, nonepithelial fibroblasts, pericytes, nucleus pulposus cells of intervertebral disc, cementoblasts/cementocytes (tooth root bonelike ewan cell secretion), odontoblasts/odontocytes (tooth dentin secretion), hyaline cartilage chondrocytes, fibrocartilage chondrocytes, elastic cartilage chondrocytes, osteoblasts/osteocytes, osteoprogenitor cells (stem cell of osteoblasts), hyalocytes of vitreous body of eye, stellate cells of perilymphatic space of ear, hepatic stellate cells (Ito cell), pancreatic stelle cells, skeletal muscle cells, satellite cells, heart muscle cells, smooth muscle cells, myoepithelial cells of iris, myoepithelial cells of exocrine glands, exocrine secretory epithelial cells (e.g., salivary gland cells, mammary gland cells, lacrimal gland cells, sweat gland cells, sebaceious gland cells, prostate gland cells, gastric glad cells, pancreatic acinar cells, pneumocytes), a hormone secreting cells (e.g., pituitary cells, neurosecretory cells, gut and respiratory tract cells, thyroid gland cells, parathyroid glad cells, adrenal gland cells, Leydig cells of testes, pancreatic islet cells), keratinizing epithelial cells, wet stratified barrier epithelial cells, neuronal cells (e.g., sensory transducer cells, autonomic neuron cells, sense organ and peripheral neuron supporting cells, and central nervous system neurons and glial cells such as interneurons, principal cells, astrocytes, oligodendrocytes, and ependymal cells).

Targeting Moiety Formats

In various embodiments, the targeting moiety of the vaccine composition, adjuvants, chimeric protein, or chimeric protein complex described herein is a protein-based agent capable of specific binding, such as an antibody or derivatives thereof. In an embodiment, the targeting moiety comprises an antibody. In some embodiments, the targeting moiety comprises a recognition domain that recognizes and/or binds an antigen or receptor on an endothelial cell, epithelial cell, mesenchymal cell, stromal cell, ECM and/or immune cell, organ cell, and/or tissue cell. In some embodiments, the immune cell is selected from a T cell, a B cell, a dendritic cell, a macrophage, a neutrophil, a mast cell, a monocyte, a red blood cell, myeloid cell, myeloid derived suppressor cell, a NKT cell, and a NK cell, or derivatives thereof. In one embodiment, the immune cell is a T cell.

In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the targeting moiety comprises antibody derivatives or formats. In some embodiments, the targeting moiety of the vaccine composition described herein is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; a Microbody; a peptide aptamer; an alterases; a plastic antibodies; a phylomer; a stradobodies; a maxibodies; an evibody; a fynomer, an armadillo repeat protein, a Kunitz domain, an avimer, an atrimer, a probody, an immunobody, a triomab, a troybody; a pepbody; a vaccibody, a UniBody; affimers, a DuoBody, a Fv, a Fab, a Fab', a $F(ab')_2$, a peptide mimetic molecule, or a synthetic molecule, as described in US Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-Jun; 3(3): 310-317.

In one embodiment, the targeting moiety comprises a single-domain antibody, such as VHH from, for example, an organism that produces VHH antibody such as a camelid, a shark, or a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain (VHH) and two constant domains (CH2 and CH3). VHHs are commercially available under the trademark of NANOBODY or NANOBODIES.

In an embodiment, the targeting moiety comprises a VHH. In some embodiments, the VHH is a humanized VHH or camelized VHH.

In some embodiments, the VHH comprises a fully human VH domain, e.g. a HUMABODY (Crescendo Biologics, Cambridge, UK). In some embodiments, fully human VH domain, e.g. a HUMABODY is monovalent, bivalent, or trivalent. In some embodiments, the fully human VH domain, e.g. a HUMABODY is mono- or multi-specific such as monospecific, bispecific, or trispecific. Illustrative fully human VH domains, e.g. a HUMABODIES are described in, for example, WO 2016/113555 and WO2016/113557, the entire disclosure of which is incorporated by reference.

In various embodiments, the targeting moiety is a protein-based agent capable of specific binding to a cell receptor, such as a natural ligand for the cell receptor. In various embodiments, the cell receptor is found on one or more immune cells, which can include, without limitation, T cells, cytotoxic T lymphocytes, T helper cells, natural killer (NK) cells, natural killer T (NKT) cells, macrophages (e.g. M1 macrophages), B cells, dendritic cells, or subsets thereof. In some embodiments, the cell receptor is found on megakaryocytes, thrombocytes, erythrocytes, mast cells, basophils, neutrophils, eosinophils, or subsets thereof.

In some embodiments, the targeting moiety is a natural ligand such as a chemokine. Illustrative chemokines that may be included in the chimeric proteins or chimeric protein complexes such as Fc-based chimeric protein complex of the invention include, but are not limited to, CCL1, CCL2, CCL4, CCL5, CCL6, CCL7, CCL8, CCL9, CCL10, CCL11, CCL12, CCL13, CCL14, CCL15, CCL16, CL17, CCL18, CCL19, CCL20, CCL21, CCL22, CCL23, CCL24, CLL25, CCL26, CCL27, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2, CX3CL1, HCC-4, and LDGF-PBP.

In some embodiments, the targeting moiety is a natural ligand, such as, FMS-like tyrosine kinase 3 ligand (Flt3L) or a truncated region thereof (e.g., which is able to bind Flt3). In some embodiments, the targeting moiety is an extracellular domain of Flt3L. In some embodiments, the targeting moiety comprising a Flt3L domain, wherein the Flt3L domain is a single chain dimer, optionally where one Flt3L domain is connected to the other Flt3L domain via one or more linkers, wherein the linker is a flexible linker. In some embodiments, the targeting moiety of the present invention comprises Flt3L domain, wherein the Flt3L domain is a single chain dimer and an Fc domain, the Fc domain optionally having one or more mutations that reduces or eliminates one or more effector functions of the Fc domain, promotes Fc chain pairing in the Fc domain, and/or stabilizes a hinge region in the Fc domain. In some embodiments, the targeting moiety recognizes CD20. In some embodiments, the targeting moiety recognizes PD-L1. In some embodiments, the targeting moiety recognizes Clec9A. In some embodiments, the targeting moiety comprises a recognition domain that recognizes and/or binds CD8 or CD4.

In an exemplary embodiment, the present vaccines, adjuvants, chimeric proteins, or chimeric protein complexes comprise a targeting moiety directed against CD8. In various embodiments, the targeting moiety directed against CD8 is a protein-based agent capable of specific binding to CD8 without functional modulation (e.g. partial or complete neutralization) of CD8. In various embodiments, the chimeric protein of the invention comprises a targeting moiety having an antigen recognition domain that recognizes an epitope present on the CD8α and/or β chains. In an embodiment, the antigen-recognition domain recognizes one or more linear epitopes on the CD8α and/or β chains. As used herein, a linear epitope refers to any continuous sequence of amino acids present on the CD8α and/or β chains. In another embodiment, the antigen-recognition domain recognizes one or more conformational epitopes present on the CD8α and/or β chains. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the present vaccines, adjuvants, chimeric proteins, or chimeric protein complexes comprise a targeting moiety that may bind to the full-length and/or mature forms and/or isoforms and/or splice variants and/or fragments and/or any other naturally occurring or synthetic analogs, variants, or mutants of human CD8α and/or p chains. In various embodiments, the targeting moiety directed against CD8 may bind to any forms of the human CD8α and/or 13chains, including monomeric, dimeric, heterodimeric, multimeric and associated forms. In an embodiment, the targeting moiety directed against CD8 may bind to the monomeric form of CD8α chain or CD8 1 chain. In another embodiment, the targeting moiety directed against CD8 may bind to a homodimeric form comprised of two CD8α chains or two CD8β chains. In a further embodiment, the targeting moiety directed against CD8 may bind to a heterodimeric form comprised of one CD8α chain and one CD8 1 chain.

In an embodiment, the CD8 binding agent comprises a targeting moiety which is an antibody. In various embodiments, the antibody is a full-length multimeric protein that includes two heavy chains and two light chains as described elsewhere herein. In some embodiments, the antibody is a chimeric antibody. In some embodiments, the antibody is a humanized antibody.

In some embodiments, the present vaccines, adjuvants, chimeric proteins, or chimeric protein complexes comprise a targeting moiety directed against CD8 which is a single-domain antibody, such as a VHH. The VHH may be derived from, for example, an organism that produces VHH antibody such as a camelid, a shark, or the VHH may be a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain ($V_H$H) and two constant domains (CH2 and CH3). VHHs are commercially available under the trademark of NANOBODY or NANOBODIES. In an embodiment, the present chimeric protein comprises a VHH.

In some embodiments, the present vaccines, adjuvants, chimeric proteins, or chimeric protein complexes comprise a targeting moiety directed against CD8 which is a VHH comprising a single amino acid chain having four "framework regions" or FRs and three "complementary determining regions" or CDRs. As used herein, "framework region" or "FR" refers to a region in the variable domain, which is located between the CDRs. As used herein, "complementary determining region" or "CDR" refers to variable regions in VHHs that contains the amino acid sequences capable of specifically binding to antigenic targets.

In various embodiments, the targeting moiety directed against CD8 comprises a VHH having a variable domain comprising at least one CDR1, CDR2, and/or CDR3 sequences.

In some embodiments, the targeting moiety comprises anti-CD8 antibody as described in WO 2019033043, the entire disclosures of which are hereby incorporated by reference. In some embodiments, the anti-CD8 antibody comprises at least one heavy chain variable region comprising the amino acid sequence of CDR H1: GFNIKDTYIH (SEQ ID NO: 37); CDR H2: RIDPANDNTLYASKFQG (SEQ ID NO: 38); CDR H2: RIDPANDNTLYARKFQG (SEQ ID NO: 39); CDR H3: GRGYGYYVFDH (SEQ ID NO: 40); or CDR H3: TRGYGYYVFDT (SEQ ID NO: 41).

In some embodiments, the anti-CD8 antibody comprises at least one light chain variable region comprising the amino acid sequence of CDR L1: SISQY (SEQ ID NO: 42); CDR L1: SISKY (SEQ ID NO: 43); CDR L2: SGSTLQ (SEQ ID NO: 44); CDR L3: HNENPL (SEQ ID NO: 45); CDR L3: HNEFPV (SEQ ID NO: 46); CDR L3: HNEFPP (SEQ ID NO: 47); CDR L3: VNEFPP (SEQ ID NO: 48); CDR L3: VNEFPV (SEQ ID NO: 49).

In some embodiments, the targeting moiety comprises anti-CD8 antibody as described in WO2019023148, the entire disclosures of which are hereby incorporated by reference. In some embodiments, the anti-CD8 antibody comprises at least one heavy chain variable region comprising the amino acid sequence of CDR H1: GFIFSNYG (SEQ ID NO: 50); CDR H2: IWYDGSNK (SEQ ID NO: 51); CDR H3: ARSYDMLTGSGDYYGL (SEQ ID NO: 52). In some embodiments, the anti-CD8 antibody comprises at least one light chain variable region comprising the amino acid sequence of CDR L1: QDITNY (SEQ ID NO: 53); CDR L2: GAS (SEQ ID NO: 553); CDR L3: QQYNNYPLT (SEQ ID NO: 54).

In some embodiments, the targeting moiety comprises anti-CD8 antibody as described in WO2015184203, the entire 20 disclosures of which are hereby incorporated by reference. In some embodiments, the anti-CD8 antibody comprises at least one heavy chain variable region comprising the amino acid sequence of CDR H1: SGYTGTDYNMH (SEQ ID NO: 55); CDR H2: YIYPYTGGTGYNQKFKN (SEQ ID NO: 56); CDR H1: DFGMN (SEQ ID NO: 57); CDR H2: LIYYDGSNKFY (SEQ ID NO: 58); CDR H3: PHYDGYYHFFDS (SEQ ID NO: 59). In some embodiments, the anti-CD8 antibody comprises at least one light chain variable region comprising the amino acid sequence of CDR L1: RASESVDSYDNSLMH (SEQ ID NO: 60); CDR L2: LASNLES (SEQ ID NO: 61); CDR L3: QQNNEDPYT (SEQ ID NO: 62); CDR L1: KGSQDINNYLA (SEQ ID NO: 63); CDR L2: NTDILHT (SEQ ID NO: 64); CDR L3: YQYNNGYT (SEQ ID NO: 65).

In some embodiments, the targeting moiety comprises anti-CD8 antibody as described in WO2018170096, the entire disclosures of which are hereby incorporated by reference. In some embodiments, the anti-CD8 antibody comprises at least one heavy chain variable region comprising the amino acid sequence of CDR H1: GYTFTSY (SEQ ID NO: 66); CDR H2: DPSDNY (SEQ ID NO: 67); CDR H3: PKSAYAFDVGGYAMDY (SEQ ID NO: 68). In some embodiments, the anti-CD8 antibody comprises at least one light chain variable region comprising the amino acid sequence of CDR L1: RTSENIDSYLT (SEQ ID NO: 69); CDR L2: AATLLAD (SEQ ID NO: 70); CDR L3: QHYYSTPWT (SEQ ID NO: 71). In some embodiments, the targeting moiety comprises anti-CD8 antibody as described in WO2014164553, the entire disclosures of which are hereby incorporated by reference. In some embodiments, the anti-CD8 antibody comprises at least one heavy chain variable region comprising the amino acid sequence of CDR H1: GFNIKD (SEQ ID NO: 72); CDR H2: RIDPANDNT (SEQ ID NO: 73); CDR H3: GYGYYVFDH (SEQ ID NO: 74). In some embodiments, the anti-CD8 antibody comprises at least one light chain variable region comprising the amino acid sequence of CDR L1: RTSRSISQYLA (SEQ ID NO: 75); CDR L2: SGSTLQS (SEQ ID NO: 76); CDR L3: QQHNENPLT (SEQ ID NO: 77).

In some embodiments, the CDR1 sequence is selected from:

```
                                        (SEQ ID NO: 148)
GFTFDDYAMS
or
                                        (SEQ ID NO: 149)
GFTFDDYAIG.
```

In some embodiments, the CDR2 sequence is selected from:

```
                                        (SEQ ID NO: 150)
TINWNGGSAEYAEPVKG
or
                                        (SEQ ID NO: 151)
CIRVSDGSTYYADPVKG.
```

In some embodiments, the CDR3 sequence is selected from:

```
                              (SEQ ID NO: 152)
KDADLVWYNLS
or
                              (SEQ ID NO: 153)
KDADLVWYNLR
or
                              (SEQ ID NO: 154)
AGSLYTCVQSIVVVPARPYYDMDY.
```

In various embodiments, the CD8 targeting moiety comprises SEQ ID NO:148, SEQ ID NO:150, and SEQ ID NO: 152.

In various embodiments, the CD8 targeting moiety comprises SEQ ID NO:148, SEQ ID NO:150, and SEQ ID NO: 153.

In various embodiments, the CD8 targeting moiety comprises SEQ ID NO:148, SEQ ID NO:150, and SEQ ID NO: 154.

In various embodiments, the CD8 targeting moiety comprises SEQ ID NO:148, SEQ ID NO:151, and SEQ ID NO: 152.

In various embodiments, the CD8 targeting moiety comprises SEQ ID NO:148, SEQ ID NO:151, and SEQ ID NO: 153.

In various embodiments, the CD8 targeting moiety comprises SEQ ID NO:148, SEQ ID NO:151, and SEQ ID NO: 154.

In various embodiments, the CD8 targeting moiety comprises SEQ ID NO:149, SEQ ID NO:150, and SEQ ID NO: 152.

In various embodiments, the CD8 targeting moiety comprises SEQ ID NO:149, SEQ ID NO:150, and SEQ ID NO:153.

In various embodiments, the CD8 targeting moiety comprises SEQ ID NO:149, SEQ ID NO:150, and SEQ ID NO: 154.

In various embodiments, the CD8 targeting moiety comprises SEQ ID NO:149, SEQ ID NO:151, and SEQ ID NO: 152.

In various embodiments, the CD8 targeting moiety comprises SEQ ID NO:149, SEQ ID NO:151, and SEQ ID NO: 153.

In various embodiments, the CD8 targeting moiety comprises SEQ ID NO:149, SEQ ID NO:151, and SEQ ID NO: 154.

In various embodiments, the CD8 targeting moiety comprises an amino acid sequence selected from the following sequences:

```
R3HCD27
                                             (SEQ ID NO: 155)
QVQLQESGGGSVQPGGSLRLSCAASGFTFDDYAMSWVRQVPGKGLEWVST

INWNGGSAEYAEPVKGRFTISRDNAKNTVYLQMNSLKLEDTAVYYCAKDA

DLVWYNLSTGQGTQVTVSSAAAYPYDVPDYGS
or

R3HCD129
                                             (SEQ ID NO: 156)
QVQLQESGGGLVQPGGSLRLSCAASGFTFDDYAMSWVRQVPGKGLEWVST

INWNGGSAEYAEPVKGRFTISRDNAKNTVYLQMNSLKLEDTAVYYCAKDA
```

-continued

```
DLVWYNLRTGQGTQVTVSSAAAYPYDVPDYGS
or

R2HCD26
                                             (SEQ ID NO: 157)
QVQLQESGGGLVQAGGSLRLSCAASGFTFDDYAIGWFRQAPGKEREGVSC

IRVSDGSTYYADPVKGRFTISSDNAKNTVYLQMNSLKPEDAAVYYCAAGS

LYTCVQSIVVVPARPYYDMDYWGKGTQVTVSSAAAYPYDVPDYGS.
```

In various embodiments, the targeting moiety comprises an amino acid sequence described in US Patent Publication No. 2014/0271462, the entire contents of which are incorporated by reference. In various embodiments, the CD8 targeting moiety comprises an amino acid sequence described in Table 0.1, Table 0.2, Table 0.3, and/or FIGS. 1A-12I of US Patent Publication No. 2014/0271462, the entire contents of which are incorporated by reference. In various embodiments, the CD8 targeting moiety comprises a HCDR1 of a HCDR1 of SEQ ID NO: 158 or 159 and/or a HCDR2 of HCDR1 of SEQ ID NO: 158 or 159 and/or a HCDR3 of HCDR1 of SEQ ID NO: 158 or 159 and/or a LCDR1 of LCDR1 of SEQ ID NO: 160 and/or a LCDR2 of LCDR1 of SEQ ID NO: 160 and/or a LCDR3 of LCDR1 of SEQ ID NO: 160, as provided below.

```
SEQ ID NO: 158:
Glu Val Gln Leu Val Glu Ser Gly Gly Gly Leu Val

Gln Pro Gly Gly Ser Leu Arg Leu Ser Cys Ala Ala

Ser Gly Phe Asn Ile Lys Asp Thr Tyr Ile His Trp

Val Arg Gln Ala Pro Gly Lys Gly Leu Glu Trp Val

Ala Arg Ile Asp Pro Ala Asn Asp Asn Thr Leu Tyr

Ala Ser Lys Phe Gln Gly Arg Ala Thr Ile Ser Ala

Asp Thr Ser Lys Asn Thr Ala Tyr Leu Gln Met Asn

Ser Leu Arg Ala Glu Asp Thr Ala Val Tyr Tyr Cys

Gly Arg Gly Tyr Gly Tyr Tyr Val Phe Asp His Trp

Gly Gln Gly Thr Leu Val Thr Val Ser Ser.

SEQ ID NO: 159:
Gln Val Gln Leu Val Gln Ser Gly Ala Glu Val Lys

Lys Pro Gly Ala Thr Val Lys Ile Ser Cys Lys Val

Ser Gly Phe Asn Ile Lys Asp Thr Tyr Ile His Trp

Val Gln Gln Ala Pro Gly Lys Gly Leu Glu Trp Met

Gly Arg Ile Asp Pro Ala Asn Asp Asn Thr Leu Tyr

Ala Ser Lys Phe Gln Gly Arg Val Thr Ile Thr Ala

Asp Thr Ser Thr Asp Thr Ala Tyr Met Glu Leu Ser

Ser Leu Arg Ser Glu Asp Thr Ala Val Tyr Tyr Cys

Ala Arg Gly Tyr Gly Tyr Tyr Val Phe Asp His Trp

Gly Gln Gly Thr Leu Val Thr Val Ser Ser.

SEQ ID NO: 160:
Asp Val Gln Ile Thr Gln Ser Pro Ser Ser Leu Ser

Ala Ser Val Gly Asp Arg Val Thr Ile Thr Cys Arg

Thr Ser Arg Ser Ile Ser Gln Tyr Leu Ala Trp Tyr
```

-continued

Gln Gln Lys Pro Gly Lys Val Pro Lys Leu Leu Ile

Tyr Ser Gly Ser Thr Leu Gln Ser Gly Val Pro Ser

Arg Phe Ser Gly Ser Gly Ser Gly Thr Asp Phe Thr

Leu Thr Ile Ser Ser Leu Gln Pro Glu Asp Val Ala

Thr Tyr Tyr Cys Gln Gln His Asn Glu Asn Pro Leu

Thr Phe Gly Gly Gly Thr Lys Val Glu Ile Lys.

In various embodiments, the CD8 binding agent comprises a VHH having a variable domain comprising at least one CDR1, CDR2, and/or CDR3 sequences.

In some embodiments, the CDR1 sequence is selected from:

(SEQ ID NO: 162)
GRSFSSYTLA;

(SEQ ID NO: 163)
GRTFSSYTMG;

(SEQ ID NO: 164)
GRTFSSYIMG;

(SEQ ID NO: 165)
GRTFSSYTMG;

(SEQ ID NO: 166)
GRTSGRTFSSYTMG;

(SEQ ID NO: 167)
GRTFSSYAMG;

(SEQ ID NO: 168)
GLTFSNYIMG;

(SEQ ID NO: 169)
GRTFSSYTMG;

(SEQ ID NO: 170)
GRTFSSDTMG;

(SEQ ID NO: 171)
GLTFSNYIMG;

(SEQ ID NO: 172)
GFTLDYYGIG;

(SEQ ID NO: 173)
GHTFSSYTMG;

(SEQ ID NO: 174)
GRTFSSYVIG;

(SEQ ID NO: 175)
GFAFDGYAIG;

(SEQ ID NO: 176)
GFAFGFFDMT;

(SEQ ID NO: 177)
GRTFSNYVIG;

(SEQ ID NO: 178)
GSIFSINVMG;

(SEQ ID NO: 179)
GRTFSNYNVG;

(SEQ ID NO: 180)
GHTFSSYTMG;

(SEQ ID NO: 181)
GRTFSTYPVG;

-continued (SEQ ID NO: 182)
GRTFSNYAMG;

(SEQ ID NO: 183)
GRTFSDYRMG;

(SEQ ID NO: 184)
GLTFSNYIMA;

(SEQ ID NO: 185)
GRTFSNSVMG;

(SEQ ID NO: 186)
GRTFSSYIIG;

(SEQ ID NO: 187)
GRTFSSYVMG;

(SEQ ID NO: 188)
GGTFSNYVMG;

(SEQ ID NO: 189)
GRTFSNYGIG;

(SEQ ID NO: 190)
GFTFDDYAIA;

(SEQ ID NO: 191)
GRTFSSYTVA;

(SEQ ID NO: 192)
GFPFDDYAIA;

(SEQ ID NO: 193)
GRTFSSYVMG;

(SEQ ID NO: 194)
GRTLSSNPMA;

(SEQ ID NO: 195)
GFTFDNYAIG;

(SEQ ID NO: 196)
GRAFSSYFMG;

(SEQ ID NO: 197)
TPTFSSYNMG;

(SEQ ID NO: 198)
GFTFDDYAIA;

(SEQ ID NO: 199)
GGTFSGYIMG;

(SEQ ID NO: 200)
GRSFSSYTIA;

(SEQ ID NO: 201)
GFSSDDYTIG;

(SEQ ID NO: 202)
GFTFDDYTIG;

(SEQ ID NO: 203)
GFSSDDYTIG;

(SEQ ID NO: 204)
GFTFDQYTIA;

(SEQ ID NO: 205)
GRTFSSYAMA;

(SEQ ID NO: 206)
GFAFDGYAIG;

(SEQ ID NO: 207)
GFSSDDYTIA;

(SEQ ID NO: 208)
GFSSDDYTIG;

-continued (SEQ ID NO: 209)
GFTFDDYTIG;

(SEQ ID NO: 210)
GFSSDDYTIG;

(SEQ ID NO: 211)
GFSSDDYTIG;

(SEQ ID NO: 212)
GFSFDDYAIA;

(SEQ ID NO: 213)
GFSSDDYTIG;

(SEQ ID NO: 214)
GFTGNDLAIG;

(SEQ ID NO: 215)
GFSSDDYTIA;

(SEQ ID NO: 216)
EGTLSSYGIG;

(SEQ ID NO: 217)
GFSSDDYTIA;

(SEQ ID NO: 218)
GFTFDDYAIA;

(SEQ ID NO: 219)
GLSSDDYTIG;

(SEQ ID NO: 220)
GLSSDDYTIG;

(SEQ ID NO: 221)
GFSSDDYTIG;

(SEQ ID NO: 222)
GFSFDDYTIG;

(SEQ ID NO: 223)
GFTFDDYAIA;

(SEQ ID NO: 224)
GFTFDDYAIG;

(SEQ ID NO: 225)
GFTFGDYTIG;

(SEQ ID NO: 226)
EGTFSSYGIG;

(SEQ ID NO: 227)
GFSSDDYTIG;

(SEQ ID NO: 228)
GVSIGDYNIG;

(SEQ ID NO: 229)
GFTFDDYTIA;

(SEQ ID NO: 300)
GFTFDDYTIA.

In some embodiments, the CDR2 sequence is selected from:

(SEQ ID NO: 331)
ASITWGGGNTY;

(SEQ ID NO: 332)
AATVWTGAGTV;

(SEQ ID NO: 333)
AAIGWSADITV;

-continued (SEQ ID NO: 334)
AFIDWSGGGTY;

(SEQ ID NO: 335)
ATITWGGGSTY;

(SEQ ID NO: 336)
AAISWSGGPTV;

(SEQ ID NO: 337)
AAITWGGGSTV;

(SEQ ID NO: 338)
AAITWSGVSTV;

(SEQ ID NO: 339)
GAIMWSGAFTH;

(SEQ ID NO: 340)
AAITWGGGSTV;

(SEQ ID NO: 341)
SCISSSDRNTY;

(SEQ ID NO: 342)
AFIDWSGGGTY;

(SEQ ID NO: 343)
AVITWSGDSTY;

(SEQ ID NO: 344)
ACISSKDGSTY;

(SEQ ID NO: 345)
SGINSIGGSTT;

(SEQ ID NO: 346)
AVVTWSGDSTY;

(SEQ ID NO: 347)
AKITNFGITS;

(SEQ ID NO: 348)
SFISWISDITY;

(SEQ ID NO: 349)
AFIDWSGGGTY;

(SEQ ID NO: 350)
AVILWSGVSTY;

(SEQ ID NO: 351)
AAIVWSGGSTY;

(SEQ ID NO: 352)
AAISSSGYHTY;

(SEQ ID NO: 353)
SCISSPDGSTY;

(SEQ ID NO: 354)
AAVLWSGVSTA;

(SEQ ID NO: 355)
VAITWDGSATT;

(SEQ ID NO: 356)
AAIGWNGGITY;

(SEQ ID NO: 357)
GFITWSGASTY;

(SEQ ID NO: 358)
AGINWSGESAD;

(SEQ ID NO: 359)
SCIERSDGSTY;

(SEQ ID NO: 360)
SCISNTDSSTY;

-continued

SCISNTDSSTY; (SEQ ID NO: 371)

AQISWSAGSIY; (SEQ ID NO: 372)

AGMSWNPGPAV; (SEQ ID NO: 373)

SCISRSDGSTY; (SEQ ID NO: 374)

ANIGWTGDMTY; (SEQ ID NO: 375)

AAIIWSGSMTY; (SEQ ID NO: 376)

SCISNTDSSTY; (SEQ ID NO: 377)

AANTWSGGPTY; (SEQ ID NO: 378)

SCISSDGSTG; (SEQ ID NO: 379)

SCYSSSDGSTG; (SEQ ID NO: 380)

SCISSDGSTG; (SEQ ID NO: 381)

GCIKSSDGTTG; (SEQ ID NO: 382)

SCISNTDSSTY; (SEQ ID NO: 383)

AAIAWSAGSTY; (SEQ ID NO: 384)

SCISSKEGSTY; (SEQ ID NO: 385)

SCISSSDGSTG; (SEQ ID NO: 386)

SCYSSRDGTTG; (SEQ ID NO: 387)

SCISSDGSTG; (SEQ ID NO: 388)

SCYSSSDGSTG; (SEQ ID NO: 389)

SCFSSSDGSTG; (SEQ ID NO: 390)

SCISNTDSSTF; (SEQ ID NO: 391)

SCYSSSDGSTG; (SEQ ID NO: 392)

SCISNTDSSTY; (SEQ ID NO: 393)

SCISSSDGSTG; (SEQ ID NO: 394)

GGINWSGDSTD; (SEQ ID NO: 395)

SCFSSSDGSAG; (SEQ ID NO: 396)

SCISNTDSSTY; (SEQ ID NO: 397)

-continued

SCFSTRDGNAG; (SEQ ID NO: 398)

SCFSSRDGSTG; (SEQ ID NO: 399)

SCFSSRDGSTG; (SEQ ID NO: 400)

SCISSDGSTG; (SEQ ID NO: 401)

SCISNTDSSTY; (SEQ ID NO: 402)

SCISSPDGSTY; (SEQ ID NO: 403)

SCYSSSDGNTG; (SEQ ID NO: 404)

GGINWSGDSTD; (SEQ ID NO: 405)

SCFSSSDGSTG; (SEQ ID NO: 406)

SCISSGDGTTY; (SEQ ID NO: 407)

SCISSDGSTG; (SEQ ID NO: 408)

SCISSDGSTG; (SEQ ID NO: 409)
and

SSISRSDGSTY. (SEQ ID NO: 410)

In some embodiments, the CDR3 sequence is selected from:

AKGLRNSDWDLRRGYEYDY; (SEQ ID NO: 411)

ADQASVPPPYGSERYDIASPSEYDY; (SEQ ID NO: 412)

ANSRAYYSSSYDLGRLASYDY; (SEQ ID NO: 413)

AAQRLGSVTDYTKYDY; (SEQ ID NO: 414)

ASVKVVAGSGIDISGSRNYDY; (SEQ ID NO: 415)

AKRLDYSATDKGVDLSDEYDY; (SEQ ID NO: 416)

AAGGSGRLRDLKVGQNYDY; (SEQ ID NO: 417)

ADSPPRTYSSGSVNLEDGSEYDY; (SEQ ID NO: 418)

VIPGRGSALPIDVGKSDEYEY; (SEQ ID NO: 419)

AAGASGRLRDLKVGQNYDY; (SEQ ID NO: 420)

ADGNVWSPPICGSAGPPPGGMDY; (SEQ ID NO: 421)

AAQRLGSVTDYTKYDY; (SEQ ID NO: 422)

-continued (SEQ ID NO: 423)
AIPPRAYSGGSYSLKDQSKYEY;

(SEQ ID NO: 424)
ADGNVWSPPICSSAGPPPGGMDY;

(SEQ ID NO: 425)
KSRSSYSNN;

(SEQ ID NO: 426)
AMPPRAYTGRSVSLKDQSKYEY;

(SEQ ID NO: 427)
LDTTGWGPPPYQY;

(SEQ ID NO: 428)
AHPPDPSRGGEWRLQTPSEYDY;

(SEQ ID NO: 429)
AAQRLGSVTDYTKYDY;

(SEQ ID NO: 430)
VPRSHFTTAQDMGQDMGAPSWYEY;

(SEQ ID NO: 431)
AVLIRYYSGGYQGLSDANEYDY;

(SEQ ID NO: 432)
VVKYLSGSYSYAGQYNF;

(SEQ ID NO: 433)
ADFNVWSPPICGSVGPPPGGMDY;

(SEQ ID NO: 434)
AHESTYYSGTYYLTDPRRYVY;

(SEQ ID NO: 435)
AVPARGLTMDLENSDIYDH;

(SEQ ID NO: 436)
AATLQVTGSYYLDLSTVDIYDN;

(SEQ ID NO: 437)
ATLFRSNGPKDLSSGYEYDY;

(SEQ ID NO: 438)
AGESGVWVGGLDY;

(SEQ ID NO: 439)
VGSANSGEFRFGWVLKPDLYNY;

(SEQ ID NO: 440)
ADGNVWSPPICGSAGPPPGGMDY;

(SEQ ID NO: 441)
ADGNVWSPPICGSAGPPPGGMDY;

(SEQ ID NO: 442)
ERGYAYCSDDGCQRTQDYDY;

(SEQ ID NO: 443)
GAARAWWSGSYDYTRMNNYDY;

(SEQ ID NO: 444)
AETSADSGEFRFGWVLKPSLYDY;

(SEQ ID NO: 445)
AAGSAYSGSYWNITMAANYDY;

(SEQ ID NO: 446)
AQRIFGAQPMDLSGDYEY;

(SEQ ID NO: 447)
ADGNVWSPPICGSAGPPPGGMDY;

(SEQ ID NO: 448)
ARDYRGIKDLDLKGDYDY;

(SEQ ID NO: 449)
ADFNVWSPPICGSIWYGPPPRGMDY;

-continued (SEQ ID NO: 450)
ADSNVWSPPICGSRWYGPPPGGMAY;

(SEQ ID NO: 451)
ADFNVWSPPICGSNWYGPPPGGMDY;

(SEQ ID NO: 452)
ADFNVWSPPICGSIWYGPPPGGMDY;

(SEQ ID NO: 453)
ADGNVWSPPICGSAGPPPGGMDY;

(SEQ ID NO: 454)
ARIITVATMRLDSDYDY;

(SEQ ID NO: 455)
ADGNVWSPPICGSAGPPPGGMDY;

(SEQ ID NO: 456)
ADSNVWSPPICGRTWYGPPPGGMDY;

(SEQ ID NO: 457)
ADFNVWSPPICGSIWYGPPPGGMAY;

(SEQ ID NO: 458)
ADFNVWSPPICGSNWYGPPPGGMDY;

(SEQ ID NO: 459)
ADFNVWSPPICGSSWYGPPPGGMDY;

(SEQ ID NO: 460)
ADFNVWSPPICGSRWYGPPPGGMEY;

(SEQ ID NO: 461)
ADGNVWSPPICGSAGPPPGGMDY;

(SEQ ID NO: 462)
ADFNVWSPPICGSRWYGPPPGGMAY;

(SEQ ID NO: 463)
ADGNVWSPPICGSAGPPPGGMDY;

(SEQ ID NO: 464)
ADSNVWSPPICGKTWYGPPPGGMDY;

(SEQ ID NO: 465)
AGESGVWVGGLDY;

(SEQ ID NO: 466)
ADSNVWSPPICGSTWYGPPPGGMAY;

(SEQ ID NO: 467)
ADGNVWSPPICGSAGPPPGGMDY;

(SEQ ID NO: 468)
ADFNVWSPPICGSRWYGPPPGGMDY;

(SEQ ID NO: 469)
ADFNVWSPPICGSRWYGPPPGGMDY;

(SEQ ID NO: 470)
ADFNVWSPPICGSRWYGPPPGGMDY;

(SEQ ID NO: 471)
ADFNVWSPPICGSIWYGPPPGGMDY;

(SEQ ID NO: 472)
ADGNVWSPPICGSAGPPPGGMDY;

(SEQ ID NO: 473)
ADFNVWSPPICGSVGPPPGGMDY;

(SEQ ID NO: 474)
ADFNVWSPPICGSSWYGPPPGGMAY;

(SEQ ID NO: 475)
AGESGVWVGGLDY;

(SEQ ID NO: 476)
ADFNVWSPPICGSSWYGPPPGGMEY;

-continued (SEQ ID NO: 477)
ADGNVWSPPICGSAGPPPGGMDY;

(SEQ ID NO: 478)
ADFNVWSPPICSSNWYGPPPRGMDY;

-continued (SEQ ID NO: 479)
ADFNVWSPPICGSIWYGPPPRGMDY.

In various embodiments, the CD8 binding agent comprises an amino acid sequence selected from the following sequences:

1CDA 7
(SEQ ID NO: 480)
QVQLQESGGGLVQAGGSLRLSCAASGRSFSSYTLAWFRQAPGKEREFVASITWGGGNTYYPDSVKGRFTISRDDAK
NTVYLQMNSLKPEDTAVYYCAAKGLRNSDWDLRRGYEYDYWGQGTQVTVSSAAAYPYDVPDYGSHHHHHH;

1CDA 12
(SEQ ID NO: 481)
QVQLQESGGGLVQDGGSLRLSCAFSGRTFSSYTMGWFRQGPGKEREFVAATVWTGAGTVYADSVKGRFTISRDNA
KNTVYLQMNSLRPEDTAVYYCAADQASVPPPYGSERYDIASPSEYDYWGQGTQVTVSSAAAYPYDVPDYGSHHHHHH;

1CDA 14
(SEQ ID NO: 482)
QVQLQESGGGLVQAGASLRLSCAASGRTFSSYIMGWFRQAPGKEREFVAAIGWSADITVYADSVKGRFTISRDNAE
NMVYLQMNSLNPEDTAVYYCAANSRAYYSSSYDLGRLASYDYWGQGTQVTVSSAAAYPYDVPDYGSHHHHHH;

1CDA 15
(SEQ ID NO: 483)
QVQLQESGGGLVQAGGSLRLSCAASGRTFSSYTMGWFRQAPGKEREFVAFIDWSGGGTYYDDSVKGRFTISRDNA
ENTVYLQMNNLEPEDTAVYYCAAAQRLGSVTDYTKYDYWGQGTQVTVSSAAAYPYDVPDYGSHHHHHH;

1CDA 17
(SEQ ID NO: 484)
QVQLQESGGGLVQAGGSLRLSCAASGRTSGRTFSSYTMGWFRQAPGKEREFVATITWGGGSTYYADSVKGRFTIS
RDNANNTVYLQMNSLKPEDTAVYYCAASVKVVAGSGIDISGSRNYDYWGQGTQVTVSSAAAYPYDVPDYGSHHHHHH;

1CDA 18
(SEQ ID NO: 485)
QVQLQESGGGLVQPGGSLRLSCLASGRTFSSYAMGWFRQAPGKEREFVAAISWSGGPTVYADHVKGRFTISRDNA
KNTVYLQVNSLKPEDTADYYCAAKRLDYSATDKGVDLSDEYDYWGQGTQVTVSSAAAYPYDVPDYGSHHHHHH;

1CDA 19
(SEQ ID NO: 486)
QVQLQESGGGLVQAGDSLRLSCAASGLTFSNYIMGWFRQAPGKEREFVAAITWGGGSTVYADSVEGRFTISRDGTK
NTVSLQMNSLLPEDTAVYYCAAAGGSGRLRDLKVGQNYDYWGQGTQVTVSSAAAYPYDVPDYGSHHHHHH;

1CDA 24
(SEQ ID NO: 487)
QVQLQESGGGLVQAGGSLRLSCAASGRTFSSYTMGWFRQAPGREREFVAAITWSGVSTVYTDSVKGRFTVSRDNA
KNTVYLQMNSLKPEDTAVYYCAADSPPRTYSSGSVNLEDGSEYDYWGQGTQVTVSSAAAYPYDVPDYGSHHHHHH;

1CDA 26
(SEQ ID NO: 488)
QVQLQESGGGLVQAGGSLRLSCAASGRTFSSDTMGWFRQAPGKEREFVGAIMWSGAFTHYADSVKGRFTISRDNA
KNTVYLQMNALKPEDTAVYYCAVIPGRGSALPIDVGKSDEYEYWGQGTQVTVSSAAAYPYDVPDYGSHHHHHH;

1CDA 28
(SEQ ID NO: 489)
QVQLQESGGGLVQAGDSLRLSCAASGLTFSNYIMGWFRQAPGKEREFVAAITWGGGSTVYADSVEGRFTISRDGTK
NTVSLQMNSLQPEDTAVYYCAAAGASGRLRDLKVGQNYDYWGQGTQVTVSSAAAYPYDVPDYGSHHHHHH;

1CDA 37
(SEQ ID NO: 490)
QVQLQESGGGLVQAGGSLRLSCAGSGFTLDYYGIGWFRQAPGKEREGVSCISSSDRNTYYADSVKGRFTISGDNAK
NTVYLQMNNLKPEDTAVYYCAADGNVWSPPICGSAGPPPGGMDYWGKGTQVTVSSAAAYPYDVPDYGSHHHHHH;

1CDA 43
(SEQ ID NO: 491)
QVQLQESGGGLVQAGGSLRLSCVASGHTFSSYTMGWFRQAPGKEREFVAFIDWSGGGTYYANSVKGRFTISRDNA
ENTVYLQMNNLKPEDTAVYYCAAAQRLGSVTDYTKYDYWGQGTQVTVSSAAAYPYDVPDYGSHHHHHH;

-continued

1CDA 45
(SEQ ID NO: 492)
QVQLQESGGGLVQAGGSLRLSCAASGRTFSSYVIGWFRQAPGKEREFVAVITWSGDSTYSSDSLKGRFTISRDNAK
NTVYLQMNALNPEDTAVYYCAAIPPRAYSGGSYSLKDQSKYEYWGQGTQVTVSSAAAYPYDVPDYGSHHHHHH;

1CDA 47
(SEQ ID NO: 493)
QVQLQESGGGLVQAEGSLKLSCISGFAFDGYAIGWFRQAPGKEREGVACISSKDGSTYYADSVKGRFTMSVDKTKN
TVYLQMSSLKPEDTAVYYCAADGNVWSPPICSSAGPPPGGMDYWGKGTQVTVSSAAAYPYDVPDYGSHHHHHH;

1CDA 48
(SEQ ID NO: 494)
QVQLQESGGGLVQPGGSLTLSCAASGFAFGFFDMTWVRQAPGKGLEWVSGINSIGGSTTYADSVKGRFTISRDNAK
NELYLQMNSLKPDDTAVYYCAKSRSSYSNNWRPPGQGTQVTVSSAAAYPYDVPDYGSHHHHHH;

1CDA 58
(SEQ ID NO: 495)
QVQLQESGGGLVQARGSLTLSCAASGRTFSNYVIGWFRQAPGEEREFVAVVTWSGDSTYSSDSLKGRFTISRDNAK
NTVYLQMNNLNPEDTAVYYCAAMPPRAYTGRSVSLKDQSKYEYWGQGTQVTVSSAAAYPYDVPDYGSHHHHHH;

1CDA 65
(SEQ ID NO: 496)
QVQLQESGGGLVQPGGSLRLSCAASGSIFSINVMGWYRQTPGKERELVAKITNFGITSYADSAQGRFTISRGNAKNT
VYLQMNSLKPEDTAVYYCNLDTTGWGPPPYQYWGQGTQVTVSSAAAYPYDVPDYGSHHHHHH;

1CDA 68
(SEQ ID NO: 497)
QVQLQESGGGLVQAGASLRLSCAASGRTFSNYNVGWFRQAPGKEREFVSFISWISDITYYSDSVKGRFIISRDNAKN
MVYLQMNSLKPEDTAVYYCAAHPPDPSRGGEWRLQTPSEYDYWGQGTQVTVSSAAAYPYDVPDYGSHHHHHH;

1CDA 73
(SEQ ID NO: 498)
QVQLQESGGGLVQAGGSLRLSCAASGHTFSSYTMGWFRQAPGKEREFVAFIDWSGGGTYYADSVKGRFTISRDNA
ENTVYLQMNNLKPEDTAVYYCAAAQRLGSVTDYTKYDYWGQGTQVTVSSAAAYPYDVPDYGSHHHHHH;

1CDA 75
(SEQ ID NO: 499)
QVQLQESGGGLVQAGGSLRLSCAASGRTFSTYPVGWFRQAPGKEREFVAVILWSGVSTYYADSVKGRFTISRDNAQ
NTVYLQMDSLKPEDTAVYYCAVPRSHFTTAQDMGQDMGAPSWYEYWGQGTQVTVSSAAAYPYDVPDYGSHHHHHH;

1CDA 86
(SEQ ID NO: 500)
QVQLQESGGGLVQAGGSLRLSCAASGRTFSNYAMGWFRQAPGKEREFVAAIVWSGGSTYYADSVKGRFTISRDNA
KNTVYLQMNSLKPEDTAVYYCAAVLIRYYSGGYQGLSDANEYDYWGQGTQVTVSSAAAYPYDVPDYGSHHHHHH;

1CDA 87
(SEQ ID NO: 501)
QVQLQESGGGLVQAGASLRLSCSASGRTFSDYRMGWFRQAPGKEREWVAAISSSGYHTYYADSVKGRFTISRDNA
KNTGYLQMSSLKPEDTAVYYCAVVKYLSGSYSYAGQYNFWGQGTQVTVSSAAAYPYDVPDYGSHHHHHH;

1CDA 88
(SEQ ID NO: 502)
QVQLQESGGGLVQAGDSLKLSCAASGLTFSNYIMAWFRQAPGKEREGVSCISSPDGSTYYADSVKGRFTISSDNAK
NTVYLQMNSLKPEDTAVYYCAADFNVWSPPICGSVGPPPGGMDYWGKGTQVTVSSAAAYPYDVPDYGSHHHHHH;

1CDA 89
(SEQ ID NO: 503)
QVQLQESGGGLVQAGGSLRLSCAASGRTFSNSVMGWFRQPPGKEREFVAAVLWSGVSTAYADSVKGRFTISRDNA
KNTVYLQMNNLKPDDTAVYYCAAHESTYYSGTYYLTDPRRYVYWGQGTQVTVSSAAAYPYDVPDYGSHHHHHH;

1CDA 92
(SEQ ID NO: 504)
QVQLQESGGGLVQAGGSLRLSCVGDGRTFSSYIIGWFRQAPGNEREFVVAITWDGSATTYADSVKGRFTVSRDSAK
NTAYLQMNSLKPEDTAVYYCAAVPARGLTMDLENSDIYDHWGRGTQVTVSSAAAYPYDVPDYGSHHHHHH;

-continued

1CDA 93
(SEQ ID NO: 505)
QVQLQESGGGLVQAGGSLRLSCAASGRTFSSYVMGWFRQALGKEREFVAAIGWNGGITYYADSVKGRFAISRDNAK
NTVYLQMNSLKPEDTAVYYCAAATLQVTGSYYLDLSTVDIYDNWGQGTQVTVSSAAAYPYDVPDYGSHHHHHH;

2CDA 1
(SEQ ID NO: 506)
QVQLQESGGGLVQAGGSLRLSCAASGGTFSNYVMGWFRQAPGKEREFVGFITWSGASTYYADSVKGRFTISRDNA
ENTVYLQMNSLKPEDTAVYYCAATLFRSNGPKDLSSGYEYDYWGQGTQVTVSSAAAYPYDVPDYGSHHHHHH;

2CDA 5
(SEQ ID NO: 507)
QVQLQESGGGLVQAGDSLRLTCTASGRTFSNYGIGWFRQAPGKEREFVAGINWSGESADYADSVKGRFTISRDNAK
NTVYLQMNSLKPEDTAVYYCAAGESGVWVGGLDYWXQGTQVTVSSAAAYPYDVPDYGSHHHHHH;

2CDA 22
(SEQ ID NO: 508)
QVQLQESGGGLVQAGGSLRLSCAASGFTFDDYAIAWFRQAPGKEREGVSCIERSDGSTYYADSVKGRFTISSDNAK
NTVYLQMNSLKPEDTAVYYCAVGSANSGEFRFGWVLKPDLYNYWGQGTQVTVSSAAAYPYDVPDYGSHHHHHH;

2CDA 28
(SEQ ID NO: 509)
QVQLQESGGGLVQAGGSLRLSCTASGRTFSSYTVAWFRQSPGKEREGISCISNTDSSTYYADSVKGRFTISSDNAKS
TVHLQMSSLKPEDTAVYYCAADGNVWSPPICGSAGPPPGGMDYWGKGTQVTVSSAAAYPYDVPDYGSHHHHHH;

2CDA 62
(SEQ ID NO: 510)
QVQLQESGGGLVQPGGSLRLSCATFGFPFDDYAIAWFRQAPGKEREGVSCISNTDSSTYYADSVKGRFTISSDNAKN
TVHLQMSSLKPEDTAVYYCAADGNVWSPPICGSAGPPPGGMDYWGKGTQVTVSSAAAYPYDVPDYGSHHHHHH;

2CDA 68
(SEQ ID NO: 511)
QVQLQESGGGLVQAGGSLRLSCAASGRTFSSYVMGWFRQAPGKEREFVAQISWSAGSIYYADSVKGRFTISNDNAK
RTVYLQMNSLKPEDTAVYYCAERGYAYCSDDGCQRTQDYDYWGQGTQVTVSSAAAYPYDVPDYGSHHHHHH;

2CDA 73
(SEQ ID NO: 512)
QVQLQESGGGLVQAGGSLRLSCAASGRTLSSNPMAWFRQAAGKEREFVAGMSWNPGPAVYADSVKGRFTISRDS
AENTVYLQMNSLKPEDTAVYYCAGAARAWWSGSYDYTRMNNYDYWGPGTQVTVSSAAAYPYDVPDYGSHHHHHH;

2CDA 74
(SEQ ID NO: 513)
QVQLQESGGGLVQAGGSLRLSCAVSGFTFDNYAIGWFRQAPGKEREGVSCISRSDGSTYYADSVRGRFTISSDNAK
NTVYLQMNSLKPEDTAVYYCAAETSADSGEFRFGWVLKPSLYDYWGQGTQVTVSSAAAYPYDVPDYGSHHHHHH;

2CDA 74 (C50S)
(SEQ ID NO: 514)
QVQLQESGGGLVQAGGSLRLSCAVSGFTFDNYAIGWFRQAPGKEREGVSSISRSDGSTYYADSVRGRFTISSDNAK
NTVYLQMNSLKPEDTAVYYCAAETSADSGEFRFGWVLKPSLYDYWGQGTQVTVSS;

2CDA 75
(SEQ ID NO: 515)
QVQLQESGGGLVQAGGSLRLSCAASGRAFSSYFMGWFRQTPGKEREFVANIGWTGDMTYYADSVKGRFTISRDNA
KNTVYLQMNSLKPEDTAVYYCAAAGSAYSGSYWNITMAANYDYWGQGTQVTVSSAAAYPYDVPDYGSHHHHHH;

2CDA 77
(SEQ ID NO: 516)
QVQLQESGGGLVQAGGSLRLSCAASTPTFSSYNMGWFRQAPGKEREFVAAIIWSGSMTYYADSMKGRFTVSIDNAK
NTVYLQMNSLKPEDTAVYYCAAQRIFGAQPMDLSGDYEYWGQGTQVTVSSAAAYPYDVPDYGSHHHHHH;

2CDA 81
(SEQ ID NO: 517)
QVQLQESGGGLVQAGGSLRLSCATFGFTFDDYAIAWFRQAPGKEREGISCISNTDSSTYYADSVKGRFTISSDSAKN
TVHLQMSSLKPEDTAVYYCAADGNVWSPPICGSAGPPPGGMDYWGKGTQVTVSSAAAYPYDVPDYGSHHHHHH;

-continued

2CDA 87

(SEQ ID NO: 518)

QVQLQESGGGLVQAGGSLRLSCKASGGTFSGYIMGWFRQAPGKEREFVAANTWSGGPTYYSDSVKGRFTISRDNA

KNTVYLQMNTLKPEDTAVYQCAARDYRGIKDLDLKGDYDYWGQGTQVTVSSAAAYPYDVPDYGSHHHHHH;

2CDA 88

(SEQ ID NO: 519)

QVQLQESGGGLVQAGDSLKLSCATSGRSFSSYTIAWFRQAPGKEREGISCISSDGSTGYADSVRGRFTISSDNAKNT

VYLQMNSLKPEDTAVYYCAADFNVWSPPICGSIWYGPPPRGMDYWGKGTQVTVSSAAAYPYDVPDYGSHHHHHH;

2CDA 89

(SEQ ID NO: 520)

QVQLQESGGGLVQAGGYLRLSCAASGFSSDDYTIGWFRQAPGKEREGISCYSSSDGSTGFADSVKGRFTISSDNAK

NTVYLQMNNLRPEDTAVYYCAADSNVWSPPICGSRWYGPPPGGMAYWGKGTQVTVSSAAAYPYDVPDYGSHHHHHH;

2CDA 91

(SEQ ID NO: 521)

QVQLQESGGGLAQVGGSLRLSCTASGFTFDDYTIGWFRQAPGKEREGISCISSDGSTGYADSVKGRFTISSDNAKNT

VYLQMNSLKPEDTAVYYCAADFNVWSPPICGSNWYGPPPGGMDYWGKGTQVTVSSAAAYPYDVPDYGSHHHHHH;

2CDA 92

(SEQ ID NO: 522)

QVQLQESGGGLVQAGGSLRLSCAASGFSSDDYTIGWFRQAPGKEREGIGCIKSSDGTTGYADSVKGRFTISSDNAK

NTVYLQMNSLKPEDTAVYYCAADFNVWSPPICGSIWYGPPPGGMDYWGKGTQVTVSSAAAYPYDVPDYGSHHHHHH;

2CDA 93

(SEQ ID NO: 523)

QVQLQESGGGLAQAGGSLRLSCAASGFTFDQYTIAWFRQAPGKEREGVSCISNTDSSTYYADSVKGRFTISSDNAK

NTVYLQMSSLKPEDTAVYYCAADGNVWSPPICGSAGPPPGGMDYWGKGTQVTVSSAAAYPYDVPDYGSHHHHHH;

2CDA 94

(SEQ ID NO: 524)

QVQLQESGGGLVQAGGSLRLSCAASGRTFSSYAMAWFRQAPGKEREFVAAIAWSAGSTYYADSVKGRFAISRDNA

ENTVYLQMNSLKPEDTAVYYCAARIITVATMRLDSDYDYWGQGTQVTVSSAAAYPYDVPDYGSHHHHHH;

2CDA 95

(SEQ ID NO: 525)

QVQLQESGGGLVQAGGSLRLSCAASGFAFDGYAIGWFRQAPGKEREGVSCISSKEGSTYYADSVKGRFTISSDNAK

NTVYLQMSSLKPEDTAVYYCAADGNVWSPPICGSAGPPPGGMDYWGKGTQVTVSSAAAYPYDVPDYGSHHHHHH;

3CDA 3

(SEQ ID NO: 526)

QVQLQESGGGLVQAGGSLRLSCAASGFSSDDYTIAWFRRAPGKEREGISCISSSDGSTGYADSVKGRFTITSDSAKN

TVYLQMNSLKPEDTAVYYCAADSNVWSPPICGRTWYGPPPGGMDYWGKGTQVTVSSAAAYPYDVPDYGSHHHHHH;

3CDA 8

(SEQ ID NO: 527)

QVQLQESGGGLVQPGGSLRLSCAASGFSSDDYTIGWFRQAPGKEREGISCYSSRDGTTGYADSVKGRFTISSDNAK

NTVYLQMNSLKPEDTAVYYCAADFNVWSPPICGSIWYGPPPGGMAYWGQGTQVTVSSAAAYPYDVPDYGSHHHHHH;

3CDA 11

(SEQ ID NO: 528)

QVQLQESGGGLVQAGGSLRLSCAASGFTFDDYTIGWFRQAPGKEREGISCISSDGSTGYADSVKGRFTISSDNAKNT

VYLQMNSLKPEDTAVYYCAADFNVWSPPICGSNWYGPPPGGMDYWGKGTQVTVSSAAAYPYDVPDYGSHHHHHH;

3CDA 18

(SEQ ID NO: 529)

QVQLQESGGGLVQAGGSLRLSCAASGFSSDDYTIGWFRQAPGKEREGISCYSSSDGSTGYADSVKGRFTISSDNAK

NTVYLQMNSLKPEDTAVYYCAADFNVWSPPICGSSWYGPPPGGMDYWGKGTQVTVSSAAAYPYDVPDYGSHHHHHH;

3CDA 19

(SEQ ID NO: 530)

QVQLQESGGGLVQAGGSLRLSCAASGFSSDDYTIGWFRQAPGKEREGISCFSSSDGSTGFADSVKGRFTISSDNAT

NTVYLEMNSLKPEDTAVYYCAADFNVWSPPICGSRWYGPPPGGMEYWGKGTQVTVSSAAAYPYDVPDYGSHHHHHH;

-continued

3CDA 21
(SEQ ID NO: 531)
QVQLQESGGGLVQAGGSLRLSCATFGFSFDDYAIAWFRQAPGKEREGISCISNTDSSTFYADSVKGRFTISSDNAKN
TVHLQMSSLKPEDTAVYYCAADGNVWSPPICGSAGPPPGGMDYWGKGTQVTVSSAAAYPYDVPDYGSHHHHHH;

3CDA 24
(SEQ ID NO: 532)
QVQLQESGGGLVQAGGSLRLSCAASGFSSDDYTIGWFRQAPGKEREGISCYSSSDGSTGFADSVKGRFTISSDNAK
NTVYLQMNSLRPEDTAVYYCAADFNVWSPPICGSRWYGPPPGGMAYWGKGTQVTVSSAAAYPYDVPDYGSHHHHHH;

3CDA 28
(SEQ ID NO: 533)
QVQLQESGGGLVQVGGSLRLSCTISGFTGNDLAIGWFRQAPGKDQREGISCISNTDSSTYYADSVKGRFTISSDNAK
NTVHLQMSSLKPEDTAVYYCAADGNVWSPPICGSAGPPPGGMDYWGKGTQVTVSSAAAYPYDVPDYGSHHHHHH;

3CDA 29
(SEQ ID NO: 534)
QVQLQESGGGLVQAGGSLRLSCAASGFSSDDYTIAWFRRAPGKEREGISCISSSDGSTGYADSVKGRFTISSDNAKN
TVYLQMTSLKPEDTAVYYCAADSNVWSPPICGKTWYGPPPGGMDYWGKGTQVTVSSAAAYPYDVPDYGSHHHHHH;

3CDA 31
(SEQ ID NO: 535)
QVQLQESGGGLVQAGDSLRLSCAGSEGTLSSYGIGWFRQAPGKEREFVGGINWSGDSTDYADSVKGRFTISRDSAK
NTVYLQMNSLKPEDTAVYYCAAGESGVWVGGLDYWGQGTQVTVSSAAAYPYDVPDYGSHHHHHH;

3CDA 32
(SEQ ID NO: 536)
QVQLQESGGGLVQAGGSLRLSCAASGFSSDDYTIAWFRRAPGKEREGISCFSSSDGSAGYADSVKGRFTVSSDNAK
NTVYLQMNSLKPEDTAVYYCAADSNVWSPPICGSTWYGPPPGGMAYWGKGTQVTVSSAAAYPYDVPDYGSHHHHHH;

3CDA 33
(SEQ ID NO: 537)
QVQLQESGGGLVQAGGSLRLSCATSGFTFDDYAIAWFRQAPGKEREGVSCISNTDSSTYYADSVKGRFTISSDNAKN
TVYLQMSSLKPEDTAVYYCAADGNVWSPPICGSAGPPPGGMDYWGKGTQVTVSSAAAYPYDVPDYGSHHHHHH;

3CDA 37
(SEQ ID NO: 538)
QVQLQESGGGLVQAGGSLRLSCEVSGLSSDDYTIGWFRQAPGKEREGFSCFSTRDGNAGYADSVKGRFTISSDNA
KNTVYLQMNNLKPEDTAVYYCAADFNVWSPPICGSRWYGPPPGGMDYWGKGTQVTVSSAAAYPYDVPDYGSHHH
HHH;

3CDA 40
(SEQ ID NO: 539)
QVQLQESGGGLVQAGGSLRLSCEVSGLSSDDYTIGWFRQAPGKKREGFSCFSSRDGSTGYADSVKGRFTISSDNAK
NTVYLQMNSLKPEDTAVYYCAADFNVWSPPICGSRWYGPPPGGMDYWGKGTQVTVSSAAAYPYDVPDYGSHHHHHH;

3CDA 41
(SEQ ID NO: 540)
QVQLQESGGGLVQAGGSLRLSCAASGFSSDDYTIGWFRQAPGKEREGFSCFSSRDGSTGYADSVKGRFTISSDNA
KNTVYLQMNSLKPEDTAVYYCAADFNVWSPPICGSRWYGPPPGGMDYWGKGTQVTVSSAAAYPYDVPDYGSHHH
HHH;

3CDA 48
(SEQ ID NO: 541)
QVQLQESGGGLVQAGGSLRLSCAASGFSFDDYTIGWFRQVPGKEREGISCISSDGSTGYADSVKGRFTISSDNAKNT
VYLQINSLKPEDTAVYYCAADFNVWSPPICGSIWYGPPPGGMDYWGKGTQVTVSSAAAYPYDVPDYGSHHHHHH;

3CDA 57
(SEQ ID NO: 542)
QVQLQESGGGLVQAGGSLRLSCATFGFTFDDYAIAWFRQAPGKEREGISCISNTDSSTYYADSVKGRFTISSDNAKN
TVHLQMSSLKPEDTAVYYCAADGNVWSPPICGSAGPPPGGMDYWGKGTQVTVSSAAAYPYDVPDYGSHHHHHH;

-continued

3CDA 65

(SEQ ID NO: 543)

QVQLQESGGGLVQAGGSLXLSCAASGFTFDDYAIGWFRQAPGKEREGVSCISSPDGSTYYADSVKGRFTISSDNAK

NTVYLQMNSLKPEDTAVYYCAADFNVWSPPICGSVGPPPGGMDYWGKGTQVTVSSAAAYPYDVPDYGSHHHHHH;

3CDA 70

(SEQ ID NO: 544)

QVQLQESGGGLVQAGASLRLSCKASGFTFGDYTIGWFRQAPGKEREGISCYSSSDGNTGYADSVKGRFTISSDNAK

NTVYLQMNSLRPEDTAVYYCAADFNVWSPPICGSSWYGPPPGGMAYWGKGTQVTVSSAAAYPYDVPDYGSHHHHHH;

3CDA 73

(SEQ ID NO: 545)

QVQLQESGGGLVQAGDSLRLSCAGSEGTFSSYGIGWFRQAPGKEREFVGGINWSGDSTDYADSVKGRFTISRDNA

KNTVYLQMNSLKPEDTAVYYCAAGESGVWVGGLDYWGQGTQVTVSSAAAYPYDVPDYGSHHHHHH;

3CDA 83

(SEQ ID NO: 546)

QVQLQESGGGLVQAGGSLRLSCAASGFSSDDYTIGWFRQAPGKEREGISCFSSSDGSTGFADSVKGRFTISSDNAT

NTVYLQMNSLKPEDTAVYYCAADFNVWSPPICGSSWYGPPPGGMEYWGKGTQVTVSSAAAYPYDVPDYGSHHHHHH;

3CDA 86

(SEQ ID NO: 547)

QVQLQESGGGLVQAGDSLRLSCTASGVSIGDYNIGWFRQAPGKEREGVSCISSGDGTTYYTDSVKGRFTISTDNAKN

TVYLQMNSLKPEDTAVYYCAADGNVWSPPICGSAGPPPGGMDYWGKGTQVTVSSAAAYPYDVPDYGSHHHHHH;

3CDA 88

(SEQ ID NO: 548)

QVQLQESGGGLVQAGGSLRLSCAASGFTFDDYTIAWFRQAPGGKEREGISCISSDGSTGYADSVKGRFTISSDNAKN

MVYLQMNSLKPEDTALYYCAADFNVWSPPICSSNWYGPPPRGMDYWGKGTQVTVSSAAAYPYDVPDYGSHHHHHH;
or

3CDA 90

(SEQ ID NO: 549)

QVQLQESGGGLVQAGGSLRLSCAASGFTFDDYTIAWFRQAPGKEREGISCISSDGSTGYADSVRGRFTISSDNAKNT

VYLQMNSLKPEDTAVYYCAADFNVWSPPICGSIWYGPPPRGMDYWGKGTQVTVSSAAAYPYDVPDYGSHHHHHH.

In various exemplary embodiments, the CD8 binding agent comprises an amino acid sequence selected from any one of the above sequences without the terminal histidine tag sequence (i.e., HHHHHH, SEQ ID NO: 550).

In some embodiments, the CD8 binding agent comprises an amino acid sequence selected from any one of the above sequences without the HA tag (i.e., YPYDVPDYGS; SEQ ID NO: 551).

In some embodiments, the CD8 binding agent comprises an amino acid sequence selected from any one of the above sequences without the AAA linker.

In some embodiments, the CD8 binding agent comprises an amino acid sequence selected from any one of the above sequences without the AAA linker, HA tag, and terminal histidine tag sequence (i.e., AAAYPYDVPDYGSHHHHHH; SEQ ID NO: 552).

In some embodiments, the targeting moiety is a CD4 binding agent that is a VHH comprising a single amino acid chain having four "framework regions" or FRs and three "complementary determining regions" or CDRs. As used herein, "framework region" or "FR" refers to a region in the variable domain that is located between the CDRs. As used herein, "complementary determining region" or "CDR" refers to variable regions in VHHs that contains the amino acid sequences capable of specifically binding to antigenic targets. In some embodiments, the targeting moiety comprises anti-CD4 antibody as described in WO2020082045, the entire disclosures of which are hereby incorporated by reference. In some embodiments, the anti-CD4 antibody comprises at least one heavy chain variable region comprising the amino acid sequence of CDRH1: GYTFTAHI (SEQ ID NO: 78); CDRH2: IKPQYGAV (SEQ ID NO: 79); or CDRH3: AR (SEQ ID NO: 554). In some embodiments, the anti-CD4 antibody comprises at least one light chain variable region comprising the amino acid sequence of CDRL1: QGVGSD (SEQ ID NO: 80); CDRL2: HTS; or CDRL3: QVLQF (SEQ ID NO: 81).

In some embodiments, the targeting moiety comprises anti-CD4 antibody as described in WO2018170096, the entire disclosures of which are hereby incorporated by reference. In some embodiments, the anti-CD4 antibody comprises at least one heavy chain variable region comprising the amino acid sequence of CDRH1: GYTFTSN (SEQ ID NO: 82); CDRH2: YPRSGN (SEQ ID NO: 83); or CDRH3: RVPYFDH (SEQ ID NO: 84). In some embodiments, the anti-CD4 antibody comprises at least one light chain variable region comprising the amino acid sequence of CDRL1: KASQSVGNNVA (SEQ ID NO: 85); CDRL2: YASNRYT (SEQ ID NO: 86); or CDRL3: QQHYSSPFT (SEQ ID NO: 87).

In some embodiments, the targeting moiety comprises anti-CD4 antibody as described in WO2016156570, the entire disclosures of which are hereby incorporated by reference. In some embodiments, the anti-CD4 antibody comprises at least one CDR1 comprising the amino acid sequence of: GYWMY (SEQ ID NO: 88); CDR1: SYSMG (SEQ ID NO: 89); CDR1: FNAMG (SEQ ID NO: 90); or CDR1: VMG (SEQ ID NO: 555). In some embodiments, the anti-CD4 antibody comprises at least one CDR2 comprising the amino acid sequence of CDR2: AISPGGG- STYYPDSVK (SEQ ID NO: 91); CDR2: AISWSGDETSY-ADSVK (SEQ ID NO: 92); CDR2: TIARAGATKY-ADSVKG (SEQ ID NO: 93); or CDR2: AVRWSSTGIYYTQYAD (SEQ ID NO: 94). In some embodiments, the anti-CD4 antibody comprises at least one CDR3 comprising the amino acid sequence of CDR3: SLTATHTYEYDY (SEQ ID NO: 95); CDR3: DRWWR-PAGLQWDY (SEQ ID NO: 96); CDR3: RVFDLPNDY (SEQ ID NO: 97); or CDR3: DTYNSNPARWDGYDF (SEQ ID NO: 98).

In some embodiments, the targeting moiety comprises anti-CD4 antibody as described in WO2012145238, the entire disclosures of which are hereby incorporated by reference. In some embodiments, the anti-CD4 antibody comprises at least one heavy chain variable region comprising the amino acid sequence of CDRH1: AYVIS (SEQ ID NO: 99); CDRH2: EIYPGSGSSYYNEKFKG (SEQ ID NO: 100); or CDRH3: SGDGSKFVY (SEQ ID NO: 101). In some embodiments, the anti-CD4 antibody comprises at least one light chain variable region comprising the amino acid sequence of CDRL1: KASQSVDYCGDSYMN (SEQ ID NO: 102); CDRL2: VASNLES (SEQ ID NO: 103); or CDRL3: QQSLQDPPT (SEQ ID NO: 104).

In some embodiments, the targeting moiety comprises anti-CD4 antibody as described in WO2008134046, the entire disclosures of which are hereby incorporated by reference. In some embodiments, the anti-CD4 antibody comprises at least one heavy chain variable region comprising the amino acid sequence of CDRH1: GYTFTSYVIH (SEQ ID NO: 105); CDRH2: YINPYNDGTDYDEKFK (SEQ ID NO: 106); or CDRH3: EKDNYATGAWFAY (SEQ ID NO: 107). In some embodiments, the anti-CD4 antibody comprises at least one light chain variable region comprising the amino acid sequence of CDRL1: KSSQSLLY-STNQKNY (SEQ ID NO: 108); CDRL2: WASTRES (SEQ ID NO: 109); or CDRL3: QQYYSYRT (SEQ ID NO: 110).

In some embodiments, the targeting moiety comprises anti-CD4 antibody as described in WO2009012944, the entire 25 disclosures of which are hereby incorporated by reference. In some embodiments, the anti-CD4 antibody comprises at least one heavy chain variable region comprising the amino acid sequence of CDRH1: SYVIH (SEQ ID NO: 111); CDRH1: GFTFSNYAMS (SEQ ID NO: 112); or CDRH2: AISDHSTNTYYP (SEQ ID NO: 113); CDRH3: EKDNYATGAWFAY (SEQ ID NO: 114); or CDRH3: ARKYGGDYDPF (SEQ ID NO: 115). In some embodiments, the anti-CD4 antibody comprises at least one light chain variable region comprising the amino acid sequence of CDRL1: KSSQSLLYSTNQKNYL (SEQ ID NO: 116); CDRL1: KSSGSLLYSTNQKNYL (SEQ ID NO: 117); CDRL1: KASQDINNY (SEQ ID NO: 118); CDRL2: WASTRES (SEQ ID NO: 119); CDRL2: YTSTLQPGVPS (SEQ ID NO: 120); CDRL3: QQYYSYRT (SEQ ID NO: 121); or CDRL3: YDNLLF (SEQ ID NO: 122).

In some embodiments, the targeting moiety comprises anti-CD4 antibody as described in WO2004005350, the entire disclosures of which are hereby incorporated by reference. In some embodiments, the anti-CD4 antibody comprises at least one heavy chain variable region comprising the amino acid sequence of CDRH1: TFGVH (SEQ ID NO: 123); CDRH1: TAGVH (SEQ ID NO: 124); or CDRH1: TFGVA (SEQ ID NO: 125); CDRH2: VIWRSGIT-DYNVPFMS (SEQ ID NO: 126); CDRH2: VIARSGIT-DYNVPFMS (SEQ ID NO: 127); CDRH2: VIWASGIT-DYNVPFMS (SEQ ID NO: 128); CDRH3: NDPGTGFAY (SEQ ID NO: 129); CDRH3: NDPGTGAAY (SEQ ID NO: 130); or CDRH3: NDPGTGFAA (SEQ ID NO: 131). In some embodiments, the anti-CD4 antibody comprises at least one light chain variable region comprising the amino acid sequence of CDRL1: RASENIYSYLA (SEQ ID NO: 132); CDRL1: RASENIYSALA (SEQ ID NO: 133); CDRL2: DAKTLAE (SEQ ID NO: 134); CDRL3: QHHYGNPPT (SEQ ID NO: 135); CDRL3: QHAYGNPPT (SEQ ID NO: 136); or CDRL3: QHHAGNPPT (SEQ ID NO: 137).

In some embodiments, the targeting moiety comprises anti-CD4 antibody as described in WO2004083247, the entire disclosures of which are hereby incorporated by reference. In some embodiments, the anti-CD4 antibody comprises at least one heavy chain variable region comprising the amino acid sequence of CDRH1: DYVIN (SEQ ID NO: 138); CDRH2: EIYPGSGSDYYNENLKD (SEQ ID NO: 139); or CDRH3: KGENGNSLAFAY (SEQ ID NO: 140). In some embodiments, the anti-CD4 antibody comprises at least one light chain variable region comprising the amino acid sequence of CDRL1: QSVDYDGDSYMN (SEQ ID NO: 141); CDRL2: AASNLES (SEQ ID NO: 142); or CDRL3: QQSIQDPCT (SEQ ID NO: 143).

In some embodiments, the targeting moiety comprises anti-CD4 antibody as described in WO2014100139, the entire disclosures of which are hereby incorporated by reference. In some embodiments, the anti-CD4 antibody comprises at least one heavy chain comprising the following amino acid sequence:

```
Anti-CD4 antibody MV1, Heavy Chain
                                        (SEQ ID NO: 144)
MEWSGVFMFLLSVTAGVHSQVQLQQSGPEVVKPGASVKMSCKASGYTFT

SYVIHWVRQKPGQGLDWIGYINPYNDGTDYDEKFKGKATLTSDTSTSTA

YMELSSLRSEDTAVYYCAREKDNYATGAWFAYWGQGTLVTVSSASTKGP

SVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCD

KTHTCPPCPAPEFEGGPSVFLFPPKPKDTLMISRTPEVTCVVVDVSHED

PEVKFNWYVDGVEVHNAKTKPREEQYNSTYRVVSVLTVLHQDWLNGKEY

KCKVSNKALPASIEKTISKAKGQPREPQVYTLPPSRDELTKNQVSLTCL

VKGFYPSDIAVEWESNGQPENNYKTTPPVLDSDGSFFLYSKLTVDKSRW

QQGNVFSCSVMHEALHNHYTQKSLSLSPGK
```

In some embodiments, the anti-CD4 antibody comprises at least one light chain comprising the following amino acid sequence:

```
Anti-CD4 antibody MV1, Light Chain
                                        (SEQ ID NO: 145)
MEWSGVFIFLLSVTAGVHSDIVMTQSPDSLAVSLGERVTMNCKSSQSLL

YSTNQKNYLAWYQQKPGQSPKLLIYWASTRESGVPDRFSGSGSGTDFTL

TISSVQAEDVAVYYCQQYYYRTFGGGTKLEIKRTVAAPSVFIFPPSDEQ

LKSGTASVVCLLNNFYPREAKVQWKVDNALQSGNSQESVTEQDSKDSTY

SLSSTLTLSKADYEKHKVYACEVTHQGLSSPVTKSFNRGEC
```

In some embodiments, the targeting moiety comprises anti-CD4 antibody as described in WO2004083247, the entire disclosures of which are hereby incorporated by reference. In some embodiments, the anti-CD4 antibody comprises at least one heavy chain comprising the following amino acid sequence:

(SEQ ID NO: 146)
EEQLVESGGGLVKPGGSLRLSCAASGFSFSDCRMYWLRQAPGKGLEWIG

VISVKSENYGANYAESVRGRFTISRDDSKNTVYLQMNSLKTEDTAVYYC

SASYYRYDVGAFAYGQGTLVTVSS

In some embodiments, the anti-CD4 antibody comprises at least one light chain comprising the following amino acid sequence:

(SEQ ID NO: 147)
DIVMTQSPDSLAVSLGERATINCRASKSVSTSGYSYIYWYQQKPGQPPK

LLIYLASILESGVPDRFSGSGSGTDFTLTISSLQAEDVAVYYCQHSREL

PTFGQGTKVEIK

In various embodiments, the vaccine composition comprises targeting moieties in various combinations. In an illustrative embodiment, the vaccine composition may comprise two targeting moieties, wherein both targeting moieties are antibodies or derivatives thereof. In another illustrative embodiment, the vaccine composition may comprise two targeting moieties, wherein both targeting moieties are natural ligands for cell receptors. In a further illustrative embodiment, the vaccine composition may comprise two targeting moieties, wherein one of the targeting moieties is an antibody or derivative thereof, and the other targeting moiety is a natural ligand for a cell receptor.

In various embodiments, the recognition domain of the targeting moiety functionally modulates (by way of non-limitation, partially or completely neutralizes) the target (e.g. antigen, receptor) of interest, e.g. substantially inhibiting, reducing, or neutralizing a biological effect that the antigen has.

In various embodiments, the recognition domain of the targeting moiety binds but does not functionally modulate the target (e.g. antigen, receptor) of interest, e.g. the recognition domain is, or is akin to, a binding antibody. For instance, in various embodiments, the recognition domain simply targets the antigen or receptor but does not substantially inhibit, reduce or functionally modulate a biological effect that the antigen or receptor has. For example, some of the smaller antibody formats described above (e.g. as compared to, for example, full antibodies) have the ability to target hard to access epitopes and provide a larger spectrum of specific binding locales. In various embodiments, the recognition domain binds an epitope that is physically separate from an antigen or receptor site that is important for its biological activity (e.g. the antigen's active site).

Such non-neutralizing binding finds use in various embodiments of the present invention, including methods in which the vaccine composition is used to, directly or indirectly, recruit active immune cells to a site of need via an effector antigen, such as any of those described herein. For example, in various embodiments, the present vaccine compositions may be used to directly or indirectly recruit cytotoxic T cells via CD8 to a site of infection in a method of treating an infection. In such embodiments, it is desirable to directly or indirectly recruit $CD8^{-}$ expressing cytotoxic T cells but not to functionally modulate the CD8 activity.

In various embodiments, the recognition domain of the targeting moiety binds to an immune modulatory antigen (e.g. immune stimulatory or immune inhibitory). In various embodiments, the immune modulatory antigen is one or more of 4-1BB, OX-40, HVEM, GITR, CD27, CD28, CD30, CD40, ICOS ligand; OX-40 ligand, LIGHT (CD258), GITR ligand, CD70, B7-1, B7-2, CD30 ligand, CD40 ligand, ICOS, ICOS ligand, CD137 ligand and TL1A.

In various embodiments, the recognition domain of the targeting moiety may be in the context of chimeric proteins or chimeric protein complexes such as Fc-based chimeric protein complex that comprises two recognition domains that have neutralizing activity, or comprises two recognition domains that have non-neutralizing (e.g. binding) activity, or comprises one recognition domain that has neutralizing activity and one recognition domain that has non-neutralizing (e.g. binding) activity.

Fc Domains

The fragment crystallizable domain (Fc domain) is the tail region of an antibody that interacts with Fc receptors located on the cell surface of cells that are involved in the immune system, e.g., B lymphocytes, dendritic cells, natural killer cells, macrophages, neutrophils, eosinophils, basophils, and mast cells. In IgG, IgA and IgD antibody isotypes, the Fc domain is composed of two identical protein fragments, derived from the second and third constant domains of the antibody's two heavy chains. In IgM and IgE antibody isotypes, the Fc domain contains three heavy chain constant domains ($C_H$ domains 2-4) in each polypeptide chain.

In some embodiments, the Fc-based chimeric protein of complex the present technology includes a Fc domain. In some embodiments, the Fc domains are from selected from IgG, IgA, IgD, IgM or IgE. In some embodiments, the Fc domains are from selected from IgG1, IgG2, IgG3, or IgG4.

In some embodiments, the Fc domains are from selected from human IgG, IgA, IgD, IgM or IgE. In some embodiments, the Fc domains are from selected from human IgG1, IgG2, IgG3, or IgG4.

In some embodiments, the Fc domains of the Fc-based chimeric protein complex comprise the CH2 and CH3 regions of IgG. In some embodiments, the IgG is human IgG. In some embodiments, the human IgG is selected from IgG1, IgG2, IgG3, or IgG4.

In some embodiments, the Fc domains comprise one or more mutations. In some embodiments, the mutation(s) to the Fc domains reduces or eliminates the effector function the Fc domains. In some embodiments, the mutated Fc domain has reduced affinity or binding to a target receptor. By way of example, in some embodiments, the mutation to the Fc domains reduces or eliminates the binding of the Fc domains to FcγR. In some embodiments, the FcγR is selected from FcγRI; FcγRIIa, 131R/R; FcγRIIa, 131 H/H, FcγRIIb; and FcγRIII. In some embodiments, the mutation to the Fc domains reduces or eliminated binding to complement proteins, such as, e.g., C1q. In some embodiments, the mutation to the Fc domains reduces or eliminated binding to both FcγR and complement proteins, such as, e.g., C1q.

In some embodiments, the Fc domains comprise the LALA mutation to reduce or eliminate the effector function of the Fc domains. By way of example, in some embodiments, the LALA mutation comprises L234A and L235A substitutions in human IgG (e.g., IgG1) (wherein the numbering is based on the commonly used numbering of the CH2 residues for human IgG1 according to EU convention (PNAS, Edelman et al., 1969; 63 (1) 78-85)).

In some embodiments, the Fc domains of human IgG comprise a mutation at 46. to reduce or eliminate the effector function of the Fc domains. By way of example, in some embodiments, the mutations are selected from L234A, L234F, L235A, L235E, L235Q, K322A, K322Q, D265A, P329G, P329A, P331G, and P331S.

In some embodiments, the Fc domains comprise the FALA mutation to reduce or eliminate the effector function of the Fc domains. By way of example, in some embodiments, the FALA mutation comprises F234A and L235A substitutions in human IgG4.

In some embodiments, the Fc domains of human IgG4 comprise a mutation at one or more of F234, L235, K322, D265, and P329 to reduce or eliminate the effector function of the Fc domains. By way of example, in some embodiments, the mutations are selected from F234A, L235A, L235E, L235Q, K322A, K322Q, D265A, P329G, and P329A.

In some embodiments, the mutation(s) to the Fc domain stabilize a hinge region in the Fc domain. By way of example, in some embodiments, the Fc domain comprises a mutation at S228 of human IgG to stabilize a hinge region. In some embodiments, the mutation is S228P.

In some embodiments, the mutation(s) to the Fc domain promote chain pairing in the Fc domain. In some embodiments, chain pairing is promoted by ionic pairing (a/k/a charged pairs, ionic bond, or charged residue pair).

In some embodiments, the Fc domain comprises a mutation at one more of the following amino acid residues of IgG to promote of ionic pairing: D356, E357, L368, K370, K392, D399, and K409.

By way of example, in some embodiments, the human IgG Fc domain comprise one of the mutation combinations in Table 1 to promote of ionic pairing.

TABLE 1

| Substitution(s) on one Fc Chain | Substitution(s) on other Fc Chain |
|---|---|
| D356K D399K | K392D K409D |
| E357R L368R | K370D K409D |
| E357R L368K | K370D K409D |
| E357R D399K | K370D K409D |
| E357R | K370D |
| L368R D399K | K392D K409D |
| L368K D399K | K392D K409D |
| L368R D399K | K409D |
| L368K D399K | K409D |
| L368R | K409D |
| L368K | K409D |
| K370D K409D | E357R D399K |
| K370D K409D | E357R L368R |
| K370D K409D | E357R L368K |
| K370D K409D | E357R D399K |
| K370D K409D | E357R L368R |
| K370D K409D | E357R L368K |
| K370D | E357R |
| K370D | E357R |
| K392D K409D | D356K D399K |
| K392D K409D | L368R D399K |
| K392D K409D | L368K D399K |
| K392D K409D | D399K |
| D399K | K392D K409D |
| D399K | K409D |
| K409D | L368R |
| K409D | L368K |
| K409D | L368R D399K |
| K409D | L368K D399K |
| K409D | L368R |
| K409D | L368K |
| K409D | L368R D399K |
| K409D | L368K D399K |
| K409D | D399K |

In some embodiments, chain pairing is promoted by a knob-in-hole mutations. In some embodiments, the Fc domain comprises one or more mutations to allow for a knob-in-hole interaction in the Fc domain. In some embodiments, a first Fc chain is engineered to express the "knob" and a second Fc chain is engineered to express the complementary "hole." By way of example, in some embodiments, human IgG Fc domain comprises the mutations of Table 2 to allow for a knob-in-hole interaction.

TABLE 2

| Substitution(s) on one Fc Chain | Substitution(s) on other Fc Chain |
|---|---|
| T366Y | Y407T |
| T366Y/F405A | T394W/Y407T |
| T366W | Y407A |
| T366W | Y407V |
| T366Y | Y407A |
| T366Y | Y407V |
| T366Y | Y407T |

In some embodiments, the Fc domains in the Fc-based chimeric protein complexes of the present technology comprise any combination of the above disclosed mutations. By way of example, in some embodiments, the Fc domain comprises mutations that promote ionic pairing and/or a knob-in-hole interaction. By way of example, in some embodiments, the Fc domain comprises mutations that have one or more of the following properties: promote ionic pairing, induce a knob-in-hole interaction, reduce or eliminate the effector function of the Fc domain, and cause Fc stabilization (e.g. at hinge).

By way of example, in some embodiments, a human IgG Fc domains comprise mutations disclosed in Table 3, which promote ionic pairing and/or promote a knob-in-hole interaction in the Fc domain.

TABLE 3

| Substitution(s) on one Fc Chain | Substitution(s) on other Fc Chain |
|---|---|
| T366W K370D | E357R Y407A |
| T366W K370D | E357R Y407V |
| T366W K409D | L368R Y407A |
| T366W K409D | L368R Y407V |
| T366W K409D | L368K Y407A |
| T366W K409D | L368K Y407V |
| T366W K409D | L368R D399K Y407A |
| T366W K409D | L368R D399K Y407V |
| T366W K409D | L368K D399K Y407A |
| T366W K409D | L368K D399K Y407V |
| T366W K409D | D399K Y407A |
| T366W K409D | D399K Y407V |
| T366W K392D K409D | D399K Y407A |
| T366W K392D K409D | D399K Y407V |
| T366W K392D K409D | D356K D399K Y407A |
| T366W K392D K409D | D356K D399K Y407V |
| T366W K370D K409D | E357R D399K Y407A |
| T366W K370D K409D | E357R D399K Y407V |
| T366W K370D K409D | E357R L368R Y407A |
| T366W K370D K409D | E357R L368R Y407V |
| T366W K370D K409D | E357R L368K Y407A |
| T366W K370D K409D | E357R L368K Y407V |
| T366W K392D K409D | L368R D399K Y407A |
| T366W K392D K409D | L368R D399K Y407V |
| T366W K392D K409D | L368K D399K Y407A |
| T366W K392D K409D | L368K D399K Y407V |
| E357R T366W | K370D Y407A |
| E357R T366W | K370D Y407V |
| T366W L368R | Y407A K409D |
| T366W L368R | Y407V K409D |
| T366W L368K | Y407A K409D |
| T366W L368K | Y407V K409D |
| T366W L368R D399K | Y407A K409D |
| T366W L368R D399K | Y407V K409D |
| T366W L368K D399K | Y407A K409D |
| T366W L368K D399K | Y407V K409D |
| T366W D399K | Y407A K409D |
| T366W D399K | Y407V K409D |
| 1366W D399K | K392D Y407A K409D |
| T366W D399K | K392D Y407V K409D |
| T366W D356K D399K | K392D Y407A K409D |

TABLE 3-continued

| Substitution(s) on one Fc Chain | Substitution(s) on other Fc Chain |
|---|---|
| T366W D356K D399K | K392D Y407V K409D |
| E357R T366W D399K | K370D Y407A K409D |
| E357R T366W D399K | K370D Y407V K409D |
| E357R T366W L368R | K370D Y407A K409D |
| E357R T366W L368R | K370D Y407V K409D |
| E357R T366W L368K | K370D Y407A K409D |
| E357R T366W L368K | K370D Y407V K409D |
| T366W L368R D399K | K392D Y407A K409D |
| T366W L368R D399K | K392D Y407V K409D |
| T366W L368K D399K | K392D Y407A K409D |

By way of example, in some embodiments, a human IgG Fc domains comprise mutations disclosed in Table 4, which promote ionic pairing, promote a knob-in-hole interaction, or a combination thereof in the Fc domain. In embodiments, the "Chain 1" and "Chain 2" of Table 4 can be interchanged (e.g. Chain 1 can have Y407T and Chain 2 can have T366Y).

TABLE 4

| Chain 1 mutation | Chain 2 mutation | Reference | IgG |
|---|---|---|---|
| T366Y | Y407T | Ridgway et al., 1996 Protein Engineering, Design and Selection, Volume 9, Issue 7, 1 Jul. 1996, Pages 617-62 | IgG1 |
| T366Y/F405A | T394W/Y407T | Ridgway et al., 1996 Protein Engineering, Design and Selection, Volume 9, Issue 7, 1 Jul. 1996, Pages 617-62 | IgG1 |
| T366W | Y407A | Atwell et al., 1997 JMB Volume 270, Issue 1, 4 Jul. 1997, Pages 26-35 | IgG1 |
| T366W | T366S/L368V/Y407A | Atwell et al., 1997 JMB Volume 270, Issue 1, 4 Jul. 1997, Pages 26-35 | IgG1 |
| T366W | L368A/Y407A | Atwell et al., 1997 JMB Volume 270, Issue 1, 4 Jul. 1997, Pages 26-35 | IgG1 |
| T366W | T366S/L368A/Y407A | Atwell e tal., 1997 JMB Volume 270, Issue 1, 4 Jul. 1997, Pages 26-35 | IgG1 |
| T366W | T366S/L368G/Y407V | Atwell et al., 1997 JMB Volume 270, Issue 1, 4 Jul. 1997, Pages 26-35 | IgG1 |
| T366W/D399C | T366S/L368A/K392C/Y407V | Merchant et al., 1998 Nature Biotechnology volume 16, pages 677-681 (1998) | IgG1 |
| T366W/K392C | T366S/L368A/D399C/Y407V | Merchant et al., 1998 Nature Biotechnology volume 16, pages 677-681 (1998) | IgG1 |
| S354C/T366W | Y349C/T366S/L368A/Y407V | Merchant et al., 1998 Nature Biotechnology volume 16, pages 677-681 (1998) | IgG1 |
| Y349C/T366W | S354C/T366S/L368A/Y407V | Merchant et al., 1998 Nature Biotechnology volume 16, pages 677-681 (1998) | IgG1 |
| E356C/T366W | Y349C/T366S/L368A/Y407V | Merchant et al., 1998 Nature Biotechnology volume 16, pages 677-681 (1998) | IgG1 |
| Y349C/T366W | E356C/T366S/L368A/Y407V | Merchant et al., 1998 Nature Biotechnology volume 16, pages 677-681 (1998) | IgG1 |
| E357C/T366W | Y349C/T366S/L368A/Y407V | Merchant et al., 1998 Nature Biotechnology volume 16, pages 677-681 (1998) | IgG1 |
| Y349C/T366W | E357C/T366S/L368A/Y407V | Merchant et al., 1998 Nature Biotechnology volume 16, pages 677-681 (1998) | IgG1 |
| D339R | K409E | Gunasekaran et al., 2010 The Journal of Biological Chemistry 285, 19637-19646. | IgG1 |

TABLE 4-continued

| Chain 1 mutation | Chain 2 mutation | Reference | IgG |
|---|---|---|---|
| D339K | K409E | Gunasekaran et al., 2010 The Journal of Biological Chemistry 285, 19637-19646. | IgG1 |
| D339R | K409D | Gunasekaran et al., 2010 The Journal of Biological Chemistry 285, 19637-19646. | IgG1 |
| D339K | K409D | Gunasekaran et al., 2010 The Journal of Biological Chemistry 285, 19637-19646. | IgG1 |
| D339K | K360D/K409E | Gunasekaran et al., 2010 The Journal of Biological Chemistry 285, 19637-19646. | IgG1 |
| D339K | K392D/K409E | Gunasekaran et al., 2010 The Journal of Biological Chemistry 285, 19637-19646. | IgG1 |
| D339K/E356K | K392D/K409E | Gunasekaran et al., 2010 The Journal of Biological Chemistry 285, 19637-19646. | IgG1 |
| D339K/E357K | K392D/K409E | Gunasekaran et al., 2010 The Journal of Biological Chemistry 285, 19637-19646. | IgG1 |
| D339K/E356K | K409E/K439D | Gunasekaran et al., 2010 The Journal of Biological Chemistry 285, 19637-19646. | IgG1 |
| D339K/E357K | K370D/K409E | Gunasekaran et al., 2010 The Journal of Biological Chemistry 285, 19637-19646. | IgG1 |
| D339K/E356K/E357K | K370D/K392D/K409E | Gunasekaran et al., 2010 The Journal of Biological Chemistry 285, 19637-19646. | IgG1 |
| S364H/F405A | Y349T/T394F | Moore et al., 2011 mAbs, 3:6, 546-557 | IgG1 |
| S364H/T394F | Y349T/F405A | Moore et al., 2011 mAbs, 3:6, 546-557 | IgG1 |
| D221R/P228R/K409R | D221E/P228E/L368E | Strop et al., 2012 JMB Volume 420, Issue 3, 13 Jul. 2012, Pages 204-219 | IgG1 |
| C223R/E225R/P228R/K409R | C223E/P228E/L368E | Strop et al., 2012 JMB Volume 420, Issue 3, 13 Jul. 2012, Pages 204-219 | IgG2 |
| F405L | K409R | Labrijn et al., 2013 PNAS Mar. 26, 2013. 110 (13) 5145-5150 | IgG1 |
| F405A/Y407V | T394W | Von Kreudenstein et al., 2013 mAbs Volume 5, 2013-Issue 5, pp.644-654 | IgG1 |
| F405A/Y407V | T3661/T394W | Von Kreudenstein et al., 2013 mAbs Volume 5, 2013-Issue 5, pp.644-654 | IgG1 |
| F405A/Y407V | T366L/T394W | Von Kreudenstein et al., 2013 mAbs Volume 5, 2013-Issue 5, pp.644-654 | IgG1 |
| F405A/Y407V | T366L/K392M/T394W | Von Kreudenstein et al., 2013 mAbs Volume 5, 2013-Issue 5, pp.644-654 | IgG1 |
| L351Y/F405A/Y407V | T366L/K392M/T394W | Von Kreudenstein et al., 2013 mAbs Volume 5, 2013-Issue 5, pp.644-654 | IgG1 |
| T350V/L351Y/F405A/Y407V | T350V/T366L/K392M/T394W | Von Kreudenstein et al., 2013 mAbs Volume 5, 2013-Issue 5, pp.644-654 | IgG1 |
| T350V/L351Y/F405A/Y407V | T350V/T366L/K392L/T394W | Von Kreudenstein et al., 2013 mAbs Volume 5, 2013-Issue 5, pp.644-654 | IgG1 |
| K409W | D339V/F405T | Choi et al., 2013 PNAS Jan. 2, 2013. 110 (1) 270-275 | IgG1 |
| K360E | Q347R | Choi et al., 2013 PNAS Jan. 2, 2013. 110 (1) 270-275 | IgG1 |
| K360E/K409W | D339V/Q347R/F405T | Choi et al., 2013 PNAS Jan. 2, 2013. 110 (1) 270-275 | IgG1 |
| Y349C/K360E/K409W | D339V/Q347R/S354C/F405T | Choi et al., 2013 PNAS Jan. 2, 2013. 110 (1) 270-275 | IgG1 |
| K392A/K409D | E356K/D399K | Leaver-Fey et al., 2016 Structure Volume 24, Issue 4, 5 Apr. 2016, Pages 641-651 | IgG1 |

TABLE 4-continued

| Chain 1 mutation | Chain 2 mutation | Reference | IgG |
|---|---|---|---|
| T366W | T366S/L358A/Y407A | Leaver-Fey et al., 2016 Structure Volume 24, Issue 4, 5 Apr. 2016, Pages 641-651 | IgG1 |
| D339M/Y407A | T336V/K409V | Leaver-Fey et al., 2016 Structure Volume 24, Issue 4, 5 Apr. 2016, Pages 641-651 | IgG1 |
| D339M/K360D/Y407A | T336V/E345R/Q347R/K409V | Leaver-Fey et al., 2016 Structure Volume 24, Issue 4, 5 Apr. 2016, Pages 641-651 | IgG1 |
| Y349S/T366V/K370Y/K409V | E357D/S364Q/Y407A | Leaver-Fey et al., 2016 Structure Volume 24, Issue 4, 5 Apr. 2016, Pages 641-651 | IgG1 |
| Y349S/T366M/K370Y/K409V | E356G/E357D/S364Q/Y407A | Leaver-Fey et al., 2016 Structure Volume 24, Issue 4, 5 Apr. 2016, Pages 641-651 | IgG1 |
| Y349S/T366M/K370Y/K409V | E357D/S364R/Y407A | Leaver-Fey et al., 2016 Structure Volume 24, Issue 4, 5 Apr. 2016, Pages 641-651 | IgG1 |

And any combination as described in Tables 1-3 of US20150284475A1

By way of example, in some embodiments, a human IgG Fc domains comprise mutations disclosed in Table 5, which reduce or eliminate FcγR and/or complement binding in the Fc domain. In embodiments, the Table 5 mutations are in both chains.

TABLE 5

| Chain 1 mutation | Reference | IgG |
|---|---|---|
| L234A/L235A | Alegre et al., 1994 Transplantation 57:1537-1543 | IgG1 |
| F234A/L235A | Alegre et al., 1994 Transplantation 57:1537-1543 | IgG4 |
| L235E | Morgan et al., 1995 Immunology. 1995 October; 86(2): 319-324. | IgG1 |
| L235E | Morgan et al., 1995 Immunology. 1995 October; 86(2): 319-324. | IgG4 |
| L235A | Morgan et al., 1995 Immunology. 1995 October; 86(2): 319-324. | IgG1 |
| G237A | Morgan et al., 1995 Immunology. 1995 October; 86(2): 319-324. | IgG1 |
| N297H | Tao and Morrison, J. Immunol. 1989; 143:2595-2601 | IgG1 |
| N297Q | Tao and Morrison, J. Immunol. 1989; 143:2595-2601 | IgG1 |
| N297K | Tao and Morrison, J. Immunol. 1989; 143:2595-2601 | IgG3 |
| N297Q | Tao and Morrison, J. Immunol. 1989; 143:2595-2601 | IgG3 |
| D265A | Idusogie et al., 2000 J Immunol Apr. 15, 2000, 164 (8) 4178-4184 | IgG1 |
| D270A, V, K | Idusogie et al., 2000 J Immunol Apr. 15, 2000, 164 (8) 4178-4184 | IgG1 |
| K322A, L, M, D, E | Idusogie et al., 2000 J Immunol Apr. 15, 2000, 164 (8) 4178-4184 | IgG1 |

TABLE 5-continued

| Chain 1 mutation | Reference | IgG |
|---|---|---|
| P329A, X | Idusogie et al., 2000 J Immunol Apr. 15, 2000, 164 (8) 4178-4184 | IgG1 |
| P331A, S, G, X | Idusogie et al., 2000 J Immunol Apr. 15, 2000, 164 (8) 4178-4184 | IgG1 |
| D265A | Idusogie et al., 2000 J Immunol Apr. 15, 2000, 164 (8) 4178-4184 | IgG1 |
| L234A | Hezareh et al., 2001 J. Virol. December 2001 vol. 75 no. 24 12161-12168 | IgG1 |
| L234A/L235A | Hezareh et al., 2001 J. Virol. December 2001 vol. 75 no. 24 12161-12168 | IgG1 |
| L234F/L235E/P331S | Oganesyan et al., 2008 Acta Cryst. (2008). D64, 700-704 | IgG1 |
| H268Q/V309L/A330S/P331S | An et al., 2009 mAbs Volume 1, 2009-Issue 6, pp. 572-579 | IgG1 |
| G236R/L328R | Moore et al., 2011 mAbs Volume 3, 2011-Issue 6, pp. 546-557 | IgG1 |
| N297G | Couch et al., 2013 Sci. Transl. Med., 5 (2013) 183ra57, 1-12 | IgG1 |
| N297G/D265A | Couch et al., 2013 Sci. Transl. Med., 5 (2013) 183ra57, 1-12 | IgG1 |
| V234A/G237A/P328S/H268A/V309L/A330S/P331S | Vafa et al., 2014 Methods Volume 65, Issue 1, 1 Jan. 2014, Pages 114-126 | IgG2 |
| L234A/L235A/P329G | Lo et al., 2016 The Journal of Biological Chemistry 292, 3900-3908 | IgG1 |
| N297D | Schlothauer et al., 2016 Protein Engineering, Design and Selection, Volume 29, Issue 10, 1 Oct. 2016, Pages 457-466 | IgG1 |
| S228P/L235E | Schlothauer et al., 2016 Protein Engineering, Design and Selection, Volume 29, Issue 10, 1 Oct. 2016, Pages 457-466 | IgG4 |
| S228P/L235E/P329G | Schlothauer et al., 2016 Protein Engineering, Design and Selection, Volume 29, Issue 10, 1 Oct. 2016, Pages 457-466 | IgG4 |
| L234F/L235A/K322Q | Borrok et al., 2017 J Pharm Sci April 2017 Volume 106, Issue 4, Pages 1008-1017 | IgG1 |
| L234F/L235Q/P331G | Borrok et al., 2017 J Pharm Sci April 2017 Volume 106, Issue 4, Pages 1008-1017 | IgG1 |
| L234F/L235Q/K322Q | Borrok et al., 2017 J Pharm Sci April 2017 Volume 106, Issue 4, Pages 1008-1017 | IgG1 |
| L234A/L235A/G237A/P328S/H268A/A330S/P331S | Tam et al., 2017 Open Access Antibodies 2017, 6(3), 12; doi:10.3390/antib6030012 | IgG1 |
| S228P/F234A/L235A | Tam et al., 2017 Open Access Antibodies 2017, 6(3), 12; doi:10.3390/antib6030012 | IgG4 |
| S228P/F234A/L235A/G237A/P238S | Tam et al., 2017 Open Access Antibodies 2017, 6(3), 12; doi:10.3390/antib6030012 | IgG4 |
| S228P/F234A/L235A/G2361/G237A/P238S | Tam et al., 2017 Open Access Antibodies 2017, 6(3), 12; doi:10.3390/antib6030012 | IgG4 |

In some embodiments, the Fc domains in the Fc-based chimeric protein complexes of the present technology are homodimeric, i.e., the Fc region in the chimeric protein complex comprises two identical protein fragments.

In some embodiments, the Fc domains in the Fc-based chimeric protein complexes of the present technology are heterodimeric, i.e., the Fc domain comprises two non-identical protein fragments.

In some embodiments, heterodimeric Fc domains are engineered using ionic pairing and/or knob-in-hole mutations described herein. In some embodiments, the heterodimeric Fc-based chimeric protein complexes have a trans orientation/configuration. In a trans orientation/configuration, the targeting moiety and signaling agent, e.g. IL-1β are, in embodiments, not found on the same polypeptide chain in the present Fc-based chimeric protein complexes.

In some embodiments, the Fc domains includes or starts with the core hinge region of wild-type human IgG1, which contains the sequence Cys-Pro-Pro-Cys. In some embodiments, the Fc domains also include the upper hinge, or parts thereof (e.g., DKTHTCPPC; see WO 2009053368), EPKSCDKTHTCPPC, or EPKSSDKTHTCPPC; see Lo et al., Protein Engineering vol. 11 no.6 pp. 495-500, 1998)).

Fc-Based Chimeric Protein Complexes

The Fc-based chimeric protein complexes of the present technology comprise at least one Fc domain disclosed herein, at least one signaling agent, e.g. IL-1β (SA) disclosed herein, e.g. IL-1β, and at least one targeting moiety TM disclosed herein.

It is understood that, the present Fc-based chimeric protein complexes may encompass a complex of two fusion proteins, each comprising an Fc domain.

In some embodiments, the Fc-based chimeric protein complex is heterodimeric. In some embodiments, the heterodimeric Fc-based chimeric protein complex has a trans orientation/configuration. In some embodiments, the heterodimeric Fc-based chimeric protein complex has a cis orientation/configuration.

In some embodiments, heterodimeric Fc domains are engineered using ionic pairing and/or knob-in-hole mutations described herein. In some embodiments, the heterodimeric Fc-based chimeric protein complexes have a trans orientation.

In a trans orientation, the targeting moiety and signaling agent are, in embodiments, not found on the same polypeptide chain in the present Fc-based chimeric protein complexes. In a trans orientation, the targeting moiety and signaling agent are, in embodiments, found on separate polypeptide chains in the Fc-based chimeric protein complexes. In a cis orientation, the targeting moiety and signaling agent are, in embodiments, found on the same polypeptide chain in the Fc-based chimeric protein complexes.

In some embodiments, where more than one targeting moiety is present in the heterodimeric protein complexes described herein, one targeting moiety may be in trans orientation (relative to the signaling agent), whereas another targeting moiety may be in cis orientation (relative to the signaling agent). In some embodiments, the signaling agent and target moiety are on the same ends/sides (N-terminal or C-terminal ends) of an Fc domain. In some embodiments, the signaling agent and targeting moiety are on different sides/ends of a Fc domain (N-terminal and C-terminal ends).

In some embodiments, where more than one targeting moiety is present in the heterodimeric protein complexes described herein, the targeting moieties may be found on the same Fc chain or on two different Fc chains in the heterodimeric protein complex (in the latter case the targeting moieties would be in trans relative to each other, as they are on different Fc chains). In some embodiments, where more than one targeting moiety is present on the same Fc chain, the targeting moieties may be on the same or different sides/ends of a Fc chain (N-terminal or/and C-terminal ends).

In some embodiments, where more than one signaling agent is present in the heterodimeric protein complexes described herein, the signaling agents may be found on the same Fc chain or on two different Fc chains in the heterodimeric protein complex (in the latter case the signaling agents would be in trans relative to each other, as they are on different Fc chains). In some embodiments, where more than one signaling agent is present on the same Fc chain, the signaling agents may be on the same or different sides/ends of a Fc chain (N-terminal or/and C-terminal ends).

In some embodiments, where more than one signaling agent is present in the heterodimeric protein complexes described herein, one signaling agent may be in trans orientation (as relates to the targeting moiety), whereas another signaling agent may be in cis orientation (as relates to the targeting moiety).

In some embodiments, the heterodimeric Fc-based chimeric protein complex does not comprise the signaling agent, e.g. IL-1β and targeting moiety on a single polypeptide.

In some embodiments, the Fc-based chimeric protein has an improved in vivo half-life relative to a chimeric protein lacking an Fc or a chimeric protein which is not a heterodimeric complex. In some embodiments, the Fc-based chimeric protein has an improved solubility, stability and other pharmacological properties relative to a chimeric protein lacking an Fc or a chimeric protein which is not a heterodimeric complex.

Heterodimeric Fc-based chimeric protein complexes are composed of two different polypeptides. In embodiments described herein, the targeting domain is on a different polypeptide than the signaling agent, e.g. IL-1β, and accordingly, proteins that contain only one targeting domain copy, and also only one signaling agent, e.g. IL-1β copy can be made (this provides a configuration in which potential interference with desired properties can be controlled).

Further, in embodiments, one targeting domain (e.g. VHH) only can avoid cross-linking of the antigen on the cell surface (which could elicit undesired effects in some cases). Further, in embodiments, one signaling agent, e.g. IL-1β may alleviate molecular "crowding" and potential interference with avidity mediated induction or restoration of effector function in dependence of the targeting domain. Further, in embodiments, heterodimeric Fc-based chimeric protein complexes can have two targeting moieties and these can be placed on the two different polypeptides. For instance, in embodiments, the C-terminus of both targeting moieties (e.g. VHHs) can be masked to avoid potential autoantibodies or pre-existing antibodies (e.g. VHH autoantibodies or pre-existing antibodies). Further, in embodiments, heterodimeric Fc-based chimeric protein complexes, e.g. with the targeting domain on a different polypeptide than the signaling agent, e.g. IL-1β (e.g. wild type signaling agent, e.g. wild type IL-1β), may favor "cross-linking" of two cell types. Further, in embodiments, heterodimeric Fc-based chimeric protein complexes can have two signaling agent, each on different polypeptides to allow more complex effector responses.

Further, in embodiments, heterodimeric Fc-based chimeric protein complexes, e.g. with the targeting domain on a different polypeptide than the signaling agent, e.g. IL-1β, combinatorial diversity of targeting moiety and signaling agent, e.g. IL-1β is provided in a practical manner. For instance, in embodiments, polypeptides with any of the targeting moieties described herein can be combined "off the shelf" with polypeptides with any of the signaling agents described herein to allow rapid generation of various combinations of targeting moieties and signaling agents in single Fc-based chimeric protein complexes.

In some embodiments, the Fc-based chimeric protein complex comprises one or more linkers. In some embodiments, the Fc-based chimeric protein complex includes a linker that connects the Fc domain, signaling agent, e.g. IL-1β(s) and targeting moiety(ies). In some embodiments, the Fc-based chimeric protein complex includes a linker that connects each signaling agent, e.g. IL-1β and targeting moiety (or, if more than one targeting moiety, a signaling agent, e.g. IL-1β to one of the targeting moieties). In some embodiments, the Fc-based chimeric protein complex includes a linker that connects each signaling agent, e.g. IL-1β to the Fc domain. In some embodiments, the Fc-based chimeric protein complex includes a linker that connects each targeting moiety to the Fc domain. In some embodiments, the Fc-based chimeric protein complex includes a linker that connects a targeting moiety to another targeting moiety. In some embodiments, the Fc-based chimeric protein complex includes a linker that connects a signaling agent, e.g. IL-1β to another signaling agent.

In some embodiments, a Fc-based chimeric protein complex comprises two or more targeting moieties. In such embodiments, the targeting moieties can be the same targeting moiety or they can be different targeting moieties.

In some embodiments, a Fc-based chimeric protein complex comprises two or more signaling agents. In such embodiments, the signaling agents can be the same targeting moiety or they can be different targeting moieties.

By way of example, in some embodiments, the Fc-based chimeric protein complex comprise a Fc domain, at least two signaling agents (SA), and at least two targeting moieties TM, wherein the Fc domain, signaling agents, and targeting moieties are selected from any of the Fc domains, signaling agents, and targeting moieties disclosed herein. In some embodiments, the Fc domain is homodimeric.

In various embodiments, the Fc-based chimeric protein complex takes the form of any of the schematics of FIGS. 1A-F.

In various embodiments, the Fc-based chimeric protein complex takes the form of any of the schematics of FIGS. 2A-H.

In various embodiments, the Fc-based chimeric protein complex takes the form of any of the schematics of FIGS. 3A-H.

In various embodiments, the Fc-based chimeric protein complex takes the form of any of the schematics of FIGS. 4A-D.

In various embodiments, the Fc-based chimeric protein complex takes the form of any of the schematics of FIGS. 5A-F.

In various embodiments, the Fc-based chimeric protein complex takes the form of any of the schematics of FIGS. 6A-J.

In various embodiments, the Fc-based chimeric protein complex takes the form of any of the schematics of FIGS. 7A-D.

In various embodiments, the Fc-based chimeric protein complex takes the form of any of the schematics of FIGS. 8A-F.

In various embodiments, the Fc-based chimeric protein complex takes the form of any of the schematics of FIGS. 9A-J.

In various embodiments, the Fc-based chimeric protein complex takes the form of any of the schematics of FIGS. 10A-F.

In various embodiments, the Fc-based chimeric protein complex takes the form of any of the schematics of FIGS. 11A-L.

In various embodiments, the Fc-based chimeric protein complex takes the form of any of the schematics of FIGS. 12A-L.

In various embodiments, the Fc-based chimeric protein complex takes the form of any of the schematics of FIGS. 13A-F.

In various embodiments, the Fc-based chimeric protein complex takes the form of any of the schematics of FIGS. 14A-L.

In various embodiments, the Fc-based chimeric protein complex takes the form of any of the schematics of FIGS. 15A-L.

In various embodiments, the Fc-based chimeric protein complex takes the form of any of the schematics of FIGS. 16A-J.

In various embodiments, the Fc-based chimeric protein complex takes the form of any of the schematics of FIGS. 17A-J.

In various embodiments, the Fc-based chimeric protein complex takes the form of any of the schematics of FIGS. 18A-F.

In various embodiments, the Fc-based chimeric protein complex takes the form of any of the schematics of FIGS. 19A-F.

In some embodiments, the signaling agents are linked to the targeting moieties and the targeting moieties are linked to the Fc domain on the same terminus (see FIGS. 1A-F). In some embodiments, the Fc domain is homodimeric.

In some embodiments, the signaling agents and targeting moieties are linked to the Fc domain, wherein the targeting moieties and signaling agents are linked on the same terminus (see FIGS. 1A-F). In some embodiments, the Fc domain is homodimeric.

In some embodiments, the targeting moieties are linked to signaling agents and the signaling agents are linked to the Fc domain on the same terminus (see FIGS. 1A-F). In some embodiments, the Fc domain is homodimeric.

In some embodiments, the homodimeric Fc-based chimeric protein complex has two or more targeting moieties. In some embodiments, there are four targeting moieties and two signaling agents, the targeting moieties are linked to the Fc domain and the signaling agents are linked to targeting moieties on the same terminus (see FIGS. 2A-H). In some embodiments, the Fc domain is homodimeric. In some embodiments, where there are four targeting moieties and two signaling agents, two targeting moieties are linked to the Fc domain and two targeting moieties are linked to the signaling agents, which are linked to the Fc domain on the same terminus (see FIGS. 2A-H). In some embodiments, the Fc domain is homodimeric. In some embodiments, where there are four targeting moieties and two signaling agents, two targeting moieties are linked to each other and one of the targeting moieties of from each pair is linked to the Fc domain on the same terminus and the signaling agents are linked to the Fc domain on the same terminus (see FIGS. 2A-H). In some embodiments, the Fc domain is homodimeric. In some embodiments, where there are four targeting moieties and two signaling agents, two targeting moieties are linked to each other, wherein one of the targeting moieties of from each pair is linked to a signaling agent, e.g. IL-1β and the other targeting moiety of the pair is linked the Fc domain, wherein the targeting moieties linked to the Fc domain are linked on the same terminus (see FIGS. 2A-H). In some embodiments, the Fc domain is homodimeric.

In some embodiments, the homodimeric Fc-based chimeric protein complex has two or more signaling agents. In some embodiments, where there are four signaling agents and two targeting moieties, two signaling agents are linked to each other and one of the signaling agents of from pair is linked to the Fc domain on the same terminus and the targeting moieties are linked to the Fc domain on the same terminus (see FIGS. 3A-H). In some embodiments, the Fc domain is homodimeric. In some embodiments, where there are four signaling agents and two targeting moieties, two signaling agents are linked to the Fc domain one the same terminus and two of the signaling agents are each linked to a targeting moiety, wherein the targeting moieties are linked to the Fc domain at the same terminus (see FIGS. 3A-H).

In some embodiments, the Fc domain is homodimeric. In some embodiments, where there are four signaling agents and two targeting moieties, two signaling agents are linked to each other and one of the signaling agents of from pair is linked to a targeting moiety and the targeting moieties are linked to the Fc domain on the same terminus (see FIGS. 3A-H). In some embodiments, the Fc domain is homodimeric.

By way of example, in some embodiments, the Fc-based chimeric protein complex comprise a Fc domain, wherein the Fc domain comprises ionic pairing mutation(s) and/or knob-in-hole mutation(s), at least one signaling agent, e.g. IL-13, and at least one targeting moiety, wherein the ionic pairing motif and/or a knob-in-hole motif, signaling agent, e.g. IL-1β, and targeting moiety are selected from any of the ionic pairing motif and/or a knob-in-hole motif, signaling agents, and targeting moieties disclosed herein. In some embodiments, the Fc domain is heterodimeric. In some embodiments, the Fc domain comprises a mutation that reduces or eliminates its effector function.

In some embodiments, the signaling agent, e.g. IL-1β is linked to the targeting moiety, which is linked to the Fc domain (see FIGS. 10A-F and 13A-F). In some embodiments, the targeting moiety is linked to the signaling agent, e.g. IL-1β, which is linked to the Fc domain (see FIGS. 10A-F and 13A-F). In some embodiments, the Fc domain is heterodimeric.

In some embodiments, the Fc domain comprises a mutation that reduces or eliminates its effector function.

In some embodiments, the signaling agent, e.g. IL-1β and targeting moiety are linked to the Fc domain (see FIGS. 4A-D, 7A-D, 10A-F, and 13A-F). In some embodiments, the targeting moiety and the signaling agent, e.g. IL-1β are linked to different Fc chains on the same terminus (see FIGS. 4A-D and 7A-D). In some embodiments, the targeting moiety and the signaling agent, e.g. IL-1β are linked to different Fc chains on different termini (see FIGS. 4A-D and 7A-D). In some embodiments, the targeting moiety and the signaling agent, e.g. IL-1β are linked to the same Fc chain (see FIGS. 10A-F and 13A-F). In some embodiments, the Fc domain is heterodimeric. In some embodiments, the Fc domain comprises a mutation that reduces or eliminates its effector function.

In some embodiments, where there are one signaling agent, e.g. IL-1β and two targeting moieties, the signaling agent, e.g. IL-1β is linked to the Fc domain and two targeting moieties can be: 1) linked to each other with one of the targeting moieties linked to the Fc domain; or 2) each linked to the Fc domain (see FIGS. 5A-F, 8A-F, 11A-L, 14A-L, 16A-J, and 17A-J). In some embodiments, the targeting moieties are linked on one Fc chain and the signaling agent, e.g. IL-1β is on the other Fc chain (see FIGS. 5A-F and 8A-F). In some embodiments, the paired targeting moieties and the signaling agent, e.g. IL-1β are linked to the same Fc chain (see FIGS. 11A-L and 14A-L). In some embodiments, a targeting moiety is linked to the Fc domain and the other targeting moiety is linked to the signaling agent, e.g. IL-1β, and the paired targeting moiety is linked to the Fc domain (see FIGS. 11A-L, 14A-L, 16A-J, and 17A-J). In some embodiments, the unpaired targeting moiety and paired targeting moiety are linked to the same Fc chain (see FIGS. 11A-L and 14A-L). In some embodiments, the unpaired targeting moiety and paired targeting moiety are linked to different Fc chains (see FIGS. 16A-J and 17A-J). In some embodiments, the unpaired targeting moiety and paired targeting moiety are linked on the same terminus (see FIGS. 16A-J and 17A-J). In some embodiments, the Fc domain is heterodimeric. In some embodiments, the Fc domain comprises a mutation that reduces or eliminates its effector function.

In some embodiments, where there are one signaling agent, e.g. IL-1β and two targeting moieties, a targeting moiety is linked to the signaling agent, e.g. IL-1β, which is linked to the Fc domain, and the unpaired targeting moiety is linked the Fc domain (see FIGS. 11A-L, 14A-L, 16A-J, and 17A-J). In some embodiments, the paired signaling agent, e.g. IL-1β and unpaired targeting moiety are linked to the same Fc chain (see FIGS. 11A-L and 14A-L). In some embodiments, the paired signaling agent, e.g. IL-1β and unpaired targeting moiety are linked to different Fc chains (see FIGS. 16A-J and 17A-J). In some embodiments, the paired signaling agent, e.g. IL-1β and unpaired targeting moiety are linked on the same terminus (see FIGS. 16A-J and 17A-J). In some embodiments, the Fc domain is heterodimeric. In some embodiments, the Fc domain comprises a mutation that reduces or eliminates its effector function.

In some embodiments, where there are one signaling agent, e.g. IL-1β and two targeting moieties, the targeting moieties are linked together and the signaling agent, e.g. IL-1β is linked to one of the paired targeting moieties, wherein the targeting moiety not linked to the signaling agent, e.g. IL-1β is linked to the Fc domain (see FIGS. 11A-L and 14A-L). In some embodiments, the Fc domain is heterodimeric. In some embodiments, the Fc domain comprises a mutation that reduces or eliminates its effector function.

In some embodiments, where there are one signaling agent, e.g. IL-1β and two targeting moieties, the targeting moieties are linked together and the signaling agent, e.g. IL-1β is linked to one of the paired targeting moieties, wherein the signaling agent, e.g. IL-1β is linked to the Fc domain (see FIGS. 11A-L and 14A-L). In some embodiments, the Fc domain is heterodimeric. In some embodiments, the Fc domain comprises a mutation that reduces or eliminates its effector function.

In some embodiments, where there are one signaling agent, e.g. IL-1β and two targeting moieties, the targeting moieties are both linked to the signaling agent, e.g. IL-1β, wherein one of the targeting moieties is linked to the Fc domain (see FIGS. 11A-L and 14A-L). In some embodiments, the Fc domain is heterodimeric. In some embodiments, the Fc domain comprises a mutation that reduces or eliminates its effector function.

In some embodiments, where there is one signaling agent, e.g. IL-1β and two targeting moieties, the targeting moieties and the signaling agent, e.g. IL-1β are linked to the Fc domain (see FIGS. 16A-J and 17A-J). In some embodiments, the targeting moieties are linked on the terminus (see FIGS. 16A-J and 17A-J). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked to the Fc domain on the same terminus and the targeting moiety is linked to the Fc domain (see FIGS. 6A-J and 9A-J).

In some embodiments, the signaling agents are linked to the Fc domain on the same Fc chain and the targeting moiety is linked on the other Fc chain (see FIGS. 18A-F and 19A-F). In some embodiments, the Fc domain is heterodimeric.

In some embodiments, the Fc domain comprises a mutation that reduces or eliminates its effector function.

In some embodiments, where there are two signaling agents and one targeting moiety, a signaling agent, e.g. IL-1β is linked to the targeting moiety, which is linked to the Fc domain and the other signaling agent, e.g. IL-1β is linked to the Fc domain (see FIGS. 6A-J, 9A-J, 12A-L, and 15A-L). In some embodiments, the targeting moiety and the unpaired signaling agent, e.g. IL-1β are linked to different Fc chains (see FIGS. 6A-J and 9A-J). In some embodiments, the targeting moiety and the unpaired signaling agent, e.g. IL-1β are linked to different Fc chains on the same terminus (see FIGS. 6A-J and 9A-J). In some embodiments, the targeting moiety and the unpaired signaling agent, e.g. IL-1β are linked to different Fc chains on different termini (see FIGS. 6A-J and 9A-J). In some embodiments, the targeting moiety and the unpaired signaling agent, e.g. IL-1β are linked to the same Fc chains (see FIGS. 12A-L and 15A-L). In some embodiments, the Fc domain is heterodimeric. In some embodiments, the Fc domain comprises a mutation that reduces or eliminates its effector function.

In some embodiments, where there are two signaling agents and one targeting moiety, the targeting moiety is linked to a signaling agent, e.g. IL-1β, which is linked to the Fc domain and the other signaling agent, e.g. IL-1β is linked to the Fc domain (see FIGS. 6A-J and 9A-J). In some embodiments, the paired signaling agent, e.g. IL-1β and the unpaired signaling agent, e.g. IL-1β are linked to different Fc chains (see FIGS. 6A-J and 9A-J). In some embodiments, the paired signaling agent, e.g. IL-1β and the unpaired signaling agent, e.g. IL-1β are linked to different Fc chains on the same terminus (see FIGS. 6A-J and 9A-J). In some embodiments, the paired signaling agent, e.g. IL-1β and the unpaired signaling agent, e.g. IL-1β are linked to different Fc chains on different termini (see FIGS. 6A-J and 9A-J). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked together and the targeting moiety is linked to one of the paired signaling agents, wherein the targeting moiety is linked to the Fc domain (see FIGS. 12A-L and 15A-L). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked together and one of the signaling agents is linked to the Fc domain and the targeting moiety is linked to the Fc domain (see FIGS. 12A-L, 15A-L, 18A-F, and 19A-F). In some embodiments, the paired signaling agents and targeting moiety are linked to the same Fc chain (see FIGS. 12A-L and 15A-L). In some embodiments, the paired signaling agents and targeting moiety are linked to different Fc chains (see FIGS. 18A-F and 19A-F). In some embodiments, the paired signaling agents and targeting moiety are linked to different Fc chains on the same terminus (see FIGS. 18A-F and 19A-F). In some embodiments, the Fc domain is heterodimeric. In some embodiments, the Fc domain comprises a mutation that reduces or eliminates its effector function.

In some embodiments, where there are two signaling agents and one targeting moiety, the signaling agents are both linked to the targeting moiety, wherein one of the signaling agents is linked to the Fc domain (see FIGS. 12A-L and 15A-L). In some embodiments, the Fc domain is heterodimeric. In some embodiments, the Fc domain comprises a mutation that reduces or eliminates its effector function.

In some embodiments, where there are two signaling agents and one targeting moiety, the signaling agents are linked together and one of the signaling agents is linked to the targeting moiety and the other signaling agent, e.g. IL-1β is linked to the Fc domain (see FIGS. 12A-L and 15A-L).

In some embodiments, where there are two signaling agents and one targeting moiety, each signaling agent, e.g. IL-13 is linked to the Fc domain and the targeting moiety is linked to one of the signaling agents (see FIGS. 12A-L and 15A-L). In some embodiments, the signaling agents are linked to the same Fc chain (see FIGS. 12A-L and 15A-L).

In some embodiments, a targeting moiety or signaling agent, e.g. IL-1β is linked to the Fc domain, comprising one or both of $C_H2$ and $C_H3$ domains, and optionally a hinge region. For example, vectors encoding the targeting moiety, signaling agent, e.g. IL-1β, or combination thereof, linked as a single nucleotide sequence to an Fc domain can be used to prepare such polypeptides.

Additional Signaling Agents

In one aspect, the present invention provides a chimeric proteins or chimeric protein complexes such as Fc-based chimeric protein complex comprising one or more signaling agents (for instance, an immune-modulating agent) in addition to the IL-1β or a variant thereof described herein. In illustrative embodiments, the chimeric proteins or chimeric protein complexes such as Fc-based chimeric protein complex may comprise two, three, four, five, six, seven, eight, nine, ten or more signaling agents in addition to the IL-1 or a variant thereof described herein. In various embodiments, the additional signaling agent is modified to have reduced affinity or activity for one or more of its receptors, which allows for attenuation of activity (inclusive of agonism or antagonism) and/or prevents non-specific signaling or undesirable sequestration of the chimeric proteins or chimeric protein complexes such as Fc-based chimeric protein complex.

In various embodiments, the additional signaling agent is antagonistic in its wild type form and bears one or more mutations that attenuate its antagonistic activity. In various embodiments, the additional signaling agent is antagonistic due to one or more mutations, e.g. an agonistic signaling agent is converted to an antagonistic signaling agent and, such a converted signaling agent, optionally, also bears one or more mutations that attenuate its antagonistic activity (e.g. as described in WO 2015/007520, the entire contents of which are hereby incorporated by reference).

In various embodiments, the additional signaling agent is selected from modified versions of cytokines, growth factors, and hormones. Illustrative examples of such cytokines, growth factors, and hormones include, but are not limited to, lymphokines, monokines, traditional polypeptide hormones, such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-a and tumor necrosis factor-R; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-β; insulin-like growth factor-I and -II; osteo inductive factors; interferons such as, for example, interferon-α, interferon-β and interferon-γ (and interferon type I, II, and Ill), colony stimulating factors (CSFs) such as macrophage-CSF (M-CSF); granulocyte-macrophage-CSF (GM-CSF); and granulocyte-CSF (G-CSF); interleukins (ILs) such as, for example, IL-1β, IL-1α, IL-2, IL-3, IL-4, IL-5, IL-6, IL-7, IL-8, IL-9, IL-10, IL-11, IL-12, IL-13, and IL-18; a tumor necrosis factor such as, for example, TNF-α or TNF-β; and other polypeptide factors including, for example, LIF and kit ligand (KL). As used herein, cytokines, growth factors, and hormones include proteins obtained from natural sources or produced from recombinant bacterial, eukaryotic or mammalian cell culture systems and biologically active equivalents of the native sequence cytokines.

In some embodiments, the additional signaling agent is a modified version of a growth factor selected from, but not limited to, transforming growth factors (TGFs) such as TGF-α and TGF-β, epidermal growth factor (EGF), insulin-like growth factor such as insulin-like growth factor-I and -II, fibroblast growth factor (FGF), heregulin, platelet-derived growth factor (PDGF), vascular endothelial growth factor (VEGF).

In an embodiment, the growth factor is a modified version of a fibroblast growth factor (FGF). Illustrative FGFs include, but are not limited to, FGF1, FGF2, FGF3, FGF4, FGF5, FGF6, FGF7, FGF8, FGF9, FGF10, FGF11, FGF12, FGF13, FGF14, murine FGF15, FGF16, FGF17, FGF18, FGF19, FGF20, FGF21, FGF22, and FGF23.

In an embodiment, the growth factor is a modified version of a vascular endothelial growth factor (VEGF). Illustrative VEGFs include, but are not limited to, VEGF-A, VEGF-B, VEGF-C, VEGF-D, and PGF and isoforms thereof including the various isoforms of VEGF-A such as $VEGF_{121}$, $VEGF_{121}$b, $VEGF_{145}$, $VEGF_{165}$, $VEGF_{165}$b, $VEGF_{189}$, and $VEGF_{206}$.

In an embodiment, the growth factor is a modified version of a transforming growth factor (TGF). Illustrative TGFs include, but are not limited to, TGF-α and TGF-β and subtypes thereof including the various subtypes of TGF-β including TGFβ1, TGFβ2, and TGFβ3.

In some embodiments, the additional signaling agent is a modified version of a hormone selected from, but not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, calcitriol, calciferol, atrial-natriuretic peptide, gastrin, secretin, cholecystokinin, neuropeptide Y, ghrelin, PYY3-36, insulin-like growth factor (IGF), leptin, thrombopoietin, erythropoietin (EPO), and angiotensinogen.

In some embodiments, the additional signaling agent is an immune-modulating agent, e.g. one or more of an interleukin, interferon, and tumor necrosis factor.

In some embodiments, the additional signaling agent is an interleukin, including for example IL-1β; IL-2; IL-3; IL-4; IL-5; IL-6; IL-7; IL-8; IL-9; IL-10; IL-11; IL-12; IL-1β; IL-14; IL-15; IL-16; IL-17; IL-18; IL-19; IL-20; IL-21; IL-22; IL- 23; IL-24; IL-25; IL-26; IL-27; IL-28; IL-29; IL-30; IL-31; IL-32; IL-33; IL-35; IL-36 or a fragment, variant, analogue, or family-member thereof. Interleukins are a group of multi-functional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons.

Interleukin activity can be determined using assays known in the art: Matthews et al., in Lymphokines and Interferens: A Practical Approach, Clemens et al., eds, IRL Press, Washington, D.C. 1987, pp. 221-225; and Orencole & Dinarello (1989) Cytokine 1, 14-20.

In some embodiments, the signaling agent is a modified version of an interferon such as interferon types I, II, and Ill.

Illustrative interferons, including for example, interferon-α-1, 2, 4, 5, 6, 7, 8, 10, 13, 14, 16, 17, and 21, interferon-β and interferon-γ, interferon κ, interferon ε, interferon τ, and interferon ω.

In embodiments, the additional signaling agent is a type I interferon. In embodiments, the type I interferon is selected from IFN-α2, IFNα1, IFN-β, IFN-γ, Consensus IFN, IFN-ε, IFN-κ, IFN-τ, IFN-δ, and IFN-ν.

In some embodiments, the additional signaling agent is a modified version of a tumor necrosis factor (TNF) or a protein in the TNF family, including but not limited to, TNF-α, TNF-β, LT-p, CD40L, CD27L, CD30L, FASL, 4-1BBL, OX40L, and TRAIL.

In various embodiments, the additional signaling agent is a modified (e.g. mutant) form of the signaling agent having one or more mutations. In various embodiments, the mutations allow for the modified signaling agent to have one or more of attenuated activity such as one or more of reduced binding affinity, reduced endogenous activity, and reduced specific bioactivity relative to unmodified or unmutated, i.e. the wild type form of the signaling agent (e.g. comparing the same signaling agent in a wild type form versus a modified (e.g. mutant) form). In various embodiments, the mutations allow for the modified signaling agent to have one or more of attenuated activity such as one or more of reduced binding affinity, reduced endogenous activity, and reduced specific bioactivity relative to unmodified or unmutated, i.e. the unmutated IL-1β. In some embodiments, the mutations which attenuate or reduce binding or affinity include those mutations which substantially reduce or ablate binding or activity. In some embodiments, the mutations which attenuate or reduce binding or affinity are different than those mutations which substantially reduce or ablate binding or activity. Consequentially, in various embodiments, the mutations allow for the signaling agent to be more safe, e.g. have reduced systemic toxicity, reduced side effects, and reduced off-target effects relative to unmutated, i.e. wild type, signaling agent (e.g. comparing the same signaling agent in a wild type form versus a modified (e.g. mutant) form). In various embodiments, the mutations allow for the signaling agent to be safer, e.g. have reduced systemic toxicity, reduced side effects, and reduced off-target effects relative to unmutated interferon, e.g. the unmutated sequence of IL-1β.

In various embodiments, the additional signaling agent is modified to have one or more mutations that reduce its binding affinity or activity for one or more of its receptors. In some embodiments, the signaling agent is modified to have one or more mutations that substantially reduce or ablate binding affinity or activity for the receptors. In some embodiments, the activity provided by the wild type signaling agent is agonism at the receptor (e.g. activation of a cellular effect at a site of therapy). For example, the wild type signaling agent may activate its receptor. In such embodiments, the mutations result in the modified signaling agent to have reduced or ablated activating activity at the receptor. For example, the mutations may result in the modified signaling agent to deliver a reduced activating signal to a target cell or the activating signal could be ablated. In some embodiments, the activity provided by the wild type signaling agent is antagonism at the receptor (e.g. blocking or dampening of a cellular effect at a site of therapy). For example, the wild type signaling agent may antagonize or inhibit the receptor. In these embodiments, the mutations result in the modified signaling agent to have a reduced or ablated antagonizing activity at the receptor. For example, the mutations may result in the modified signaling agent to deliver a reduced inhibitory signal to a target cell or the inhibitory signal could be ablated. In various embodiments, the signaling agent is antagonistic due to one or more mutations, e.g. an agonistic signaling agent is converted to an antagonistic signaling agent (e.g. as described in WO 2015/007520, the entire contents of which are hereby incorporated by reference) and, such a converted signaling agent, optionally, also bears one or more mutations that reduce its binding affinity or activity for one or more of its receptors or that substantially reduce or ablate binding affinity or activity for one or more of its receptors.

In some embodiments, the reduced affinity or activity at the receptor is inducible or restorable by attachment with one or more of the targeting moieties or upon inclusion in the Fc-based chimeric protein complex disclosed herein. In other embodiments, the reduced affinity or activity at the receptor is not substantially inducible or restorable by the activity of one or more of the targeting moieties or upon inclusion in the Fc-based chimeric protein complex disclosed herein.

In various embodiments, the additional signaling agent is active on target cells because the targeting moiety(ies) compensates for the missing/insufficient binding (e.g., without limitation and/or avidity) required for substantial activation. In various embodiments, the modified signaling agent is substantially inactive en route to the site of therapeutic activity and has its effect substantially on specifically targeted cell types which greatly reduces undesired side effects.

In some embodiments, the additional signaling agent may include one or more mutations that attenuate or reduce binding or affinity for one receptor (i.e., a therapeutic receptor) and one or more mutations that substantially reduce or ablate binding or activity at a second receptor. In such embodiments, these mutations may be at the same or at different positions (i.e., the same mutation or multiple mutations). In some embodiments, the mutation(s) that reduce binding and/or activity at one receptor is different than the mutation(s) that substantially reduce or ablate at another receptor.

In some embodiments, the mutation(s) that reduce binding and/or activity at one receptor is the same as the mutation(s) that substantially reduce or ablate at another receptor. In some embodiments, the present chimeric proteins or chimeric protein complexes such as Fc-based chimeric protein complexes have a modified signaling agent that has both mutations that attenuate binding and/or activity at a therapeutic receptor and therefore allow for a more controlled, on-target therapeutic effect (e.g. relative wild type signaling agent) and mutations that substantially reduce or ablate binding and/or activity at another receptor and therefore reduce side effects (e.g. relative to wild type signaling agent).

In some embodiments, the substantial reduction or ablation of binding or activity is not substantially inducible or restorable with a targeting moiety or upon inclusion in the Fc-based chimeric protein complex disclosed herein. In some embodiments, the substantial reduction or ablation of binding or activity is inducible or restorable with a targeting moiety or upon inclusion in the Fc-based chimeric protein complex disclosed herein. In various embodiments, substantially reducing or ablating binding or activity at a second receptor also may prevent deleterious effects that are mediated by the other receptor. Alternatively, or in addition, substantially reducing or ablating binding or activity at the other receptor causes the therapeutic effect to improve as there is a reduced or eliminated sequestration of the therapeutic chimeric proteins or chimeric protein complexes such as Fc-based chimeric protein complexes away from the site of therapeutic action. For instance, in some embodiments, this obviates the need of high doses of the chimeric proteins or chimeric protein complexes such as Fc-based chimeric protein complexes that compensate for loss at the other receptor. Such ability to reduce dose further provides a lower likelihood of side effects.

In various embodiments, the additional modified signaling agent comprises one or more mutations that cause the signaling agent to have reduced, substantially reduced, or ablated affinity, e.g. binding (e.g. $K_D$) and/or activation (for instance, when the modified signaling agent is an agonist of its receptor, measurable as, for example, $K_A$ and/or $EC_{50}$) and/or inhibition (for instance, when the modified signaling agent is an antagonist of its receptor, measurable as, for example, $K_i$ and/or $IC_{50}$), for one or more of its receptors. In various embodiments, the reduced affinity at the signaling agent's receptor allows for attenuation of activity (inclusive of agonism or antagonism). In such embodiments, the modified signaling agent has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor relative to the wild type signaling agent. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent (including, by way of non-limitation, relative to the unmutated IL-1β).

In embodiments wherein the chimeric proteins or chimeric protein complexes such as Fc-based chimeric protein complex has mutations that reduce binding at one receptor and substantially reduce or ablate binding at a second receptor, the attenuation or reduction in binding affinity of a modified signaling agent for one receptor is less than the substantial reduction or ablation in affinity for the other receptor. In some embodiments, the attenuation or reduction in binding affinity of a modified signaling agent for one receptor is less than the substantial reduction or ablation in affinity for the other receptor by about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, or about 95%. In various embodiments, substantial reduction or ablation refers to a greater reduction in binding affinity and/or activity than attenuation or reduction.

In various embodiments, the additional modified signaling agent comprises one or more mutations that reduce the endogenous activity of the signaling agent to about 75%, or about 70%, or about 60%, or about 50%, or about 40%, or about 30%, or about 25%, or about 20%, or about 10%, or about 5%, or about 3%, or about 1%, e.g., relative to the wild type signaling agent (including, by way of non-limitation, relative to the unmutated IL-1β).

In various embodiments, the additional modified signaling agent comprises one or more mutations that cause the signaling agent to have reduced affinity and/or activity for a receptor of any one of the cytokines, growth factors, and hormones as described herein.

In some embodiments, the additional modified signaling agent comprises one or more mutations that cause the signaling agent to have reduced affinity for its receptor that is lower than the binding affinity of the targeting moiety(ies) for its(their) receptor(s). In some embodiments, this binding affinity differential is between signaling agent/receptor and targeting moiety/receptor on the same cell. In some embodiments, this binding affinity differential allows for the signaling agent, e.g. mutated signaling agent, to have localized, on-target effects and to minimize off-target effects that underlie side effects that are observed with wild type signaling agent. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold.

Receptor binding activity may be measured using methods known in the art. For example, affinity and/or binding activity may be assessed by Scatchard plot analysis and computer-fitting of binding data (e.g. Scatchard, 1949) or by 5 reflectometric interference spectroscopy under flow through conditions, as described by Brecht et al. (1993), the entire contents of all of which are hereby incorporated by reference.

The amino acid sequences of the wild type signaling agents described herein are well known in the art. Accordingly, in various embodiments the additional modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known wild type amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments the additional modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the additional modified signaling agent comprises an amino acid sequence having one or more amino acid mutations. In some embodiments, the one or more amino acid mutations may be independently selected from substitutions, insertions, deletions, and truncations.

In some embodiments, the amino acid mutations are amino acid substitutions, and may include conservative and/or non-conservative substitutions as described herein.

As described herein, the additional modified signaling agents bear mutations that affect affinity and/or activity at one or more receptors. In various embodiments, there is reduced affinity and/or activity at a therapeutic receptor, e.g. a receptor through which a desired therapeutic effect is mediated (e.g. agonism or antagonism). In various embodiments, the modified signaling agents bear mutations that substantially reduce or ablate affinity and/or activity at a receptor, e.g. a receptor through which a desired therapeutic effect is not mediated (e.g. as the result of promiscuity of binding).

The receptors of any modified signaling agents, e.g., one of the cytokines, growth factors, and hormones as described herein, are known in the art.

Linkers and Functional Groups

In some embodiments, the vaccine composition, adjuvant, chimeric protein or chimeric protein complex optionally comprises one or more linkers. In some embodiments, the vaccine composition, adjuvant, chimeric protein or chimeric protein complex such as Fc-based chimeric protein complex comprises a linker connecting the targeting moiety and the signaling agent (e.g., IL-1β or a variant thereof). In some embodiments, the vaccine composition, adjuvant, chimeric protein or chimeric protein complex comprises a linker within the signaling agent (e.g., IL-1β or a variant thereof). In some embodiments, the linker may be utilized to link various functional groups, residues, or moieties as described herein to the vaccine composition, adjuvant, chimeric protein or chimeric protein complex. In some embodiments, the linker is a single amino acid or a plurality of amino acids that does not affect or reduce the stability, orientation, binding, neutralization, and/or clearance characteristics of the binding regions and the binding protein. In various embodiments, the linker is selected from a peptide, a protein, a sugar, or a nucleic acid.

In some embodiments vectors encoding the vaccine composition, adjuvant, chimeric protein, or chimeric protein complex linked as a single nucleotide sequence to any of the linkers described herein are provided and may be used to prepare such vaccine composition, adjuvant, chimeric protein or chimeric protein complex. In embodiments, the substituents of the Fc-based chimeric protein complex are expressed as nucleotide sequences in a vector.

In some embodiments, the linker length allows for efficient binding of a targeting moiety and the signaling agent (e.g., IL-1β or a variant thereof) to their receptors. For instance, in some embodiments, the linker length allows for efficient binding of one of the targeting moieties and the signaling agent to receptors on the same cell. In some embodiments the linker length is at least equal to the minimum distance between the binding sites of one of the targeting moieties and the signaling agent to receptors on the same cell. In some embodiments the linker length is at least twice, or three times, or four times, or five times, or ten times, or twenty times, or 25 times, or 50 times, or one hundred times, or more the minimum distance between the binding sites of one of the targeting moieties and the signaling agent to receptors on the same cell.

As described herein, the linker length allows for efficient binding of one of the targeting moieties and the signaling agent to receptors on the same cell, the binding being sequential, e.g. targeting moiety/receptor binding preceding signaling agent/receptor binding.

In some embodiments, there are two linkers in a single chimera, each connecting the signaling agent to a targeting moiety. In various embodiments, the linkers have lengths that allow for the formation of a site that has a disease cell and an effector cell without steric hindrance that would prevent modulation of the either cell.

The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present chimeric proteins or chimeric protein complexes such as Fc-based chimeric protein complex.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide. In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In some embodiments directed to chimeric proteins or chimeric protein complexes such as Fc-based chimeric protein complexes having two or more targeting moieties, a linker connects the two targeting moieties to each other and this linker has a short length and a linker connects a targeting moiety and a signaling agent this linker is longer than the linker connecting the two targeting moieties. For example, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is (Gly$_4$Ser), where n is from about 1 to about 8, e.g. 1, 2, 3, 4, 5, 6, 7, or 8 (SEQ ID NO:2-SEQ ID NO:9, respectively). In an embodiment, the linker sequence is GGSGGSGGGGSGGGGS (SEQ ID NO: 10). Additional illustrative linkers include, but are not limited to, linkers having the sequence LE, GGGGS (SEQ ID NO:2), (GGGGS), (n=1-4) (SEQ ID NO:2-SEQ ID NO:5), (Gly)a (SEQ ID NO:11), (Gly)$_6$ (SEQ ID NO:12), (EAAAK), (n=1-3) (SEQ ID NO:13-SEQ ID NO:15), A(EAAAK),A (n=2-5) (SEQ ID NO:16-SEQ ID NO:19), AEAAAKEAAAKA (SEQ ID NO:16), A(EAAAK)$_4$ALEA $(EAAAK)_4A$ (SEQ ID NO:21), PAPAP (SEQ ID NO:22), KESGSVSSEQLAQFRSLD (SEQ ID NO:23), EGKSSGSGSESKST (SEQ ID NO:24), GSAGSAAGSGEF (SEQ ID NO:25), and (XP), with X designating any amino acid, e.g., Ala, Lys, or Glu. In various embodiments, the linker is GGS or a repeat thereof wherein the GGS sequence is repeated 1 to 8 times (SEQ ID NO: 556-563). In some embodiments, the linker is GGGS or a repeat thereof wherein the GGGS sequence is repeated 1 to 8 times (SEQ ID NO: 564-571).

In some embodiments, the linker is one or more of GGGSE (SEQ ID NO: 26), GSESG (SEQ ID NO: 27), GSEGS (SEQ ID NO: 28), GEGGSGEGSSGEGSSSEGGGSEGGGSEGGGSEGGS (SEQ ID NO: 29), and a linker of randomly placed G, S, and E every 4 amino acid intervals.

In various embodiments, the linker may be functional. For example, without limitation, the linker may function to improve the folding and/or stability, improve the expression, improve the pharmacokinetics, and/or improve the bioactivity of the present vaccine composition, adjuvant, chimeric protein or chimeric protein complex. In another example, the linker may function to target the vaccine composition, adjuvant, chimeric protein or chimeric protein complex to a particular cell type or location.

In various embodiments, the vaccine composition, adjuvant, chimeric protein or chimeric protein complex may include one or more functional groups, residues, or moieties. In various embodiments, the one or more functional groups, residues, or moieties are attached or genetically fused to any of the signaling agents or targeting moieties described herein. In some embodiments, such functional groups, residues or moieties confer one or more desired properties or functionalities to the chimeric proteins or chimeric protein complexes such as Fc-based chimeric protein complex of the invention. Examples of such functional groups and of techniques for introducing them into the chimeric proteins or chimeric protein complexes such as Fc-based chimeric protein complex are known in the art, for example, see Remington's Pharmaceutical Sciences, 16th ed., Mack Publishing Co., Easton, Pa. (1980).

In various embodiments, each of the chimeric proteins or chimeric protein complexes such as Fc-based chimeric protein complex may by conjugated and/or fused with another agent to extend half-life or otherwise improve pharmacodynamic and pharmacokinetic properties. In some embodiments, the chimeric proteins or chimeric protein complexes such as Fc-based chimeric protein complex may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In various embodiments, each of the individual chimeric proteins or chimeric protein complexes such as Fc-based chimeric protein complex is fused to one or more of the agents described in BioDrugs (2015) 29:215-239, the entire contents of which are hereby incorporated by reference.

In some embodiments, the functional groups, residues, or moieties comprise a suitable pharmacologically acceptable polymer, such as poly(ethyleneglycol) (PEG) or derivatives thereof (such as methoxypoly(ethyleneglycol) or mPEG).

In some embodiments, attachment of the PEG moiety increases the half-life and/or reduces the immunogenecity of the chimeric proteins or chimeric protein complexes such as Fc-based chimeric protein complex. Generally, any suitable form of pegylation can be used, such as the pegylation used in the art for antibodies and antibody fragments (including but not limited to single domain antibodies such as VHHs); see, for example, Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO04060965, the entire contents of which are hereby incorporated by reference. Various reagents for pegylation of proteins are also commercially available, for example, from Nektar Therapeutics, USA. In some embodiments, site-directed pegylation is used, in particular via a cysteine-residue (see, for example, Yang et al., Protein Engineering, 16, 10, 761-770 (2003), the entire contents of which is hereby incorporated by reference). In some embodiments, the vaccine composition, adjuvant, chimeric protein or chimeric protein complex is modified so as to suitably introduce one or more cysteine residues for attachment of PEG, or an amino acid sequence comprising one or more cysteine residues for attachment of PEG may be fused to the amino- and/or carboxy-terminus of the chimeric proteins or chimeric protein complexes such as Fc-based chimeric protein complex, using techniques known in the art. In some embodiments, the functional groups, residues, or moieties comprise N-linked or O-linked glycosylation. In some embodiments, the N-linked or O-linked glycosylation is introduced as part of a co-translational and/or post-translational modification.

In some embodiments, the functional groups, residues, or moieties comprise one or more detectable labels or other signal-generating groups or moieties. Suitable labels and techniques for attaching, using and detecting them are known in the art and, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled VHHs and polypeptides of the invention may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label.

In some embodiments, the functional groups, residues, or moieties comprise a tag that is attached or genetically fused to the vaccine composition, adjuvant, chimeric protein or chimeric protein complex. In some embodiments, the vaccine composition, adjuvant, chimeric protein or chimeric protein complex may include a single tag or multiple tags. The tag for example is a peptide, sugar, or DNA molecule that does not inhibit or prevent binding of the chimeric proteins or chimeric protein complexes such as Fc-based chimeric protein complex to its target or any other antigen of interest. In various embodiments, the tag is at least about:

three to five amino acids long, five to eight amino acids long, eight to twelve amino acids long, twelve to fifteen amino acids long, or fifteen to twenty amino acids long. Illustrative tags are described for example, in U.S. Patent Publication No. US2013/0058962. In some embodiment, the tag is an affinity tag such as glutathione-S-transferase (GST) and histidine (His) tag. In an embodiment, the vaccine composition, adjuvant, chimeric protein or chimeric protein complex complex comprises a His tag.

In some embodiments, the functional groups, residues, or moieties comprise a chelating group, for example, to chelate one of the metals or metallic cations. Suitable chelating groups, for example, include, without limitation, diethylenetriaminepentaacetic acid (DTPA) or ethylenediaminetetraacetic acid (EDTA).

In some embodiments, the functional groups, residues, or moieties comprise a functional group that is one part of a specific binding pair, such as the biotin-(strept)avidin binding pair. Such a functional group may be used to link the chimeric proteins or chimeric protein complexes such as Fc-based chimeric protein complex of the invention to another protein, polypeptide or chemical compound that is bound to the other half of the binding pair, i.e., through formation of the binding pair. For example, the adjuvant, chimeric protein or chimeric protein complex may be conjugated to biotin, and linked to another protein, polypeptide, compound or carrier conjugated to avidin or streptavidin. For example, such a conjugated chimeric proteins or chimeric protein complexes such as Fc-based chimeric protein complex may be used as a reporter, for example, in a diagnostic system where a detectable signal-producing agent is conjugated to avidin or streptavidin. Such binding pairs may, for example, also be used to bind the chimeric proteins or chimeric protein complexes such as Fc-based chimeric protein complex to a carrier, including carriers suitable for pharmaceutical purposes. One non-limiting example are the liposomal formulations described by Cao and Suresh, *Journal of Drug Targeting,* 8, 4, 257 (2000). Such binding pairs may also be used to link a therapeutically active agent to the chimeric proteins or chimeric protein complexes such as Fc-based chimeric protein complex of the invention.

Production of Chimeric Proteins or Chimeric Protein Complexes Such as Fc-Based Chimeric Protein Complex Methods for producing the chimeric proteins or chimeric protein complexes such as Fc-based chimeric protein complex of the invention are described herein. For example, DNA sequences encoding the chimeric proteins or chimeric protein complexes such as Fc-based chimeric protein complex of the invention (e.g., DNA sequences encoding the signaling agent (e.g., IL-1β or a variant thereof) and the targeting moiety and the linker) can be chemically synthesized using methods known in the art. Synthetic DNA sequences can be ligated to other appropriate nucleotide sequences, including, e.g., expression control sequences, to produce gene expression constructs encoding the desired chimeric proteins or chimeric protein complexes such as Fc-based chimeric protein complex. Accordingly, in various embodiments, the present invention provides for isolated nucleic acids comprising a nucleotide sequence encoding the chimeric proteins or chimeric protein complexes such as Fc-based chimeric protein complex of the invention.

Nucleic acids encoding the chimeric proteins or chimeric protein complexes such as Fc-based chimeric protein complex of the invention can be incorporated (ligated) into expression vectors, which can be introduced into host cells through transfection, transformation, or transduction techniques. For example, nucleic acids encoding the chimeric proteins or chimeric protein complexes such as Fc-based chimeric protein complex of the invention can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the chimeric proteins or chimeric protein complexes such as Fc-based chimeric protein complex of the invention. Accordingly, in various embodiments, the present invention provides expression vectors comprising nucleic acids that encode the chimeric proteins or chimeric protein complexes such as Fc-based chimeric protein complex of the invention. In various embodiments, the present invention additional provides host cells comprising such expression vectors.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The vaccine composition, adjuvant, chimeric protein or chimeric protein complex such as Fc-based chimeric protein complex of the invention can be produced by growing a host cell transfected with an expression vector encoding the chimeric proteins or chimeric protein complexes such as Fc-based chimeric protein complex under conditions that permit expression of the protein. Following expression, the protein can be harvested and purified using techniques well known in the art, e.g., affinity tags such as glutathione-S-transferase (GST) and histidine tags or by chromatography.

Accordingly, in various embodiments, the present invention provides for a nucleic acid encoding a chimeric proteins or chimeric protein complexes such as Fc-based chimeric protein complex of the present invention. In various embodiments, the present invention provides for a host cell comprising a nucleic acid encoding a chimeric proteins or chimeric protein complexes such as Fc-based chimeric protein complex of the present invention.

In various embodiments, IL-1β, its variant, or a chimeric proteins or chimeric protein complexes such as Fc-based chimeric protein complex comprising the IL-1β or its variant may be expressed in vivo, for instance, in a patient. For example, in various embodiments, the IL-1β, its variant, or a chimeric proteins or chimeric protein complexes such as Fc-based chimeric protein complex comprising the IL-1β or its variant may administered in the form of nucleic acid which encodes for the IL-1β or its variant or chimeric proteins or chimeric protein complexes such as Fc-based chimeric protein complex comprising IL-1β or its variant. In various embodiments, the nucleic acid is DNA or RNA. In some embodiments, the IL-1β, its variant, or a chimeric proteins or chimeric protein complexes such as Fc-based chimeric protein complex comprising the IL-1β or its variant is encoded by a modified mRNA, i.e. an mRNA comprising one or more modified nucleotides. In some embodiments, the modified mRNA comprises one or modifications found in U.S. Pat. No. 8,278,036, the entire contents of which are hereby incorporated by reference. In some embodiments, the modified mRNA comprises one or more of m5C, m5U, m6A, s2U, ψ, and 2'-O-methyl-U. In some embodiments, the present invention relates to administering a modified mRNA encoding one or more of the present chimeric proteins or chimeric protein complexes such as Fc-based chimeric protein complex. In some embodiments, the present invention relates to gene therapy vectors comprising the same. In some embodiments, the present invention relates to gene therapy methods comprising the same. In various embodiments, the nucleic acid is in the form of an oncolytic virus, e.g. an adenovirus, reovirus, measles, herpes simplex, Newcastle disease virus or vaccinia.

In various embodiments, the chimeric proteins or chimeric protein complexes such as Fc-based chimeric protein complex comprises a targeting moiety that is a VHH. In various embodiments, the VHH is not limited to a specific biological source or to a specific method of preparation. For example, the VHH can generally be obtained: (1) by isolating the $V_H$H domain of a naturally occurring heavy chain antibody; (2) by expression of a nucleotide sequence encoding a naturally occurring $V_H$H domain; (3) by "humanization" of a naturally occurring $V_H$H domain or by expression of a nucleic acid encoding a such humanized $V_H$H domain; (4) by "camelization" of a naturally occurring VH domain from any animal species, such as from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known in the art; (7) by preparing a nucleic acid encoding a VHH using techniques for nucleic acid synthesis known in the art, followed by expression of the nucleic acid thus obtained; and/or (8) by any combination of one or more of the foregoing.

In an embodiment, the chimeric proteins or chimeric protein complexes such as Fc-based chimeric protein complex comprises a VHH that corresponds to the $V_H$H domains of naturally occurring heavy chain antibodies directed against a target of interest. In some embodiments, such $V_H$H sequences can generally be generated or obtained by suitably immunizing a species of Camelid with a molecule of based on the target of interest (e.g., CD8, etc.) (i.e., so as to raise an immune response and/or heavy chain antibodies directed against the target of interest), by obtaining a suitable biological sample from the Camelid (such as a blood sample, or any sample of B-cells), and by generating $V_H$H sequences directed against the target of interest, starting from the sample, using any suitable known techniques. In some embodiments, naturally occurring $V_H$H domains against the target of interest can be obtained from naive libraries of Camelid $V_H$H sequences, for example, by screening such a library using the target of interest or at least one part, fragment, antigenic determinant or epitope thereof using one or more screening techniques known in the art. Such libraries and techniques are, for example, described in WO 9937681, WO 0190190, WO 03025020 and WO 03035694, the entire contents of which are hereby incorporated by reference. In some embodiments, improved synthetic or semi-synthetic libraries derived from naive $V_H$H libraries may be used, such as $V_H$H libraries obtained from naive $V_H$H libraries by techniques such as random mutagenesis and/or CDR shuffling, as for example, described in WO 0043507, the entire contents of which are hereby incorporated by reference. In some embodiments, another technique for obtaining $V_H$H sequences directed against a target of interest involves suitably immunizing a transgenic mammal that is capable of expressing heavy chain antibodies (i.e., so as to raise an immune response and/or heavy chain antibodies directed against the target of interest), obtaining a suitable biological sample from the transgenic mammal (such as a blood sample, or any sample of B-cells), using any suitable known techniques. For example, for this purpose, the heavy chain antibody-expressing mice and the further methods and techniques described in WO 02085945 and in WO 04049794 (the entire contents of which are hereby incorporated by reference) can be used.

In an embodiment, the chimeric proteins or chimeric protein complexes such as Fc-based chimeric protein complex comprises a VHH that has been "humanized" i.e., by replacing one or more amino acid residues in the amino acid sequence of the naturally occurring $V_H$H sequence (and in particular in the framework sequences) by one or more of the amino acid residues that occur at the corresponding position(s) in a VH domain from a conventional 4-chain antibody from a human being. This can be performed using humanization techniques known in the art. In some embodiments, possible humanizing substitutions or combinations of humanizing substitutions may be determined by methods known in the art, for example, by a comparison between the sequence of a VHH and the sequence of a naturally occurring human VH domain. In some embodiments, the humanizing substitutions are chosen such that the resulting humanized VHHs still retain advantageous functional properties. Generally, as a result of humanization, the VHHs of the invention may become more "human-like," while still retaining favorable properties such as a reduced immunogenicity, compared to the corresponding naturally occurring $V_H$H domains. In various embodiments, the humanized VHHs of the invention can be obtained in any suitable manner known in the art and thus are not strictly limited to polypeptides that have been obtained using a polypeptide that comprises a naturally occurring $V_H$H domain as a starting material.

In an embodiment, the chimeric proteins or chimeric protein complexes such as Fc-based chimeric protein complex comprises a VHH that has been "camelized," i.e., by replacing one or more amino acid residues in the amino acid sequence of a naturally occurring VH domain from a conventional 4-chain antibody by one or more of the amino acid residues that occur at the corresponding position(s) in a $V_H$H domain of a heavy chain antibody of a camelid. In some embodiments, such "camelizing" substitutions are inserted at amino acid positions that form and/or are present at the VH-VL interface, and/or at the so-called Camelidae hallmark residues (see, for example, WO9404678, the entire contents of which are hereby incorporated by reference). In some embodiments, the VH sequence that is used as a starting material or starting point for generating or designing the camelized VHH is a VH sequence from a mammal, for example, the VH sequence of a human being, such as a VH3 sequence. In various embodiments, the camelized VHHs can be obtained in any suitable manner known in the art and thus are not strictly limited to polypeptides that have been obtained using a polypeptide that comprises a naturally occurring VH domain as a starting material.

In various embodiments, both "humanization" and "camelization" can be performed by providing a nucleotide sequence that encodes a naturally occurring $V_H$H domain or VH domain, respectively, and then changing, in a manner known in the art, one or more codons in the nucleotide sequence in such a way that the new nucleotide sequence encodes a "humanized" or "camelized" VHH, respectively. This nucleic acid can then be expressed in a manner known in the art, so as to provide the desired VHH of the invention. Alternatively, based on the amino acid sequence of a naturally occurring $V_HH$ domain or VH domain, respectively, the amino acid sequence of the desired humanized or camelized VHH of the invention, respectively, can be designed and then synthesized de novo using techniques for peptide synthesis known in the art. Also, based on the amino acid sequence or nucleotide sequence of a naturally occurring $V_HH$ domain or VH domain, respectively, a nucleotide sequence encoding the desired humanized or camelized VHH, respectively, can be designed and then synthesized de novo using techniques for nucleic acid synthesis known in the art, after which the nucleic acid thus obtained can be expressed in a manner known in the art, so as to provide the desired VHH of the invention. Other suitable methods and techniques for obtaining the VHHs of the invention and/or nucleic acids encoding the same, starting from naturally occurring VH sequences or $V_HH$ sequences, are known in the art, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a VHH of the invention or a nucleotide sequence or nucleic acid encoding the same.

Pharmaceutically Acceptable Salts and Excipients

The vaccine composition, adjuvant, chimeric protein or chimeric protein complex described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science,* 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In various embodiments, the present invention pertains to vaccine composition, adjuvant, chimeric protein or chimeric protein complex described herein and a pharmaceutically acceptable carrier or excipient. Any vaccine composition, adjuvant, chimeric protein or chimeric protein complex described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in Remington's Pharmaceutical Sciences 1447-1676 (Alfonso R. Gennaro eds., 19th ed. 1995), incorporated herein by reference.

The present invention includes the described vaccine composition, adjuvant, chimeric protein or chimeric protein complex in various formulations. Any inventive vaccine composition, adjuvant, chimeric protein or chimeric protein complex described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, dessicated powder, or any other form suitable for use. In yet another embodiment, the vaccine composition is formulated as a liquid.

Where necessary, the inventive the vaccine composition, adjuvant, chimeric protein or chimeric protein complex can also include a solubilizing agent. Also, the agents can be delivered with a suitable vehicle or delivery device as known in the art. Combination therapies outlined herein can be co-delivered in a single delivery vehicle or delivery device.

The formulations comprising the inventive the vaccine composition, adjuvant, chimeric protein or chimeric protein complex of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any compositions (and/or additional agents) described herein is formulated in accordance with routine procedures as a composition adapted for a mode of administration described herein. Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. In some embodiments, the vaccine composition, the adjuvant, and/or the antigen are formulated for administration intravenously. In embodiments, the vaccine composition, the adjuvant and/or the antigen are formulated for administration to the lung. In embodiments, the vaccine composition, the adjuvant and/or the antigen are formulated for administration by inhalation. In embodiments, the vaccine composition, the adjuvant and/or the antigen are formulated for administration via aerosol or nebulizer. In some embodiments, the vaccine composition, the adjuvant and/or the antigen are formulated for administration liquid nebulization, dry powder dispersion and meter-dose administration.

Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream.

In one embodiment, the vaccine composition, adjuvant, chimeric protein or chimeric protein complex described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation.

Moreover, where in tablet or pill form, the compositions can be coated to delay disintegration and absorption in the gastrointestinal tract thereby providing a sustained action over an extended period. Selectively permeable membranes surrounding an osmotically active driving vaccine compositions described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive vaccine composition, adjuvant, chimeric protein or chimeric protein complex described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used. Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the vaccine composition, adjuvant, chimeric protein or chimeric protein complex to be administered according to the present invention will vary according to the particular dosage form, and the mode of administration. Many factors that may modify the action of the vaccine composition, adjuvant, chimeric protein or chimeric protein complex (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the vaccine composition, adjuvant, chimeric protein or chimeric protein complex is in a range of about 0.01 μg/kg to about 100 mg/kg of body weight of the subject, about 0.01 μg/kg to about 10 mg/kg of body weight of the subject, or about 0.01 μg/kg to about 1 mg/kg of body weight of the subject for example, about 0.01 μg/kg, about 0.02 μg/kg, about 0.03 μg/kg, about 0.04 μg/kg, about 0.05 μg/kg, about 0.06 μg/kg, about 0.07 μg/kg, about 0.08 μg/kg, about 0.09 μg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, or about 100 mg/kg body weight, inclusive of all values and ranges therebetween.

Individual doses of the vaccine composition, adjuvant, chimeric protein or chimeric protein complex can be administered in unit dosage forms (e.g., tablets, capsules, or liquid formulations) containing, for example, from about 1 μg to about 100 mg, from about 1 μg to about 90 mg, from about 1 μg to about 80 mg, from about 1 μg to about 70 mg, from about 1 μg to about 60 mg, from about 1 μg to about 50 mg, from about 1 μg to about 40 mg, from about 1 μg to about 30 mg, from about 1 μg to about 20 mg, from about 1 μg to about 10 mg, from about 1 μg to about 5 mg, from about 1 μg to about 3 mg, from about 1 μg to about 1 mg per unit dosage form, or from about 1 μg to about 50 μg per unit dosage form. For example, a unit dosage form can be about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29, about 30 μg, about 35 μg, about 40 μg, about 45 μg, about 50 μg, about 60 μg, about 70 μg, about 80 μg, about 90 μg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, inclusive of all values and ranges therebetween.

In one embodiment, the vaccine composition, adjuvant, chimeric protein or chimeric protein complex is administered at an amount of from about 1 μg to about 100 mg daily, from about 1 μg to about 90 mg daily, from about 1 μg to about 80 mg daily, from about 1 μg to about 70 mg daily, from about 1 μg to about 60 mg daily, from about 1 μg to about 50 mg daily, from about 1 μg to about 40 mg daily, from about 1 μg to about 30 mg daily, from about 1 μg to about 20 mg daily, from about 01 μg to about 10 mg daily, from about 1 μg to about 5 mg daily, from about 1 μg to about 3 mg daily, or from about 1 μg to about 1 mg daily. In various embodiments, the vaccine composition, adjuvant, chimeric protein or chimeric protein complex is administered at a daily dose of about 1 μg, about 2 μg, about 3 μg, about 4 μg, about 5 μg, about 6 μg, about 7 μg, about 8 μg, about 9 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29, about 30 μg, about 35 μg, about 40 μg, about 45 μg, about 50 μg, about 60 μg, about 70 μg, about 80 μg, about 90 μg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg, inclusive of all values and ranges therebetween.

In accordance with certain embodiments of the invention, the vaccine composition, adjuvant, chimeric protein or chimeric protein complex may be administered, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year. In an embodiment, the vaccine composition, adjuvant, chimeric protein or chimeric protein complex is administered about three times a week.

In various embodiments, the vaccine composition, adjuvant, chimeric protein or chimeric protein complex may be administered for a prolonged period. For example, the vaccine composition comprising chimeric proteins or chimeric protein complexes may be administered as described herein for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, or at least about 12 weeks.

For example, the vaccine composition may be administered for 12 weeks, 24 weeks, 36 weeks or 48 weeks. In some embodiments, the vaccine composition is administered for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months. In some embodiments, the vaccine composition may be administered for at least about 1 year, at least about 2 years, at least about 3 years, at least about 4 years, or at least about 5 years.

Combination Therapy and Additional Therapeutic Agents

In various embodiments, the vaccine composition, adjuvant, chimeric protein or chimeric protein complex of the present invention is co-administered in conjunction with additional therapeutic agent(s). Co-administration can be simultaneous or sequential.

In one embodiment, the additional therapeutic agent and the vaccine composition, adjuvant, chimeric protein or chimeric protein complex of the present invention are administered to a subject simultaneously. The term "simultaneously" as used herein, means that the additional therapeutic agent and the vaccine composition are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the vaccine composition, adjuvant, chimeric protein or chimeric protein complex can be by simultaneous administration of a single formulation (e.g., a formulation comprising the additional therapeutic agent and the vaccine composition) or of separate formulations (e.g., a first formulation including the additional therapeutic agent and a second formulation including the vaccine composition).

Co-administration does not require the therapeutic agents to be administered simultaneously, if the timing of their administration is such that the pharmacological activities of the additional therapeutic agent and the vaccine composition, adjuvant, chimeric protein or chimeric protein complex overlap in time, thereby exerting a combined therapeutic effect. For example, the additional therapeutic agent and the vaccine composition, adjuvant, chimeric protein or chimeric protein complex can be administered sequentially. The term "sequentially" as used herein means that the additional therapeutic agent and the vaccine composition are administered with a time separation of more than about 60 minutes. For example, the time between the sequential administration of the additional therapeutic agent and the vaccine composition can be more than about 60 minutes, more than about 2 hours, more than about 5 hours, more than about 10 hours, more than about 1 day, more than about 2 days, more than about 3 days, more than about 1 week apart, more than about 2 weeks apart, or more than about one month apart. The optimal administration times will depend on the rates of metabolism, excretion, and/or the pharmacodynamic activity of the additional therapeutic agent and the vaccine composition, adjuvant, chimeric protein or chimeric protein complex being administered.

Co-administration also does not require the therapeutic agents to be administered to the subject by the same route of administration. Rather, each therapeutic agent can be administered by any appropriate route, for example, parenterally or non-parenterally.

In some embodiments, the vaccine composition, adjuvant, chimeric protein or chimeric protein complex herein acts synergistically when co-administered with another therapeutic agent. In such embodiments, the vaccine composition, adjuvant, chimeric protein or chimeric protein complex and the additional therapeutic agent may be administered at doses that are lower than the doses employed when the agents are used in the context of monotherapy.

In some embodiments, inclusive of, without limitation, infectious disease applications, the present invention pertains to anti-infectives as additional therapeutic agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

Additional therapeutic agents, e.g. for coronavirus-related methods, include, for example, one or more of acyclovir, ganciclovir, remdesivir; favipiravir; galidesivir; prezcobix; lopinavir and/or ritonavir and/or arbidol; mRNA-1273; recombinant proteins such as agonists, antagonists, blockers, or decoy mimetics of the viral spike protein, or agonists, antagonists, blockers, or decoy mimetics of the ACE2 protein; stem cell-derived exosomes; lopinavir/ritonavir and/or ribavirin and/or IFN-alpha, IFN-beta, IFN-gamma; xiyanping; anti-VEGF-A agents (e.g. Bevacizumab, ranibizumab, aflibercept, and others); fingolimod; carrimycin; hydroxychloroquine chloroquine; darunavir and cobicistat; prednisone, prednisolone, methylprednisolone; fluocinalone, brilacidin; leronlimab (PRO 140); and thalidomide. In various embodiments, the present adjuvatns are administered to a patient undergoing treatment with one or more additional therapeutic agents. In various embodiments, additional therapeutic agents include anti-virals, anti-inflammatories, agents that reduce vascular leakage and tissue edema, antifibrotic agents. Additional therapeutic agents, include, for example, one or more of acyclovir, ganciclovir, remdesivir; favipiravir; galidesivir; prezcobix; lopinavir and/or ritonavir and/or arbidol; mRNA-1273; recombinant proteins such as agonists, antagonists, blockers, or decoy mimetics of the viral spike protein, or agonists, antagonists, blockers, or decoy mimetics of the ACE2 protein; stem cell-derived exosomes; lopinavir/ritonavir and/or ribavirin and/or IFN-alpha, IFN-beta, IFN-gamma; xiyanping; anti-VEGF-A agents (e.g. Bevacizumab, ranibizumab, aflibercept, and others); fingolimod; carrimycin; hydroxychloroquine chloroquine; darunavir and cobicistat; prednisone, prednisolone, methylprednisolone; fluocinalone, brilacidin; leronlimab (PRO 140); and thalidomide.

In some embodiments, the additional therapeutic agents include convalescent plasma, i.e., plasma from a donor subject (e.g. a human subject) who has recovered from the viral infection, e.g., SARS-CoV-2. In some embodiments, the additional therapeutic agents include plasma from a donor subject (e.g. a human subject) comprising IgG and IgM antibodies directed against a virus disclosed herein that causes an infection or a disease, e.g., SARS-CoV-2.

In some embodiments, the present invention relates to combination therapy with one or more chimeric agents described in WO 2013/10779, WO 2015/007536, WO 2015/007520, WO 2015/007542, and WO 2015/007903, the entire contents of which are hereby incorporated by reference in their entireties.

In some embodiments, the vaccine composition, adjuvant, chimeric protein or chimeric protein complex includes derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

In still other embodiments, the vaccine composition, adjuvant, chimeric protein or chimeric protein complex further comprise a cytotoxic agent, comprising, in illustrative embodiments, a toxin, a chemotherapeutic agent, a radioisotope, and an agent that causes apoptosis or cell death. Such agents may be conjugated to a composition described herein.

The vaccine composition, adjuvant, chimeric protein or chimeric protein complex described herein may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, *vinca* alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and *Pseudomonas* toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the vaccine composition comprising chimeric proteins or chimeric protein complexes, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, Iodine-125, Carbon-14, Sulfur-35, Tritium and Phosphorus-32.

Methods of Treatment or Vaccination

Methods and compositions described herein have application to treating or vaccinating against various diseases and disorders, including, e.g., infectious diseases. Further, any of the disclosed vaccine compositions, adjuvants, chimeric proteins, or chimeric protein complexes may be for use in the treating/vaccinating against, or the manufacture of a medicament for treating, various diseases and disorders, including, infections.

In some embodiments, the vaccine composition, adjuvant, chimeric protein or chimeric protein complex described herein are suitable for vaccinating against, preventing, or mitigating a disease or disorder is an infectious disease. In some embodiments, the disease or disorder is selected from diphtheria, tetanus, pertussis, influenza, pneumonia, hepatitis A, hepatitis B, polio, yellow fever, Human Papillomavirus (HPV) infection, anthrax, rabies, Japanese Encephalitis, meningitis, measles, mumps, rubella, gastroenteritis, smallpox, typhoid fever, varicella (chickenpox), rotavirus, and shingles.

One aspect of the present invention is related to a method for vaccinating a subject against an infectious disease, comprising administering: (a) administering an adjuvant comprising a chimeric protein or chimeric protein complex, comprising: (i) a mutant IL-1β, (ii) one or more targeting moieties, said targeting moieties comprising recognition domains which specifically bind to an antigen or receptor of interest; and (iii) a connector between (i) and (ii), the connector being: (1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii) or (2) a flexible linker that connects (i) and (ii); wherein the mutant IL-13 is characterized by low affinity or activity at the IL-1 receptor; and (b) an antigen which is suitable for inducing an immune response.

In some embodiments, the infectious disease is an infection with a pathogen, optionally selected from a bacterium, virus, fungus, or parasite. In some embodiments, the virus is: (a) an influenza virus, optionally selected from Type A, Type B, Type C, and Type D influenza viruses, (b) a member of the Coronaviridae family, optionally selected from a betacoronavirus, optionally selected from severe acute respiratory syndrome coronavirus 2 (SARS-CoV-2), SARS-CoV, Middle East Respiratory Syndrome-Corona Virus (MERS-CoV), HCoV-HKU1, and HCoV-OC43 or an alphacoronavirus, optionally selected from HCoV-NL63 and HCoV-229E, or (c) a member of Picornaviridae family, optionally selected from Rhinovirus A or Rhinovirus B.

Coronavirus infection 2019 (COVID-19), caused by SARS-CoV-2 (e.g., 2019-nCoV), is a disease thought to be originated from the bat. COVID-19 causes severe respiratory distress and this RNA virus strain has been the cause of a worldwide outbreak that was declared a major threat to public health and worldwide emergency. Phylogenetic analysis of the complete genome of 2019-nCoV revealed that the virus was most closely related (89.1% nucleotide similarity) to a group of SARS-like coronaviruses (genus Betacoronavirus, subgenus Sarbecovirus). Wu et al., A new coronavirus associated with human respiratory disease in China. Nature, Feb. 3, 2020. 2019-nCoV is thought to spread from person-to-person and the spread may be possible from contact with infected surfaces or objects.

In some embodiments, the virus is SARS-CoV-2. In some embodiments, the antigen is a 2019-nCoV protein, or an antigenic fragment thereof, optionally selected from spike surface glycoprotein, membrane glycoprotein M, envelope protein E, and nucleocapsid phosphoprotein N. In some embodiments, the antigen is the S1 or S2 subunit of the spike surface glycoprotein, or an antigenic fragment thereof.

In an embodiment, the spike surface glycoprotein comprises the amino acid sequence of SEQ ID NO: 31:

```
MFVFLVLLPLVSSQCVNLTTRTQLPPAYTNSFTRGVYYPDKVFRSSVLH
STQDLFLPFFSNVTWFHAIHVSGTNGTKRFDNPVLPFNDGVYFASTEKS
NIIRGWIFGTTLDSKTQSLLIVNNATNVVIKVCEFQFCNDPFLGVYYHK
NNKSWMESEFRVYSSANNCTFEYVSQPFLMDLEGKQGNFKNLREFVFKN
IDGYFKIYSKHTPINLVRDLPQGFSALEPLVDLPIGINITRFQTLLALH
RSYLTPGDSSSGWTAGAAAYYVGYLQPRTFLLKYNENGTITDAVDCALD
PLSETKCTLKSFTVEKGIYQTSNFRVQPTESIVRFPNITNLCPFGEVFN
ATRFASVYAWNRKRISNCVADYSVLYNSASFSTFKCYGVSPTKLNDLCF
TNVYADSFVIRGDEVRQIAPGQTGKIADYNYKLPDDFTGCVIAWNSNNL
DSKVGGNYNYLYRLFRKSNLKPFERDISTEIYQAGSTPCNGVEGFNCYF
PLQSYGFQPTNGVGYQPYRVVVLSFELLHAPATVCGPKKSTNLVKNKCV
NFNFNGLTGTGVLTESNKKFLPFQQFGRDIADTTDAVRDPQTLEILDIT
PCSFGGVSVITPGTNTSNQVAVLYQDVNCTEVPVAIHADQLTPTWRVYS
TGSNVFQTRAGCLIGAEHVNNSYECDIPIGAGICASYQTQTNSPRRARS
VASQSIIAYTMSLGAENSVAYSNNSIAIPTNFTISVTTEILPVSMTKTS
VDCTMYICGDSTECSNLLLQYGSFCTQLNRALTGIAVEQDKNTQEVFAQ
VKQIYKTPPIKDFGGFNFSQILPDPSKPSKRSFIEDLLFNKVTLADAGF
IKQYGDCLGDIAARDLICAQKFNGLTVLPPLLTDEMIAQYTSALLAGTI
TSGWTFGAGAALQIPFAMQMAYRFNGIGVTQNVLYENQKLIANQFNSAI
GKIQDSLSSTASALGKLQDVVNQNAQALNTLVKQLSSNFGAISSVLNDI
LSRLDKVEAEVQIDRLITGRLQSLQTYVTQQLIRAAEIRASANLAATKM
SECVLGQSKRVDFCGKGYHLMSFPQSAPHGVVFLHVTYVPAQEKNFTTA
PAICHDGKAHFPREGVFVSNGTHWFVTQRNFYEPQIITTDNTFVSGNCD
WVIGIVNNTVYDPLQPELDSFKEELDKYFKNHTSPDVDLGDISGINASV
VNIQKEIDRLNEVAKNLNESLIDLQELGKYEQYIKWPWYIWLGFIAGLI
AIVMVTIMLCCMTSCCSCLKGCCSCGSCCKFDEDDSEPVLKGVKLHYT
```

In an embodiment, the membrane glycoprotein precursor M comprises the amino acid sequence of SEQ ID NO: 32:

```
MADSNGTITVEELKKLLEQWNLVIGFLFLTWICLLQFAYANRNRFLYII
KLIFLWLLWPVTLACFVLAAVYRINWITGGIAIAMACLVGLMWLSYFIA
SFRLFARTRSMWSFNPETNILLNVPLHGTILTRPLLESELVIGAVILRG
HLRIAGHHLGRCDIKDLPKEITVATSRTLSYYKLGASQRVAGDSGFAAY
SRYRIGNYKLNTDHSSSSDNIALLVQ
```

In an embodiment, the envelope protein E comprises the amino acid sequence of SEQ ID NO: 33:

```
MYSFVSEETGTLIVNSVLLFLAFVVFLLVTLAILTALRLCAYCCNIVNV
SLVKPSFYVYSRVKNLNSSRVPDLLV
```

In an embodiment, the nucleocapsid phosphoprotein N comprises the amino acid sequence of SEQ ID NO: 34:

MSDNGPQNQRNAPRITFGGPSDSTGSNQNGERSGARSKQRRPQGLPNNT

ASWFTALTQHGKEDLKFPRGQGVPINTNSSPDDQIGYYRRATRRIRGGD

GKMKDLSPRWYFYYLGTGPEAGLPYGANKDGIIWVATEGALNTPKDHIG

TRNPANNAAIVLQLPQGTTLPKGFYAEGSRGGSQASSRSSSRSRNSSRN

STPGSSRGTSPARMAGNGGDAALALLLLDRLNQLESKMSGKGQQQQGQT

VTKKSAAEASKKPRQKRTATKAYNVTQAFGRRGPEQTQGNFGDQELIRQ

GTDYKHWPQIAQFAPSASAFFGMSRIGMEVTPSGTWLTYTGAIKLDDKD

PNFKDQVILLNKHIDAYKTFPPTEPKKDKKKKADETQALPQRQKKQQTV

TLLPAADLDDFSKQLQQSMSSADSTQA

In various embodiments, the subject is afflicted with coronavirus disease 2019 (COVID-19). In additional embodiments, the subject is elderly and/or afflicted with one or more comorbidities, including, but not limited to, hypertension and/or diabetes. A subject afflicted with a coronavirus infection can acquire symptoms including, but not limited to, fever, tiredness, dry cough, aches and pains, shortness of breath and other breathing difficulties, diarrhea, upper respiratory symptoms (e.g. sneezing, runny nose, nasal congestion, cough, sore throat), pneumonia, pneumonia respiratory failure, hepatic and renal insufficiency, acute respiratory distress syndrome (ARDS), and a cytokine imbalance.

In some embodiments, the virus is an influenza virus. In some embodiments, the antigen is an influenza viral antigen, optionally selected from hemagglutinin (HA) protein, matrix 2 (M2) protein, and neuraminidase, or an antigenic fragment thereof.

In some embodiments, the antigens described herein have at least about 90%, or at least about 95%, or at least about 97%, or at least about 98%, or at least about 99% identity with its wild type sequence. In some embodiments, the spike surface glycoprotein, membrane glycoprotein M, envelope protein E, and nucleocapsid phosphoprotein N have at least about 90%, or at least about 95%, or at least about 97%, or at least about 98%, or at least about 99% identity with their sequences as shown above.

In various embodiments, the SARS-CoV-2 surface glycoprotein comprises the amino acid sequence of SEQ ID NO:31.

In various embodiments, the SARS-CoV-2 fragment comprises amino acid residues F486, N487, Q493, Q498, T500, N501 of the SARS-CoV-2 surface glycoprotein, having the amino acid sequence of SEQ ID NO: 31, that interact with the α1 helix of the ACE2 receptor.

In some embodiments, the SARS-CoV-2 peptide is a fragment of the SARS-CoV-2 RBD or the spike protein, including the wild type or a variant (also referred to as lineages). In some embodiments, the SARS-CoV-2 peptide is a fragment of SEQ ID NO: 31 or a variant thereof. In embodiments, the wild type SARS-CoV-2 coronavirus is the "Wuhan strain."

In embodiments, the present vaccine is pan-antigenic, thus providing immune response to the wild type (e.g., "Wuhan strain") and numerous variants of the coronavirus. In embodiments, the present vaccine comprises one or more peptides of the wild type and/or a variants of the spike proteins, or RBD thereof. Accordingly, in various embodiments, the vaccine includes two or more peptides of a respective variant, lineage, or strain of a coronavirus protein. For example, the variants can include a coronavirus protein having a mutation (e.g., without limitation, a substitution, deletion, or insertion) in any part of the spike, or the RBD thereof, protein, such as in the S1 subunit (e.g., in the RBD of the Spike protein), or in the S2 subunit. In some embodiments, a mutation is in a glycosylation site of the Spike protein.

In some embodiments, the variant (also referred to as lineages) is one or more of B.1.1.7, B.1.351, B.1.617.2, B.1.427, B.1.429, B.1.525, B.1.526, B.1.617.1, B.1.617.3, B.1, B.1.1.28, B.1.2, CAL.20C, B.6, P.1, and P.2 variants and/or any other variants, or antigenic fragments thereof. In some embodiments, the lineages include A.1, A.2, A.3, A.4, A.5, A.6, A.7, A.8, A.9, B, B.1, B.1.1, B.1.1.1, B.2, B.3, B.4, B.5, B.6, B.7, B.9, B.10, B.11, B.12, B.13, B.14, B.15, B.16, B.17, B.18, B.19, B.20, B.21, B.22, B.23, B.24, B.25, B.26, B.27, C.1, C.2, C.3, D.1, and D2.

In some embodiments, the SARS-CoV-2 variant is B.1.1.7, also known as the Alpha variant. In embodiments, the B.1.1.7 ("Alpha") variant comprises one or more mutations selected from 69del, 70del, 144del, (E484K*), (S494P*), N501Y, A570D, D614G, P681H, T7161, S982A, and D1118H (K1191N*), relative to the amino acid sequence of SEQ ID NO: 31 or an antigenic fragment thereof.

In some embodiments, the SARS-CoV-2 variant is B.1.351, also known as the Beta variant. In embodiments, the B.1.351 ("Beta") variant comprises one or more mutations selected from D80A, D215G, 241del, 242del, 243del, K417N, E484K, N501Y, D614G, and A701V, relative to the amino acid sequence of SEQ ID NO: 31 or an antigenic fragment thereof.

In some embodiments, the SARS-CoV-2 variant is B.1.617.2, also known as the Delta variant. In embodiments, the B.1.617.2 ("Delta") variant comprises one or more mutations selected from T19R, (G142D*), 156del, 157del, R158G, L452R, T478K, D614G, P681R, and D950N, relative to the amino acid sequence of SEQ ID NO: 31 or an antigenic fragment thereof.

In some embodiments, the SARS-CoV-2 variant is P.1, also known as the Gamma variant. In embodiments, the P.1 ("Gamma") variant comprises one or more mutations selected from L18F, T20N, P26S, D138Y, R190S, K417T, E484K, N501Y, D614G, H655Y, and T10271, relative to the amino acid sequence of SEQ ID NO: 31 or an antigenic fragment thereof.

In some embodiments, the SARS-CoV-2 variant is B.1.427, also known as the Epsilon variant. In embodiments, the B.1.427 ("Epsilon") variant comprises one or more mutations selected from L452R and D614G, relative to the amino acid sequence of SEQ ID NO: 31 or an antigenic fragment thereof.

In some embodiments, the SARS-CoV-2 variant is B.1.429, also known as the Epsilon variant. In embodiments, the B.1.429 ("Epsilon") variant comprises one or more mutations selected from S131, W152C, L452R, and D614G, relative to the amino acid sequence of SEQ ID NO: 31 or an antigenic fragment thereof.

In some embodiments, the SARS-CoV-2 variant is B.1.525, also known as the Eta variant. In embodiments, the B.1.525 ("Eta") variant comprises one or more mutations selected from A67V, 69del, 70del, 144del, E484K, D614G, Q677H, and F888L, relative to the amino acid sequence of SEQ ID NO: 31 or an antigenic fragment thereof.

In some embodiments, the SARS-CoV-2 variant is B.1.526, also known as the Iota variant. In embodiments, the B.1.526 ("Iota") variant comprises one or more mutations selected from L5F, (D80G*), T951, (Y144-*), (F157S*), D253G, (L452R⁺), (S477N*), E484K, D614G, A701V, (T859N*), (D950H*), and (Q957R⁺), relative to the amino acid sequence of SEQ ID NO: 31 or an antigenic fragment thereof.

In some embodiments, the SARS-CoV-2 variant is B.1.617.1, also known as the Kappa variant. In embodiments, the B.1.617.1 ("Kappa") variant comprises one or more mutations selected from (T951), G142D, E154K, L452R, E484Q, D614G, P681R, and Q1071H, relative to the amino acid sequence of SEQ ID NO: 31 or an antigenic fragment thereof.

In some embodiments, the SARS-CoV-2 variant is B.1.617.3. In embodiments, the B.1.617.3 variant comprises one or more mutations selected from T19R, G142D, L452R, E484Q, D614G, P681R, D950N, relative to the amino acid sequence of SEQ ID NO: 31 or an antigenic fragment thereof.

In some embodiments, the SARS-CoV-2 variant is P.2, also known as the Zeta variant. In embodiments, the P.2 ("Zeta") variant comprises one or more mutations selected from E484K, (F565L⁺), D614G, and V1176F, relative to the amino acid sequence of SEQ ID NO: 31 or an antigenic fragment thereof.

In some embodiments, a variant is a SARS-CoV-2 protein having a variation in a glycosylation site of a Spike protein.

In some embodiments, a variant is a Spike protein having one or more of D614G, E484K, N501Y, K417N, S477G, and S477N mutations relative to the amino acid sequence of SEQ ID NO: 31 or an antigenic fragment thereof.

In some embodiments, a variant is a Spike protein having a mutation in the RBD of the Spike protein. In some embodiments, the mutation in the RBD of the Spike protein is a mutation in a glycosylation site in the RBD.

In some embodiments, a variant is a Spike protein having a mutation outside the RBD of the Spike protein.

Another aspect of the present invention is related to a method for vaccinating a subject against an influenza infection, comprising administering: (a) administering an adjuvant comprising a chimeric protein or chimeric protein complex, comprising: (i) a mutant IL-1β, (ii) one or more targeting moieties, said targeting moieties comprising recognition domains which specifically bind to an antigen or receptor of interest; and (iii) a connector between (i) and (ii), the connector being: (1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii) or (2) a flexible linker that connects (i) and (ii); wherein the mutant IL-13 is characterized by low affinity or activity at the IL-1 receptor; and (b) an influenza antigen which is suitable for inducing an immune response.

Yet another aspect of the present invention is related to a method for vaccinating a subject against a severe acute respiratory syndrome coronavirus 2 (SARS-CoV-2) infection comprising administering: (a) administering an adjuvant comprising a chimeric protein or chimeric protein complex, comprising: (i) a mutant IL-1β, (ii) one or more targeting moieties, said targeting moieties comprising recognition domains which specifically bind to an antigen or receptor of interest; and (iii) a connector between (i) and (ii), the connector being: (1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii) or (2) a flexible linker that connects (i) and (ii); wherein the mutant IL-1β is characterized by low affinity or activity at the IL-1 receptor; and (b) a SARS-CoV-2 antigen which is suitable for inducing an immune response.

Another aspect of the invention is related to a method for treating a subject afflicted with an infectious disease, comprising administering a chimeric protein or chimeric protein complex, comprising: (i) a mutant IL-1β, (ii) one or more targeting moieties, said targeting moieties comprising recognition domains which specifically bind to an antigen or receptor of interest; and (iii) a connector between (i) and (ii), the connector being: (1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii) and/or (2) a flexible linker that connects (i) and (ii); wherein the mutant IL-1β is characterized by low affinity or activity at the IL-1 receptor. For example, in embodiments, the invention is related to a method for treating a subject afflicted with an a coronavirus (e.g. SARS-CoV-2) or influenza infection. In such embodiments, the adjuvant is administered to a patient who has a low level or moderate infection and the adjuvant causes a boost to the natural immune response to the infection occurring in the patient.

In some embodiments, the present invention relates to the treatment or vaccination of patients who are naive to antiviral therapy. In other embodiments, the present invention relates to the treatment or vaccination of patients who did not respond to previous antiviral therapy. In some embodiments, the present vaccine compositions may be used to vaccinate relapsed patients.

In various embodiments, the vaccine compositions of the invention provide improved safety compared to, e.g., untargeted IL-1β or an unmodified, wild type IL-1β or a modified IL-1β (e.g., pegylated IL-1β). In illustrative embodiments, administration of the vaccine composition is associated with minimal side effects such as those side effects associated with the use of the untargeted IL-1β or an unmodified, wild type IL-1β or a modified IL-1β (e.g., influenza-like symptoms, myalgia, leucopenia, thrombocytopenia, neutropenia, depression, and weight loss).

In some embodiments, the vaccine composition of the invention shows improved therapeutic activity compared to untargeted IL-1β or an unmodified, wild type IL-1β, or a modified IL-1β (e.g., pegylated IL-1β). In some embodiments, the vaccine composition of the invention shows improved pharmacokinetic profile (e.g., longer serum half-life and stability) compared to untargeted IL-1β or an unmodified, wild type IL-1β or a modified IL-1β (e.g., pegylated IL-1β).

Kits

The invention also provides kits for the administration of any agent described herein. The kit is an assembly of materials or components, including at least one of the compositions described herein. Thus, in some embodiments, the kit contains at least one of the compositions described herein. The exact nature of the components configured in the kit depends on its intended purpose. In one embodiment, the kit is configured for the purpose of treating or vaccinating human subjects.

Instructions for use may be included in the kit. Instructions for use typically include a tangible expression describing the technique to be employed in using the components of the kit to effect a desired outcome, such as to treat an infectious disease or vaccinate against such diseases. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label that indicates the contents and/or purpose of the kit and/or its components.

Definitions

As used herein, "a," "an," or "the" can mean one or more than one.

Unless specifically stated or obvious from context, as used herein, the term "or" is understood to be inclusive and covers both "or" and "and".

Further, the term "about" when used in connection with a referenced numeric indication means the referenced numeric indication plus or minus up to 10% of that referenced numeric indication, e.g., within (plus or minus) 10%, 9%, 8%, 7%, 6%, 5%, 4%, 3%, 2%, 1%, 0.5%, 0.1%, 0.05%, or 0.01% of the stated value. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified.

As used herein, the word "include," and its variants, is intended to be non-limiting, such that recitation of items in a list is not to the exclusion of other like items that may also be useful in the compositions and methods of this technology.

Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of." As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein. This invention is further illustrated by the following non-limiting examples.

EXAMPLES

Figure 1A:
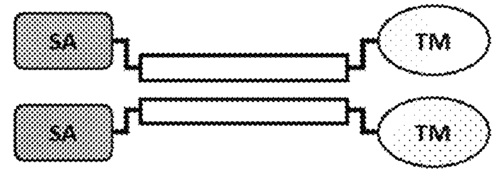
Figure 1B:
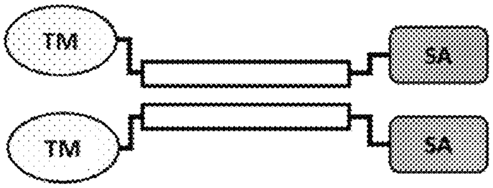
Figure 1C:
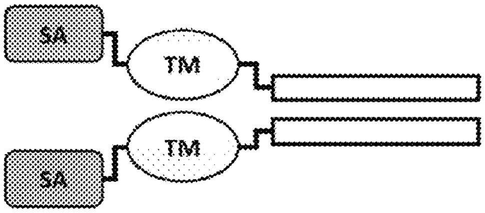
Figure 1D:
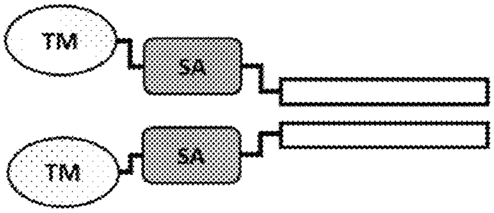
Figure 1E:
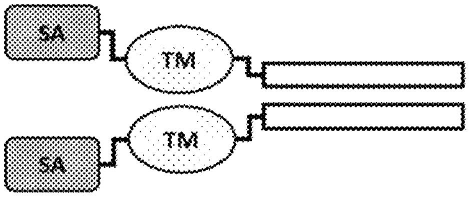
Figure 1F:
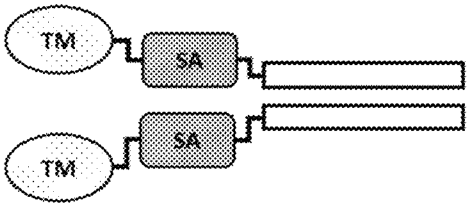
Figure 2A:
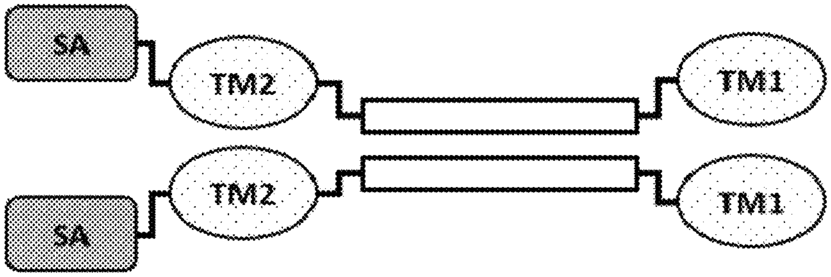
Figure 2B:
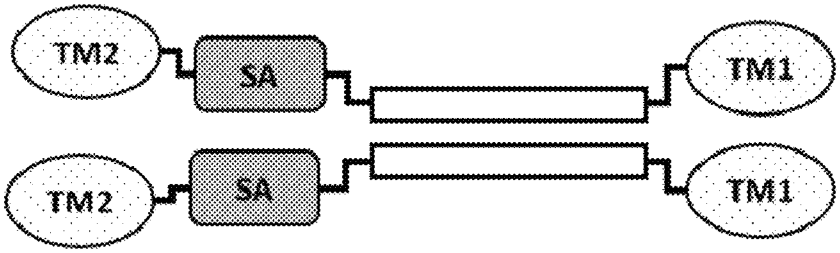
Figure 2C:
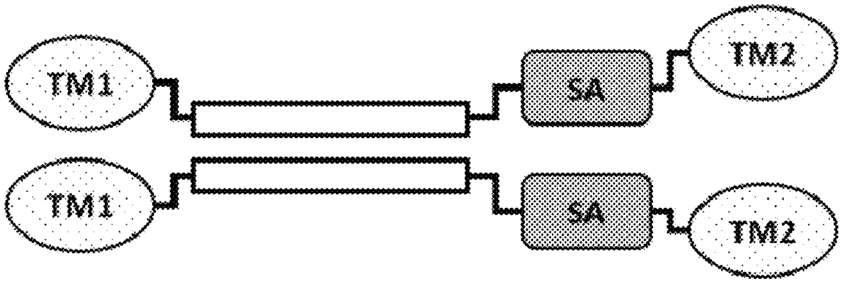
Figure 2D:
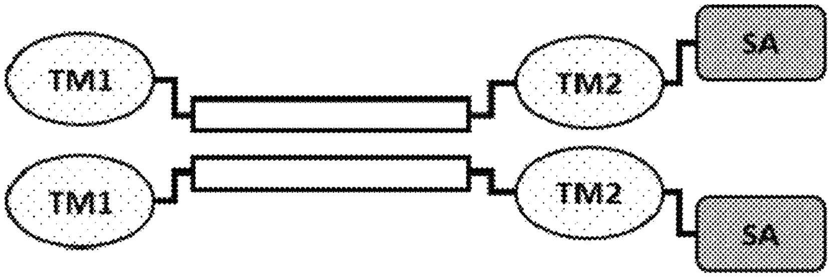
Figure 3A:
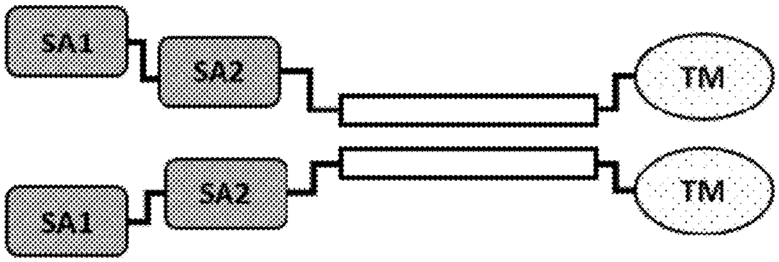
Figure 3B:
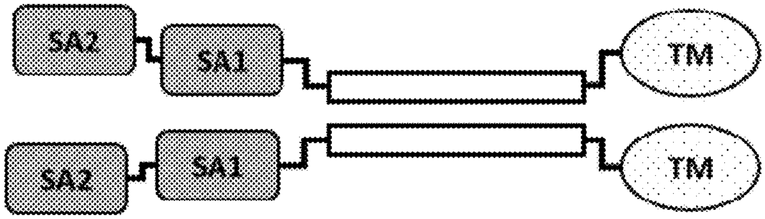
Figure 3C:
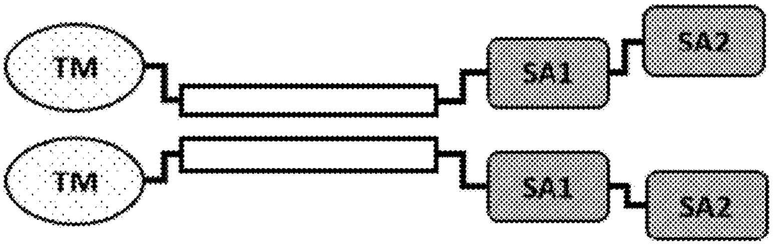
Figure 3D:
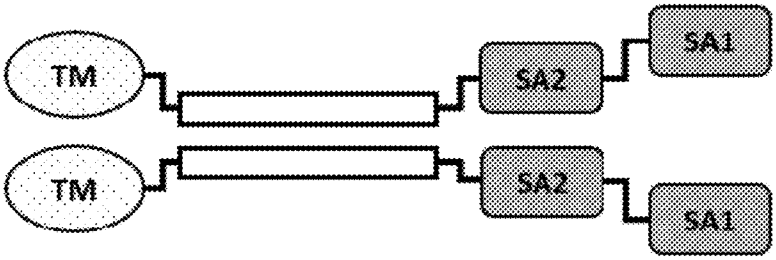
Figure 3E:
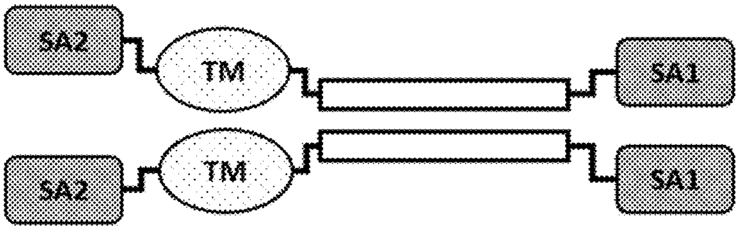
Figure 3F:
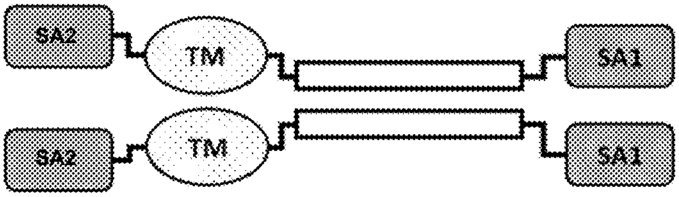
Figure 3G:
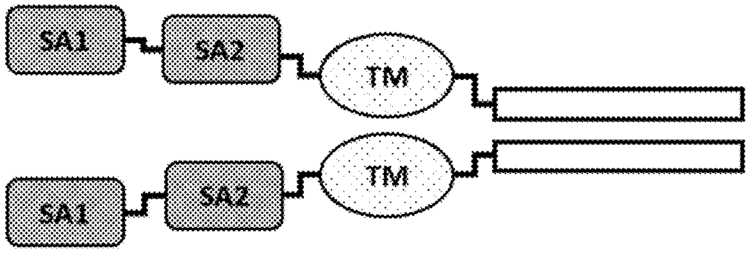
Figure 3H:
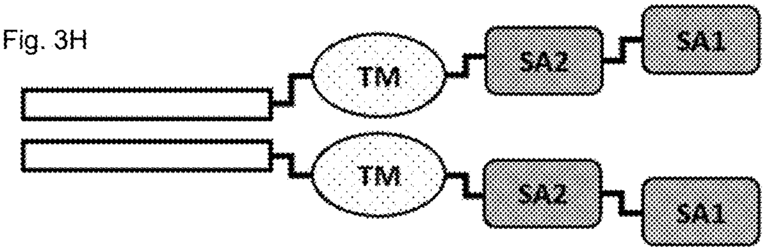
Figure 4A:
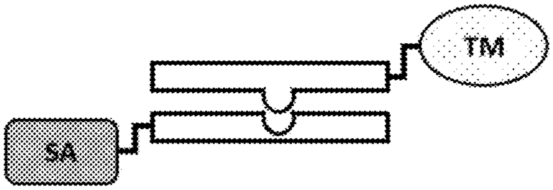
Figure 4B:
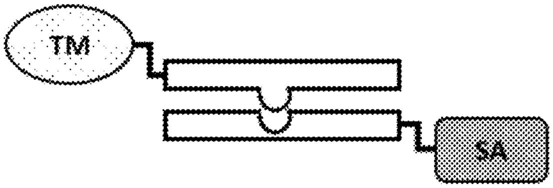
Figure 4C:
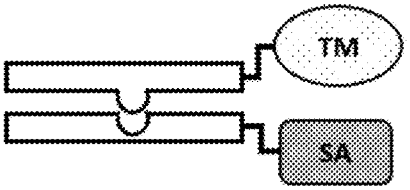
Figure 4D:
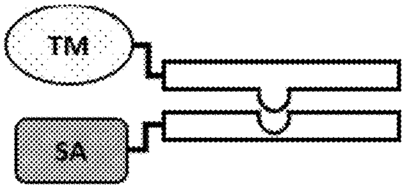
Figure 5A:
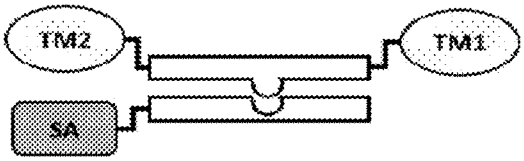
Figure 5B:
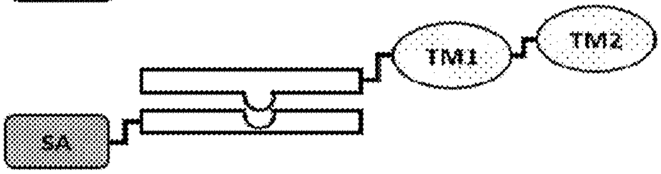
Figure 5C:
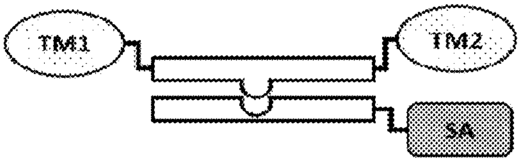
Figure 5D:
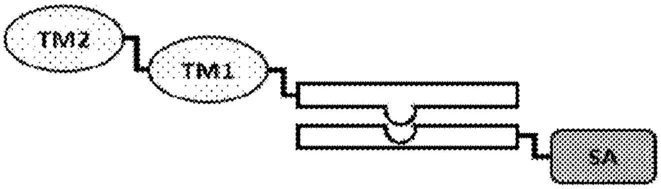
Figure 5E:
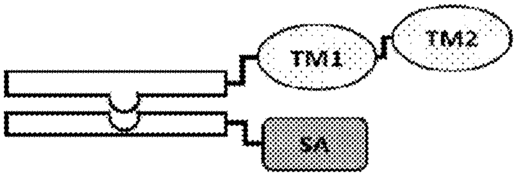
Figure 5F:
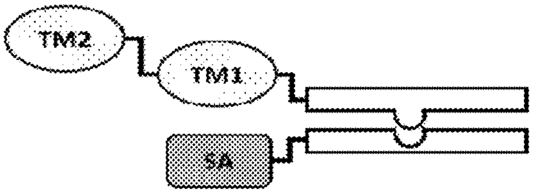
Figure 6A:
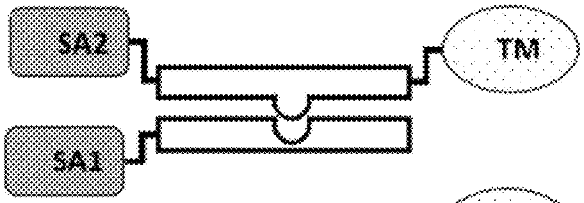
Figure 6B:
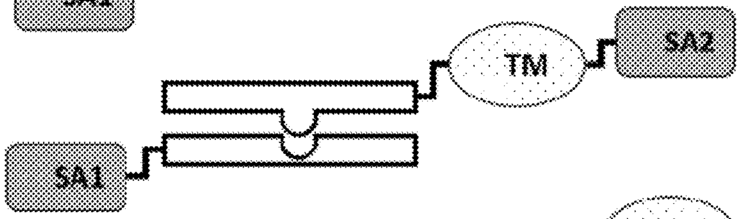
Figure 6C:
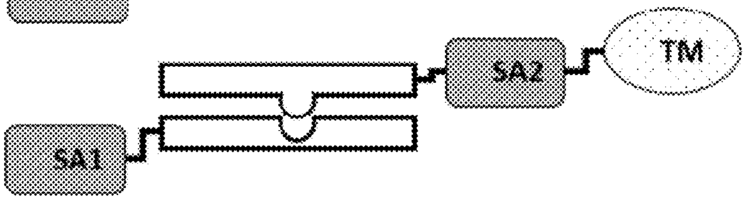
Figure 6D:
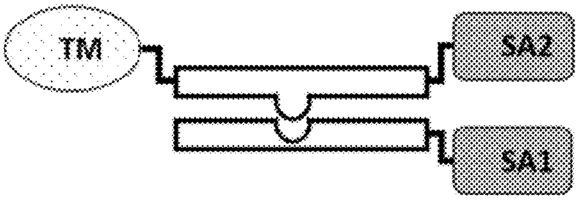
Figure 6E:
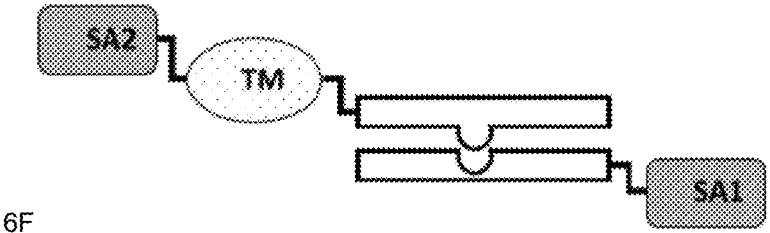
Figure 6F:
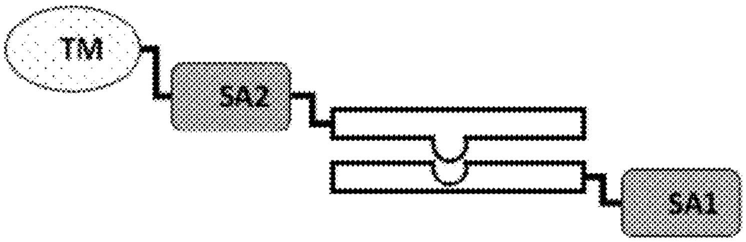
Figure 6G:
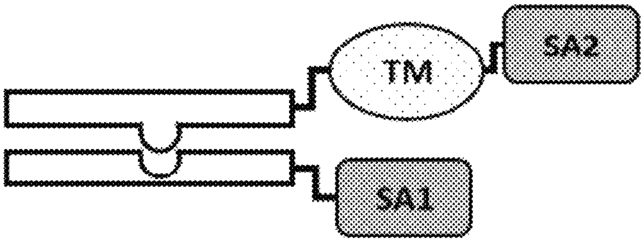
Figure 6H:
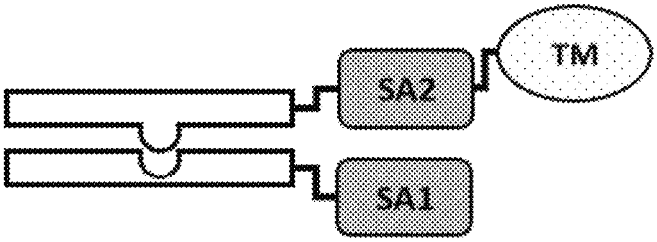
Figure 6I:
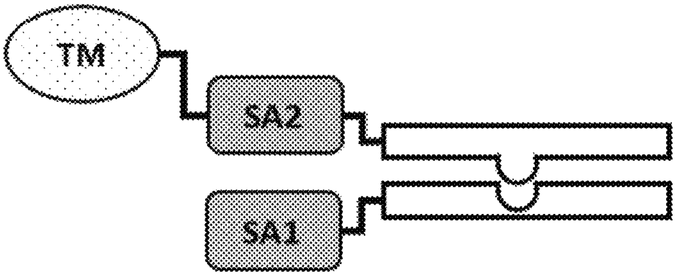
Figure 6J:
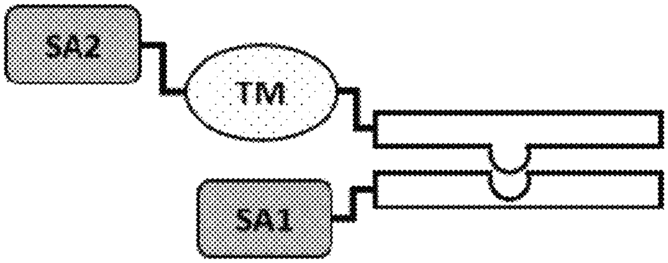
Figure 7A:
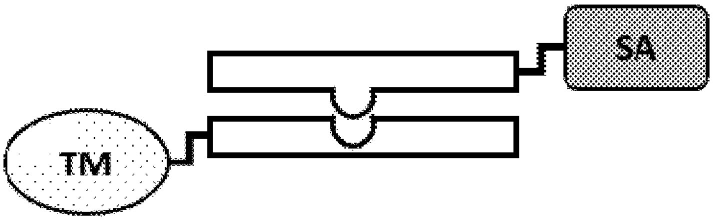
Figure 7B:
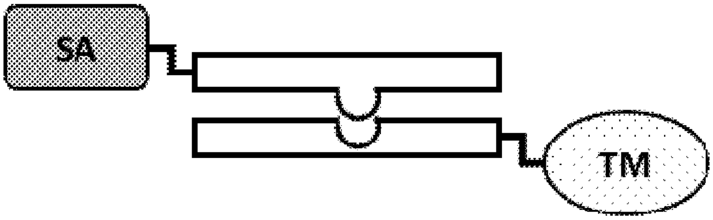
Figure 7C:
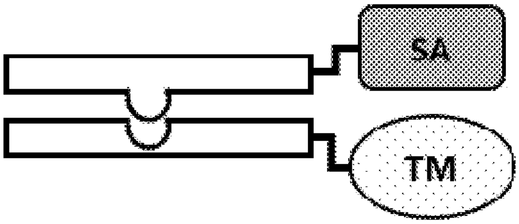
Figure 7D:
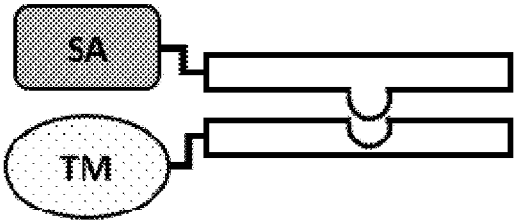
Figure 8A:
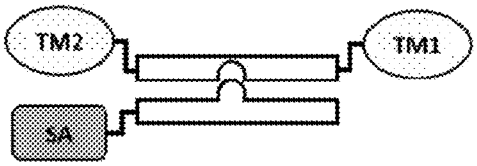
Figure 8B:
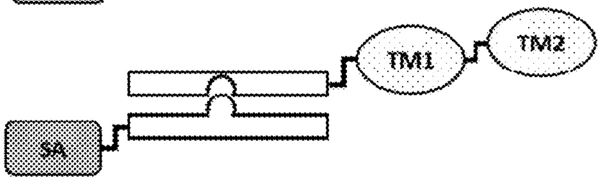
Figure 8C:
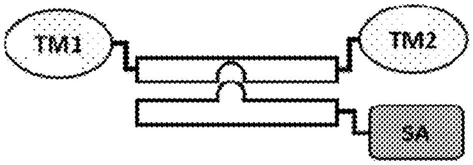
Figure 8D:
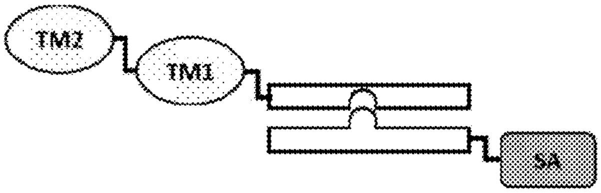
Figure 8E:
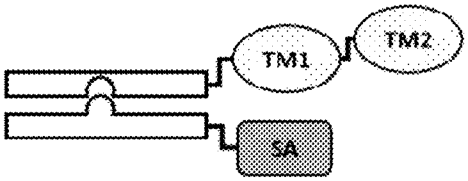
Figure 8F:
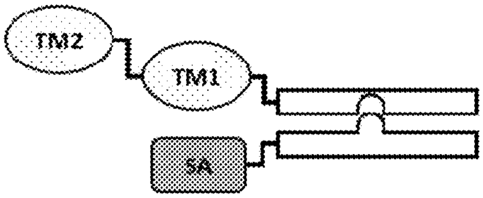
Figure 9A:
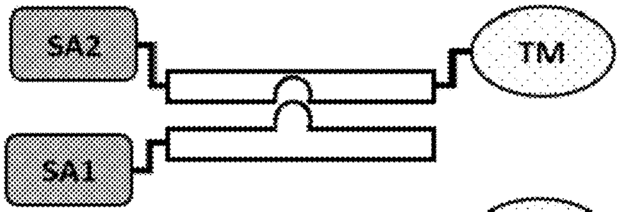
Figure 9B:
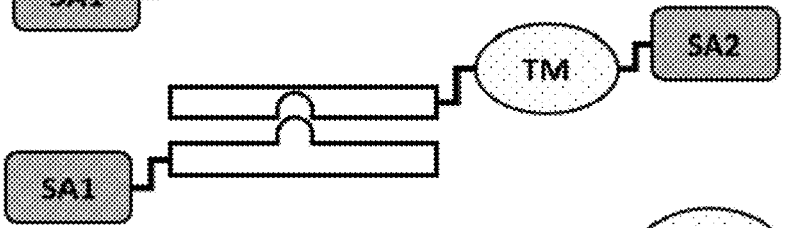
Figure 9C:
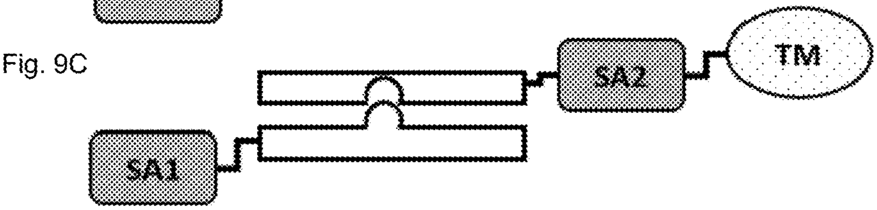
Figure 9D:
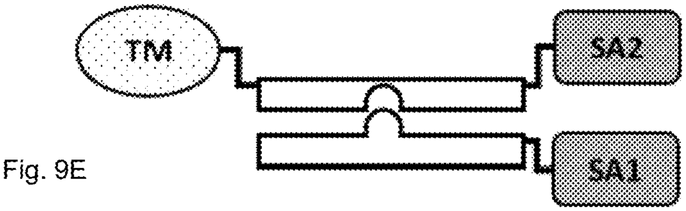
Figure 9E:
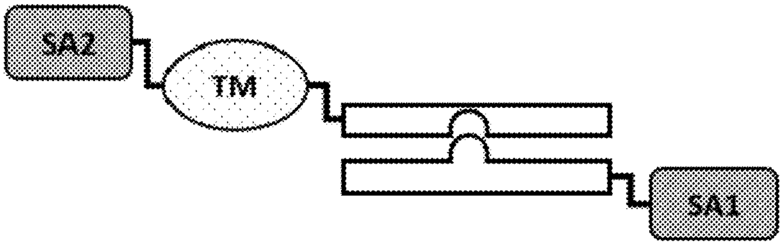
Figure 9F:
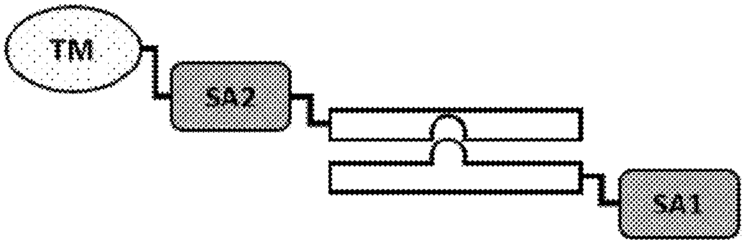
Figure 9G:
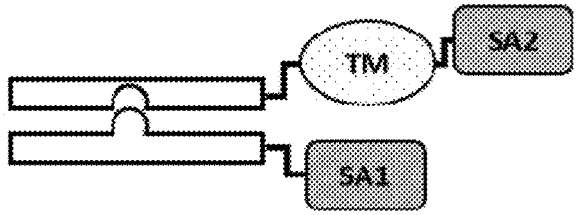
Figure 9H:
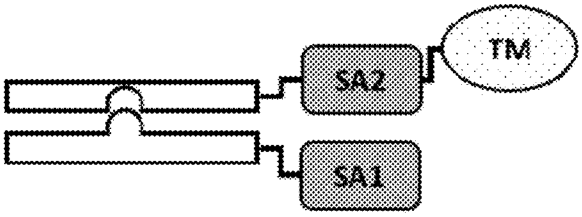
Figure 9I:
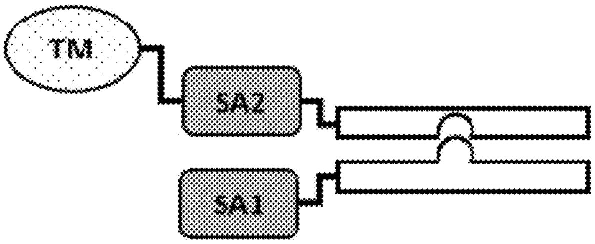
Figure 9J:
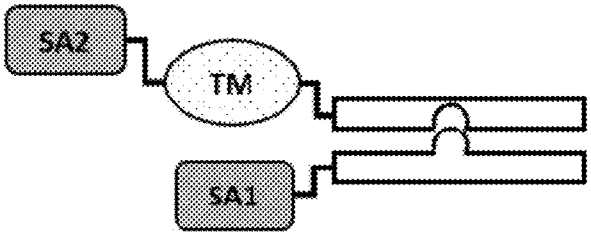
Figure 10A:
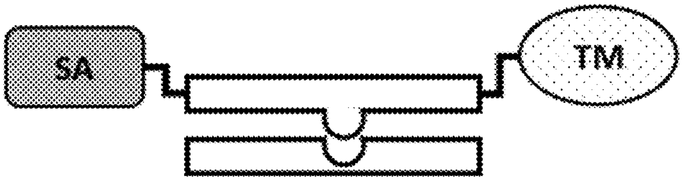
Figure 10B:
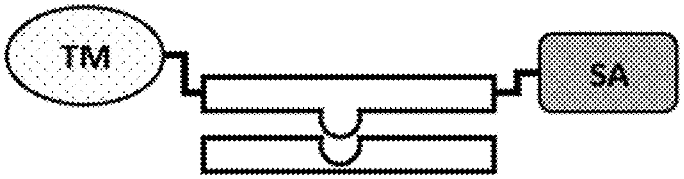
Figure 10C:
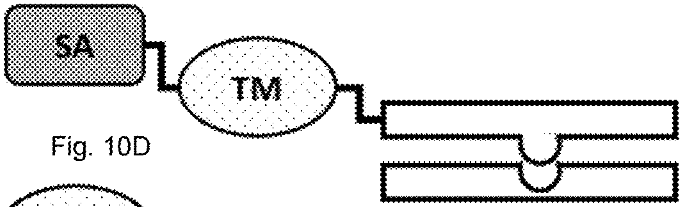
Figure 10D:
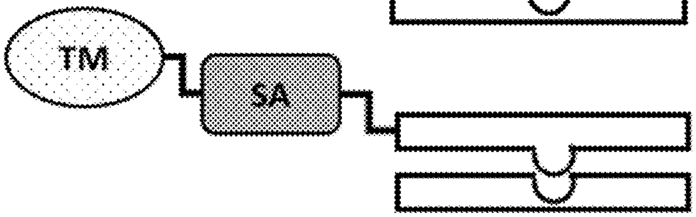
Figure 10E:
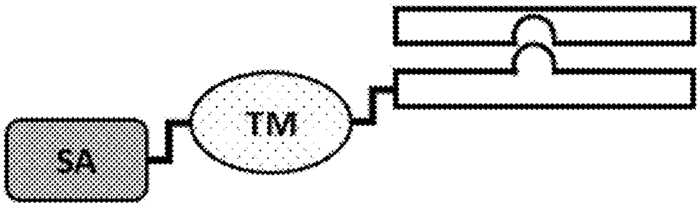
Figure 10F:
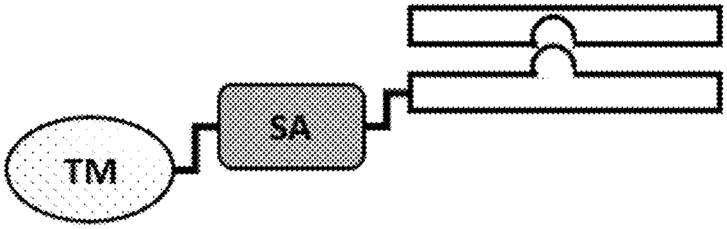
Figure 11A:
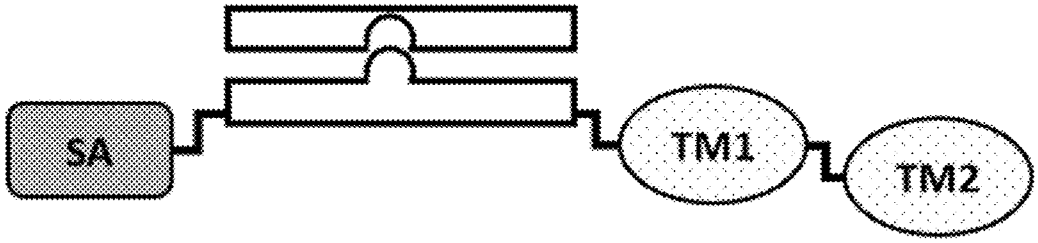
Figure 11B:
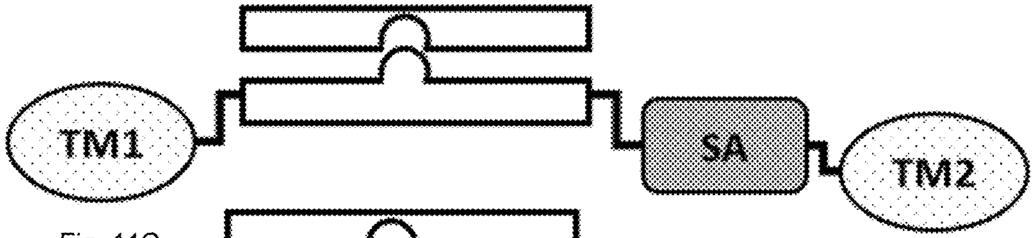
Figure 11C:
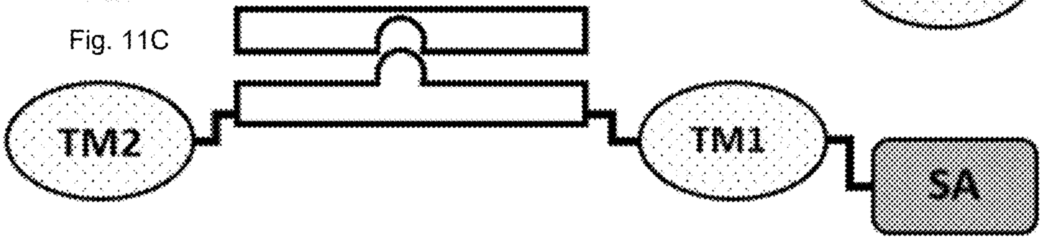
Figure 11D:
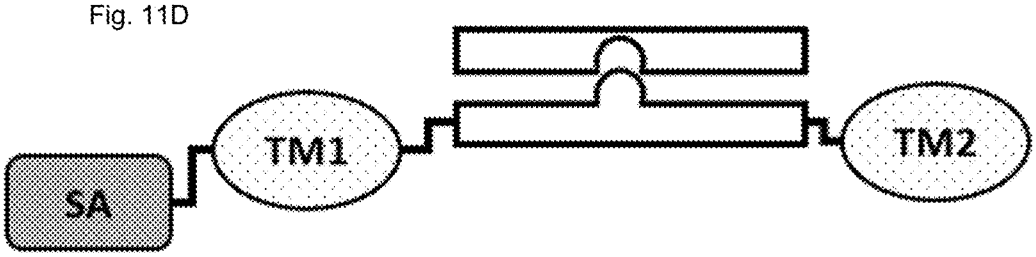
Figure 11E:
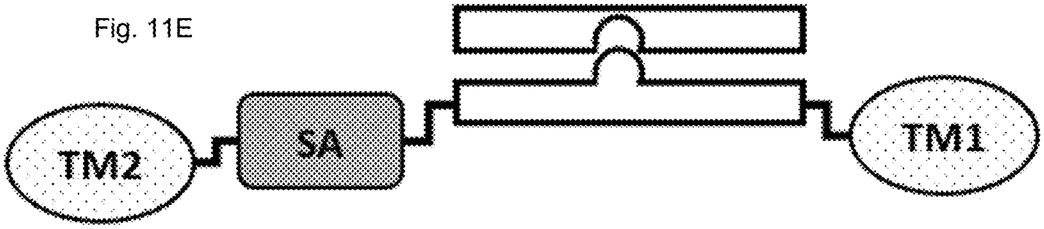
Figure 11F:
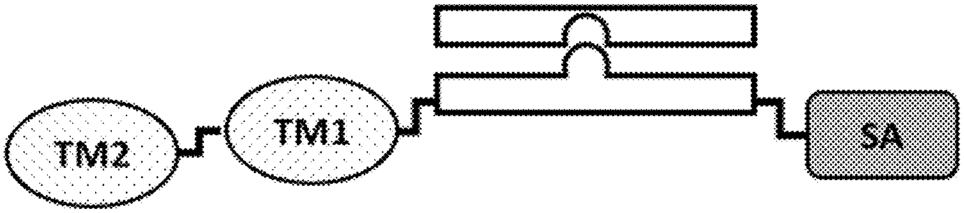
Figure 11G:
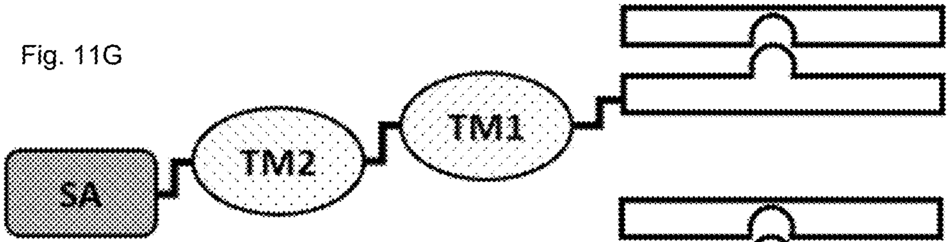
Figure 11H:
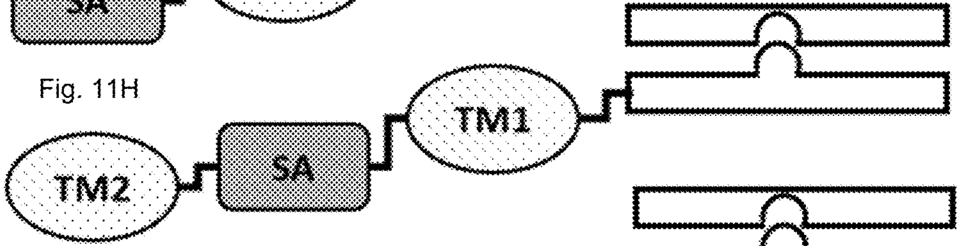
Figure 11I:
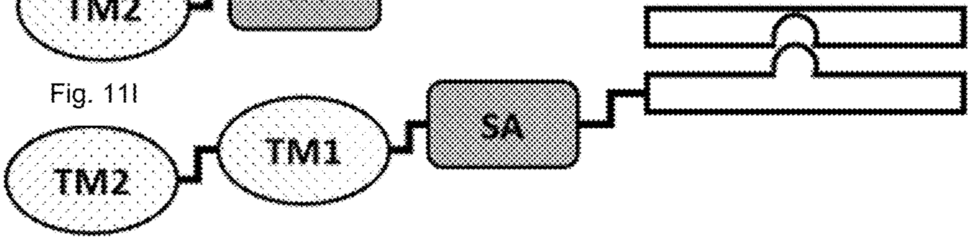
Figure 11J:
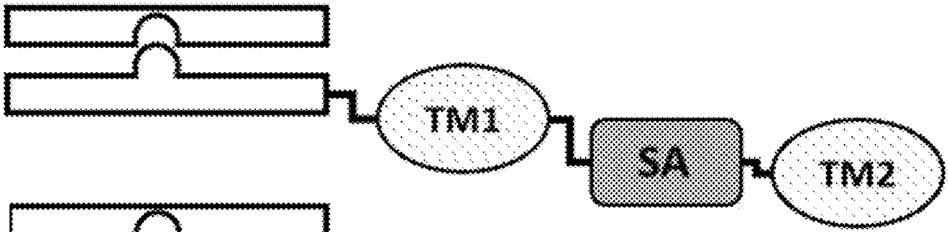
Figure 11K:
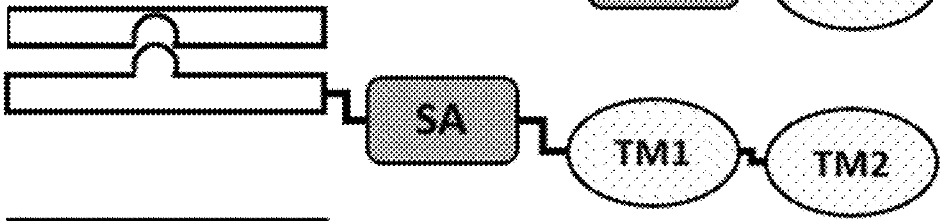
Figure 11L:
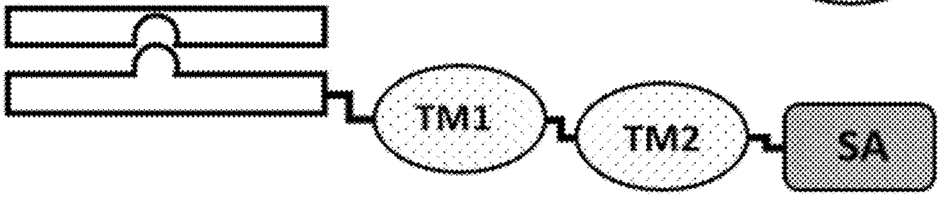
Figure 12A:
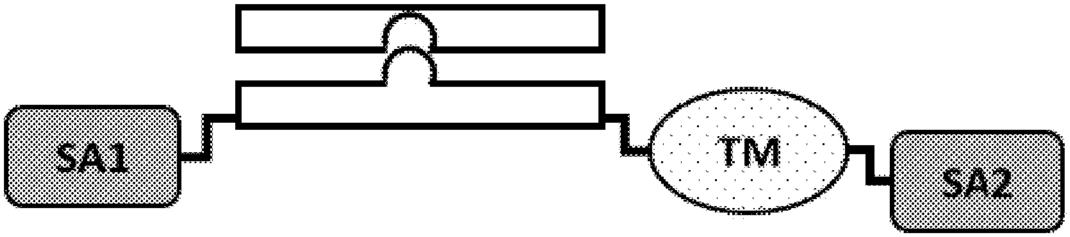
Figure 12B:
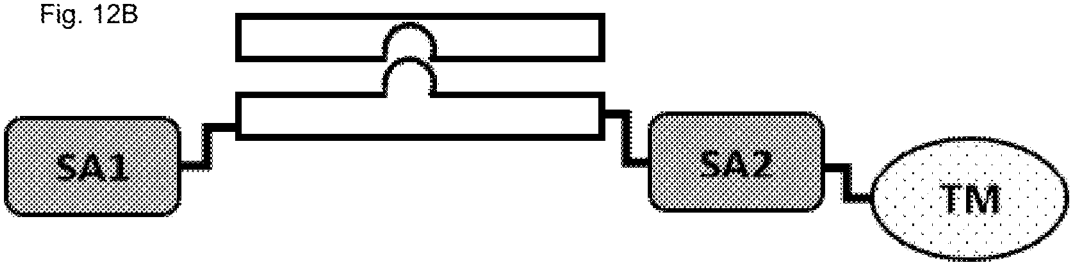
Figure 12C:
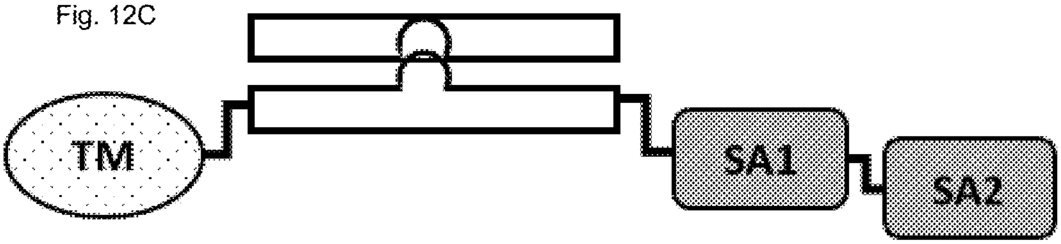
Figure 12D:
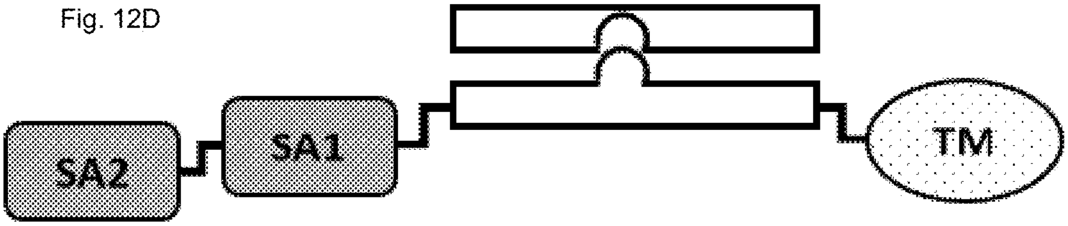
Figure 12E:
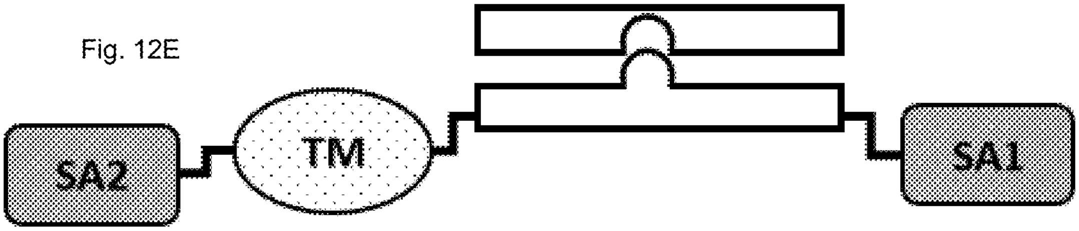
Figure 12F:
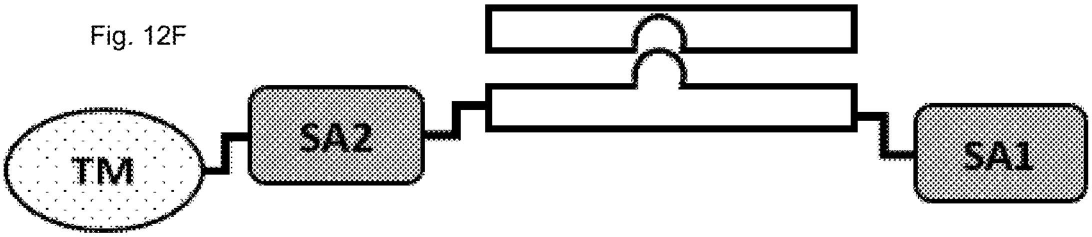
Figure 12G:
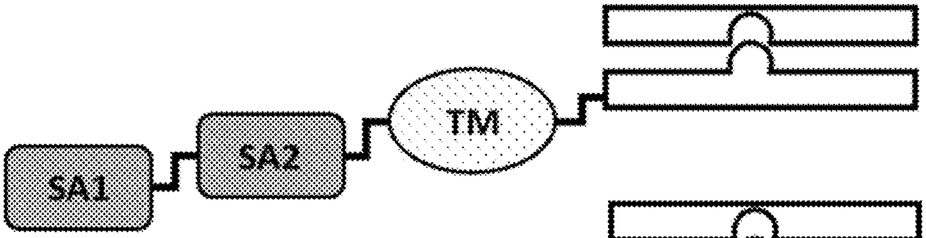
Figure 12H:
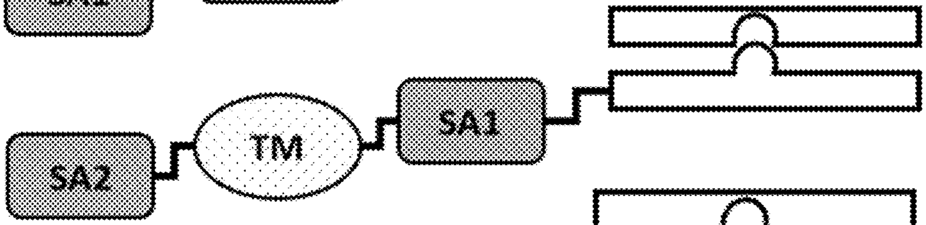
Figure 12I:
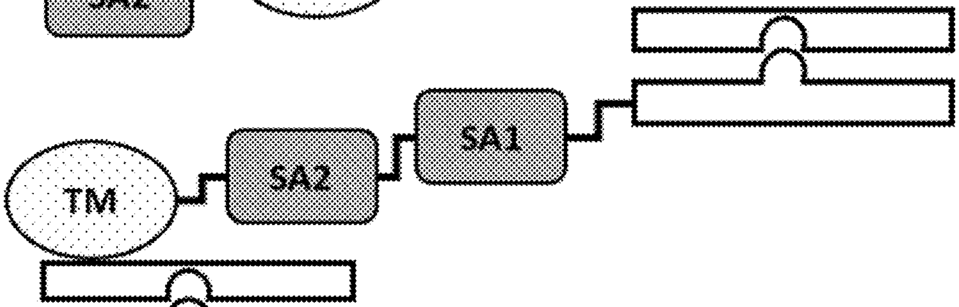
Figure 12J:
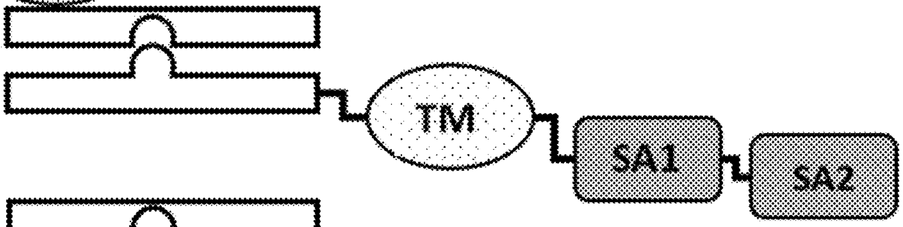
Figure 12K:
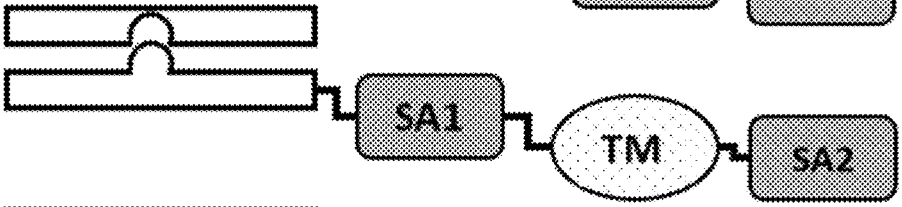
Figure 12L:
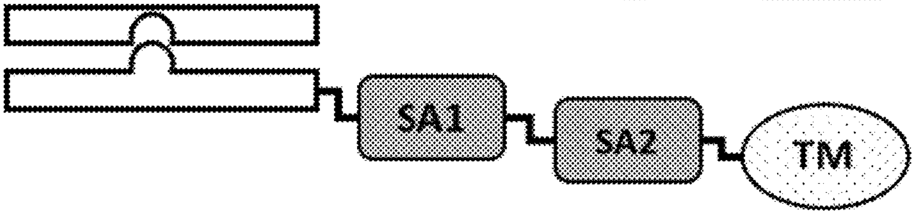
Figure 13A:
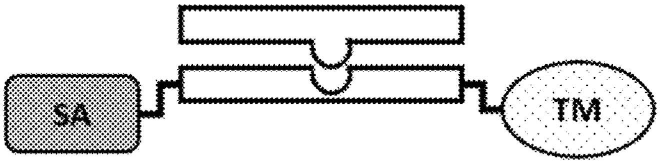
Figure 13B:
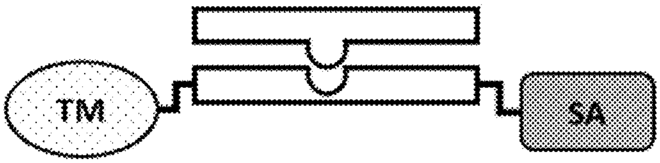
Figure 13C:
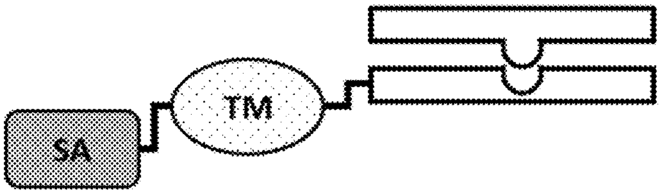
Figure 13D:
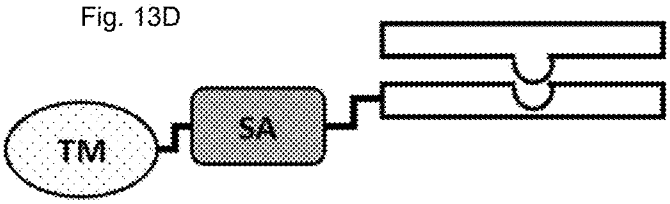
Figure 13E:
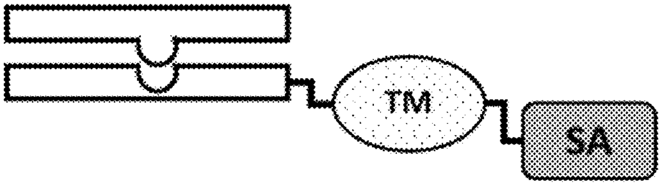
Figure 13F:
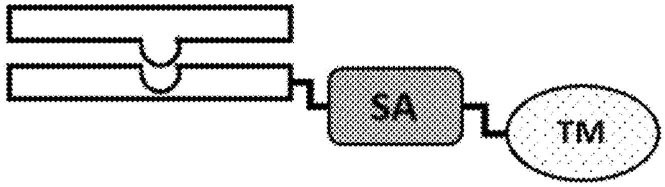
Figure 14A:
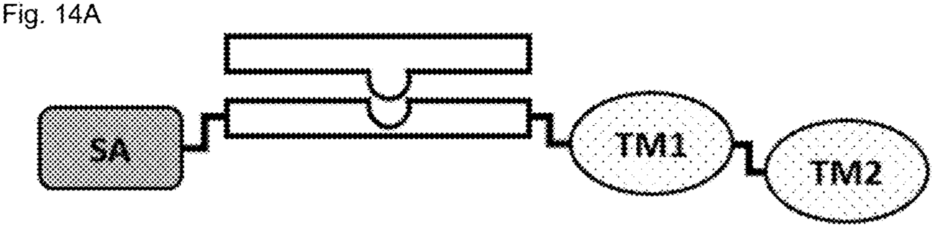
Figure 14B:
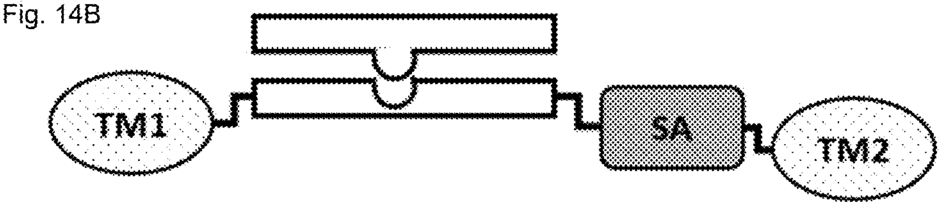
Figure 14C:
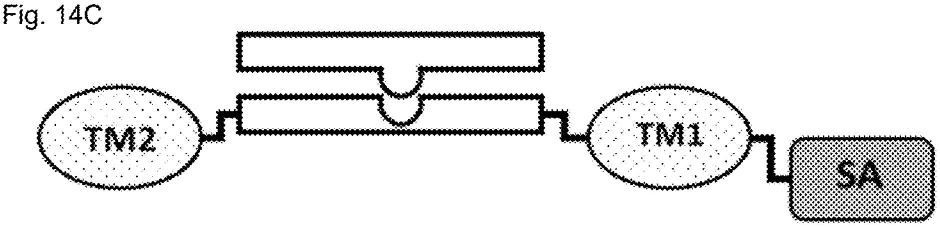
Figure 14D:
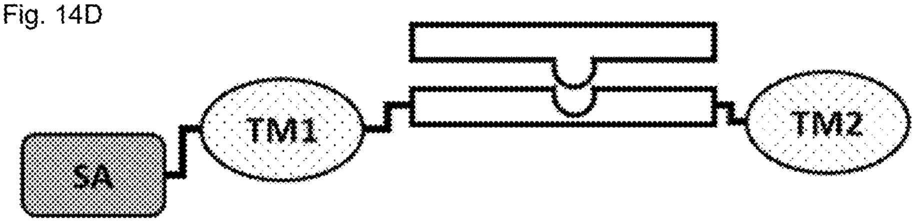
Figure 14E:
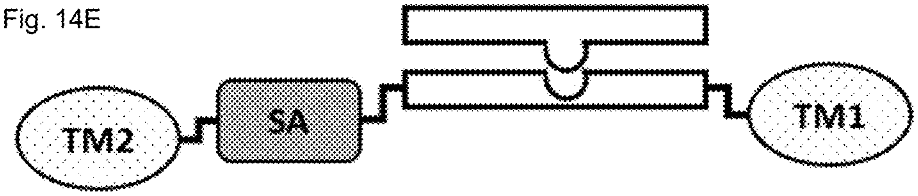
Figure 14F:
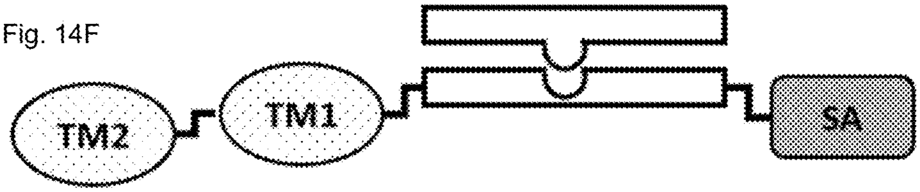
Figure 14G:
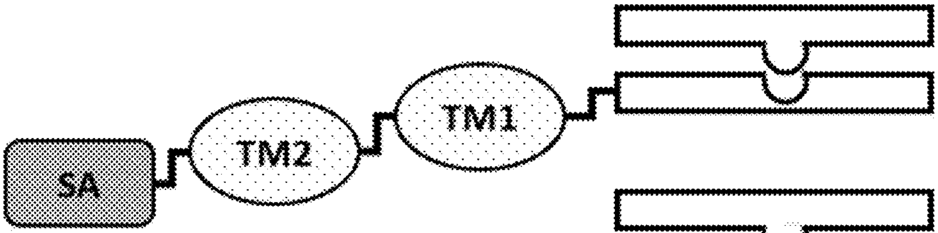
Figure 14H:
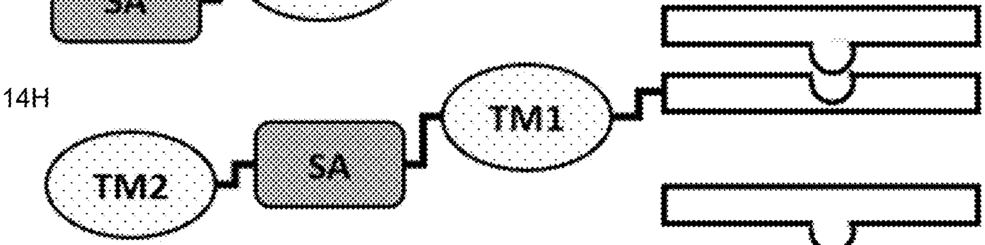
Figure 14I:
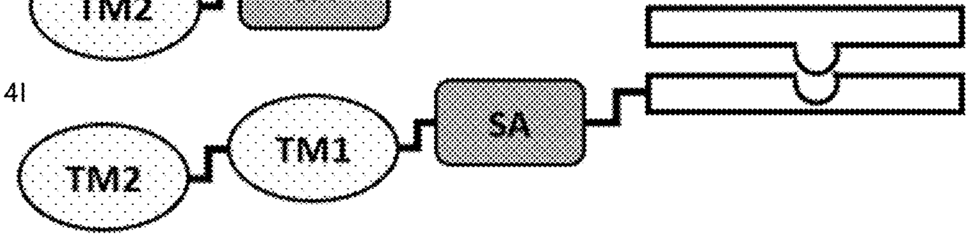
Figure 14J:
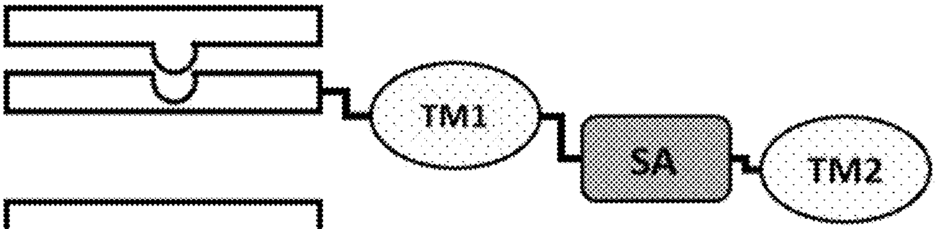
Figure 14K:
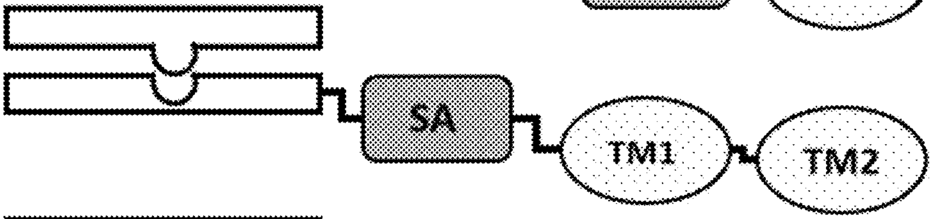
Figure 14L:
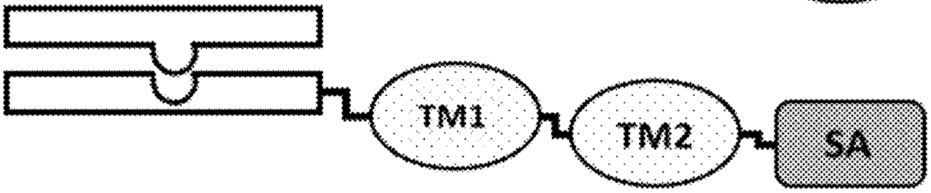
Figure 15A:
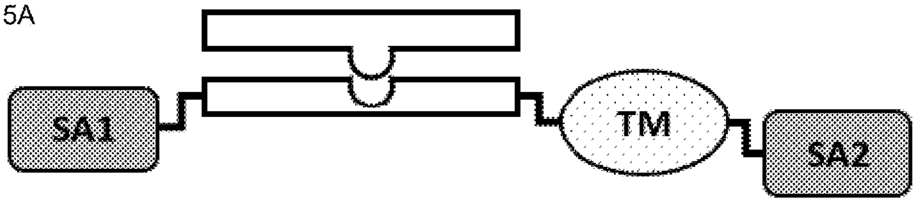
Figure 15B:
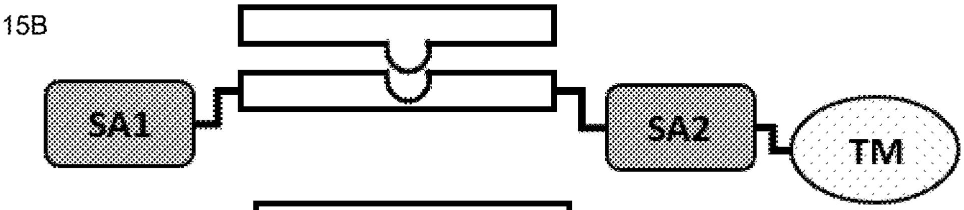
Figure 15C:
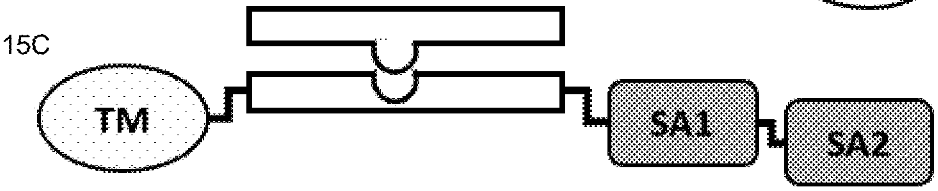
Figure 15D:
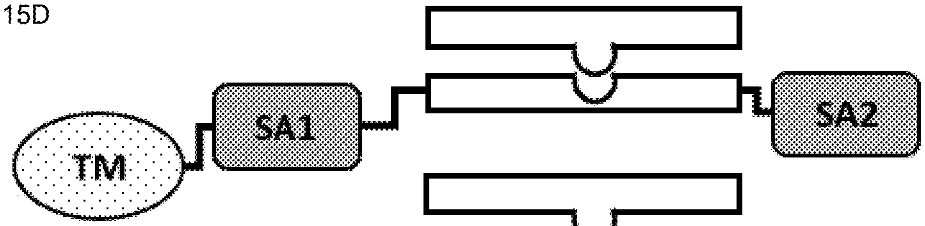
Figure 15E:
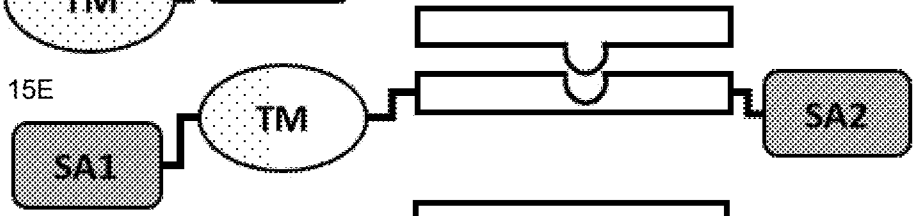
Figure 15F:
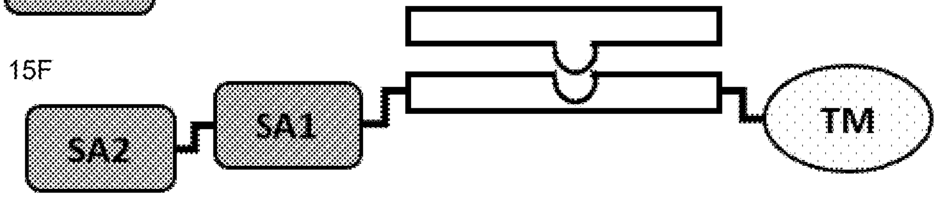
Figure 15G:
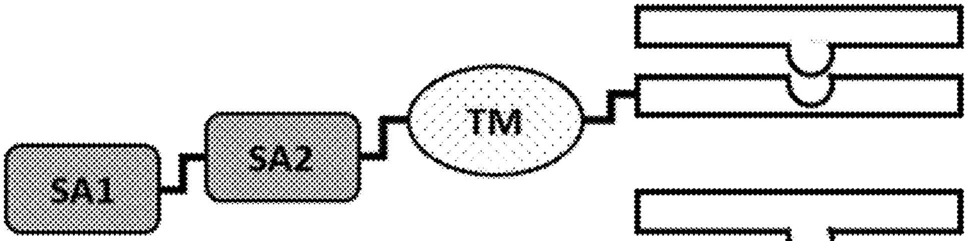
Figure 15H:
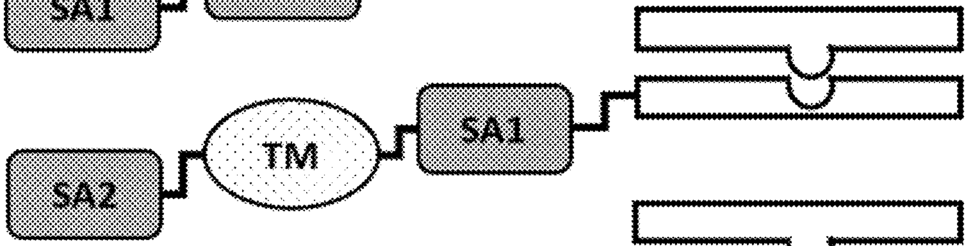
Figure 15I:
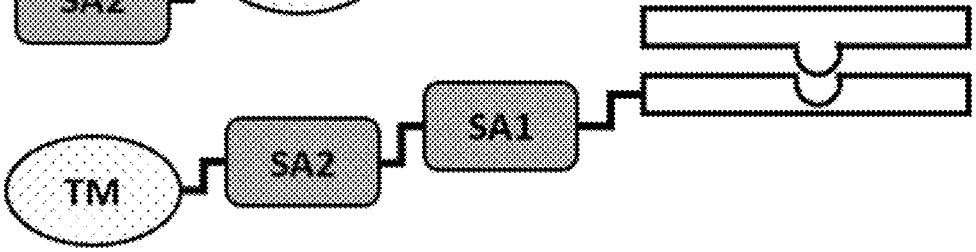
Figure 15J:
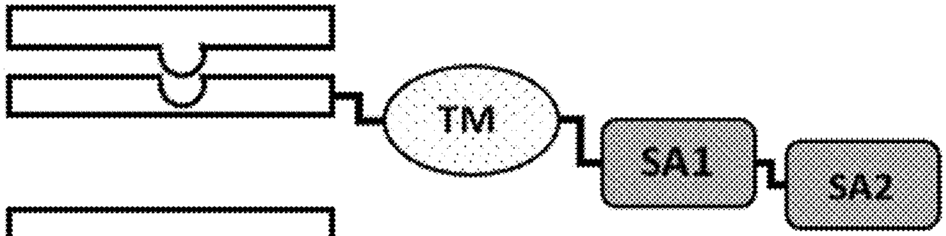
Figure 15K:
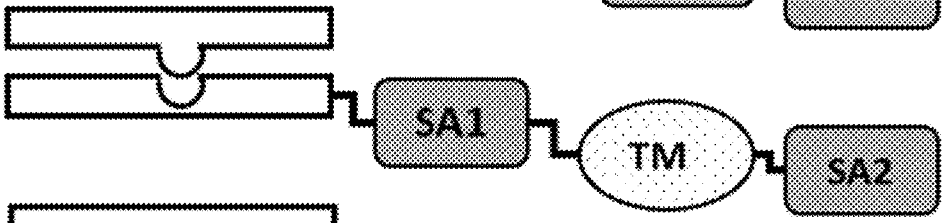
Figure 15L:
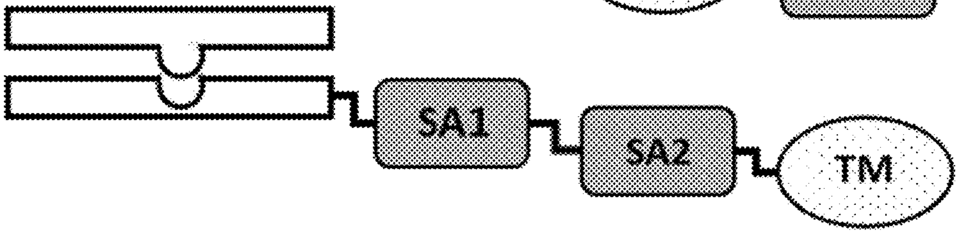
Figure 16A:
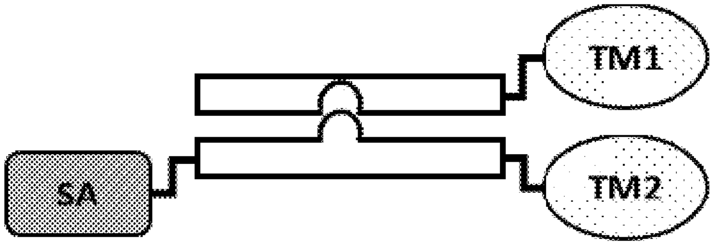
Figure 16B:
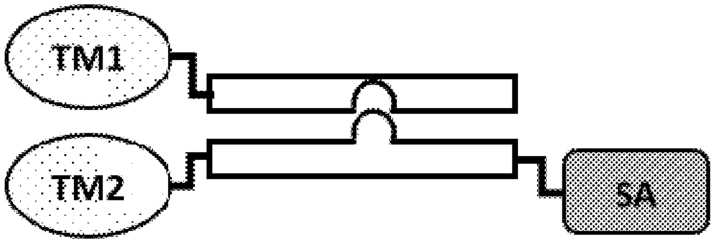
Figure 16C:
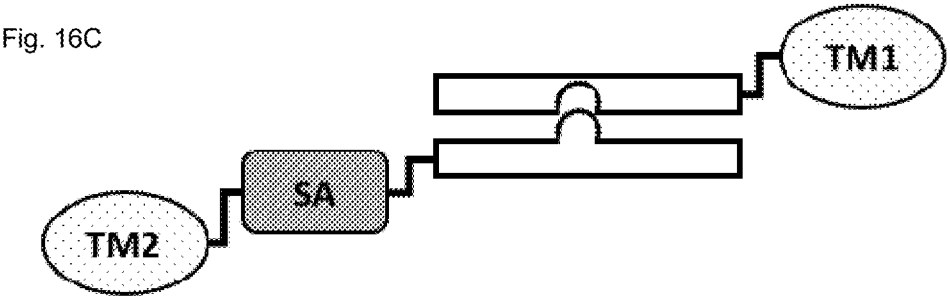
Figure 16D:
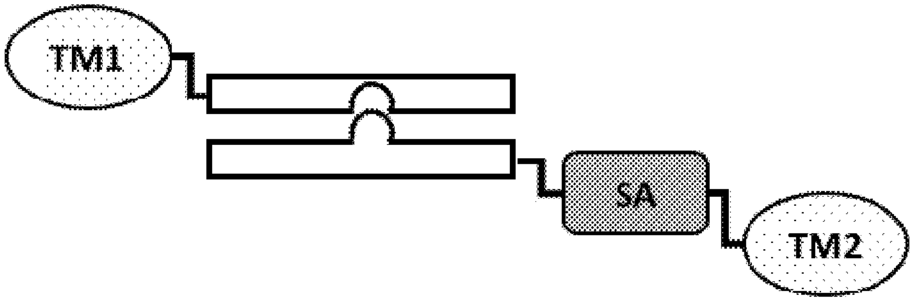
Figure 16E:
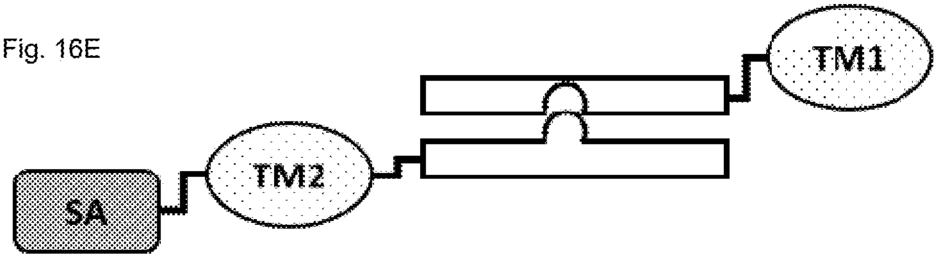
Figure 16F:
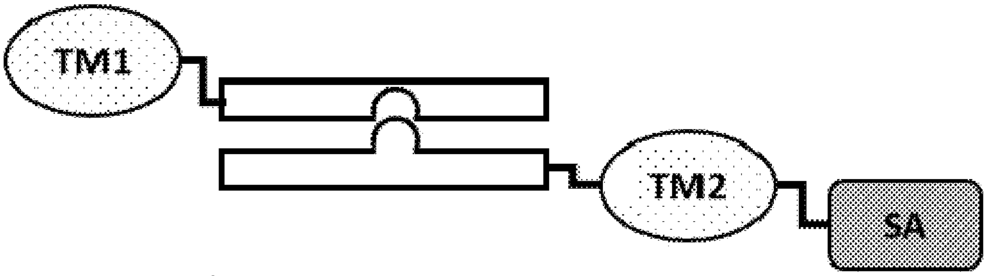
Figure 16G:
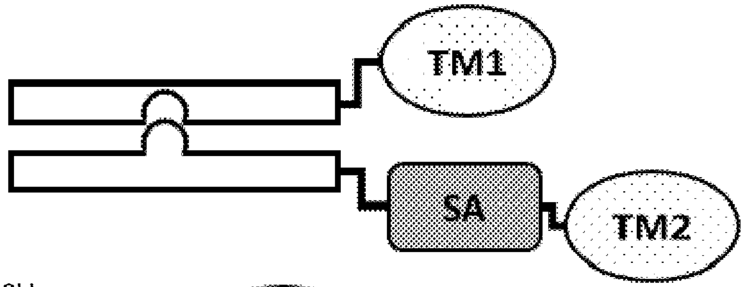
Figure 16H:
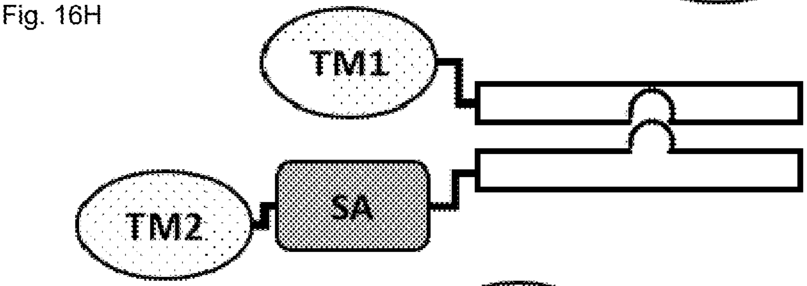
Figure 16I:
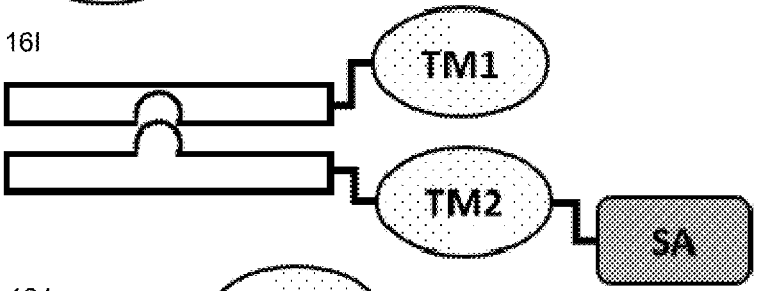
Figure 16J:
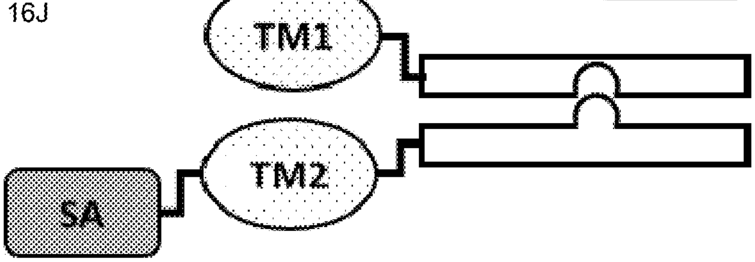
Figure 17A:
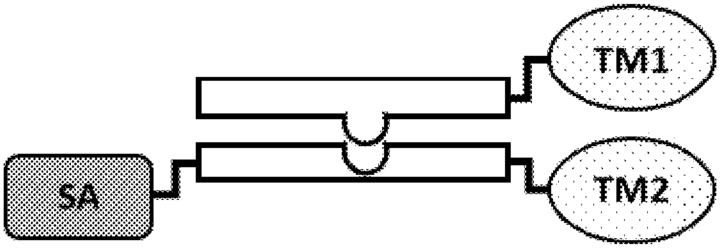
Figure 17B:
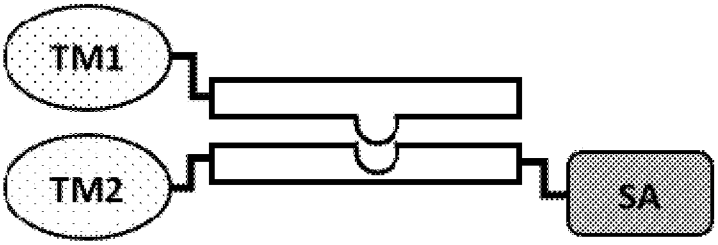
Figure 17C:
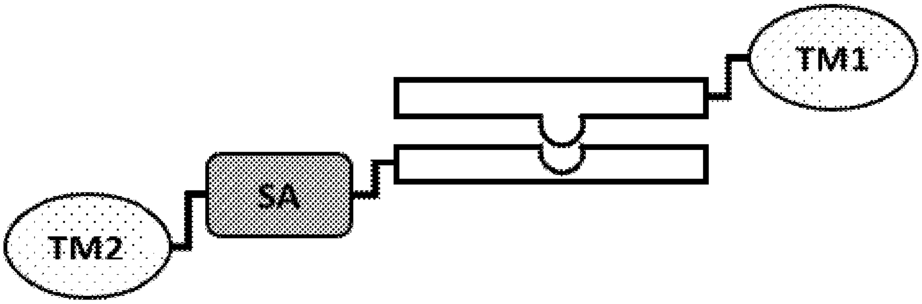
Figure 17D:
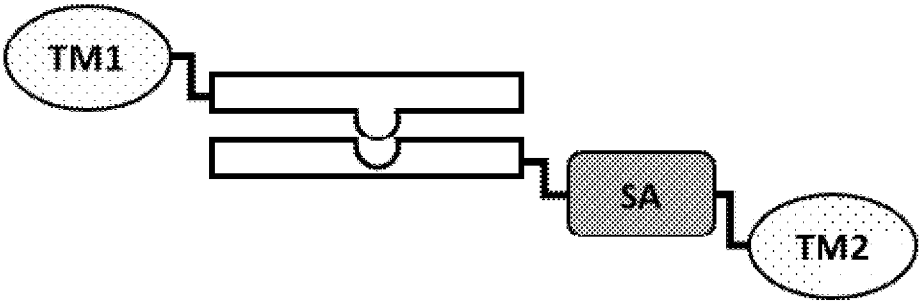
Figure 17E:
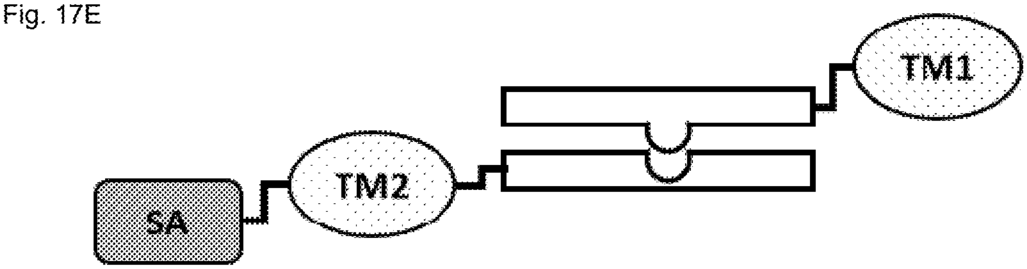
Figure 17F:
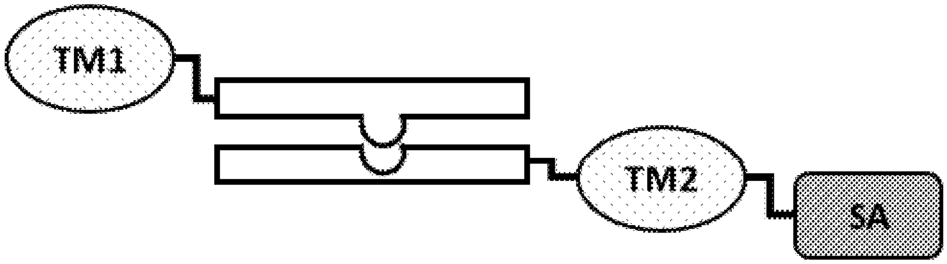
Figure 17G:
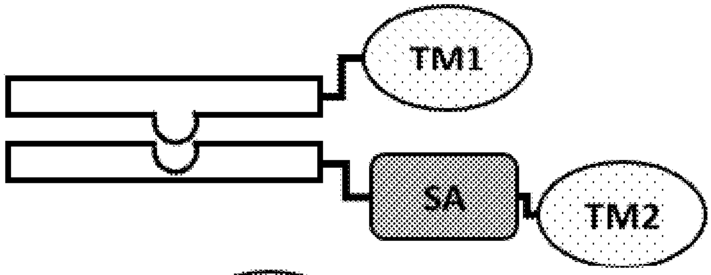
Figure 179H:
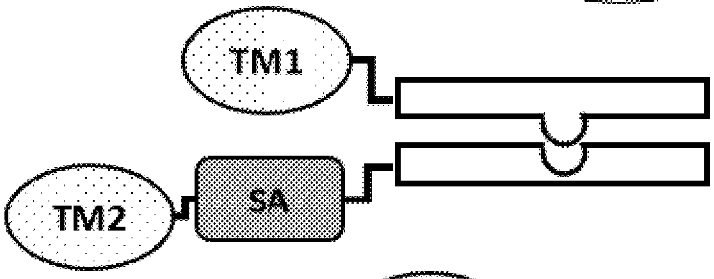
Figure 17I:
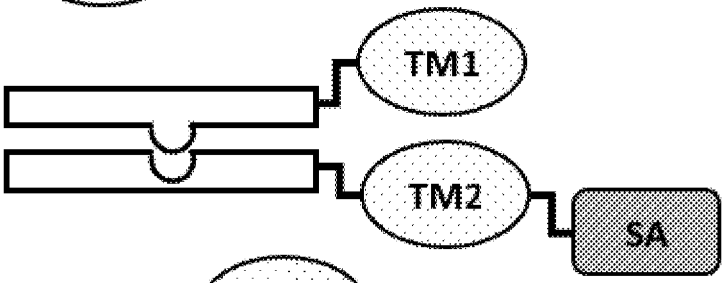
Figure 17J:
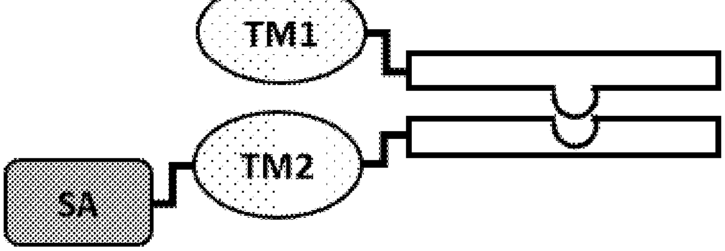
Figure 18A:
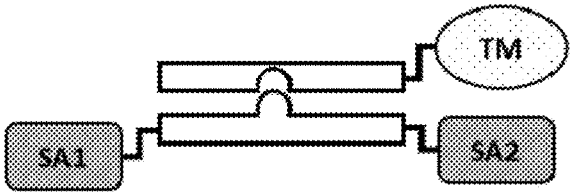
Figure 18B:
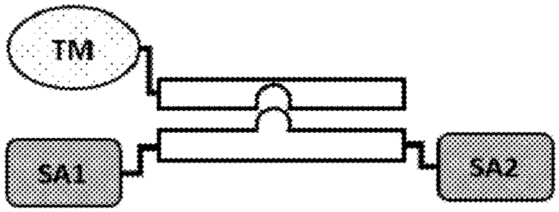
Figure 18C:
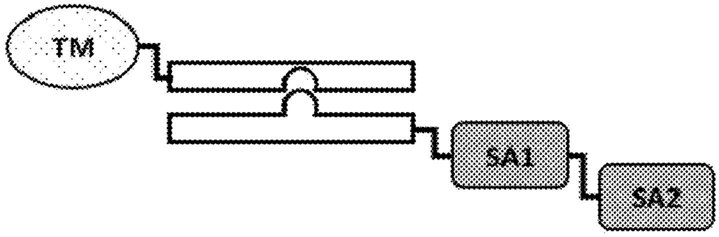
Figure 18D:
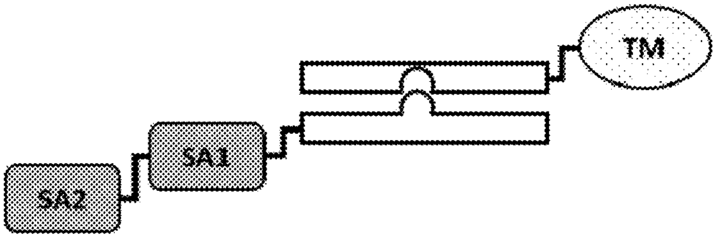
Figure 18E:
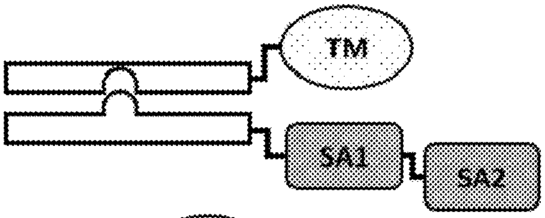
Figure 18F:
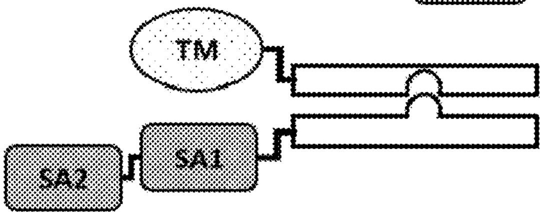
Figure 19A:
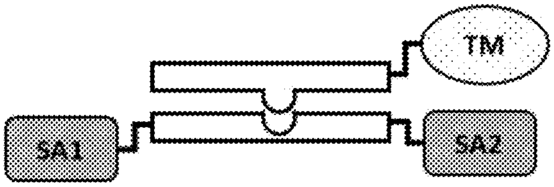
Figure 19B:
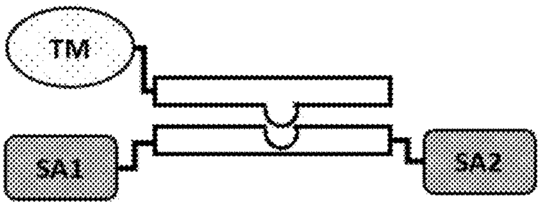
Figure 19C:
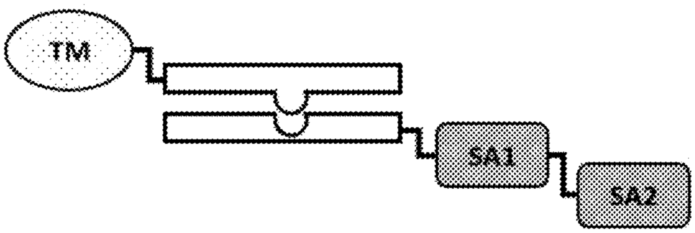
Figure 19D:
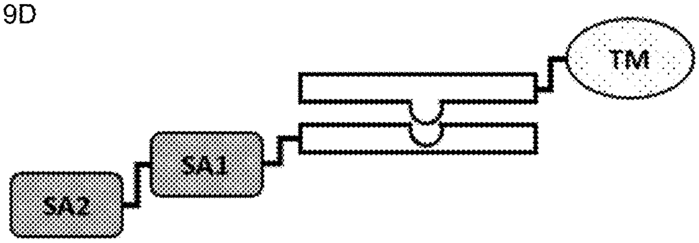
Figure 19E:
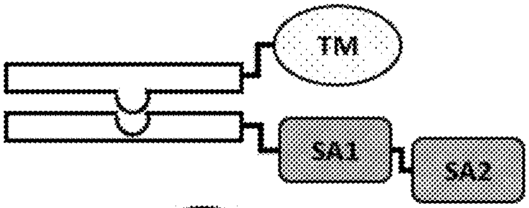
Figure 19F:
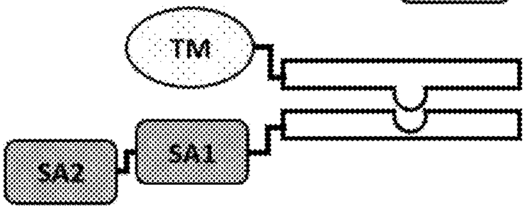
Figure 20:
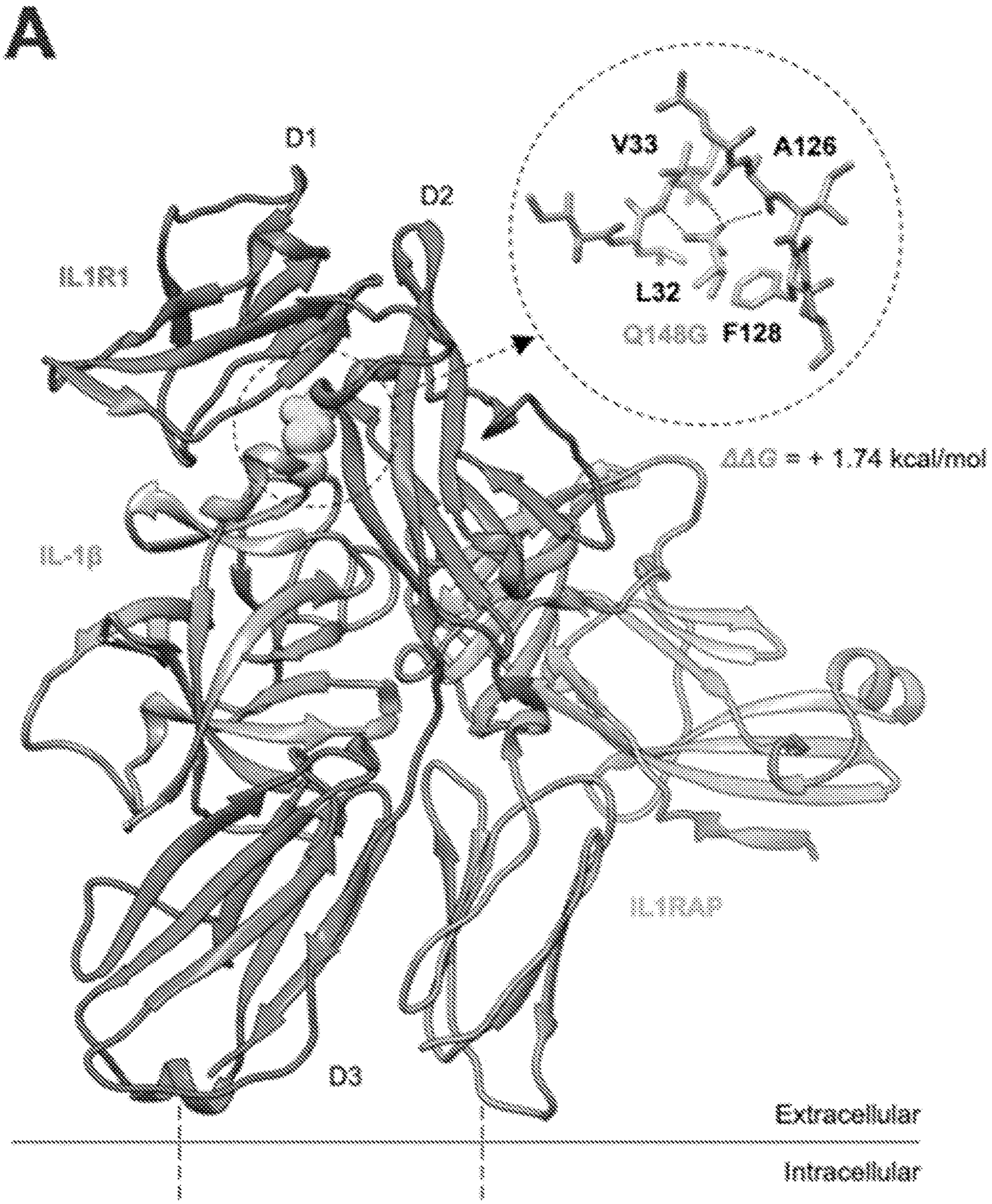
FIGS. 20A-G shows that Q148G is an IL-1β mutant with strongly reduced biological activity that can be reactivated upon targeting using CD8α sdAbs (single domain antibodies). Panel A shows a model of the IL-1R complex, consisting of the IL-1R1 (red, domains D1-D3) and IL-1RAP (orange) receptor subunits together with the IL-1β ligand, showing a detail of the Q148G mutation. Panel B shows NF-κB-driven luciferase reporter gene expression in HEK-Blue-IL1R cells. NF-κB activity is normalized to background and expressed as fold induction. WT IL-1β activity is shown as reference. Each data point represents the mean of four independent experiments±s.e.m. Panel C. Blueprint of the CD8α ALN-1 design: IL-1β Q148G is coupled by a 20×GGS linker to a sdAb binding mouse CD8α. The Bcl110 sdAb fusion is used as an untargeted control. The C-terminal 9×His-tag allows for protein purification. Panel D shows a representative SDS-PAGE protein gel demonstrating purity after recombinant production in HEK-293F cells. Panel E shows a proof-of-concept for CD8α ALN-1 targeting using NF-κB-driven luciferase reporter gene expression in HEK-Blue-IL1R cells, transiently transfected with or without CD8α. The activities of WT IL-1β and CD8α WT IL-1β are shown as reference. Each data point represents the mean of at least five independent experiments±s.e.m. Panel F shows nuclear translocation of NF-κB's p65 subunit in HEK-Blue-IL1R cells, assessed by confocal microscopy. HEK-Blue-IL1R cells were either transiently transfected with CD8α or empty plasmid DNA, mixed in a 1:1-ratio and plated 24 h prior to stimulation. Nuclei were stained with DAPI, NF-κB p65 Ser-536 and CD8α were stained with antibodies conjugated with AlexaFluor 647 or AlexaFluor 488 fluorochromes, respectively. The activities of vehicle, WT IL-1β and untargeted ALN-1 are included as controls. The scale bar (white) indicates 50 m. Panel G shows induction of NF-κB-, p38 MAPK- and AP-1-driven target genes in human 132 1N1 astrocytes transiently transfected with CD8α or an irrelevant target protein, evaluated by RT-qPCR. Data are normalized to WT IL-1β-induced gene expression and bars represent the mean±s.e.m. of two independent experiments. In each set of histograms, the left bar represents CD8α ALN-1 (CD8α+ cells); the middle bar represents Untargeted ALN-1 (CD8α+ cells); and the right bar represents CD8α ALN-1 (irrelevant target cells). See also FIG. 27.
Figure 20:
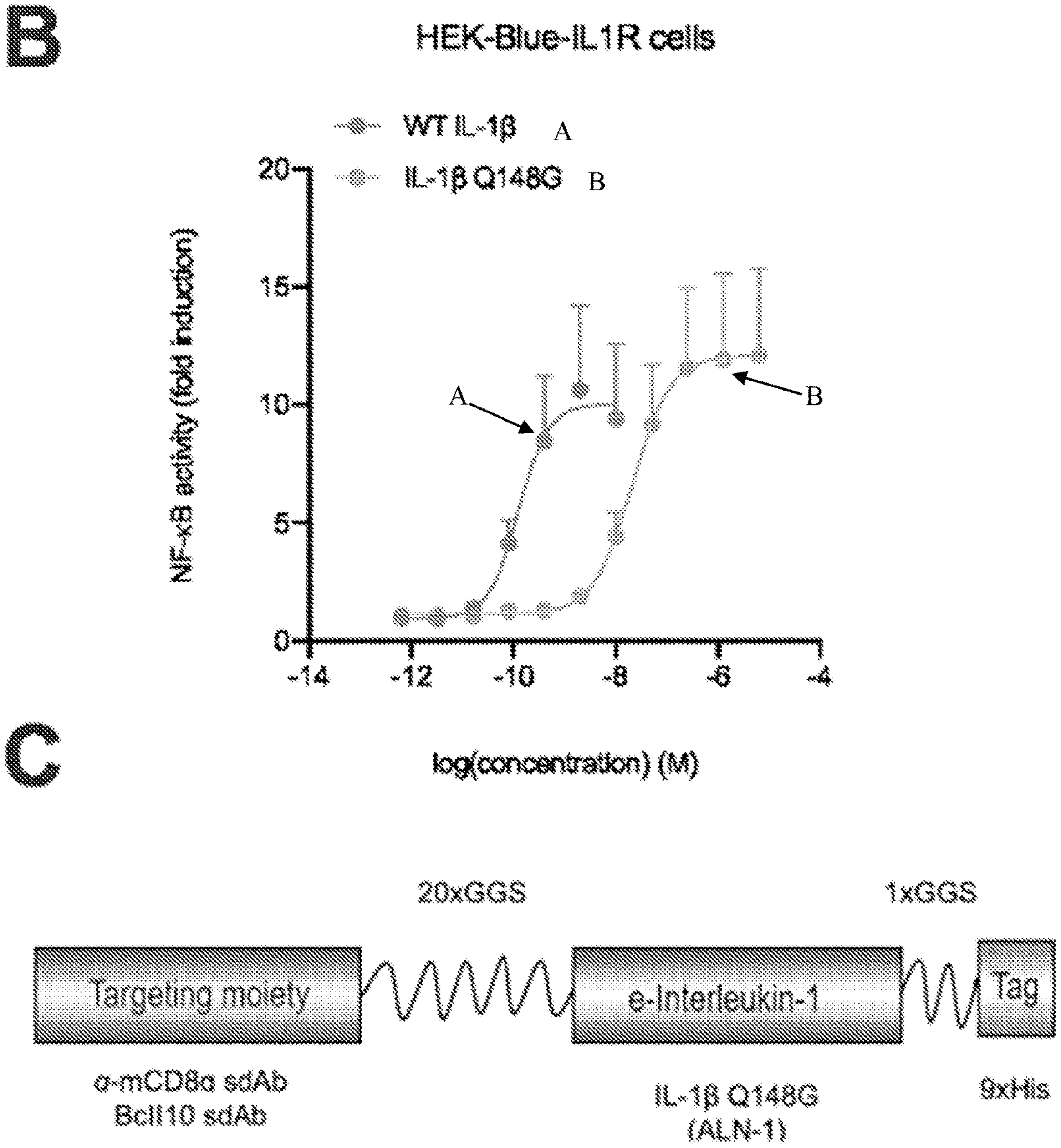
Figure 20:
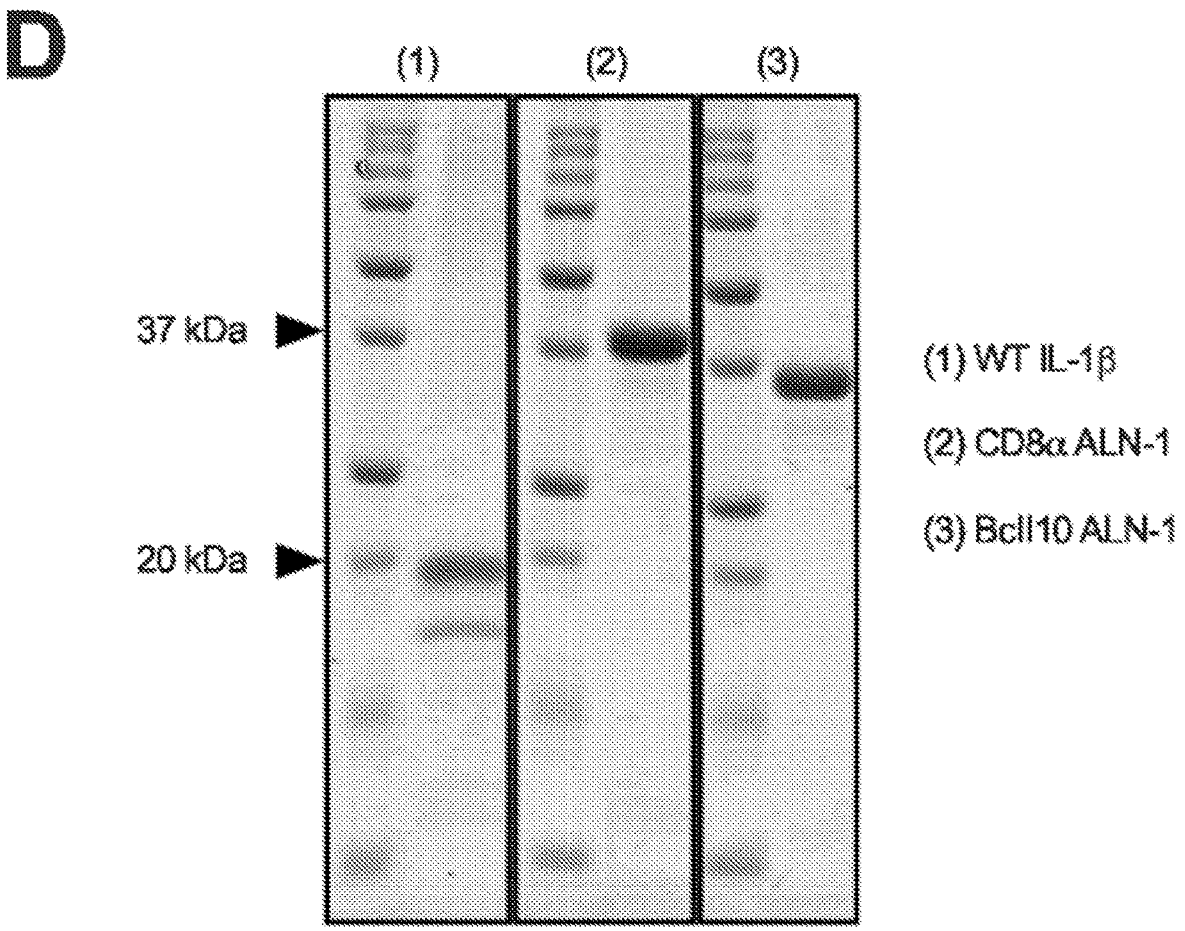
Figure 20:
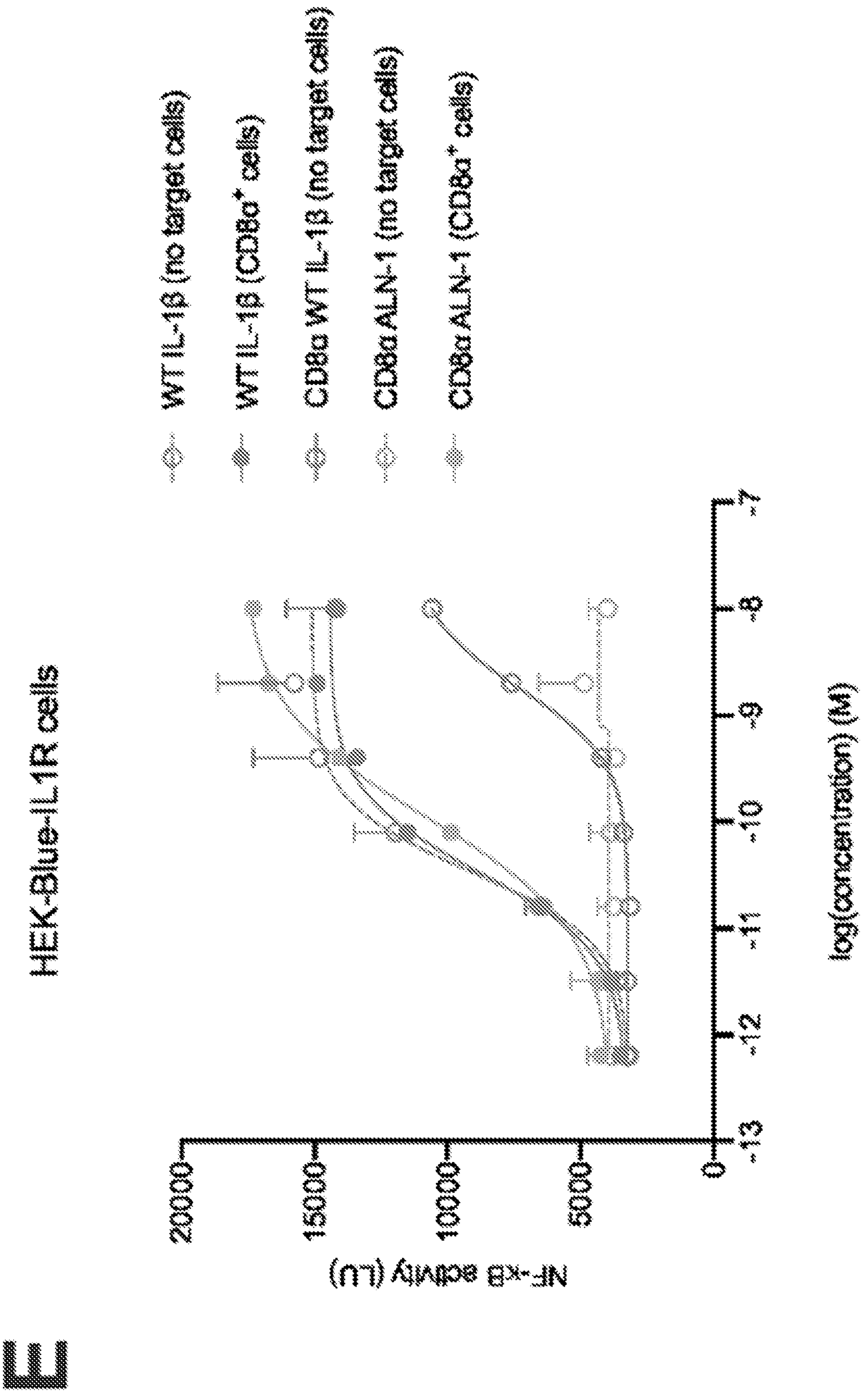
Figure 20:
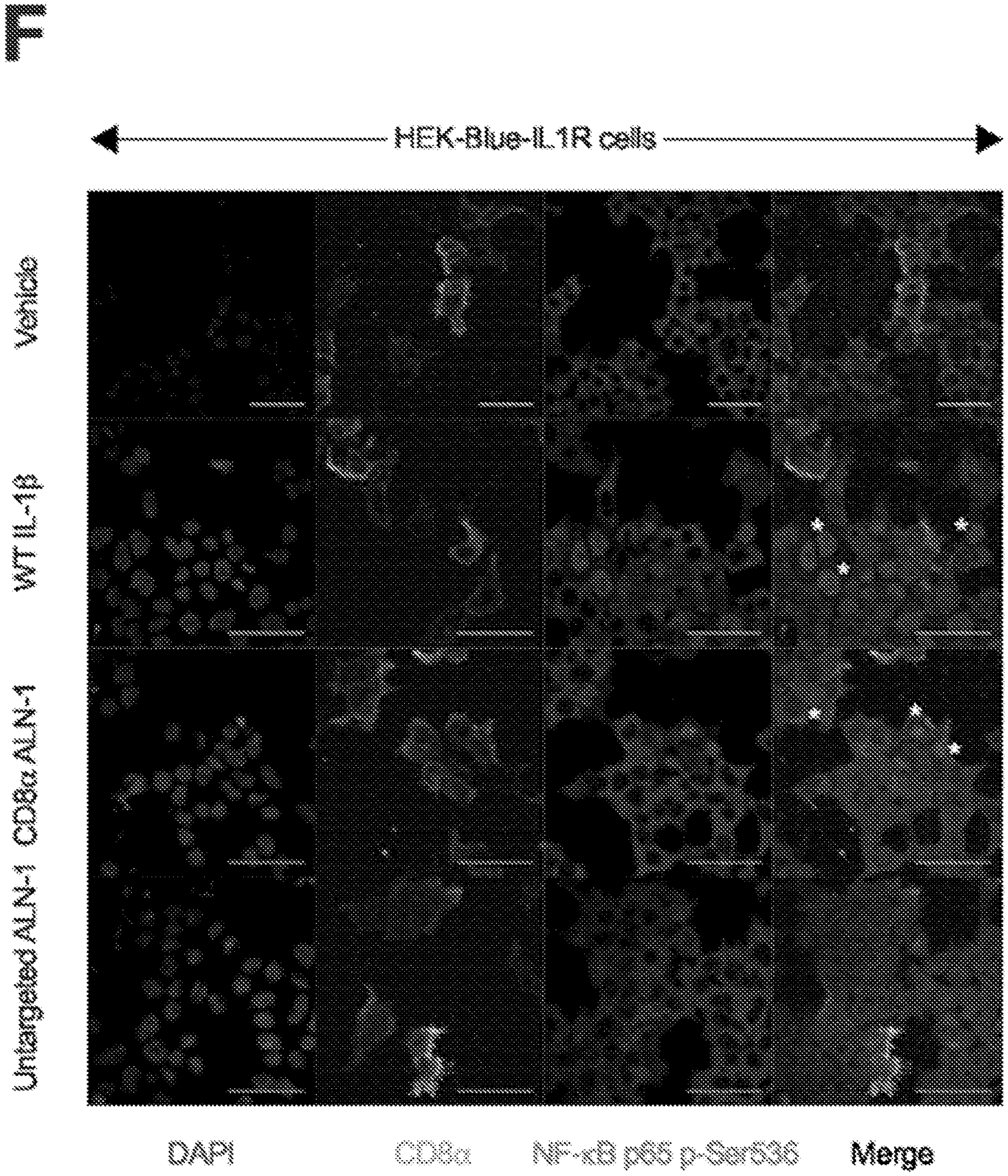
Figure 20:
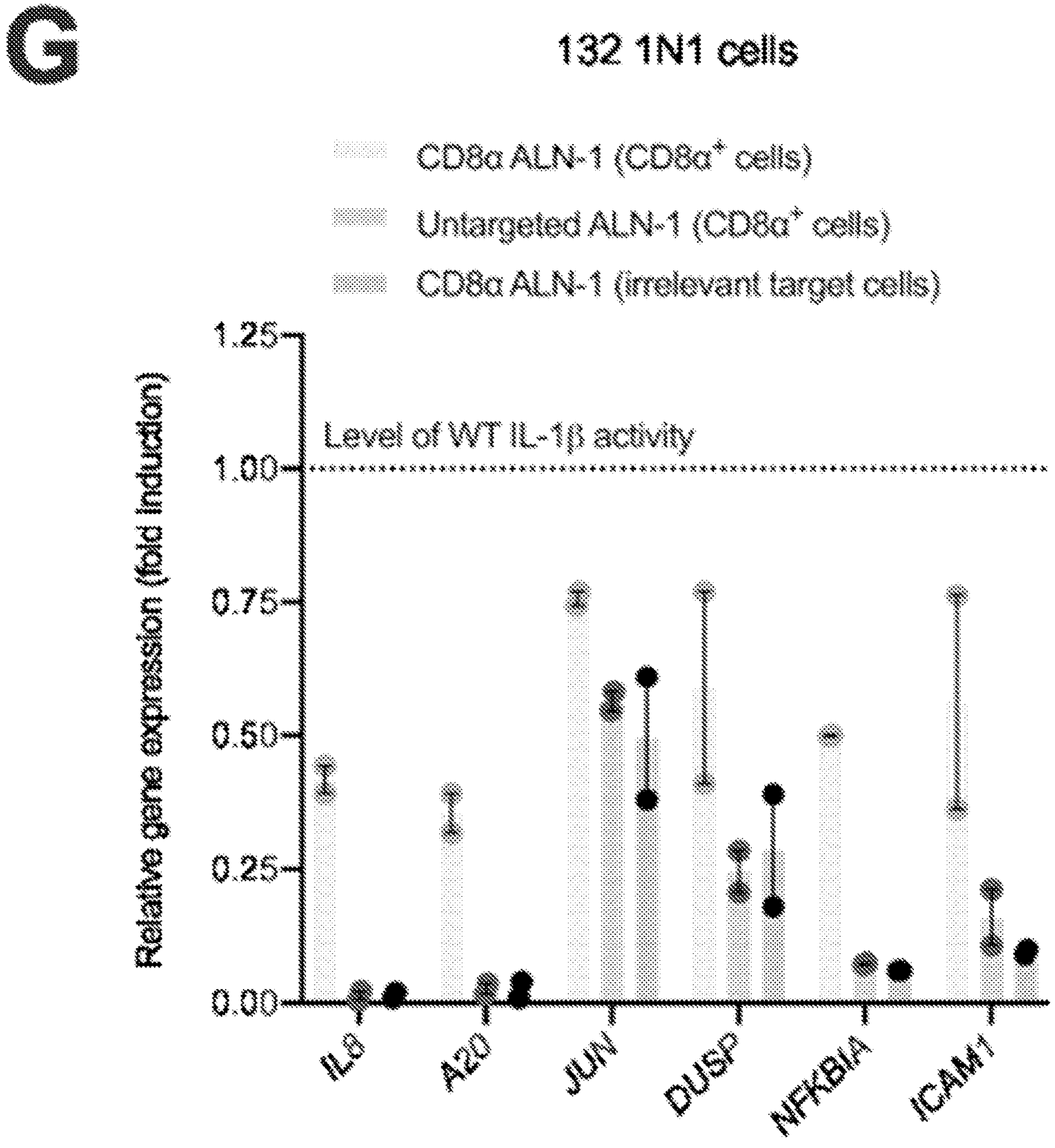

Example 1: Q148G is an IL-1β Mutant with Strongly Reduced Biological Activity that can be Completely Reactivated Upon Targeting Using CD8α Sdabs We generated several human IL-1β mutants, predicted to have reduced biological activity (FIG. 20A). Of these, the IL-13 mutant Q148G (FIG. 20A) was selected for further study. Q148 is an important residue for IL-1R1 binding, located in one of two known cytokine-receptor contact areas. Within this interface, 118 Å$^2$ of the amino acid's accessible surface becomes buried while it makes multiple connections with the IL-1R1: two direct contacts with F128 and L32 and three hydrogen bonds with the backbone amides of V33 and A126 of the receptor subunit (FIG. 20A). Mutating the glutamine at position 148 to glycine destabilizes the interaction with 1.74 kcal/mol, as predicted by Fold-X. This leads to an approximately 168-fold reduction in activity compared with WT IL-1β (FIG. 20B), as measured by NF-κB-driven expression of a luciferase reporter in HEK-293 cells stably transfected with the mouse IL-1R complex (HEK-Blue-IL1R).

Figure 27:
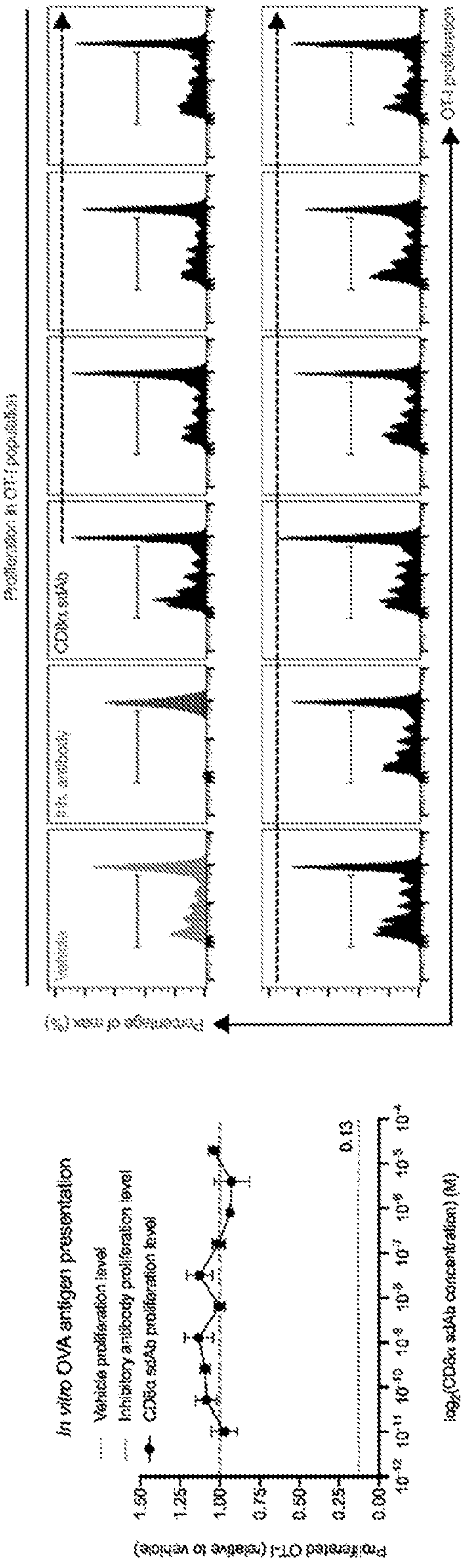
FIGS. 27A-C. Panel A shows that the CD8α sdAb does not interfere with $CD8^+$ T cell activation in vitro. The CD8α sdAb was tested (20 M top concentration and 1:5 serial dilution) in vitro using the OT-I co-culture system. OT-I activation was assessed by flow cytometry after 72 h of culture by evaluating proliferation (CTV dilution). Staining with CD3 and CD4 antibodies. OT-I cells were detected as single cells (based on FSC/SSC) that stained $CD3^+CD4$-$CTV^{labeled}$. Left: Quantification of OT-I proliferation. Shown is mean proliferation under treatment conditions relative to vehicle±s.e.m. of one experiment. Treatment with inhibitory antibody is shown as control. Right: Representative histograms illustrating unaltered OT-I proliferation in the presence of the CD8α sdAb. Panel B shows heat maps showing gene expression (relative to vehicle) of IL8, A20, JUN, DUSP, NFKBIA and ICAM1 in $CD8\alpha^+$ 132 1N1 human astrocytes upon stimulation with WT IL-1β, CD8α ALN-1 or untargeted ALN-1. Representative heat maps of two independent experiments. Panel C shows the biological activity of CD8α ALN-1 upon targeting is dependent on the level of target antigen expression. NF-κB-driven luciferase reporter gene expression induced by CD8α ALN-1 (1 nM) in HEK-Blue-IL1R cells, transiently transfected with CD8α (50 ng top concentration and 1:5 serial dilution). Top: NF-κB activity is normalized to p3-galactosidase activity and expressed as fold induction compared to the activity of WT IL-13 (1 nM) for every tested DNA concentration. Each data point represents the mean of two independent experiments±s.e.m. Untargeted Bcll10 ALN-1 (1 nM) is included as control. Bottom: Representative Western Blot image of total HEK-Blue-IL1R cell lysates, demonstrating decreasing CD8α protein (37 kDa) levels with decreasing levels of plasmid DNA. Tubulin (50 kDa) is included as loading control. Staining with primary antibodies against Flag-tag (Sigma F7425) and tubulin (Sigma T6199). Secondary detection with HRP-conjugated antibodies against rabbit and mouse IgG (GE Healthcare). Detection by chemiluminescence using the Amersham Imager 680 (GE Healthcare).
Figure 27:
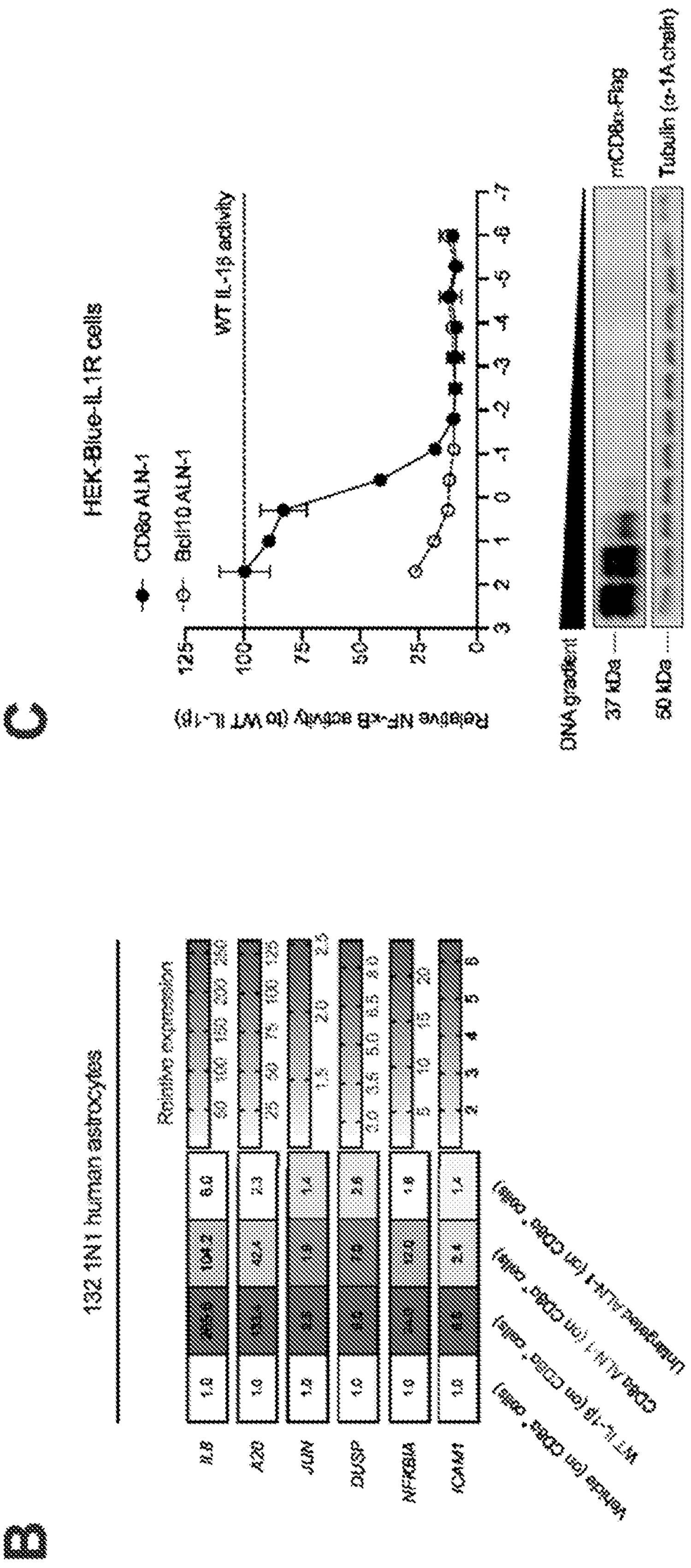

To locally reactivate IL-1β Q148G by targeting to cell type-specific surface molecules, we genetically fused the mutant cytokine to a sdAb that is specific for mouse CD8α, thereby creating the CD8α ALN-1 (FIG. 20C). This sdAb was found not to impede the activation of CD8$^+$ T cells during antigen presentation in vitro (FIG. 27A). This is important, as different anti-CD8 antibodies with the potential to interfere with CTL activation have been described before. As a negative control for targeting, we made a genetic fusion with a Bcll10 sdAb, which is directed against bacterial p3-lactamase. These fusion proteins were produced in mammalian HEK-F cells and subsequently purified using the built-in 9×His-tag (FIG. 20D). We measured an approximately 60-fold reduction in the biological activity of WT IL-1β after N-terminal coupling to the CD8α sdAb (FIG. 20E), meaning that the specific activity of CD8α ALN-1 is approximately 9000-fold lower than that of WT. Next, we evaluated CD8α ALN-1's reactivation-by-targeting on cells transiently transfected with CD8α. We found that the agonistic activity of CD8α ALN-1 could be fully restored up to WT level on CD8α$^+$ cells, while CD8α ALN-1 remained completely inactive on cells lacking the sdAb target. This was demonstrated by measuring NF-κB activation via reporter gene (FIG. 20E) and confocal microscopy (FIG. 20F) experiments in HEK-Blue-IL1R cells. Nuclear translocation of the NF-κB p65 subunit upon CD8α ALN-1 treatment occurred only in CD8α$^+$ cells, whereas WT IL-1β induced NF-κB activation independently of CD8α expression and untargeted ALN-1 did not show any activity. Additionally, we evaluated IL-1R signaling further downstream by measuring the expression of selected NF-κB, p38 MAPK and AP-1 target genes via RT-qPCR analysis in human 132 1N1 astrocytes, which endogenously express the IL-1R complex and were transiently transfected with CD8α or an irrelevant target protein. We found that the induction of most genes (IL8, A20, NFKBIA and ICAM1) was only restored upon targeting of CD8α ALN-1 to CD8α*cells, while the expression of other genes (JUN and DUSP) was only partially restored (FIG. 20G). Noteworthy, the JUN, DUSP and ICAM1 transcripts were less strongly induced upon WT IL-1β stimulation (FIG. 27B). Moreover, we found that the biological activity of CD8α ALN-1 upon targeting is dependent on the level of target antigen expression (FIG. 27C).

Altogether, these findings illustrate that Q148G, an IL-1β mutant with strongly reduced biological activity; can regain WT activity upon its targeting using a CD8α-specific sdAb.

Figure 21:
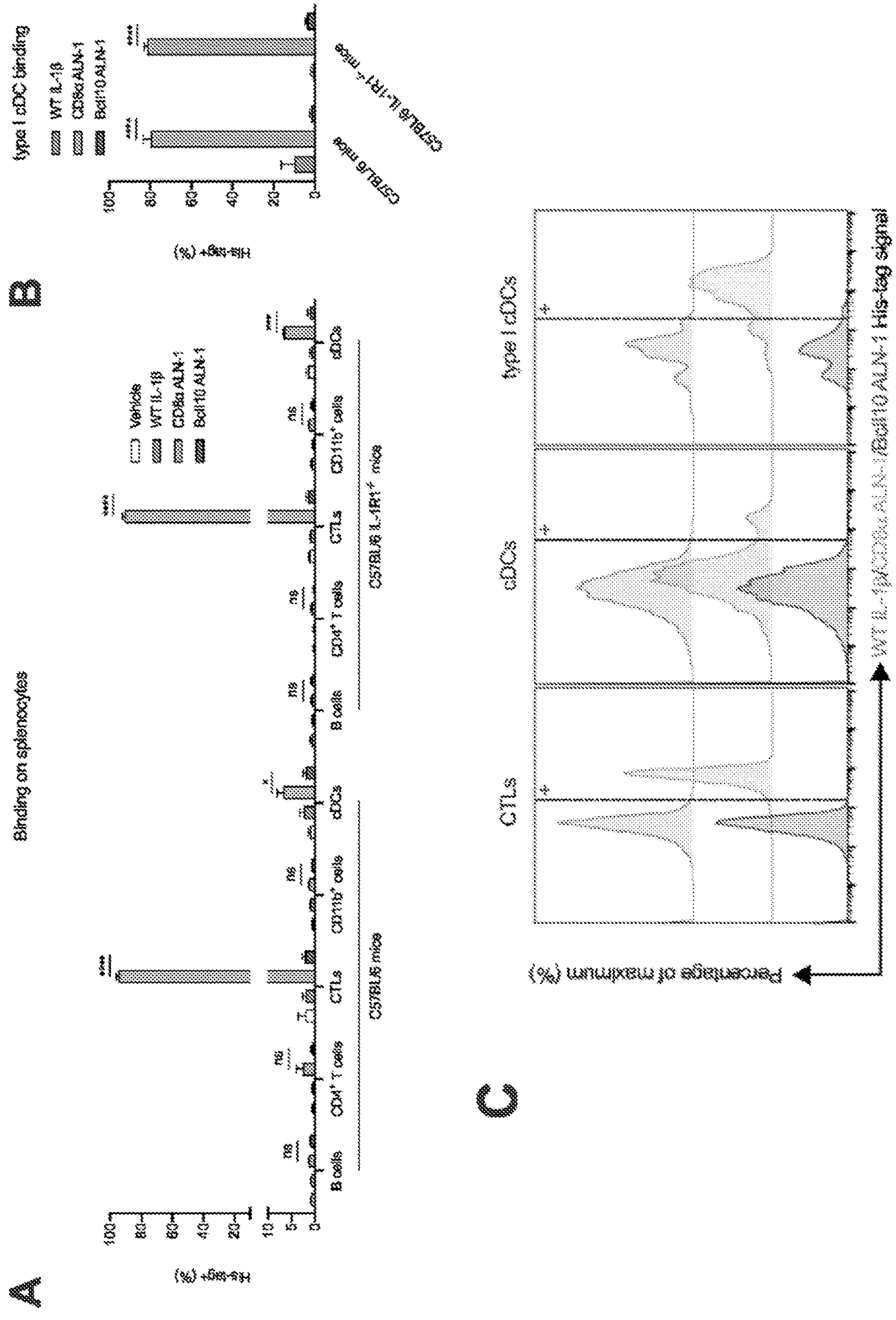
FIGS. 21A-H shows that CD8α ALN-1 promotes antigen-dependent proliferation and activation. Panel A shows flow cytometric detection of CD8α ALN-1 binding in vitro within different immune cell populations (spleen) from WT or IL-1R1$^{-/-}$ C57BL/6 mice. In the set of histograms, the bars represent, from left to right: Vehicle; WT IL-1B; CD8α ALN-1; and Bcl110 ALN-1. Panel B shows flow cytometric detection of CD8α ALN-1 binding in vitro within the XCR1$^{+}$ cDC population (spleen) from WT or IL-1R1$^{-/-}$ C57BL/6 mice. In the set of histograms, the bars represent, from left to right: WT IL-1B; CD8α ALN-1 and Bcl110 ALN-1. In A and B, controls include vehicle, WT IL-1β and untargeted Bcl110 ALN-1 binding. Bars represent the mean His-tag*fraction (%) in the annotated cell population±s.e.m. of three independent experiments. **, p<0.0001; *, p<0.001; *, p<0.05; ns, p≥0.05 compared with the binding of untargeted Bcl110 ALN-1 by unpaired Student's t-test (two-tailed). Panel C shows representative histograms demonstrating binding of CD8α ALN-1 on CTLs, cDCs and type I cDCs. Binding of vehicle, WT IL-1β and untargeted Bcl110 ALN-1 are shown as controls. Panel D shows representative histograms showing titration of CD8α ALN-1 binding on CTLs and cDCs, assessed by flow cytometry. Molecules were titrated in the same concentration range shown in panels (Panel E) and (Panel F). Panel E and Panel F show quantification of CD8α ALN-1's binding affinity on CTLs and cDCs. Each data point represents the mean fluorescence intensity (MFI) of the His-tag signal in CTL population±s.e.m. or the mean His-tag+ fraction (%) in the cDC population±s.e.m of three independent experiments. Panel G shows flow cytometry analysis of OT-I proliferation (CFSE dilution, left) and activation (CD25 upregulation, right) in in vitro OT-I co-cultures. OT-I cells were defined as CD3$^{+}$CD4-CFSE$^{labeled}$ cells. Each bar represents the mean fold induction (CFSE dilution or CD25 upregulation under treatment conditions relative to the vehicle signal)±s.e.m. of at least three independent experiments. **, p<0.0001; , p<0.01; *, p<0.05; ns, p≥0.05 by one-way ANOVA with Tukey's multiple comparisons test. Panel H shows representative histograms illustrating OT-I proliferation and upregulation of CD25 in the divided OT-I subset. See also FIGS. 28 and 29.
Figure 21:
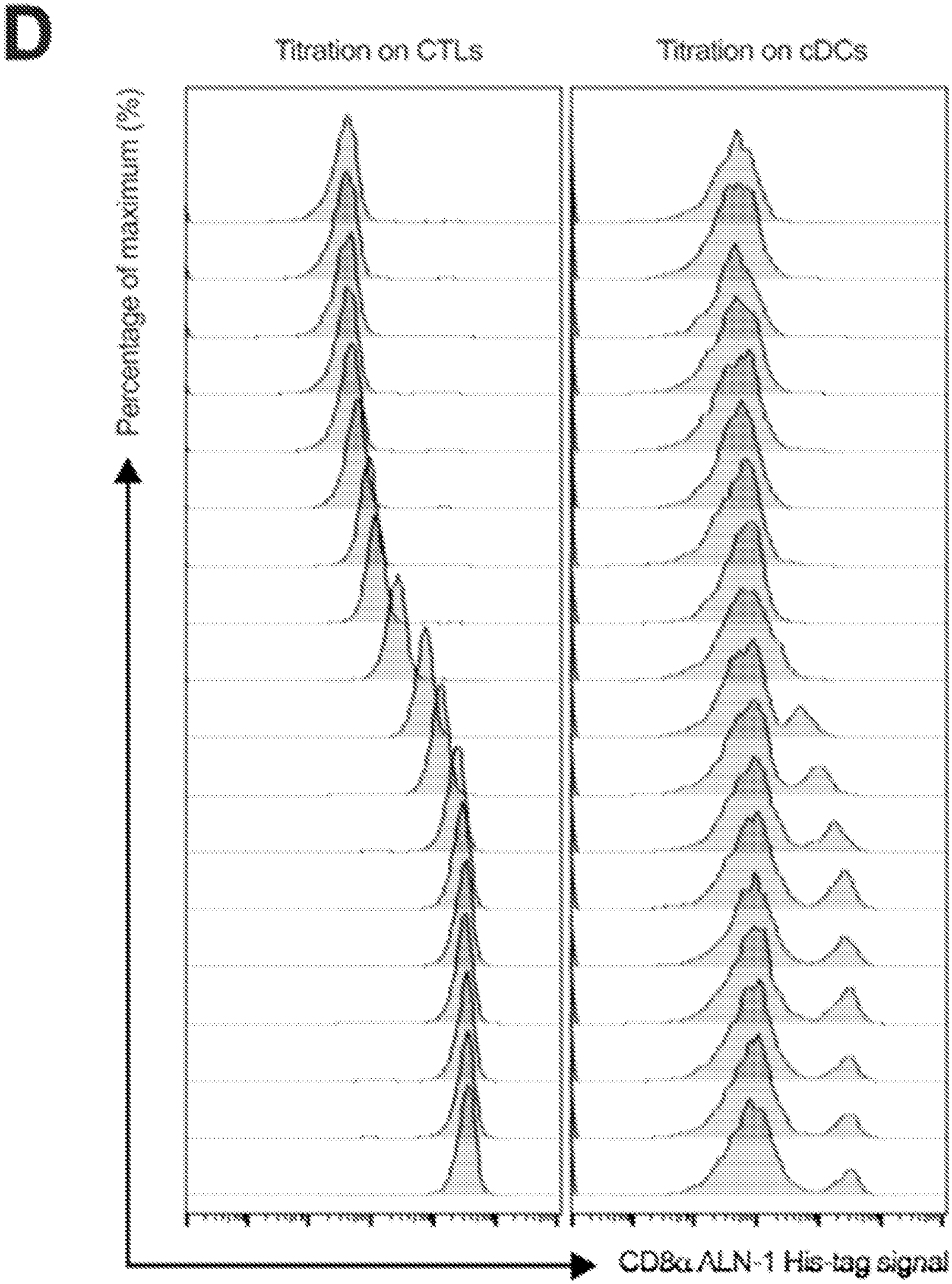
Figure 21:
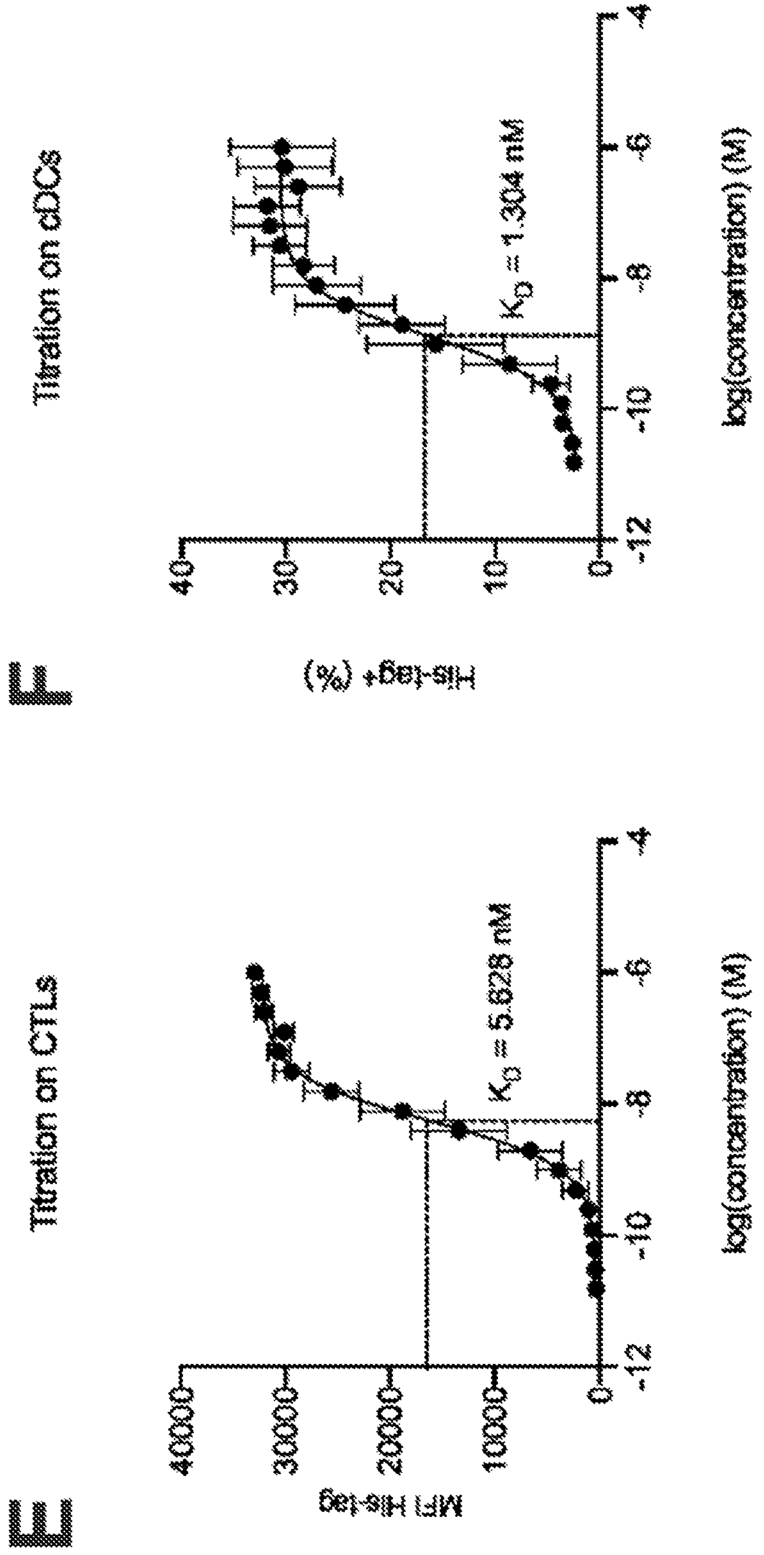
Figure 21:
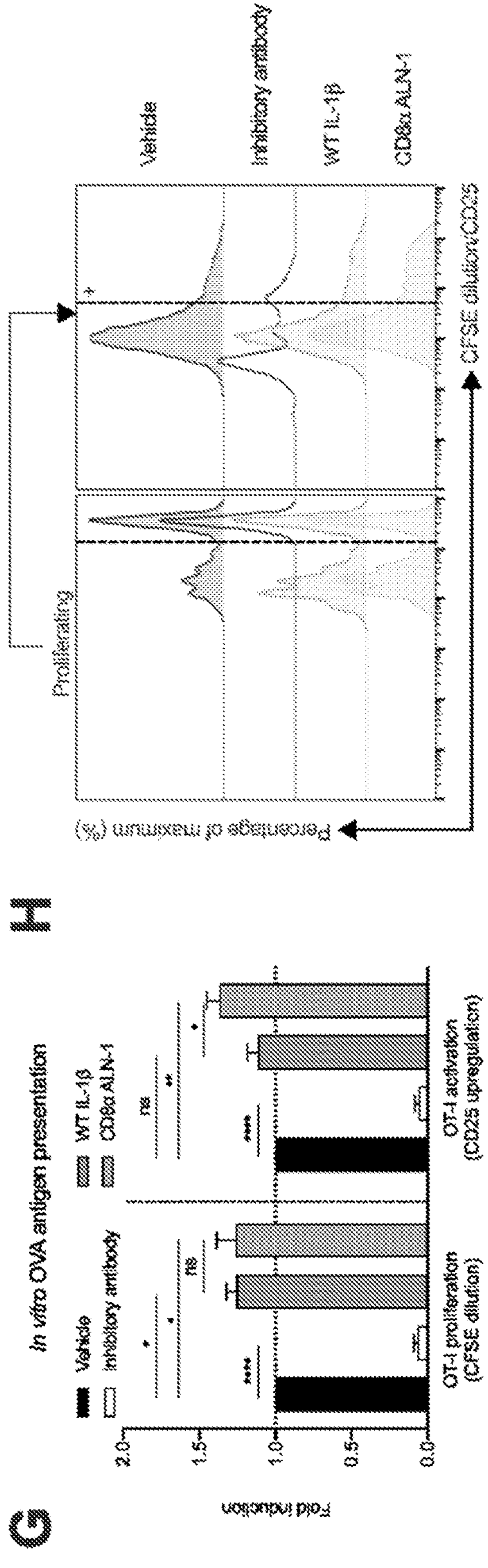
Figure 28:
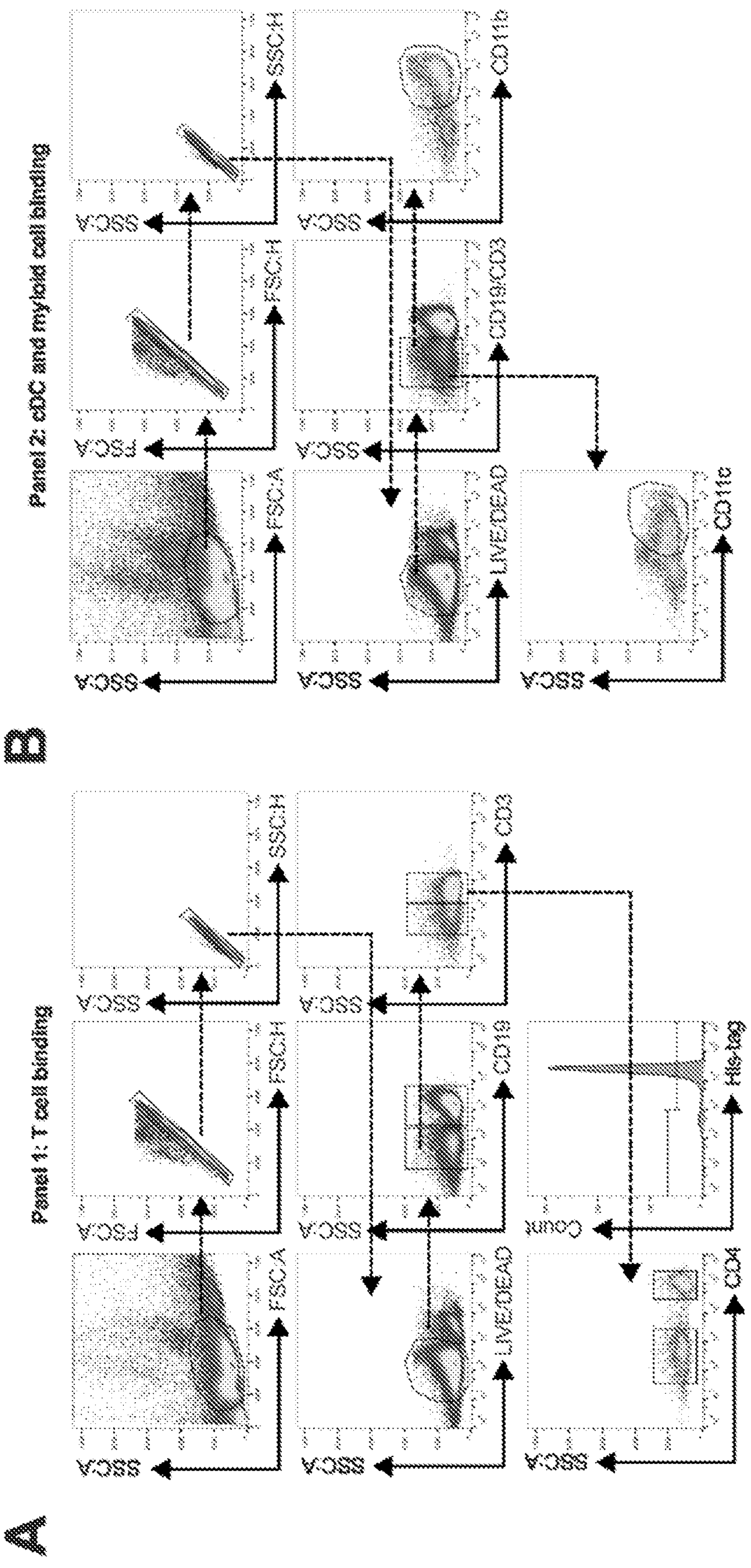
FIGS. 28A-E. Panels A-D show the gating strategy for the detection of CD8α ALN-1 binding in C57BL/6 (IL-1R1/) splenocyte pools. Staining with LIVE/DEAD, CD19, CD3, CD4, CD11b, CD11c, XCR1 and anti-His-tag antibodies. Panel E Left: CD8α ALN-1 does not bind NK cells in a mixed pool of WT C57BL/6 splenocytes, whereas strong CTL targeting is present. Bars represent the mean His-tag signal (MFI) in the annotated cell populations±s.e.m. of two independent experiments. Controls include vehicle, WT IL-1β and untargeted Bcll10 ALN-1 binding. Representative histograms are included below the graph. Panel E Right: Gating strategy for this analysis. Staining with LIVE/DEAD, CD19, CD3, CD4, NK1.1 (clone PK136, 108707, BioLegend) and anti-His-tag antibodies. NK cells were identified as $CD19^-CD3^-NK1.1^+$. In the set of histograms, the bars represent, from left to right: Vehicle; WT IL-1β (1 nM); CD8α ALN-1 (1 nM); and Bcll10 ALN-1 (1 nM).
Figure 28:
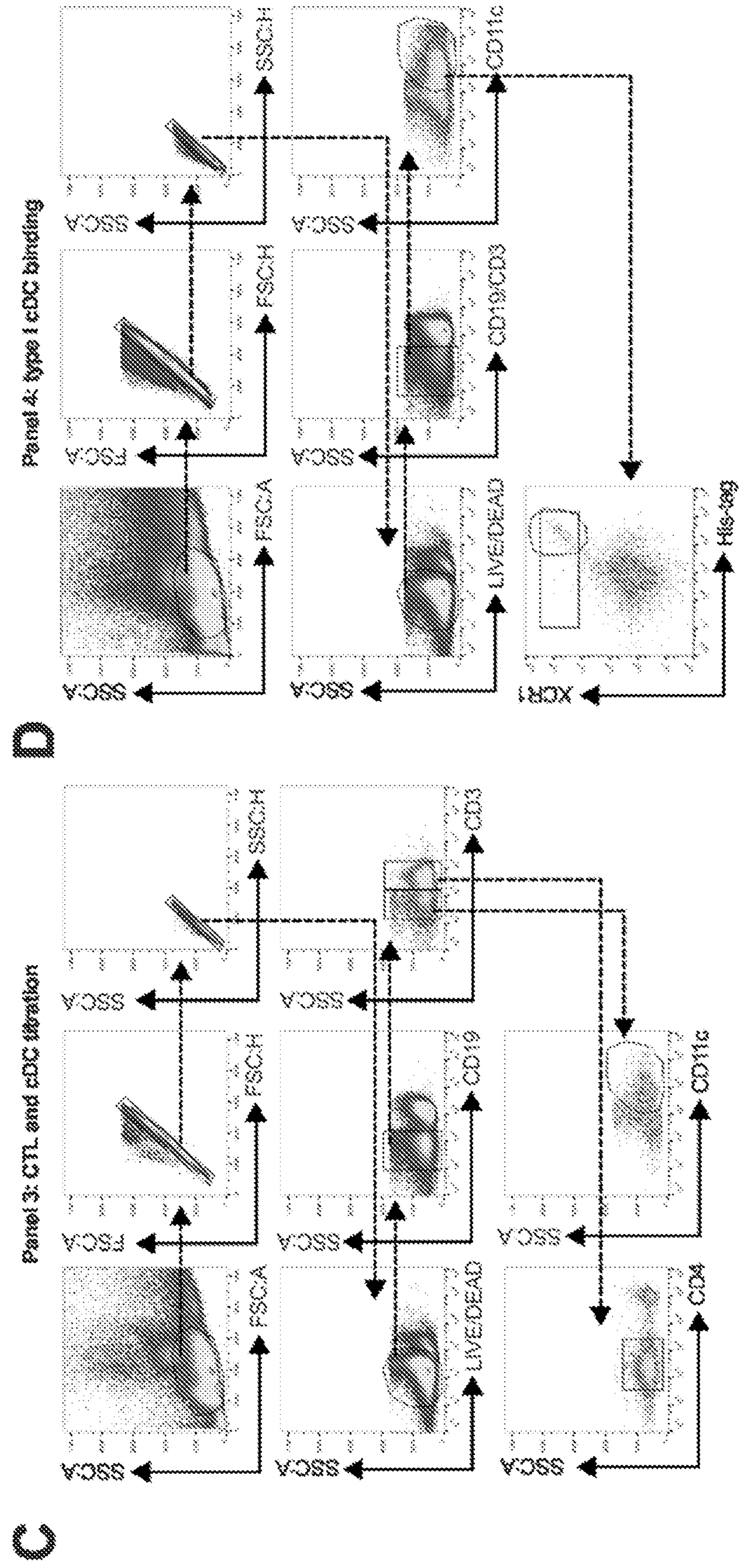
Figure 28:
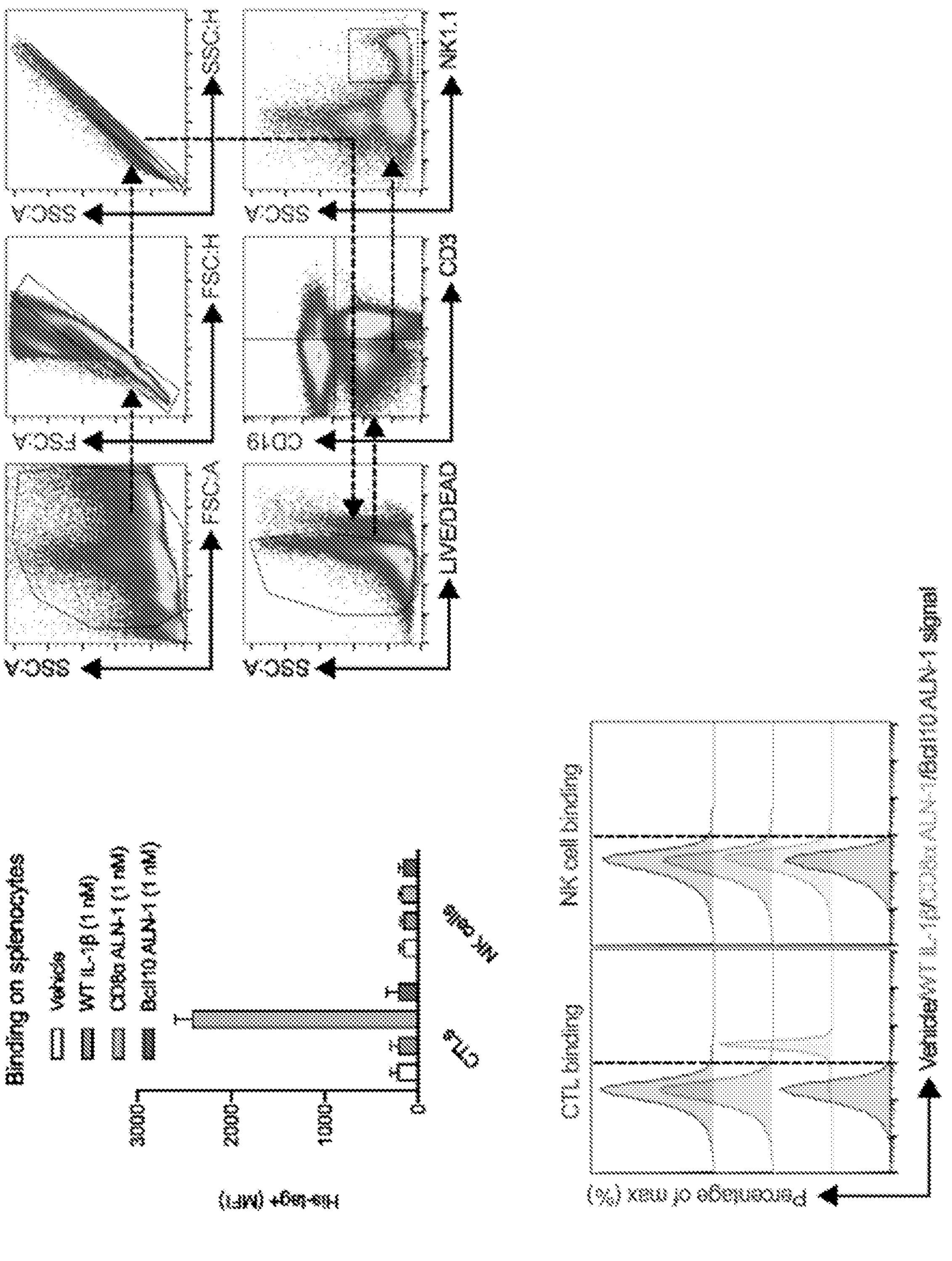

Example 2: CD8α ALN-1 Promotes Antigen-Dependent Proliferation and Activation Due to the cross-reactivity of human IL-1β in mouse we could further evaluate the specificity and affinity of CD8α ALN-1 on murine splenocytes in vitro using flow cytometry (gating strategy in FIGS. 28A-D). In this mixed population of cells, two different cellular subsets specifically bound CD8α ALN-1: CD4-T cells, corresponding to cytotoxic T lymphocytes (CTLs), and conventional DCs (cDCs) (FIG. 21A and FIG. 21C). Furthermore, the cDCs targeted by CD8α ALN-1 expressed XCR1, identifying them as type I cDCs, which are known to be CD8α$^+$ in mice (FIGS. 21B-C). We did not observe binding of CD8α ALN-1 to any other immune cell type tested (FIGS. 21A-C), including NK cells (FIG. 28E). No binding could be detected for WT IL-1β and untargeted Bcll10 ALN-1 (FIGS. 21A-C). The importance of this sdAb is confirmed by the observation that CD8α ALN-1 binding remained intact on IL-1R1$^{-/-}$ splenocytes (FIGS. 21A-B). Titration of the CD8α sdAb on the CTL and cDC subsets showed that this targeting moiety binds with nanomolar affinity ($K_D$ of 25 5.6 nM for CTL binding and 1.3 nM for cDC binding) (FIGS. 21D-F).

Figure 29:
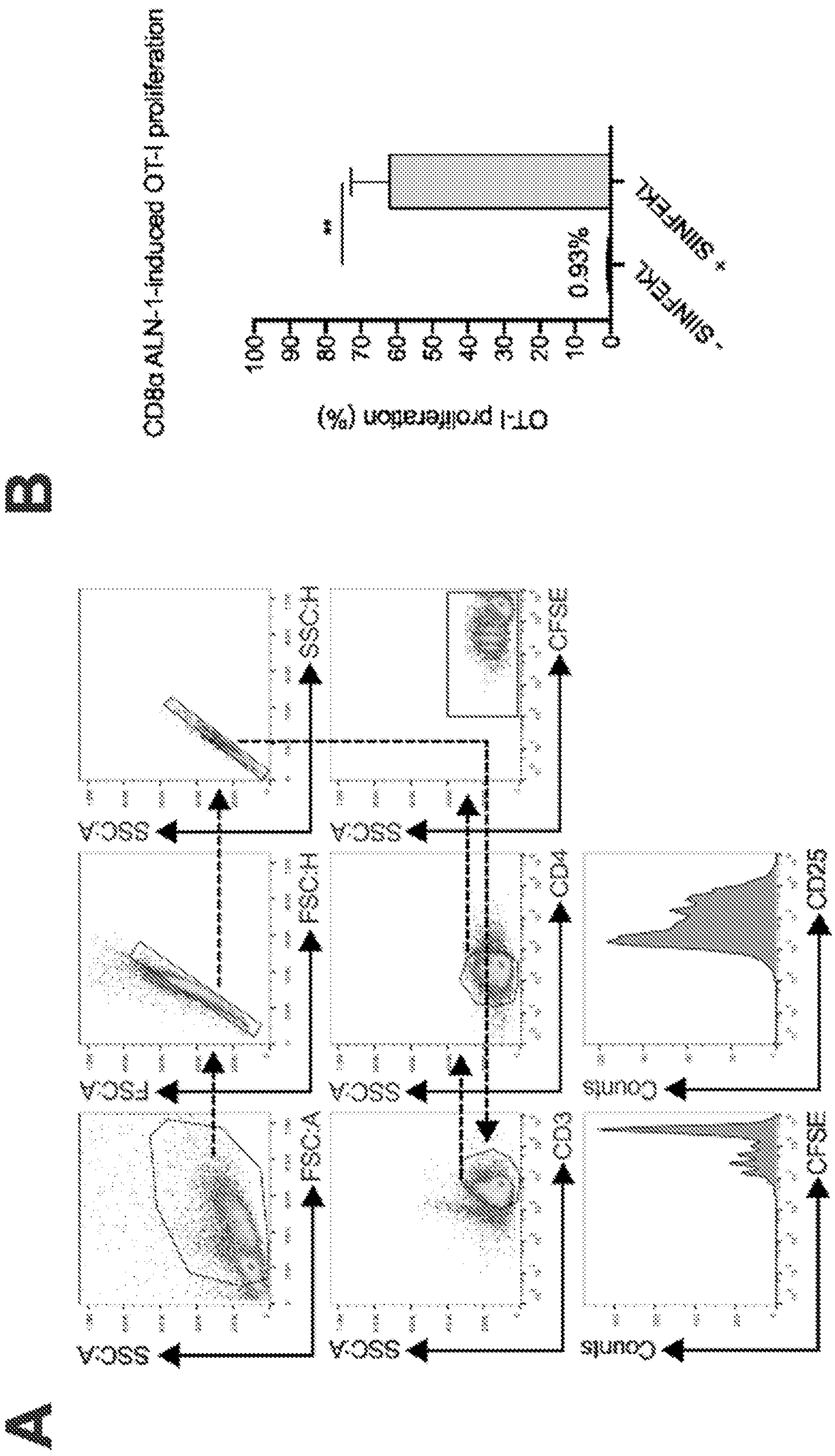
FIGS. 29A-D. Panel A shows the gating strategy for OT-I coculture experiments. Staining with CD3, CD4 and CD25 antibodies and detection of $CD3^+CD4$-$CFSE^{labeled}$ OT-I cells. Proliferation is calculated as a measure of CSE dilution.
Figure 29:
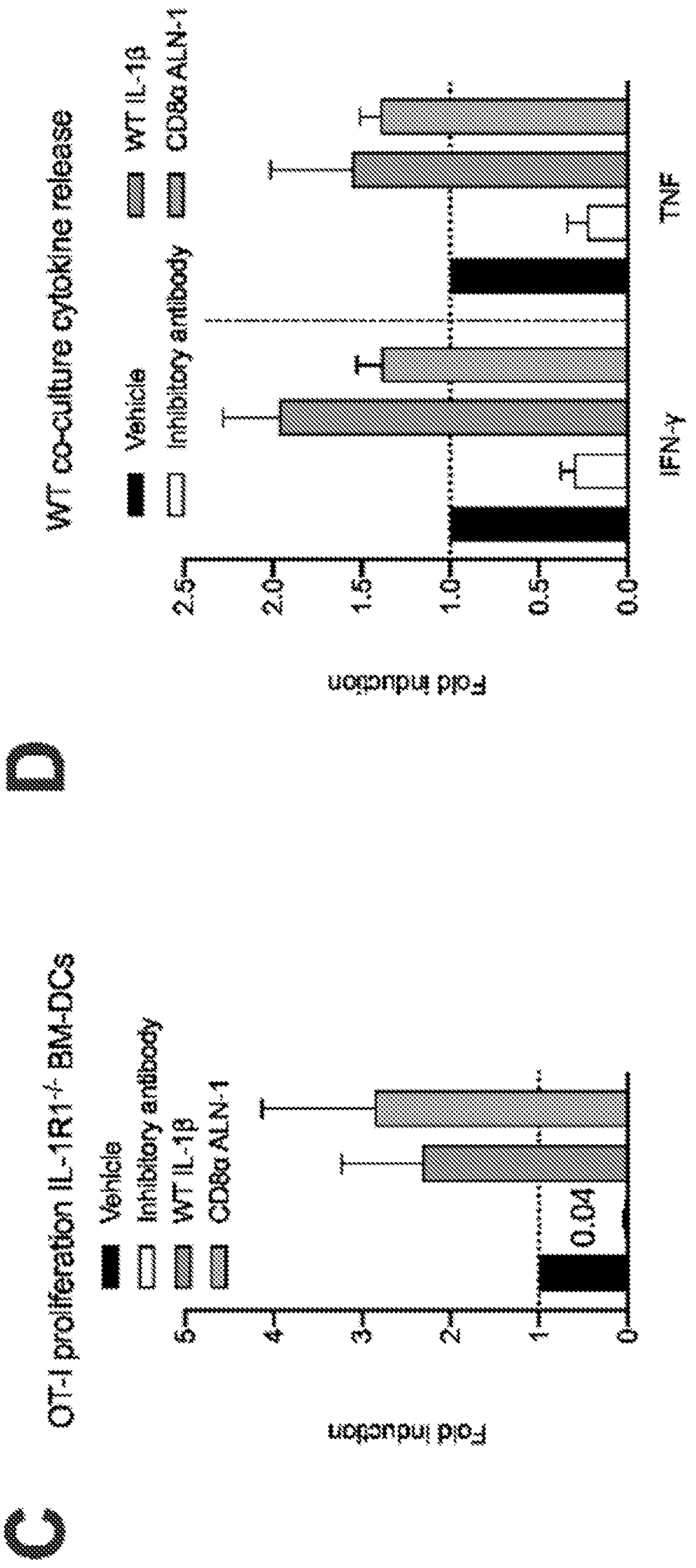

To address the potential adjuvant capacity of CD8α ALN-1 in vitro, we used the OT-I co-culture system. We found that, despite high background proliferation of antigen-exposed OT-I cells, CD8α ALN-1 (like WT IL-1β) further promoted SIINFEKL peptide-dependent proliferation of OT-I cells (FIGS. 21G-H, left; gating strategy in FIG. 29A). This effect completely depended on presentation of antigen by bone marrow-derived DCs (BM-DCs) to OT-I cells (FIG. 29B). Similar results were obtained using IL-1R1$^{-/-}$ BM-DCs in the co-cultures, suggesting that CD8α ALN-1 acts directly on the antigen-specific CTLs (FIG. 29C). Moreover, treatment with CD8α ALN-1 led to an enhanced upregulation of CD25 (IL-2Ra) in the dividing OT-1 cell subset (FIGS. 21G-H, right) and augmented release of the effector cytokines tumor necrosis factor (TNF) and IFN-γ, indicative for enhanced CTL activation (FIG. 29D).

In conclusion, we demonstrated that CD8α ALN-1 can efficiently deliver IL-1β activity to CD8$^+$ T cells, leading to an enhanced antigen-specific T cell response in vitro.

Figure 22:
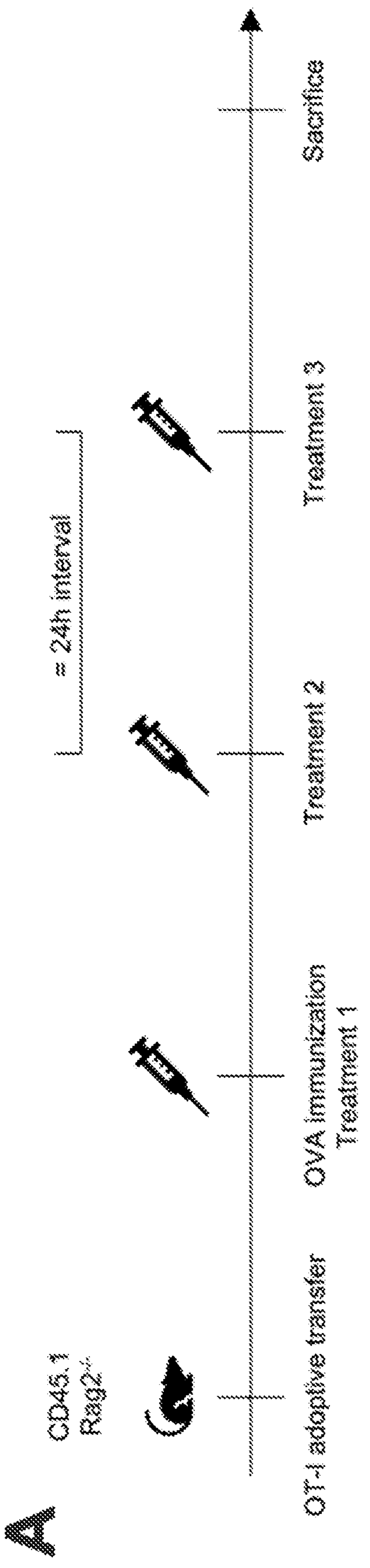
FIGS. 22A-J shows that CD8α ALN-1 induces CD8$^{+}$ T cell proliferation and effector functions in response to antigen in vivo. Panel A shows a schematic representation of the adoptive transfer experiment. C57BL/6 mice received an intravenous (i.v.) transfer of OT-1 cells. OVA (100 g) was delivered intraperitoneally (i.p.) one day later. Together with OVA, mice received three treatments with either LPS (25 g), WT IL-1β (5 g), CD8α ALN-1 or untargeted Bcl110 ALN-1 (10 g) (i.p. every 24 h). Flow cytometry was performed one day after the last treatment. Panel B shows representative flow cytometry histograms illustrating enhanced OT-1 proliferation in C57BL/6 recipient mice upon treatment with OVA and CD8α ALN-1. Controls include the OT-1 response without OVA (PBS) and with OVA alone or combined with LPS, WT IL-1β or untargeted Bcl110 ALN-1. Panel C and Panel D show quantification of OT-1 proliferation in C57BL/6 (Panel C) or C57BL/6 IL-1R14-(Panel D) recipient mice, visualized as stacked histograms. Individual stacks show the mean percentages of total proliferating OT-1 cells in a certain stage of cell division±s.e.m. Shown is a pool of two independent experiments with n=6 (Panel C) or 10 (Panel D) mice/group combined. **, p<0.01; *, p<0.05; ns, p≥0.05 for comparison of cell frequencies in the ultimate (sixth) fraction of division by Kruskal-Wallis test with Dunn's multiple comparisons test (Panel C) or unpaired Mann-Whitney U test (two-tailed) (Panel D). Panel E shows CD44/CD62L expression as a measure of CTL activation in spleens of C57BL/6 recipient mice. Each bar represents mean percentages of CTLs with the CD44$^{+}$CD62L$^{-}$ phenotype±s.e.m. of a pool of two independent experiments with n=6 mice/group combined. *, p<0.05 by one-way ANOVA with Tukey's multiple comparisons test. Panel F shows schematic representation of the in vivo killing experiment. C57BL/6 mice received one i.p. OVA (100 g) treatment together with three treatments with either LPS (25 g), WT IL-1β (5 g), CD8α ALN-1 or untargeted Bcl110 ALN-1 (10 g) (i.p. every 24 h). One week after OVA delivery, a 1:1-mixture of splenocytes (either CTV$^{high}$ labeled and SIINFEKL-loaded or CTV$^{low}$ labeled and non-loaded) was i.v. transferred. Flow cytometry to assess SIINFEKL-directed cytolytic activity was performed one day post-transfer. Panel G shows representative histograms illustrating SIINFEKL-directed cytolytic activity in C57BL/6 mice induced upon treatment with OVA and CD8α ALN-1. Controls include the response without OVA (PBS) and with OVA alone or combined with LPS, WT IL-1β or untargeted Bcll10 ALN-1. Panel H shows quantification of SIINFEKL-specific target cell lysis. Panel I shows one week after initial OVA immunization, induction of SIINFEKL-specific $CD8^+$ T cell responses in spleens of treated mice were measured by IFN-γ ELISPOT and quantified. Panel J shows representative ELISPOT pictures are shown, depicting the number of spots after treatment with: i. OVA alone, ii. OVA and WT IL-1β, iii. OVA and CD8α ALN-1 and iv. OVA and untargeted Bcll10 ALN-1. In (Panel H) and (Panel I), data points represent individual mice±s.e.m. of a pool of two independent experiments with n=10 mice/group combined. **, p<0.0001; *, p<0.001; *, p<0.05; ns, p≥0.05 by Kruskal-Wallis test with Dunn's multiple comparisons test. See also FIGS. 30 and 31.
Figure 22:
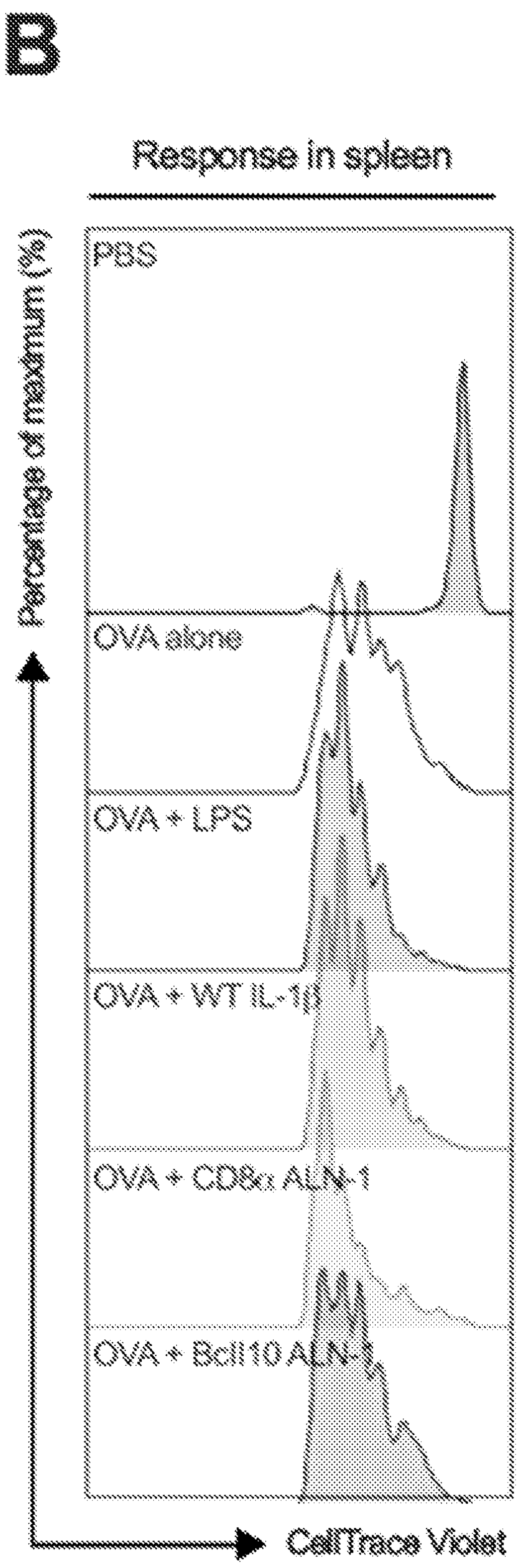
Figure 22:
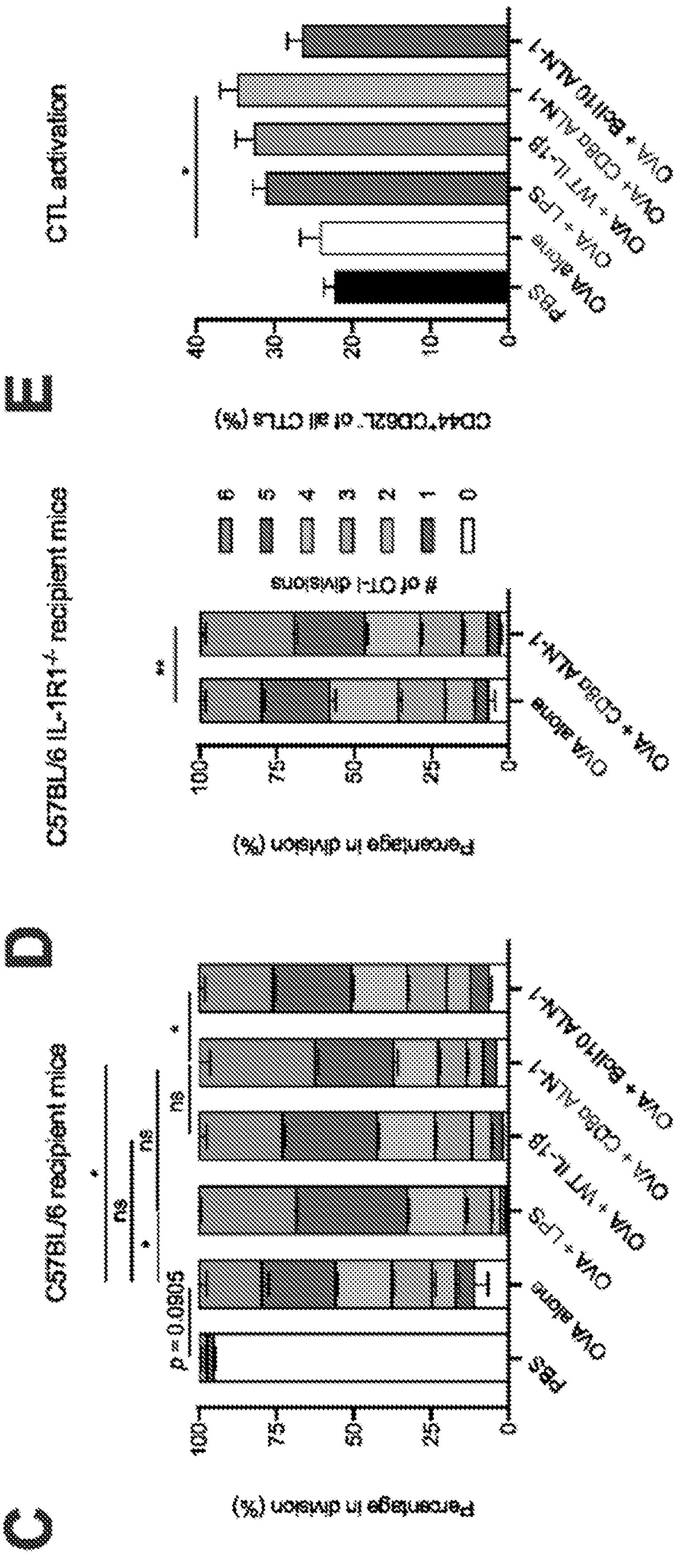
Figure 22:
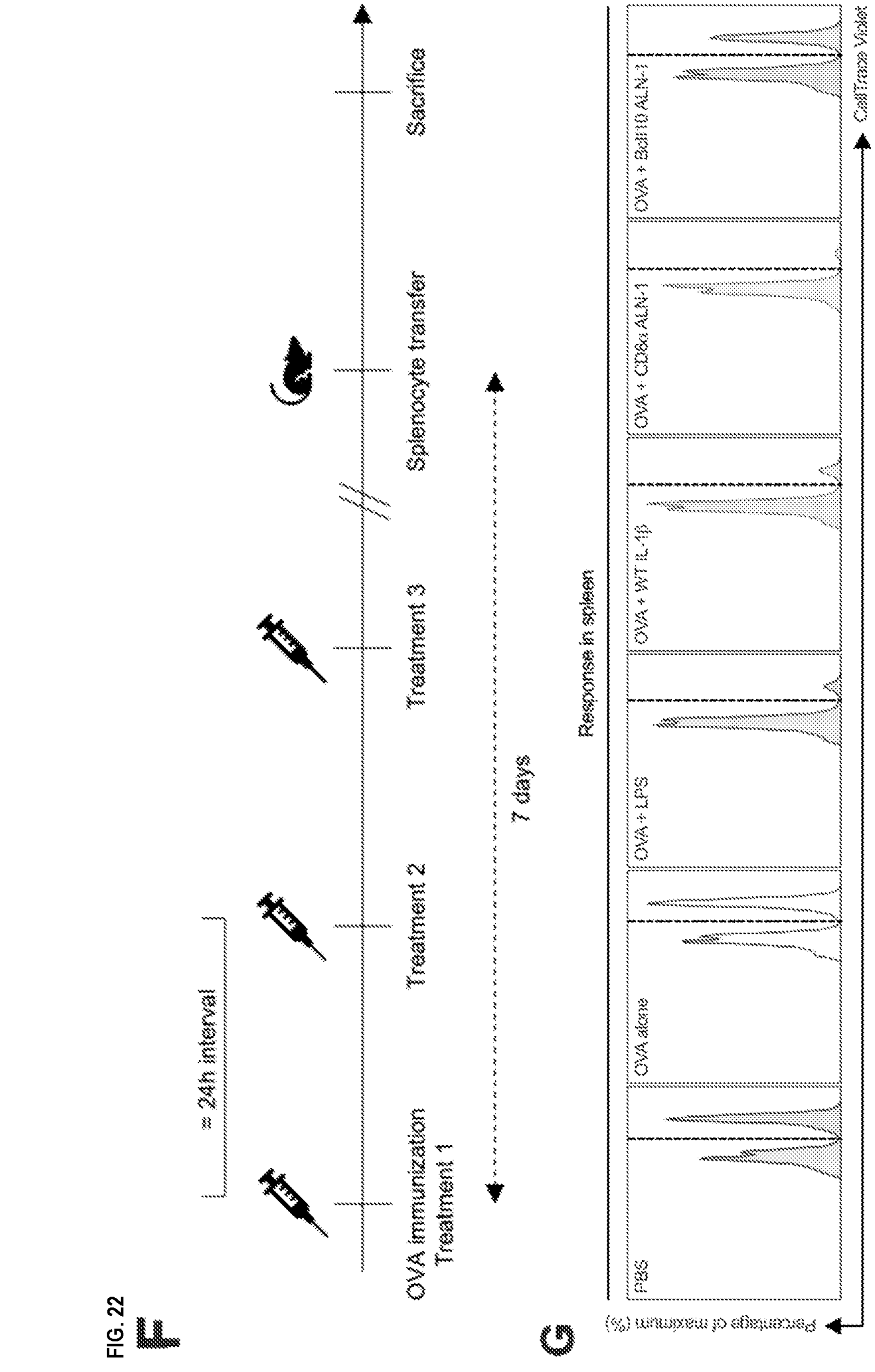
Figure 22:
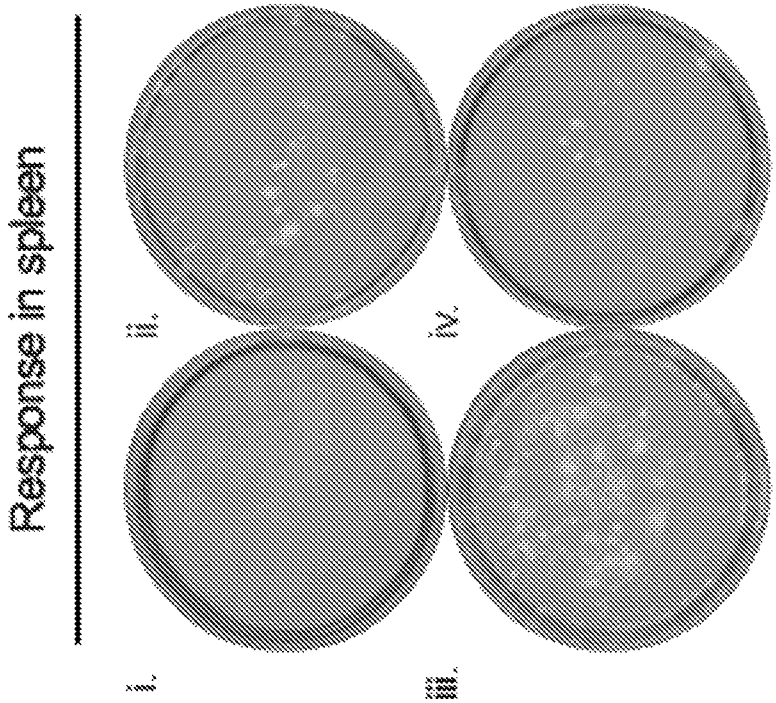
Figure 30:
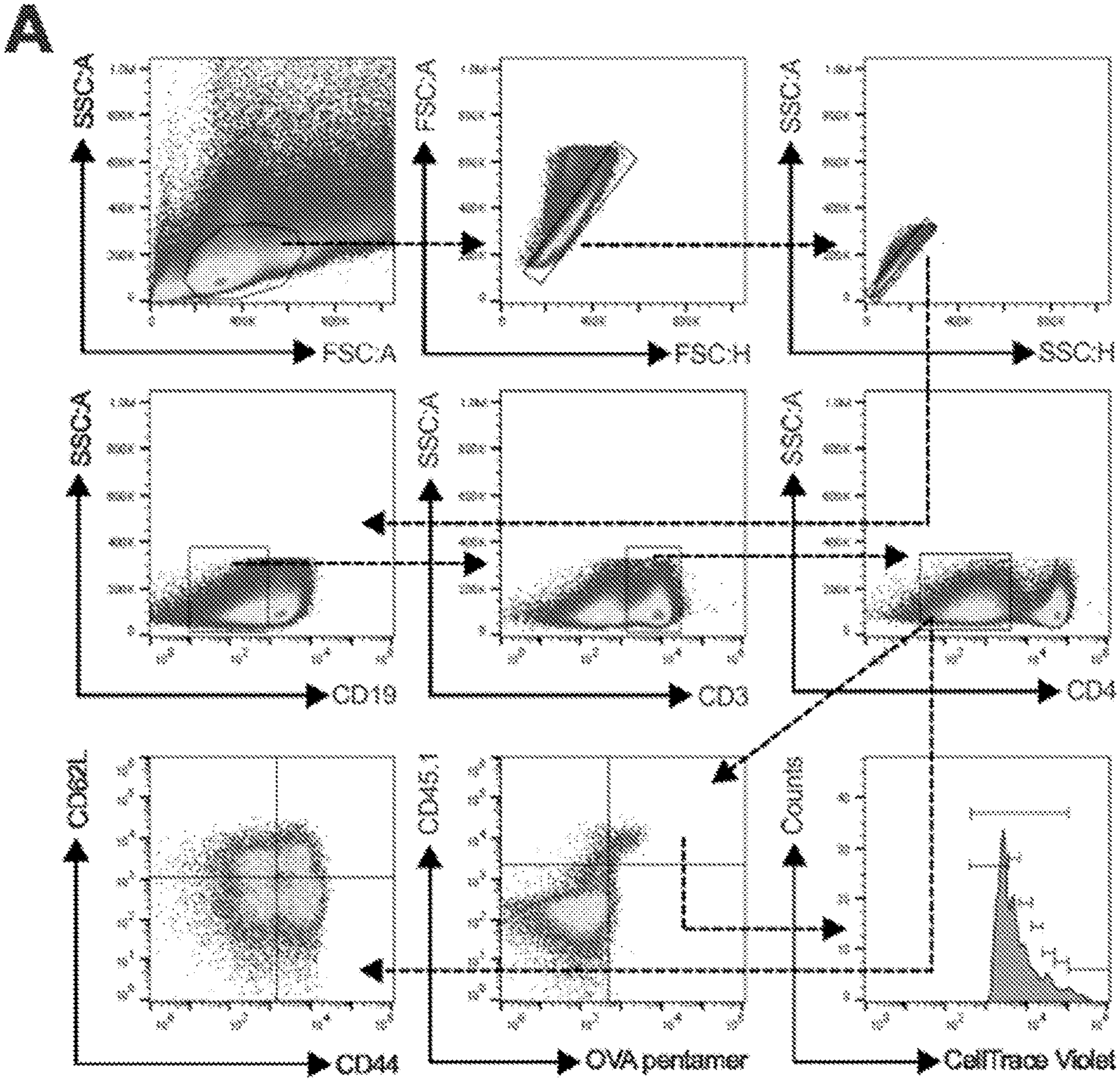
Figure 30:
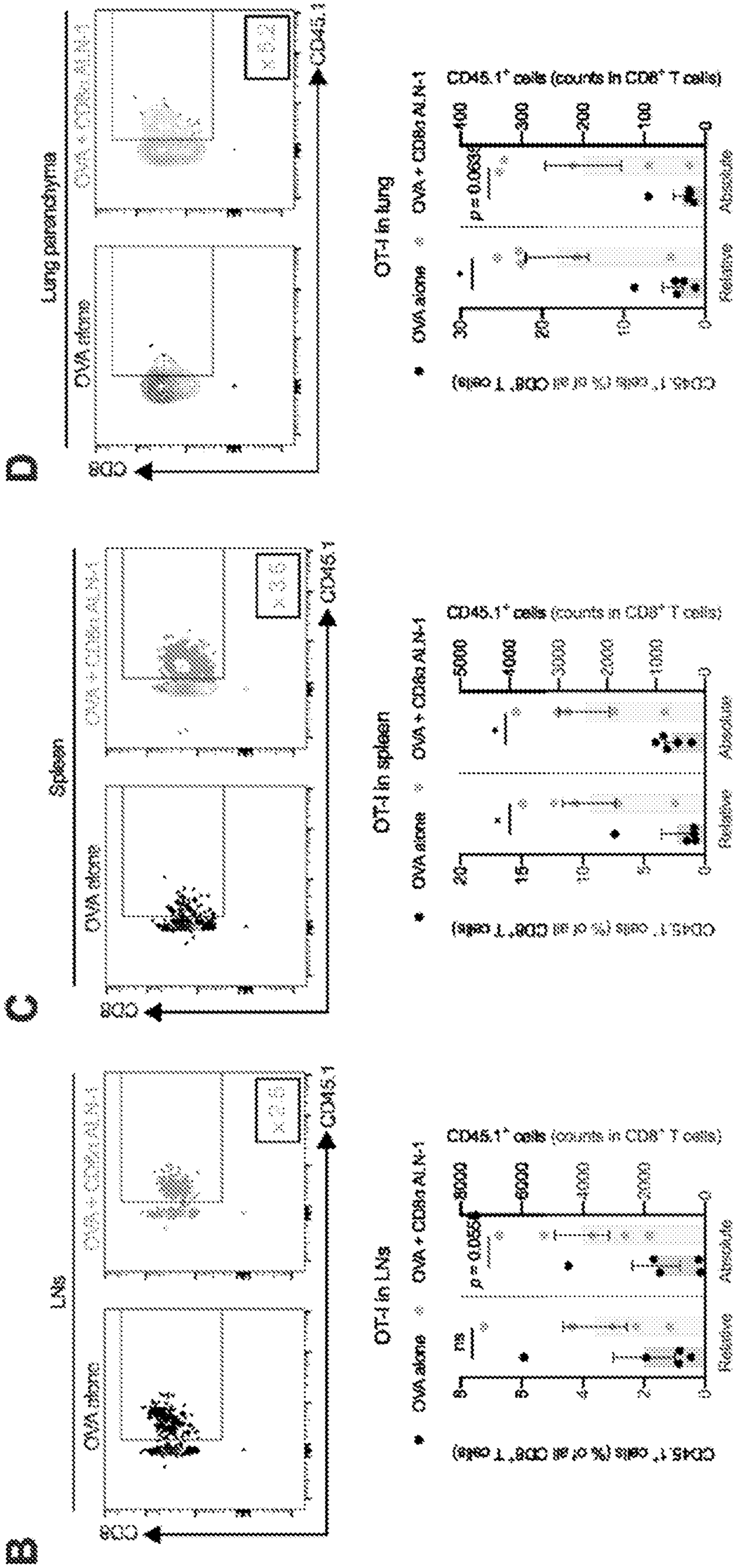
Figure 30:
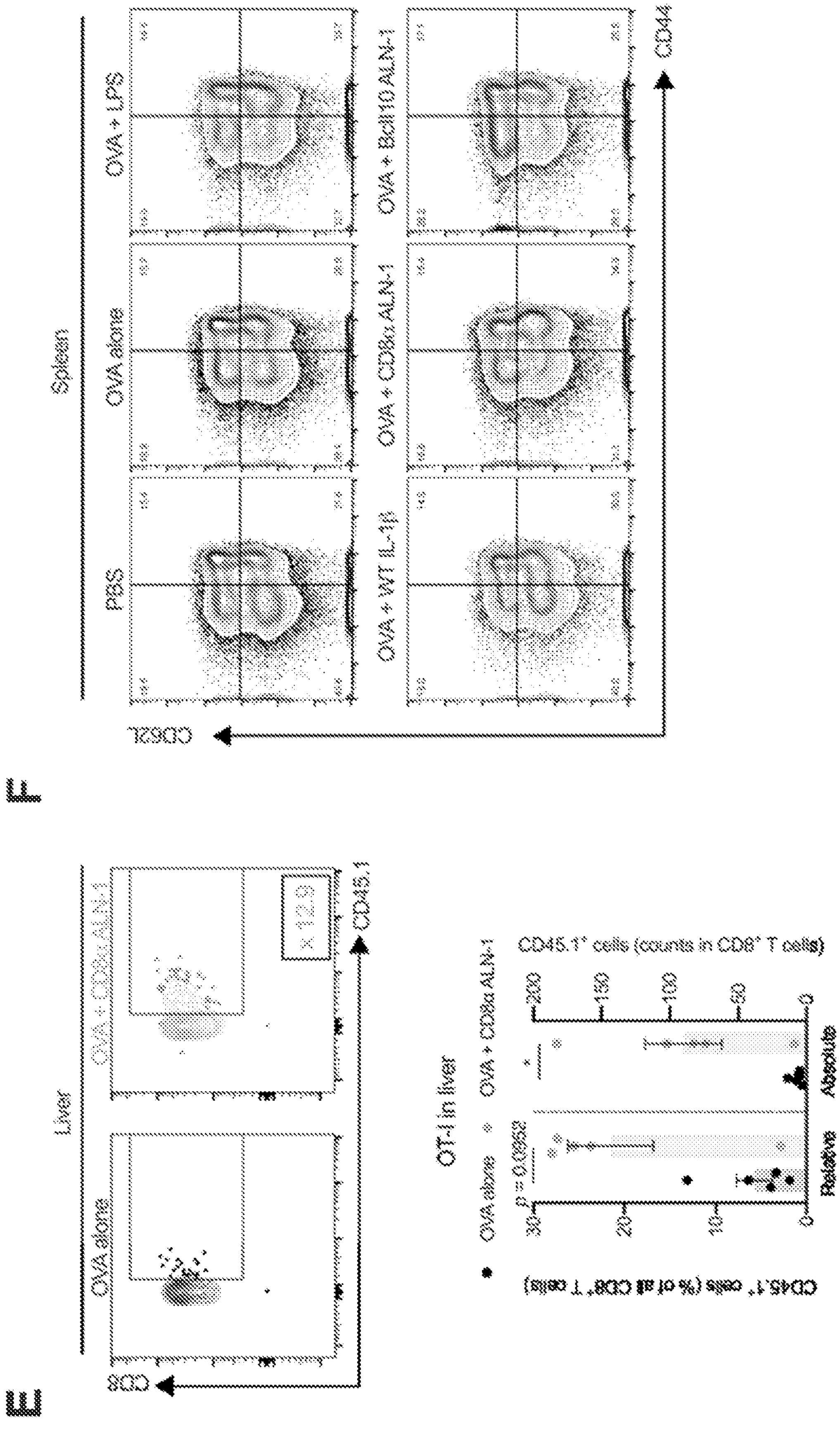

Example 3: CD8α ALN-1 Induces CD8+ T Cell Proliferation and Effector Functions in Response to Antigen In Vivo To investigate whether CD8α ALN-1 displays cellular adjuvant activity in vivo, as was earlier reported for WT IL-1β, we first performed OT-1 adoptive transfer experiments (FIG. 22A; gating strategy in FIG. 30A). In this model, intraperitoneal (i.p.) immunization of mice with OVA alone already resulted in the proliferation of OT-1 cells compared with mice treated without antigen (PBS) (FIGS. 22B-C). Co-administration of OVA and LPS (used as a positive control adjuvant) further increased OT-1 division. Characteristic for this effect is the significant increase in the fraction of OT-1 cells in the latest stage of cell proliferation (i.e. the sixth CellTrace Violet (CTV) dilution peak) compared with immunization with OVA alone. Similar to the effect of LPS, CD8α ALN-1 significantly enhanced OVA-induced OT-1 proliferation. No significant effect of untargeted Bcl110 ALN-1 was observed when compared with immunization with OVA alone. When using C57BL/6 IL-1R1' recipient mice, the observed CD8α ALN-1 effect on proliferation remained intact (FIG. 22D), indicating that CD8α ALN-1 acts directly on the OT-1 cells. We found that treatment with OVA and CD8α ALN-1 increased the fraction of OT-1 cells within the total $CD8^+$ T cell population and the absolute numbers of OT-1 cells both in lymphoid (lymph nodes (LNs) and spleen) and peripheral (liver and lungs) organs compared with delivery of OVA alone (FIGS. 30B-E). Moreover, CTL activation was enhanced in the spleens of mice treated with OVA and CD8α ALN-1 compared with mice immunized with OVA alone, as indicated by the simultaneous upregulation of CD44 and downregulation of CD62L (FIG. 22E; representative dot plots in FIG. 30F).

We next explored whether CD8α ALN-1 could also boost endogenous OVA-specific $CD8^+$ T cell activity using an in vivo killing assay (FIG. 22F; gating strategy and splenocyte labeling in FIGS. 31A-B). No antigen-specific target cell killing was observed in mice immunized with OVA alone, while cytolytic activity was strongly promoted upon co-administration of LPS, WT IL-1β and CD8α ALN-1 (FIGS. 22G-H). In this assay, CD8α ALN-1 was found to be equally efficacious as high-dose LPS and WT IL-1β. Conversely, treatment with OVA and untargeted Bcl110 ALN-1 had no significant effect on target cell killing compared with OVA immunization alone.

ELISPOT analysis revealed an increase in the numbers of SIINFEKL-specific $CD8^+$ T cells that produced IFN-γ in mice that had been treated with OVA and WT IL-1β or CD8α ALN-1 compared with mice immunized with OVA alone (FIGS. 22I-J). In agreement with the results from the in vivo killing experiment, the effect of CD8α ALN-1 was comparable to that of WT IL-1β. Some residual activity of the combination of OVA with untargeted Bcl110 ALN-1 was apparent in the ELISPOT. These data demonstrate that CD8α ALN-1 stimulates antigen-specific CTL responses in vivo.

Figure 23:
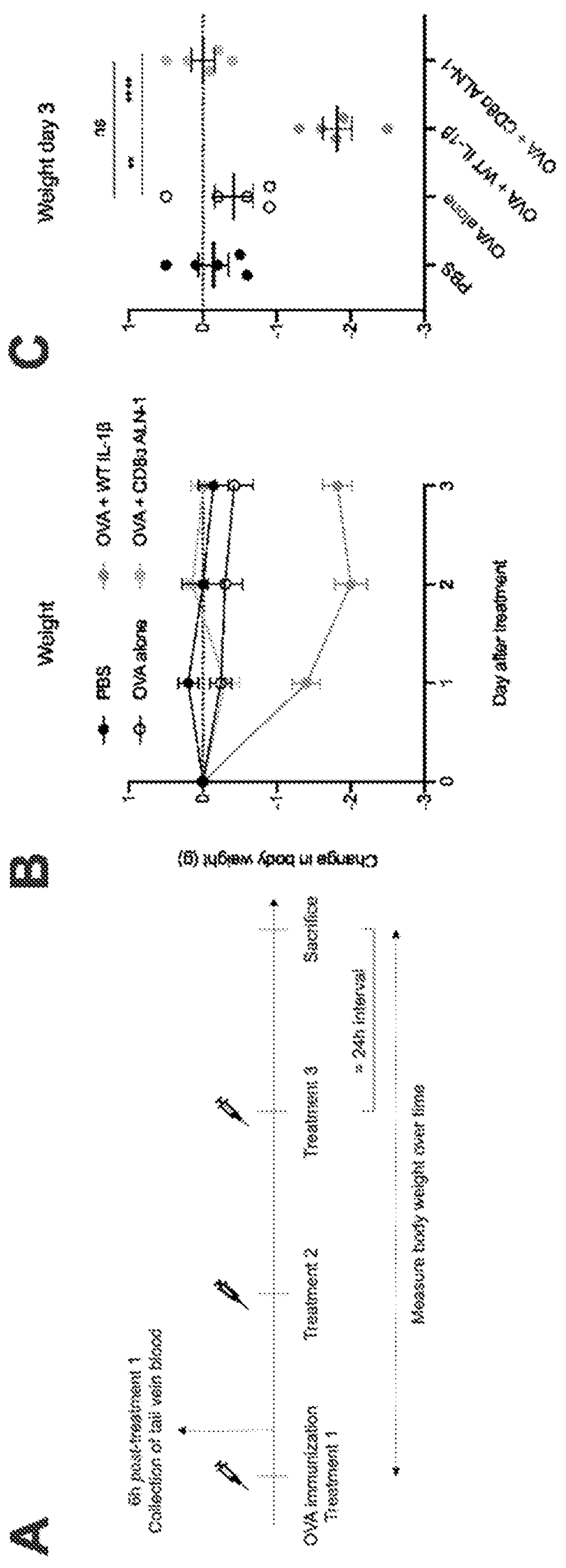
FIGS. 23A-I shows that systemic treatment of mice with antigen in combination with CD8α ALN-1 is completely free of toxicity. Panel A shows a schematic representation of the toxicity experiment. C57BL/6 mice received one i.p. OVA (100 μg) treatment together with three treatments with either WT IL-1β (5 μg) or CD8α ALN-1 (10 μg) (i.p. every 24 h). Controls include mice treated with PBS or OVA alone. Tail vein blood was sampled 6 h after the first treatment and body weight was tracked over time. Panel B and Panel C show change in body weight over time (Panel B) or after three days of treatment (Panel C). Data points represent the mean (Panel B) or individual mice (Panel C)±s.e.m. of a representative of two independent experiments with n=5 mice/group. Panels D-I show hematological analysis of fresh EDTA-coated blood (Panels E-I) or plasma derived from this blood (Panel D), showing systemic IL-6 levels (Panel D), platelet counts (Panel E) and mean platelet volumes (Panel F), total white blood cell counts (Panel G), lymphocyte counts (Panel H) and neutrophil counts (Panel I). Data points represent individual mice±s.e.m. of a pool of two independent experiments with n=10 mice/group combined. **, p<0.0001; *, p<0.001; **, p<0.01*, p<0.05; ns, p≥0.05 by one-way ANOVA with Tukey's multiple comparisons test (Panel C) and (Panel G) or by Kruskal-Wallis test with Dunn's multiple comparisons test (Panel D), (Panel E), (Panel F) and (Panel H). See also FIG. 32.
Figure 23:
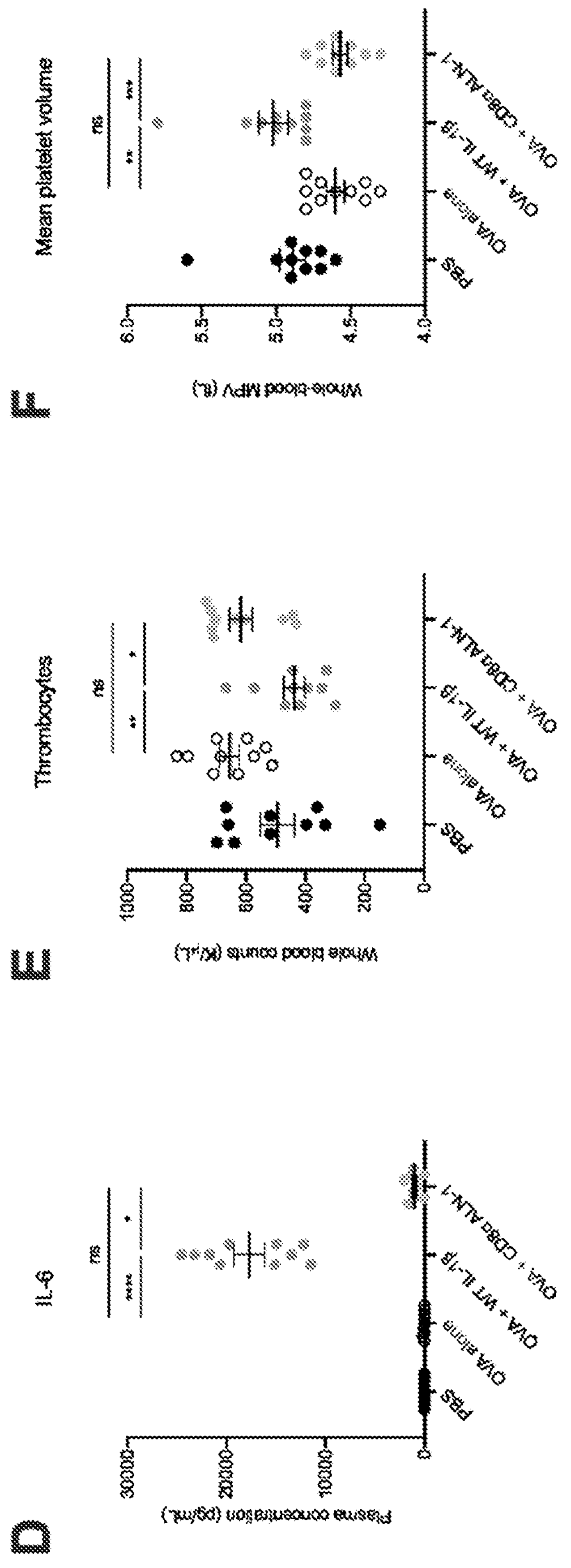
Figure 23:
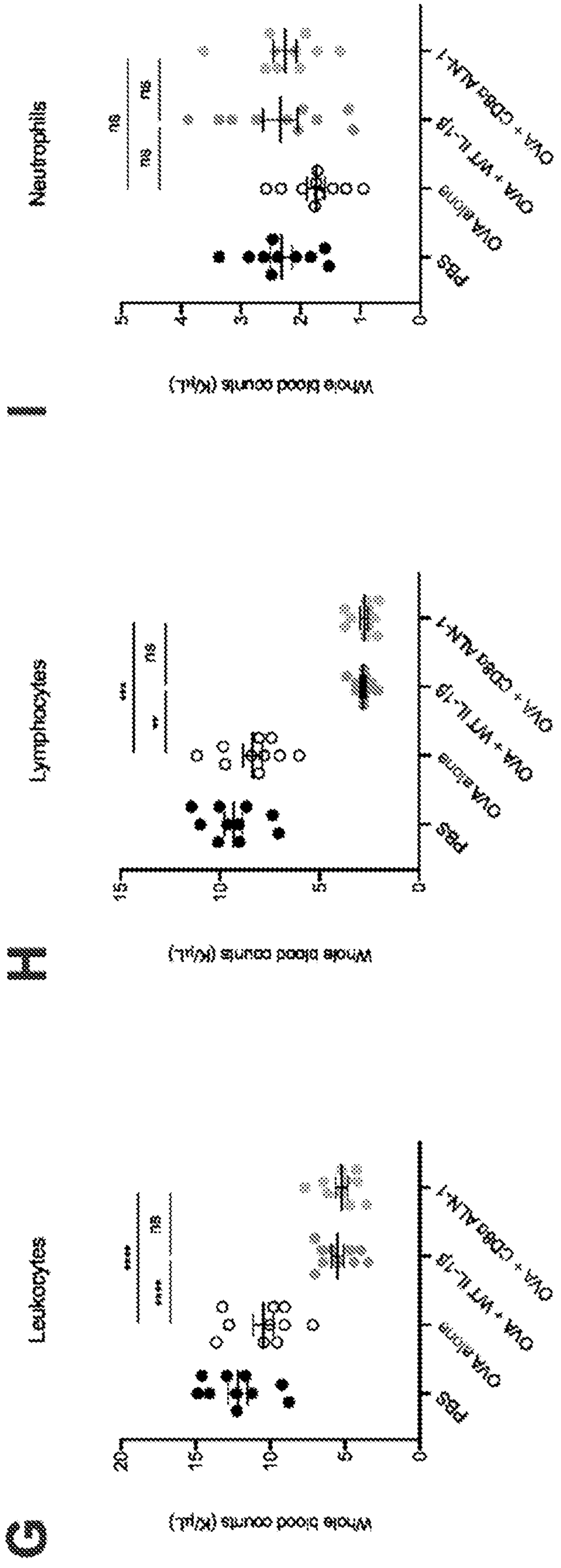

Example 4: Systemic Treatment of Mice with Antigen in Combination with CD8α ALN-1 is Completely Free of Toxicity Because WT IL-1β is well known for its capacity to induce systemic inflammation, we addressed the safety of the immunization strategy described above. As a measure of morbidity, we measured mouse body weight over time and evaluated the systemic release of IL-6 in blood, sampled 6 h after the first treatment. In these samples, we also looked for abnormalities in different hematological parameters (FIG. 23A). We found that repeated delivery of WT IL-1β leads to detrimental side effects, such as severe body weight loss (FIGS. 23B-C), systemic release of IL-6 (FIG. 23D) and platelet destruction (FIGS. 23E-F), whereas treatment with a corresponding dose of CD8α ALN-1 had no significant effects on these parameters. Intriguingly, both WT IL-1β and CD8α ALN-1 elicit leukopenia (FIG. 23G), which we found is primarily due to a reduction in circulating lymphocytes (FIG. 23H) as the level of neutrophils remains unaltered (FIG. 23I).

We looked further into this leukopenia and observed that, based on Hemavet 950FS measurements, this decrease in circulating lymphocytes is apparent 6 h after treatment and is thereafter further maintained when CD8α ALN-1 is repeatedly administered (FIG. 32A). Using flow cytometry, we further investigated which lymphocyte subpopulations were exactly affected (see FIG. 32B for the gating strategy) and observed drops in absolute counts for all evaluated cell types (FIG. 32C).

Together, these data show that overall wellbeing of mice is improved when IL-1β activity is restricted to $CD8^+$ T cells.

Figure 24:
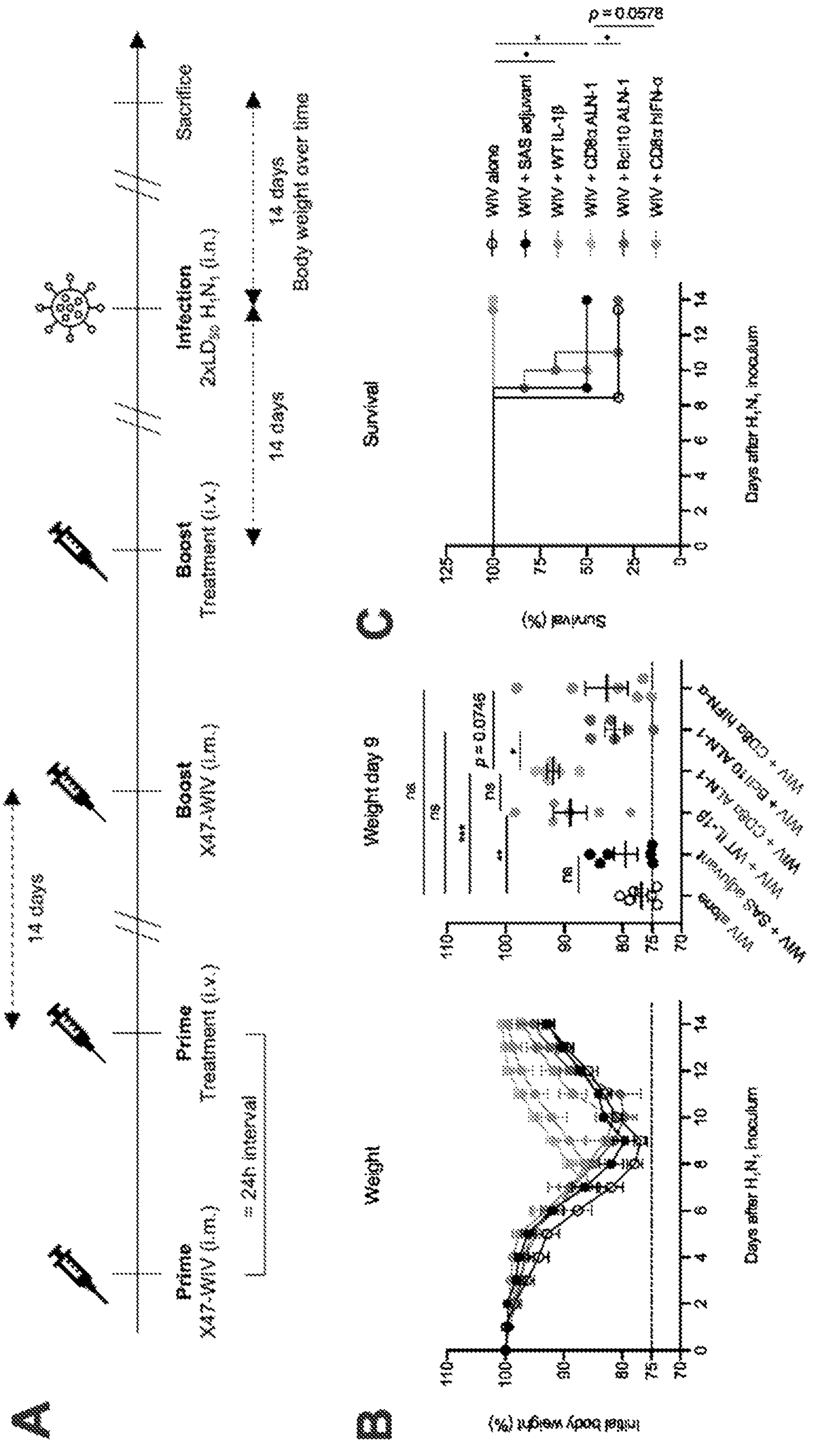
FIGS. 24A-I shows that an influenza vaccine adjuvanted with CD8α ALN-1 protects mice against viral infection. Panel A shows a schematic representation of the prime-boost prophylactic influenza vaccination experiment. BALB/c mice were immunized intramuscularly (i.m.) with X47 WIV (15 μg), either alone or combined with SAS adjuvant (15 g i.m. together with WIV), WT IL-1β (5 g), CD8α ALN-1, untargeted Bcll10 ALN-1 or CD8α hIFNα2 (10 g i.v. 24 h post-WIV). An identical boost treatment was delivered two weeks later. A heterosubtypic pH1N1 virus that shares strongly conserved T cell epitopes with X47 WIV was used to infect the mice two weeks later (intranasally (i.n), $2\times LD_{50}$). Panel B shows a change in body weight over time (left) or after nine days of infection (right) of mice challenged i.n. with a high inoculum of pH1N1 influenza virus. Data points represent the mean (left) or individual mice (right)±s.e.m. of a representative of two independent experiments with n=6 mice/group. *, p<0.001; , p<0.01; *, p<0.05 by one-way ANOVA with Tukey's multiple comparisons test. Panel C shows a Kaplan-Meier curve, representing survival of mice during pH1N1 influenza virus infection. Each data point represents the mean survival (%)±s.e.m. of a representative of two independent experiments with n=6 mice/group. *, p<0.05 by log-rank testing. Panels D-I shows change in body weight (%) over time of virus-infected mice for each individual treatment, including WIV alone (Panel D) or combined with SAS (Panel E), WT IL-1β (Panel F), CD8α ALN-1 (Panel G), untargeted Bcll10 ALN-1 (Panel H) and CD8α hIFNα2 (Panel I).
Figure 24:
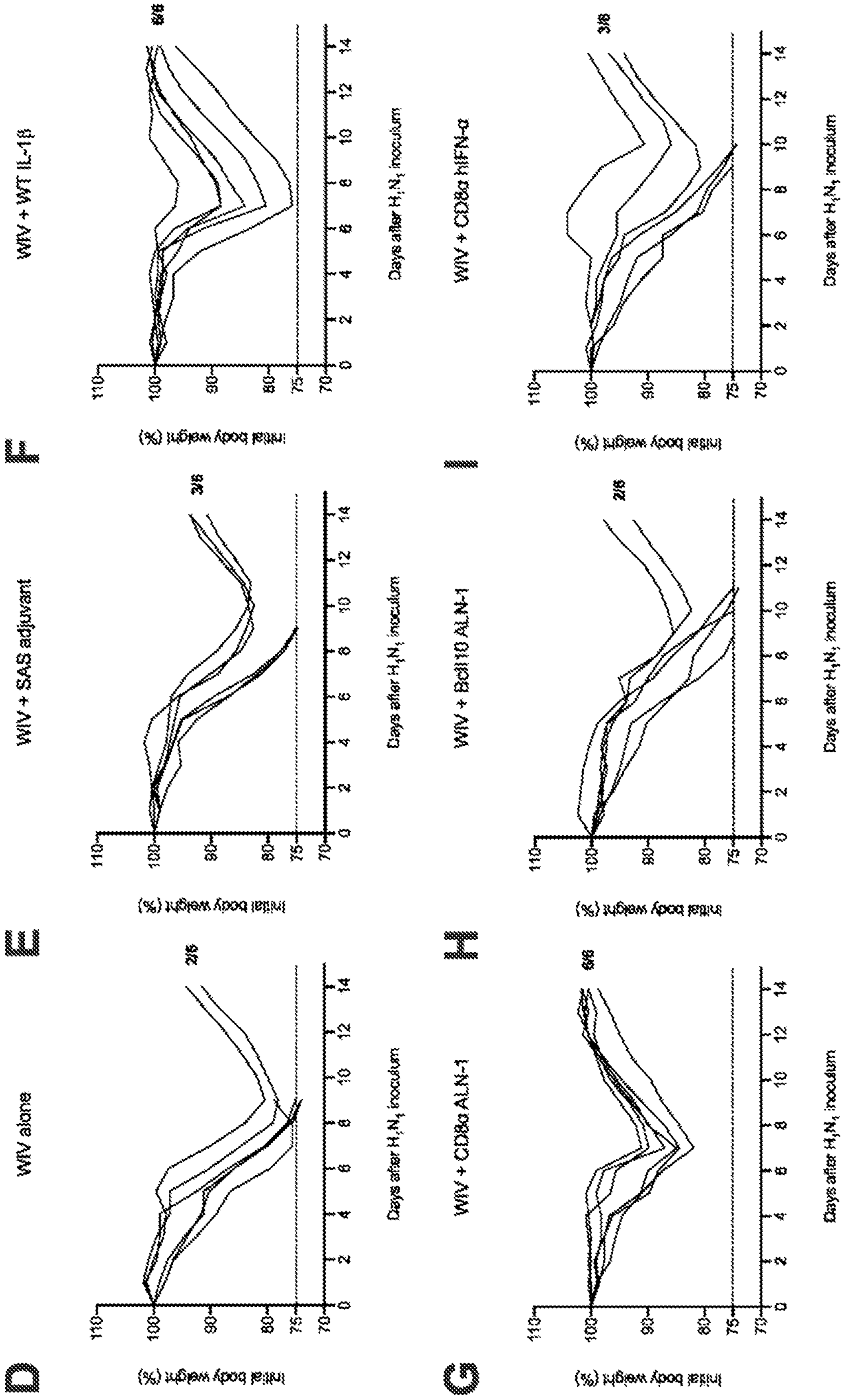

Example 5: An Influenza Vaccine Adjuvanted with CD8α ALN-1 Protects Mice Against Viral Infection Adjuvants promoting T cell responses against conserved influenza epitopes could be critical in the search for a universal influenza vaccine. Therefore, we evaluated the efficacy of CD8α ALN-1 as an adjuvant in a prime-boost vaccination strategy, using whole-inactivated X47 (H3N2) virus (WIV) as source of viral antigen, to protect against challenge infection with a heterosubtypic H1N1 2009 pandemic (pH1N1) influenza virus, a mouse-adapted derivative from a clinical isolate responsible for the 2009 flu pandemic (FIG. 24A). Protection in this model is expected to depend predominantly on T cell responses as mainly T cell epitopes are conserved between heterosubtypic X47 and pH1N1. We found that all mice vaccinated with CD8α ALN-1 survived the challenge infection with pH1N1 (FIGS. 24B-I). Treatment with WIV and CD8α ALN-1 was as efficacious as treatment with WIV an WT IL-1β. Four out of six mice immunized with WIV alone succumbed to the infection. This suggests that CD8α ALN-1 treatment induces potent cross-protective antiviral immunity. Interestingly, vaccination with CD8α ALN-1 also outperforms the commercial Sigma Adjuvant System (SAS), an oil-in-water emulsion containing MPLA, for which no significant difference with WIV alone could be observed. Moreover, no protection compared to the WIV only vaccine was observed when using untargeted Bcl110 ALN-1 or a CD8α sdAb coupled to human IFNα2. As human IFNα2 is inactive in mice and has a molecular weight comparable to WT IL-1β, this molecule is used as control for possible effects via the CD8α sdAb.

Altogether, these data show that CD8α ALN-1 can be used as an adjuvant to protect against influenza A virus infection by prime-boost vaccination.

Example 6: The Protective Antiviral Effect of CD8α ALN-1 Correlates with the Induction of Strong and Long-Lasting Influenza-Specific T Cell Responses in Lung and Lymphoid Tissues Influenza virus nucleoprotein (NP) is a conserved internal antigen, known for its ability to mount strong and long-lasting T cell responses. Functionally, NP is an RNA-binding protein that encapsulates the viral genome and is required for RNA transcription, replication and viral genome packaging.

Figure 25:
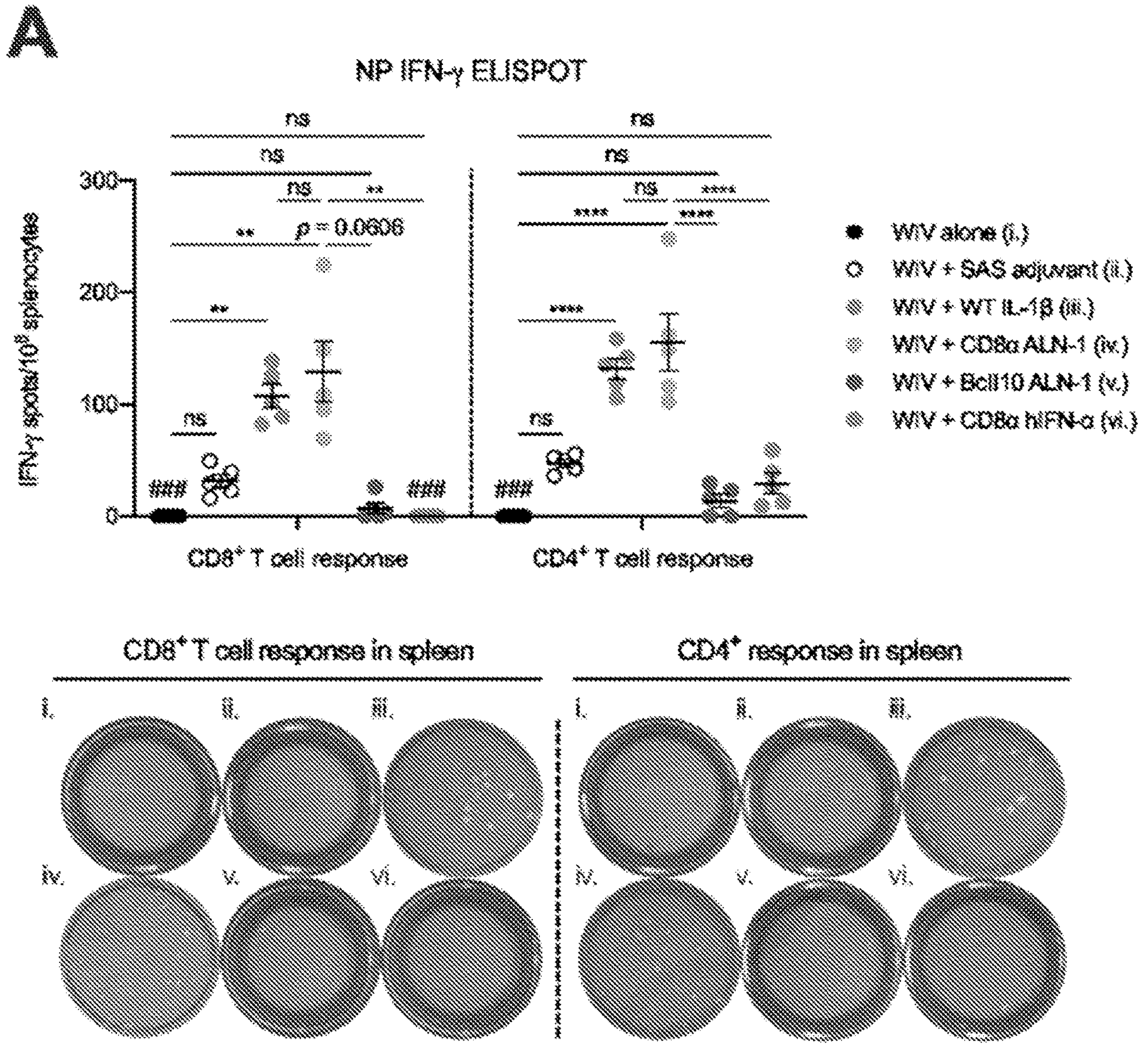
FIGS. 25A-C shows that the protective antiviral effect of CD8α ALN-1 correlates with the induction of strong and long-lasting influenza-specific T cell responses in lung and lymphoid tissues. Panel A shows induction of NP-specific $CD8^+$ and $CD4^+$ T cell responses in spleens of vaccinated mice two weeks after boost administration, measured by IFN-γ ELISPOT. Below the graph, representative ELISPOT pictures are shown, depicting the number of spots after treatment with: i. WIV alone, ii. WIV and SAS, iii. WIV and WT IL-1β, iv. WIV and CD8α ALN-1, v. WIV and untargeted Bcll10 ALN-1 and vi. WIV and CD8α hIFNα2. In the graph above, bars represent the mean±s.e.m. of a representative of two independent experiments with n=5 mice/group. **, p<0.0001; , p<0.01; ns, p 0.05 by Kruskall-Wallis test with Dunn's multiple comparisons test (CD8 ELISPOT) or one-way ANOVA with Tukey's multiple comparisons test (CD4 ELISPOT). Undetectable responses are indicated by ###. Panel B shows the detection of NP-specific $CD8^+$ T cells in the lung-draining LNs (upper histograms) and lung parenchyma (lower histograms) of mice vaccinated with WIV and WT IL-1β or CD8α ALN-1, seven days post-pH1N1 influenza A virus infection. In the NP-pentamer*CTL population, $T_{CM}$, $T_{EM}$, and $T_{RM}$ cells are identified in LNs and/or lung parenchyma. Bars on the right represent the mean±s.e.m. of a representative of two independent experiments with n=5 mice/group. *, p<0.05; ns, p 0.05 by unpaired Student's t-test (two-tailed). In each set of histograms, the left bar represents WIV+CD8 ALN-1 and the right bar represents WIV+WT IL-1β. Panel C shows flow cytometric detection of NP-specific $CD8^+$ T cells in the lungs of surviving mice that were vaccinated with WIV and WT IL-1β or CD8α ALN-1, 50 days post-pH1N1 influenza A virus infection. Left-Representative histograms showing the fraction of NP-pentamer*cells in the $CD8^+$ T cell population. Right: Bars represent the mean±s.e.m. of one experiment with n=5 (WT IL-1β) or 6 (CD8α ALN-1) mice/group. ns, p≥0.05 by unpaired Student's t-test (two-tailed). See also FIG. 33.
Figure 25:
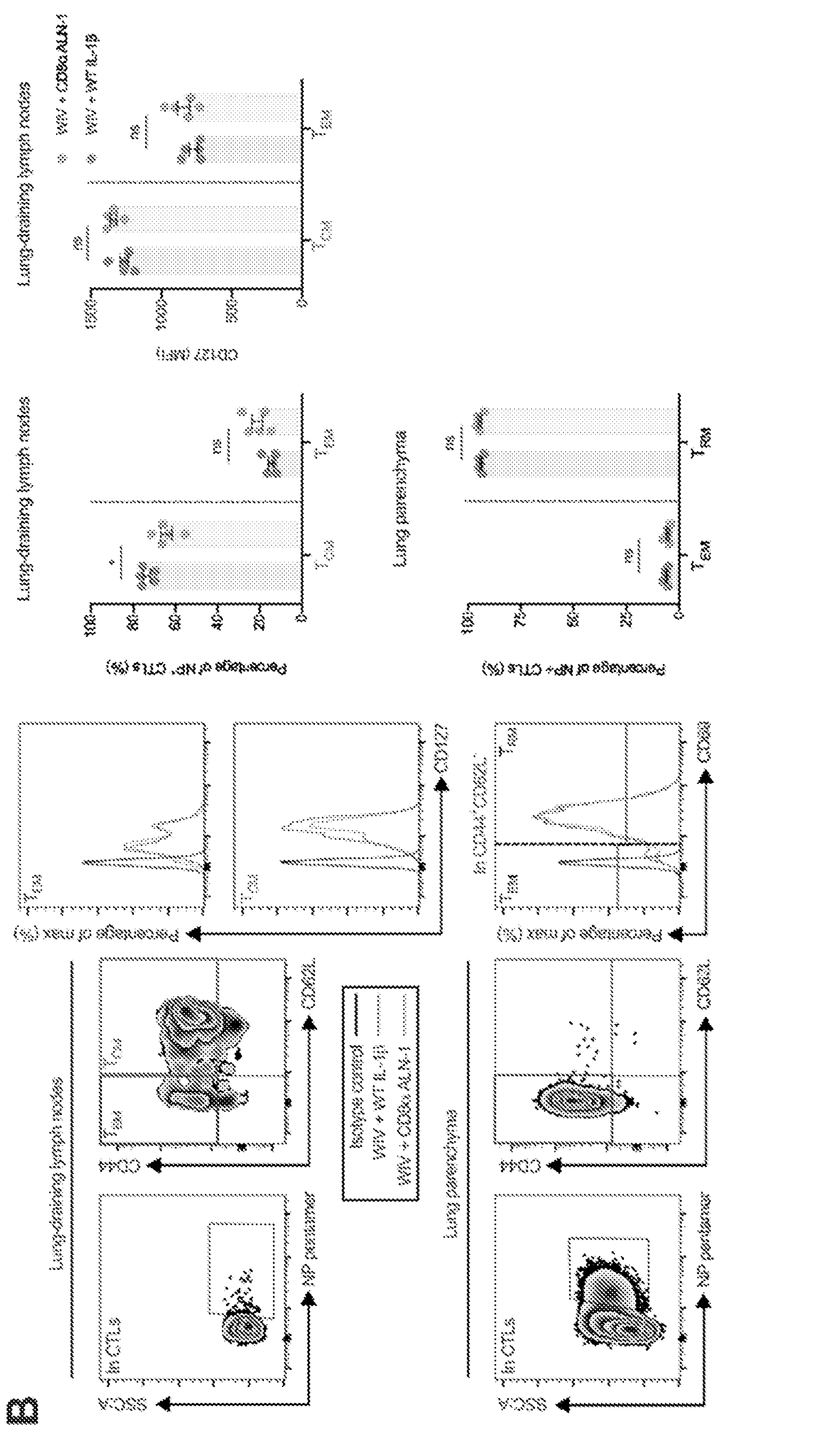
Figure 25:
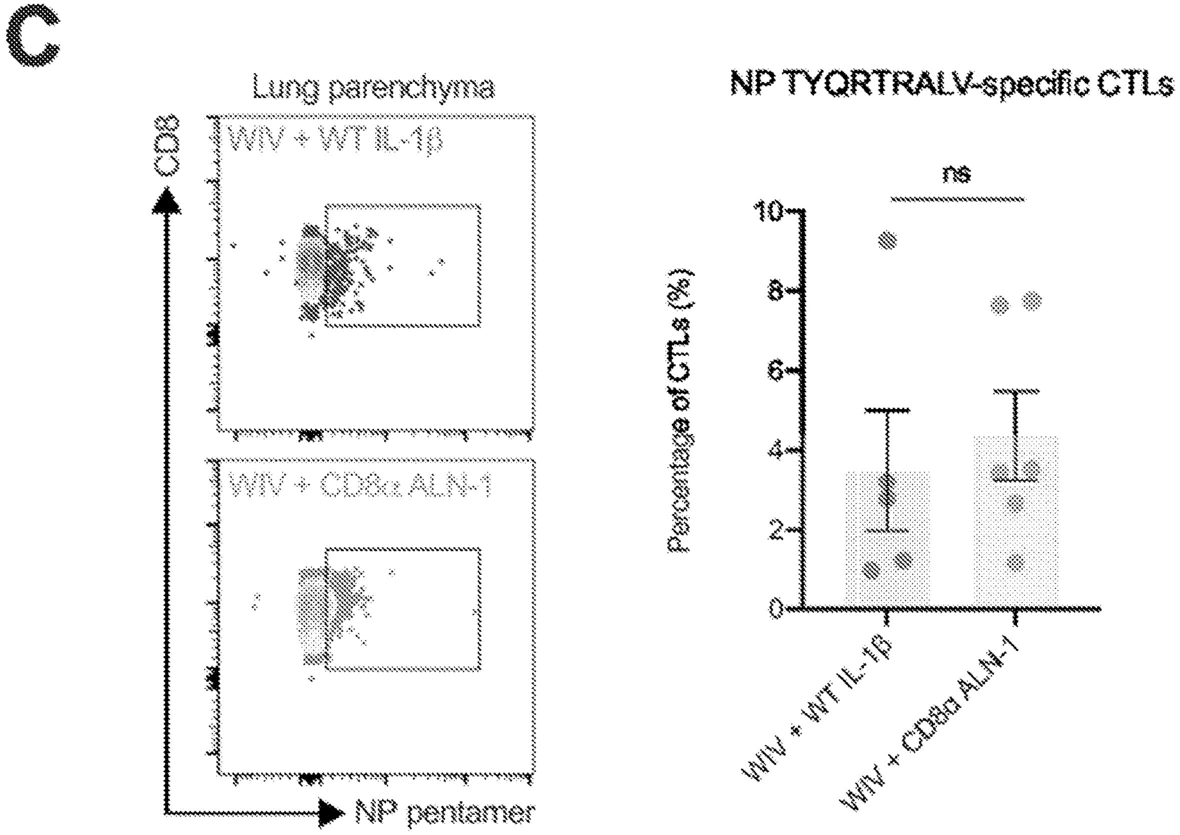

We sampled mice on different time points before, during and after pH1N1 virus encounter to evaluate whether vaccination with WIV combined with CD8α ALN-1 induces NP-specific T cell responses. Two weeks after the boost, we observed a significantly stronger increase in the number of splenic NP-specific IFN-γ producing $CD8^+$ and $CD4^+$ T cells in mice that had been vaccinated with WIV and CD8α ALN-1 compared with mice immunized with WIV alone (FIG. 25A). CD8α ALN-1 proved to be as efficacious as WT IL-1β to induce these responses. The combinations of WIV with either SAS, untargeted Bcll10 ALN-1 or CD8α hIFNα2 had no significant effect, which is consistent with their inability to enhance survival.

We further characterized the NP-specific $CD8^+$ T cells, induced upon vaccination with both WT IL-1β and CD8α ALN-1, in lung-draining mediastinal LNs and lung parenchyma of mice, one week post-influenza A virus challenge using flow cytometry (FIG. 25B; gating strategy in FIGS. 33A-B). In the draining LNs, the bulk of these NP-specific $CD8^+$ T cells showed a $CD62L^+CD44^+$ expression pattern, representing a central memory T cell ($T_{CM}$) pool. A much smaller fraction consisted of $CD62L^-CD44^+$cells, which identify as effector memory T cells ($T_{EM}$). Consistent with this profile, higher expression of the pro-survival marker CD127 (IL-7Ra) was found in the $T_{CM}$ subset compared to the $T_{EM}$ cells.

In the functional lung parenchyma, most of the retrieved NP-specific $CD8^+$ T cells were positive for the residency marker CD69, which is indicative for a tissue-resident ($T_{RM}$) phenotype. A smaller proportion of antiviral CTLs in the lung were CD69-$T_{EM}$ cells. In both LNs and lung, we found no significant differences for the evaluated parameters between mice treated with WT IL-1β and CD8α ALN-1. Moreover, we found that NP-specific $CD8^+$ T cells were still present in the lungs of mice vaccinated with WT IL-1β and CD8α ALN-1 by day 50 after pH1N1 infection (FIG. 25C; gating strategy in FIG. 33C).

Example 7: The Transcriptional Landscape of CD8+ T Cells Isolated from Vaccinated Mice During Influenza Virus Infection Supports the Cellular Adjuvant Effect of CD8α ALN-1

The previous data clearly demonstrate that vaccination of mice with WIV and CD8α ALN-1 raises potent and long-lasting $CD8^+$ and $CD4^+$ T cell responses, directed against the viral NP antigen. In order to better understand how selective IL-1β activity on $CD8^+$ T cells establishes these effects, we performed RNA sequencing and looked into transcriptomic changes in CTLs. For this, we sorted $CD8^+$ T cells from the lung parenchyma and lung-draining mediastinal LNs of mice vaccinated with either WIV alone or combined with WT IL-1β or CD8α ALN-1, one week after viral challenge (see FIGS. 34A-B for the gating strategy).

Figure 26:
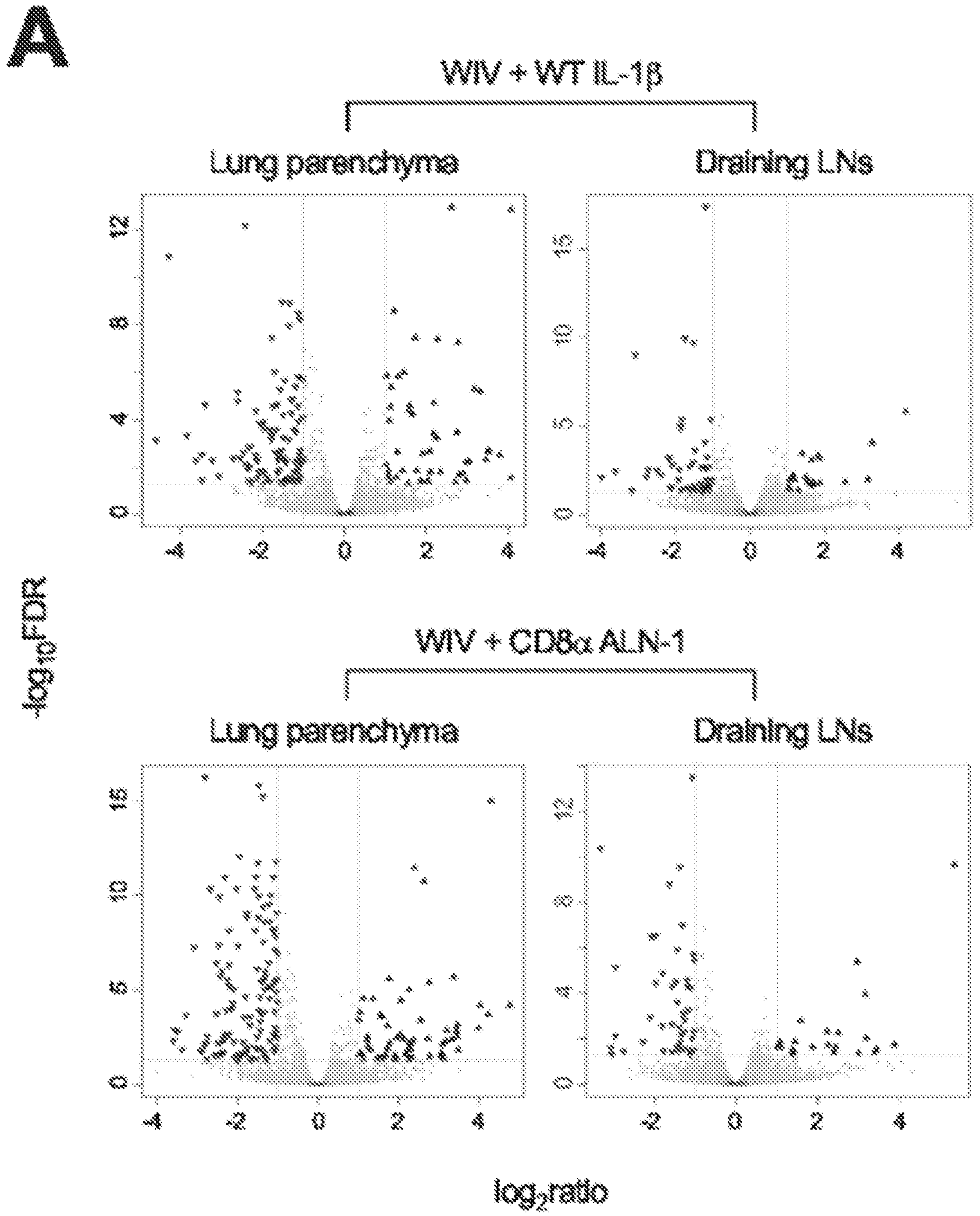
FIGS. 26A-D shows that the transcriptional landscape of $CD8^+$ T cells isolated from vaccinated mice during influenza virus infection supports the cellular adjuvant effect of CD8α ALN-1. Panel A shows volcano plots showing all genes found differentially up-(blue) or downregulated (red) in $CD8^+$ T cells sorted from lung parenchyma (left) or lung-draining mediastinal LNs (right) of mice vaccinated with WIV and WT IL-1β (up) or CD8α ALN-1 (down), compared with mice treated with WIV alone. Significance is indicated by a False Discovery Rate (FDR)<0.05 and an absolute $\log_2$ fold-change>1. Panel B shows heat maps of all statistically significant DEGs (differentially expressed genes) identified in $CD8^+$ T cells isolated from lungs (left map) or draining LNs (right map) of mice vaccinated with WIV and WT IL-1β (left columns) or CD8α ALN-1 (right column). Cells summarize the $\log_2$ fold-change in the gene expression level of n=3 mice/group, compared to treatment with WIV alone. Clusters indicate DEGs shared between (i.) or unique for treatment with WT IL-1β (iii.) and/or CD8α ALN-1 (ii.). Within these clusters, genes are organized by increasing FDR. Panel C shows top five of up- and downregulated GO biological processes, clustered using the DAVID bioinformatics tool based on the lists of DEGs identified in lungs and draining LNs. Panel D shows a graphical representation of the subcellular localization of gene products with a known association with regulation of $CD8^+$ T cell activation and memory development (based on literature). See also FIG. 34.
Figure 26:
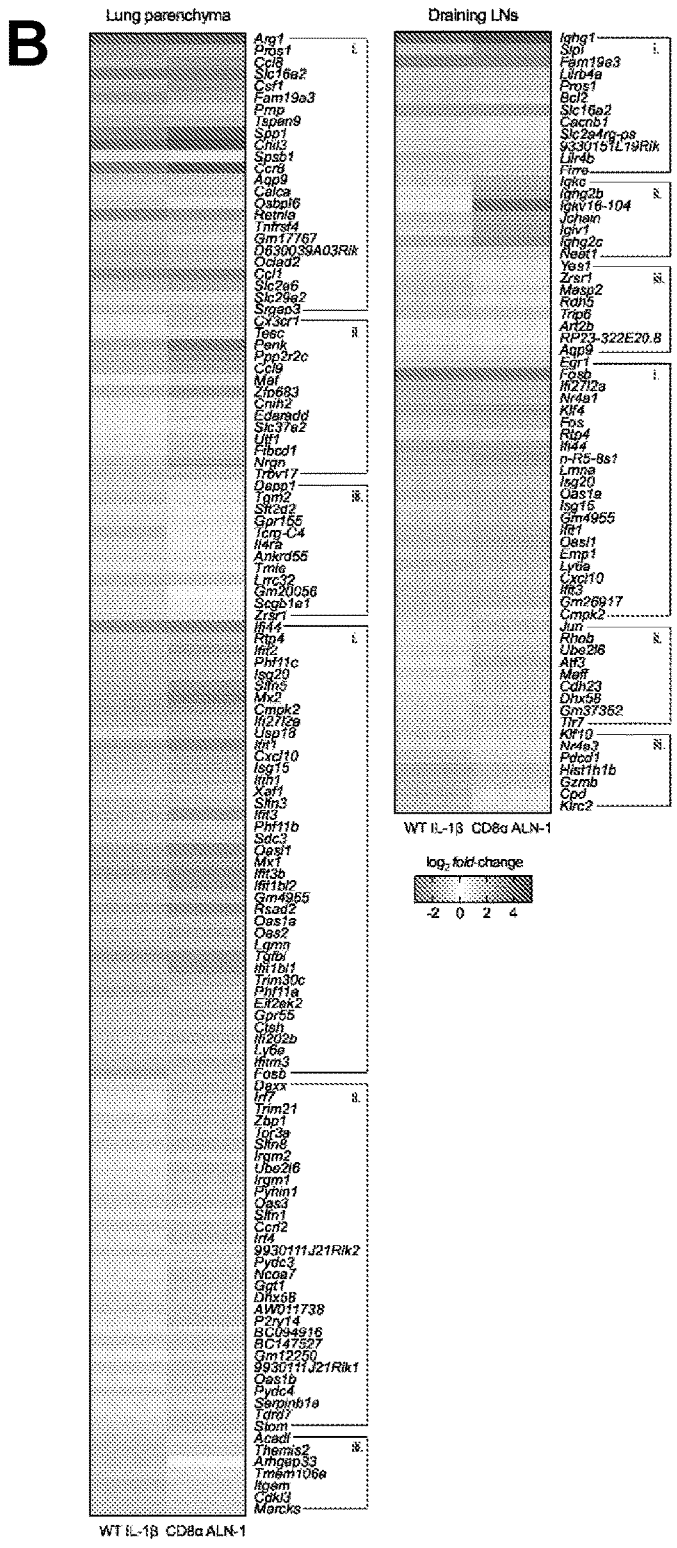
Figure 26:
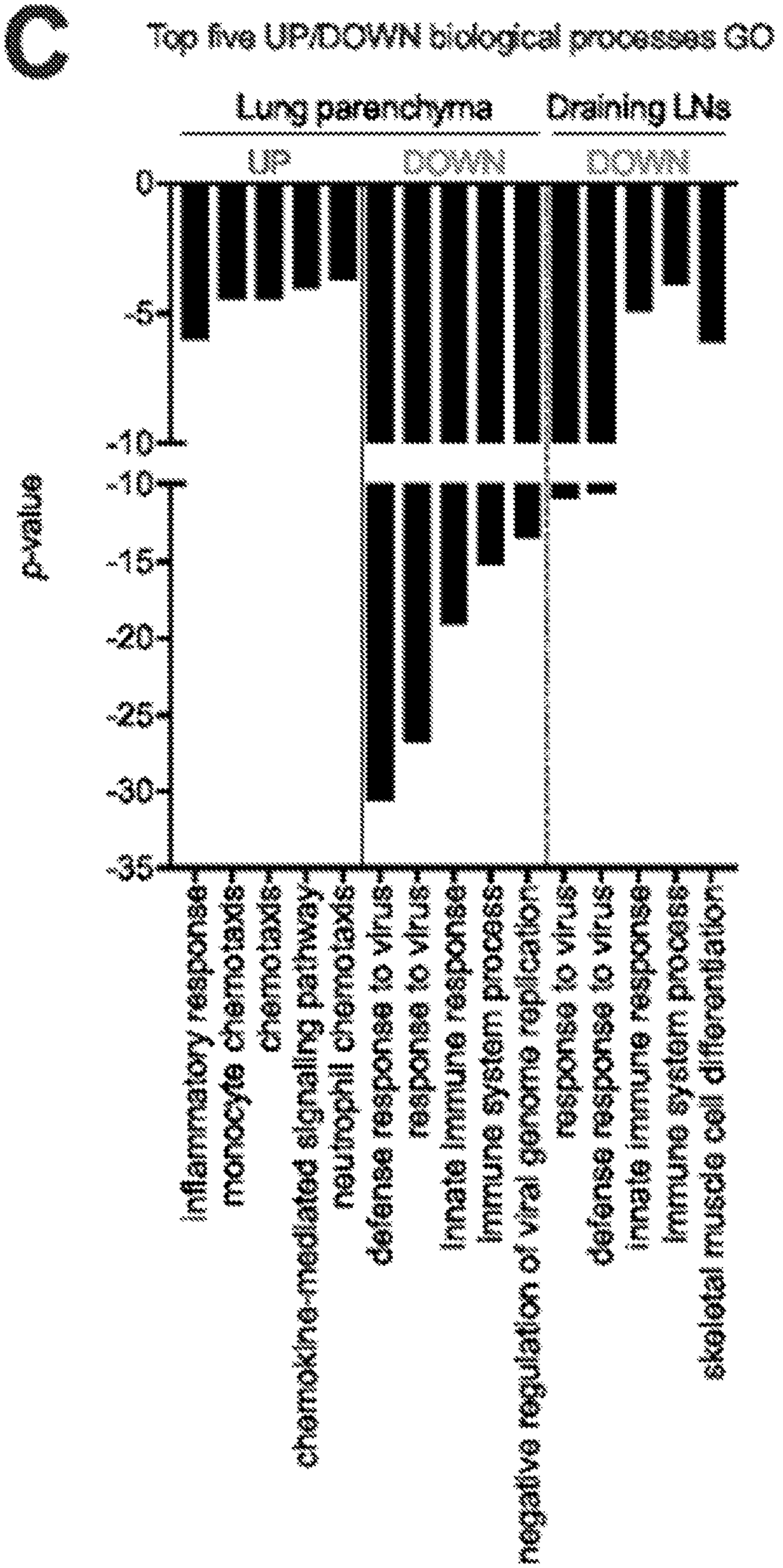
Figure 26:
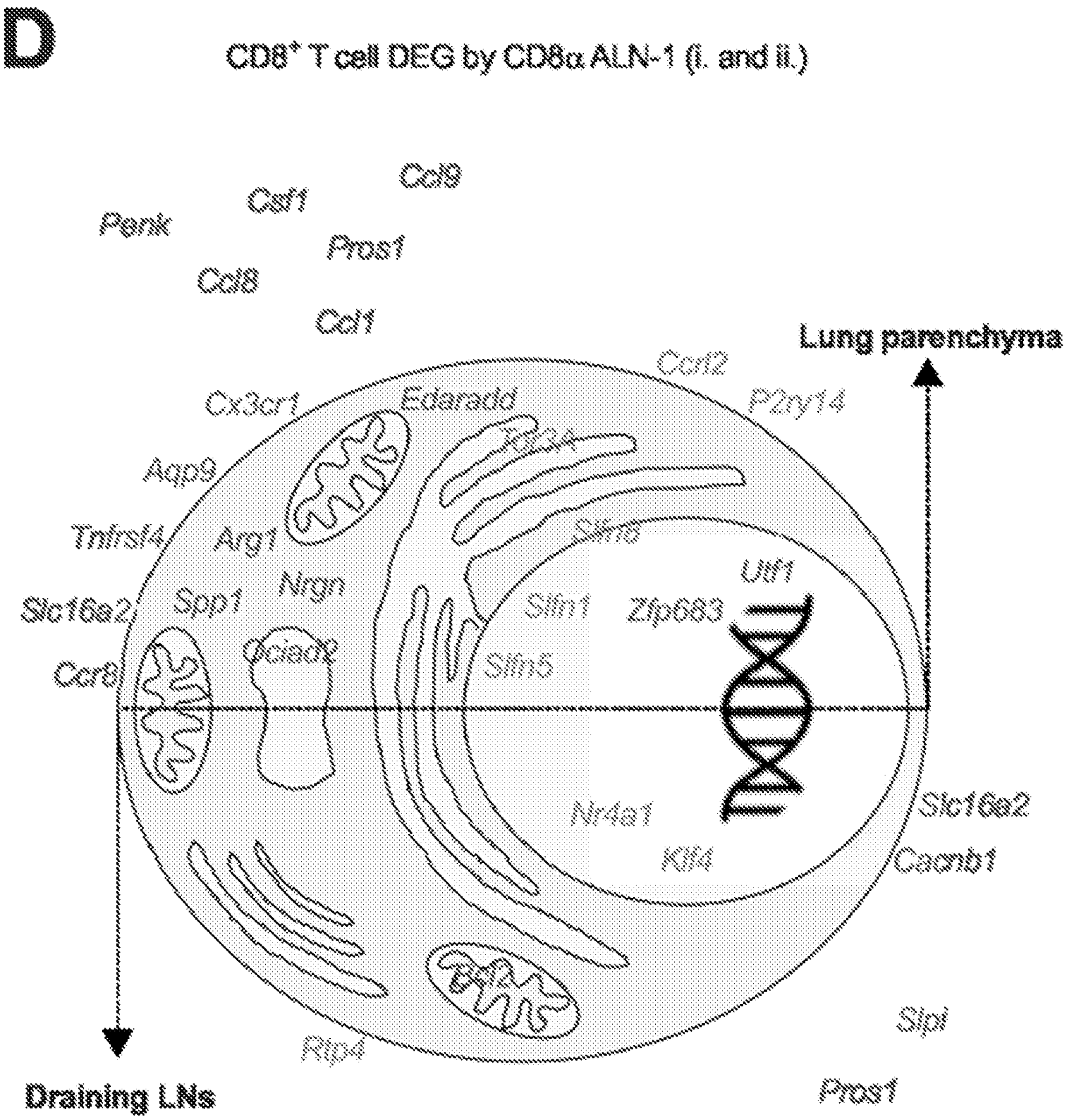

The transcriptome of $CD8^+$ T cells isolated from mice vaccinated with WIV and WT IL-1β or CD8α ALN-1 was significantly altered in lung (50 up- and 76 downregulated genes) and to a lesser extent in draining LNs (27 up- and 38 downregulated genes) compared with mice vaccinated with WIV alone (FIGS. 26A-B, FIG. 34C). For mice vaccinated with WIV and WT IL-1β or CD8α ALN-1, all genes that were found to be significantly up- or downregulated compared to WIV alone vaccinated mice are summarized in Supplementary Table 2.

We summarized the gene ontology (GO) biological processes (BPs) associated with these transcriptome changes by performing DAVID bioinformatics analysis using the differentially expressed genes (DEGs) in lung or draining LNs as input. Among the top-five most upregulated BPs were the inflammatory response and different chemotactic processes, indicative for immune cell recruitment to the site of viral infection (FIG. 26C). Furthermore, this GO analysis indicated that genes associated with the antiviral response to influenza (e.g. lfi2712a, Isg20, Oas1a, Isg15, Ifit1, Oas11 and Ifit3) were strongly enriched in mice vaccinated with WIV alone as compared to mice vaccinated with WT IL-1β or CD8α ALN-1.

We performed a structured literature search to correlate the identified transcriptional changes in $CD8^+$ T cells to the enhanced T cell responses and survival rates after viral challenge observed in mice vaccinated with WT IL-1β or CD8α ALN-1. We found that several transcripts with previously reported roles in long-term survival of T cells (e.g. Cacnb1, Bc12 and Aqp9 and Arg1), installation of peripheral residency (e.g. Zfp683 or Hobio, activity of T cells (e.g. Pros1 and Tnfrsf4) and T cell effector functions (e.g. Cx3cr1) were significantly upregulated in $CD8^+$ T cells isolated from mice vaccinated with WT IL-1β and CD8α ALN-1. On the other hand, downregulation of several Schlafen-family genes (e.g. Slfn 1, 3, 5 and 8) was found in these cells, which has been described before as a consequence of CTL activation, allowing T cells to exit a quiescent state. We further summarized DEGs with known importance for different $CD8^+$ T cell-related processes in FIG. 7D.

Remarkably, in draining LNs from mice vaccinated with WIV and CD8α ALN-1, we retrieved several genes associated with the immunoglobulin response (e.g. Igkc, Ighg2b and Jchain), mediated by B lymphocytes. These results are probably due to sample contamination with small amounts of B cells (FIG. 26B).

Altogether, these transcriptomics data indicate that WT IL-1β and CD8α ALN-1 provoke changes in the transcriptome of $CD8^+$ T cells that are in line with the generation of potent and active CTLs both in lung parenchyma and draining LNs.

Example 8: Methods of Examples 1-7

In Silico Analyses of the IL-1β/Receptor Interactions

Effects of mutations on the IL-1β/receptor interactions were predicted using the crystal structure of the human IL-1β with the extracellular fragments of its receptors (PDB code 1DEP). The average of five calculations with the FoldX 4.0 command PSSM was used to predict the AAG of the IL-1β Q148G mutant on its interaction with the IL-1R1. Buried surface area of the mutated residue and contacts of the mutated residue were derived using PDB-ePISA and by visualization of the crystal structure using UCSF Chimera.

Molecular Cloning and Recombinant Protein Production and Purification.

The Q148G mutation was introduced in the coding sequence of human IL-1β by site-directed mutagenesis (Q5© Hot Start High-Fidelity DNA Polymerase, M0493L, New England BioLabs Inc.) (5'-GAAGGCACTG-CATCTGGGTGGCCAGGACATGGAACAGC-3' (forward) (SEQ ID NO: 35); 5'-GCTGTTCCATGTCCTGGC-CACCCAGATGCAGTGCCTTC-3' (reverse complement) (SEQ ID NO: 36), primers were synthesized and purified by Eurogentec). Anti-mouse CD8α and Bcll10 sdAbs were generated by the VIB Protein Service Facility. WT IL-1β, CD8α WT IL-1β, CD8α ALN-1, Bcll10 ALN-1 and CD8α hIFNα2 were constructed in an in-house developed vector (pmTW). Plasmid DNA was purified from the supernatant of DH10B *E. coli* bacteria (18290-015, Thermo Fisher Scientific) after overnight growth (37° C., 175 rpm) by anion exchange chromatography, using the NucleoBond® PC 2000 system (740525, Machery Nagel). Proteins were produced in FreeStyle™ 293-F cells (R79007, Thermo Fisher Scientific), grown in suspension and transfected at a density of 1.2×10$^6$ cells/mL in 300 mL of FreeStyle™ 293 expression medium (12338026, Thermo Fisher Scientific) using the PEI-25k transfection reagent (600 g) (23966-2, Poly-Sciences Inc.), complexed with DNA (300 g). Additional medium (100 mL) was added 72 h post-transfection and 48 h later the supernatant was collected and filtered. Proteins were purified overnight at 4° C. by immobilized metal affinity chromatography (IMAC), using nickel ion-loaded sepharose resins (17526801, GE Healthcare). Resins were washed with two column volumes of 20 mM imidazole (8.14223.0250, Merck Millipore) in PBS (14190-169, Thermo Fisher Scientific) and proteins were eluted with 400 mM imidazole in PBS. Imidazole was exchanged with PBS by gel filtration using PD-10 columns (17-0851-01, GE Healthcare). Protein concentrations were determined by measuring absorbance at 280 nm. Purity was assessed by SDS-PAGE and Instant Blue (EP ISB1L, Expedeon) staining of the protein gel.

Cell Lines and Culture Conditions.

HEK-Blue-IL1R cells (hkb-il1r, Invivogen) and 132 1N1 human astrocytes were cultured in DMEM (41966-052, Thermo Fisher Scientific) supplemented with 10% fetal bovine serum (10270-106, Thermo Fisher Scientific), following conditions specified by the provider. All cells were grown at 37° C. in a humidified atmosphere containing 5% $CO_2$ and tested negative for contamination with *mycoplasma* (Venor™GeM *Mycoplasma* Detection Kit, PCR-based, MP0025, Sigma-Aldrich). No full authentication of the cell lines was performed.

In Vitro Bio-Activity and Activation-by-Targeting Proof of Concept Experiments.

For reporter gene experiments, HEK-Blue-IL1R cells were plated 24 h prior to transfection in 75 cm$^2$ flasks (1×10$^6$ cells/flask). Cells were transfected with 1 g of NF-κB-3 kB-Luc reporter gene DNA, using calcium phosphate precipitation. In the activation-by-targeting experiments, this transfection mix was additionally complemented with 10 g of DNA encoding mouse CD8α or an irrelevant target (pMET7 vector). Transfected cells were plated in 96-black bottom well plates 24 h post-transfection (1×10$^5$ cells/well). Cells were stimulated 24 h later with WT IL-1β, CD8α WT IL-1β or CD8α ALN-1 in a concentration range. Cells were lysed 6 h post-stimulation and incubated with luciferase substrate, after which luminescence was measured on an Envision luminometer. NF-κB activity was calculated as fold induction by normalization to the activity in unstimulated cells (bio-activity experiments) or cells stimulated with WT IL-13 (activation-by-targeting experiments).

Confocal Microscopy.

For confocal imaging, HEK-Blue-IL1R cells were seeded in 6-well plates (2.5×10$^5$ cells/well). The next day, cells were transfected with either DNA encoding Flag-tagged mouse CD8α or empty vector DNA (both 0.5 g) using lipofectamine-2000 (11668019, Thermo Fisher Scientific). 24 h later, transfected cells were detached using enzyme-free cell dissociation buffer (13151014, Thermo Fisher Scientific), washed and resuspended in DMEM with 10% fetal bovine serum in a 1:1-ratio (50,000 cells/mL). Next, cells (200 μL/well) were transferred to 8-well chambered coverslips (80826, Ibidi), coated with poly-L-lysine (P4707, Sigma-Aldrich). After 24 h, cells were treated for 30 min with vehicle or WT IL-1β, CD8α ALN-1 or untargeted ALN-1 (0.5 nM). At the end of the stimulation, cells were rinsed with PBS, containing $Ca^{2+}$and $Mg^{2+}$ (14040133, Thermo Fisher Scientific) and fixed for 15 min at room temperature in paraformaldehyde in PBS (4%). After three PBS washes, cells were permeabilized with Triton X-100 in PBS (0.1%) for 10 min and blocked in BSA in PBS (1%) for another 10 min at room temperature. Samples were then incubated overnight (4° C.) with mouse anti-Flag (2000× diluted) (F3165, Sigma) and rabbit anti-p65 (400× diluted) (sc-372, Santa Cruz) in BSA in PBS (1%). After three washes in PBS, cells were incubated for 30 min at room temperature (dark) with anti-rabbit Alexa 568 (500× diluted) (Al0042, Thermo Fisher Scientific) and anti-mouse Alexa 488 (Al1029, Thermo Fisher Scientific) (500× diluted) in BSA in PBS (1%). DAPI (2 μg/ml) was added to the secondary antibody mix to stain the nuclei. Next, cells were washed four times in PBS and covered with propyl gallate mounting medium. Images were acquired using a 60× 1.35 NA objective on an Olympus IX-81 laser scanning confocal microscope and analyzed using Fluoview 1000 software.

RNA isolation and RT-qPCR. 132 1N1 cells were seeded in 6-well plates (2.5×10$^5$ cells/well). The next day, cells were transfected with 0.5 g of DNA encoding mouse CD8α or an irrelevant target protein using lipofectamine-2000. 24 h later transfected cells were detached using trypsin-EDTA (25300096, Thermo Fisher Scientific), washed with PBS and resuspended in DMEM, supplemented with 10% fetal bovine serum (2×10$^5$ cells/mL). Cells were transferred to 24-well plates (1×10$^5$ cells/well) and stimulated the next day with vehicle or WT IL-1β, CD8α ALN-1 or untargeted ALN-1 (0.5 nM). After 6 h of treatment, cells were washed with PBS and total RNA was extracted using the RNeasy Mini Kit (74104, Qiagen). Reverse transcription was performed on 0.5 μg of total RNA using the PrimeScript RT Reagent kit (RR037A, Takara). For real-time cDNA amplification we used the LightCycler® 480 SYBR Green I Mastermix (04707516001, Roche) and the primers listed in Supplementary Table 1. Samples were amplified and analyzed using the LightCycler® 480 System (Roche). Relative quantification of mRNA expression was performed using ΔΔCt analysis with HPRT as reference gene.

Mice

All mice were housed under pathogen-free conditions in individually ventilated cages, placed in a temperature-controlled environment with a 12 h day/12 h night cycle. Mice received food and water adlibitum. Female C57BL/6 and BALB/c mice were purchased from Charles River Laboratories. OT-I transgenic CD45.1 C57BL/6 Rag2$^{-/-}$ mice and C57BL/6 IL-1R1$^{-/-}$ mice were bred at our own facility. All mice were between 7-12 weeks of age at the start of experiments. All animal experiments followed the guidelines of the Federation of European Laboratory Animal Science Association (FELASA) and were approved by Ethical Committees of Ghent University (ECD 17/80k, ECD 18/127k, ECD 16/07 and ECD 2018/86). For all experiments, mice were allocated to groups randomly. The investigators were not blinded during data collection nor analysis.

Binding Studies on Murine Splenocytes In Vitro.

Spleens were isolated from C57BL/6 or C57BL/6 IL-1R1$^{-/-}$ mice, collected in PBS and passed through 70 m nylon strainers by mashing. Red blood cells were lysed with a home-made lysis buffer (155 mM $Na_4Cl$, 12 mM $NaHCO_3$ and 127 M EDTA in PBS pH 7.4). Cells were resuspended in home-made FACS buffer (1% FBS, 0.09% sodium azide and 0.05 mM EDTA in PBS), plated in a 96-well plate (1×10$^6$ cells/well) and incubated for 2 h at 4° C. with WT IL-1β, CD8α ALN-1 or Bcll10 ALN-1 (10 nM for type I cDC binding, 1 nM for binding on all other cell subsets, concentration range for titration experiments). Cells were stained in FACS buffer with anti-CD16/32 (100× dilution) (Thermo Fisher Scientific) to block Fc receptors, followed by staining with LIVE/DEAD Fixable Aqua (1000× dilution) (Thermo Fisher Scientific), CD19 AF700 (500× dilution) (clone eBio1D3, 56-0193-82, Thermo Fisher Scientific), CD3 AF700 (clone 17A2, 56-0032-82, Thermo Fisher Scientific) or PE-Cy7 (250× dilution) (clone 145-2C11, 552774, BD Biosciences), CD4 PE (250× dilution) (clone RM4-5, 553048, BD Biosciences), CD11b PE-Cy7 (250× dilution) (clone M1/70, 101215, BioLegend), CD11c APC (100× dilution) (clone N418, 117310, BioLegend), XCR1 PE (100× dilution) (clone ZET, 148204, BioLegend) and His-tag FITC (2000× dilution) (clone 6G2A9, A01620, GenScript). Cells were recorded on a four-laser Attune Nxt flow cytometer (Thermo Fisher Scientific) and data were analyzed using FlowJo software (Treestar). First, we selected single cells based on FSC/SSC and living cells based on negativity for LIVE/DEAD. Within this subset, we described $CD19^+$cells as B cells, CD19-/$CD3^+$/$CD4^+$cells as $CD4^+$ T cells, CD19-/$CD3^+$/CD4-cells as CD4-T cells (corresponding to CTLs), CD19-/$CD3^-$/CD11c*as cDCs, CD19-/$CD3^-$/CD11c*/$XCR1^+$ cells as type I cDCs and CD19-/$CD3^-$/CD11b*cells as myeloid cells.

In Vitro OT-Co-Culture Assay.

Bone marrow was isolated from tibias and femurs of C57BL/6 mice by flushing the bones with PBS. Red blood cells were lysed as described above and cells were seeded in 6-well plates ($1\times10^5$ cells/mL) in RPMI-1640 (61870-044, Thermo Fisher Scientific), supplemented with 5% Fetal Clone I (FCI), recombinant mouse GM-CSF (20 ng/mL), gentamicin (100 g/mL) (15710-049, Thermo Fisher Scientific) and 50 M 3-mercaptoethanol (21985-023, Thermo Fisher Scientific). After 10 days of culture, mature BM-DCs were plated in 6-wells ($2.5\times10^6$ cells/mL) and pulsed with 10 pM, 100 pM or 1 nM SIINFEKL ($OVA_{257-264}$) (AS-60193-1, AnaSpec) for 1 h at 37° C., 5% $CO_2$. Spleens were isolated from OT-I transgenic CD45.1 C57BL/6 Rag2/mice and processed to single cells as described before. $CD8^+$ T cells were purified by negative selection using magnetic-activated cell sorting (MACS) (130-104-075, Miltenyi Biotec), following the manufacturer's instructions. These purified OT-I cells express a transgenic T cell receptor (TCR), recognizing SIINFEKL. Cell were subsequently labeled with 5 M carboxyfluorescein succinimidyl ester (CFSE) (65-0850-84, Thermo Fisher Scientific) and plated ($1\times10^5$ cells/well) together with the loaded BM-DCs ($1\times10^4$ cells/well) in 96-well plates for 72 h, supplemented with inhibitory antibody (2000× dilution) (clone CT-CD8α, MA5-17594, Thermo Fisher Scientific), WT IL-1β or CD8α ALN-1 (1 nM). Following this co-culture, cells were stained in FACS buffer with anti-CD16/32, CD3 PE-Cy7, CD4 PE and CD25 APC (100× dilution) (clone PC61.5, 17-0251-81, Thermo Fisher Scientific). Samples were recorded on the Attune Nxt flow cytometer and data were analyzed using FlowJo software.

First, we selected single cells based on FSC/SSC. Within this subset, we described OT-I cells as $CD3^+$/CD4-/CFSE-$^{labeled}$. TNF (DY410, R&D Systems) and IFN-γ (CMC4033, Thermo Fisher Scientific) were detected in the conditioned supernatant by ELISA, following the manufacturer's instructions.

In Vivo OT-1 Proliferation Experiments.

$CD8^+$ OT-I cells were isolated and MACS-purified as described above. Purified cells were labeled with 5 M CellTrace Violet (CTV) (C34557, Thermo Fisher Scientific), according to the manufacturer's instructions, and i.v. adoptively transferred in C57BL/6 recipient mice ($1.5\times10^6$ cells/mouse in 200 L PBS). One day post-transfer, recipient mice were immunized i.p. with endotoxin-free full-length OVA protein (100 g/mouse in 50 L PBS) (vac-pova-100, Invivogen).

Starting together with the antigen delivery, mice received additional i.p. treatments with LPS (25 g/mouse) (tlrl-eklps, Invivogen), WT IL-1β (5 g/mouse), CD8α ALN-1 (10 g/mouse) or Bcl110 ALN-1 (10 g/mouse, all in 100 L PBS) every 24 h for three consecutive days. One day after the last adjuvant treatment, spleens were isolated and processed to single cells as described above and stained in FACS buffer with anti-CD16/32, CD19 AF700, CD3 PE-Cy7 (250× dilution), CD4 PE, CD45.1 BV605 (100× dilution) (clone A20, 110737, BioLegend), SIINFEKL in H-2 kB pentamer APC (10 L/sample, following the manufacturer's instructions) (F093-4A, ProImmune), CD44 PerCP-Cy5.5 (100× dilution) (clone IM7, 103032, BioLegend) and CD62L PE-Cy7 (100× dilution) (clone MEL-14, 104428, BioLegend). Cells were recorded on the Attune Nxt flow cytometer and data were analyzed using FlowJo software. Single cells were selected based on FSC/SSC. OT-I cells were described as CD19-/$CD3^+$/CD4-/$CD45.1^+$/SIINFEKL in H-2 kB pentamer*/$CTV^{labeled}$.

In vivo killing experiments.

Splenocytes were isolated from C57BL/6 mice, processed to single cells as described earlier and suspended in RPMI-1640, supplemented with 10% fetal bovine serum. Half of these splenocytes were pulsed with SIINFEKL (10 g/mL) for 2 h at 37° C., 5% $CO_2$, while the remaining cells were left unloaded. Peptide-loaded cells were labeled with 5 M CTV, according to the manufacturer's instructions, while unloaded cells were labeled with a 10-foldlower concentration of CTV (500 nM). Both splenocyte pools were subsequently mixed in a 1:1-ratio and i.v. transferred ($1\times10^7$ cells/mouse in 200 μL PBS) in recipient mice, five days after the last adjuvant treatment (the immunization strategy applied is presented earlier for the in vivo OT-1 proliferation experiments). One day post-transfer, splenocytes were isolated from recipient mice, processed to single-cell suspensions and recorded on the Attune Nxt flow cytometer. Transferred cells 5 were identified as $CTV^{labeled}$ cells after single cell selection using FSC/SSC. Data were analyzed using FlowJo software, allowing to calculate the percentage of antigen-specific killing as: 100−[100×(% $CTV^{high}$ treated mice/% $CTV^{low}$ treated mice)/(% $CTV^{high}$ PBS-treated mice/% $CTV^{low}$–PBS-treated mice)]. Prior to transfer, correct CTV labeling and peptide presentation was accounted using flow cytometry, by staining the splenocyte pools in FACS buffer with a SIINFEKL in H-2 kB PE antibody (100× dilution) (clone 25-D1.16, 141603, BioLegend).

Hematological Analyses.

Six hours after the initial delivery of OVA and adjuvant, blood was sampled from the tail vein of treated mice, collected in EDTA-coated microcuvette tubes (Sarstedt) and analyzed in a Hemavet 950FS whole blood counter (Drew Scientific). For the analysis of IL-6 in plasma, blood was centrifuged at 14,000×g for 10 min at 4° C., after which the cytokine concentration was determined by ELISA (431302, BioLegend), according to the manufacturer's instruction.

Influenza Viruses and Viral Infection Procedures.

X47 (H3N2) and pH1N1 (A/Belgium/145-MA/2009, a mouse-adapted virus derived from a clinical isolate of the H1N1 2009 pandemic virus) were grown on Madin-Darby canine kidney (MDCK) cells in serum-free RPMI-1640, complemented with L-1-tosylamide-2-phenylethyl chloromethyl ketone (TPCK)-treated trypsin (T1426, Sigma-Aldrich). WIV was prepared as described earlier. BALB/c mice were primed by an i.m. injection of whole-inactivated X47 virus (WIV) (15 g/mouse in 50 L PBS), followed by an i.v. injection with WT IL-1β (5 g/mouse), CD8α ALN-1 (10 g/mouse), Bcll10 ALN-1 (10 g/mouse) or CD8α hIFNa2 (10 g/mouse, all in 200 L PBS) 24 h post-WIV delivery. SAS adjuvant (15 g/mouse) (S6322-1VL, Sigma-Aldrich) was i.m. co-administered with WIV. An identical boost treatment was administered two weeks after priming. Two weeks post-boost, mice were challenged i.n. under mild isoflurane anesthesia (Abbott Animal Health) with 2×$LD_{50}$ of the pH1N1 in 50 L PBS. The body weight of the mice was determined daily, during 14 days, after infection and mice that had lost 25% or more of their initial body weight were euthanized. All influenza virus infections were conducted in a biosafety level 2+accredited animal facility.

IFN-γEnzyme-Linked Immunospot (ELISPOT) Assays.

For the OVA-specific IFN-γ ELISPOT assays, spleens were isolated from C57BL/6 mice seven days after the initial OVA immunization and first adjuvant treatment. For the NP-specific IFN-γ ELISPOT assays, spleens were isolated 30 from BALB/c mice two weeks after the boost treatment. Splenocytes were processed to single-cell suspensions as described above and seeded (2.5×$10^5$ cells/well) in a 96 well-plate, pre-coated with an anti-IFN-γ antibody (CT317-T2, U-CyTech biosciences), in the presence of peptide (5 g/mL) for 24 h. The ELISPOT was further developed according to the manufacturer's instructions. The peptides used for restimulation of the cells were the MHC-I epitopes $OVA_{257-264}$ (SIINFEKL) and $NP_{147-155}$ (TYQRTRALV) and the MHC-II epitopes $NP_{206-229}$ (FWRGENGRKTRSAYER-MCNILKGK), $NP_{55-77}$ (RLIQNSLTIERMVLSAFDERNK) and $NP_{182-205}$ (AVKGVGTMVMELIRMIKRGINDRN) (NP peptides were synthesized and purified by GenScript).

Analyses of T Cell Status in Lungs and Draining Lymph Nodes Upon Influenza Infection.

One week post-pH1N1 inoculum, mice were euthanized by overdose with ketamine (80 mg/kg) (Eurovet) and xylazine (5 mg/kg) (Bayer) in 500 μL PBS (i.p.) and perfused with PBS, supplemented with heparin (50 IU/mL) (H5515-100KU, Sigma-Aldrich). Lungs and lung-draining mediastinal LNs were isolated and collected in ice-cold PBS, supplemented with DnaseI (5 IU/mL) (4536282001, Sigma-Aldrich) and liberase (50 μg/mL) (5401119001, Sigma-Aldrich). Lungs were chopped finely using scissors and further minced mechanically using GentleMACS (Miltenyi Biotec). The obtained cell suspension was incubated for 30 min at 4° C. (while rotating) and subjected to another round of GentleMACS mincing. Red blood cells were lysed, as described before and finally cells were passed through 70 m nylon strainers.

LNs were mashed, passed through 70 m nylon strainers and incubated with DNaseI (5 IU/mL) and liberase (50 μg/mL) in PBS for 30 min at 4° C. (while rotating). Single cells isolated from lung and LNs were stained in FACS buffer with anti-CD16/32, LIVE/DEAD Fixable Aqua, CD45 APC-Cy7 (500× dilution) (clone 30-Fl1, 103116, BioLegend), CD3 PE-Cy7, CD4 BV605 (250× dilution) (clone RM4-5, 100547, BioLegend), CD8 PerCP-Cy5.5 (250× dilution) (clone 53-6.7, 100733, BioLegend), TYQR-TRALV in H-2 kB pentamer APC (10 L/sample, following the manufacturer's instructions) (F098-4A, ProImmune), CD44 BV711 (100× dilution) (clone IM7, 103057, BioLegend), CD62L PE (100× dilution) (clone MEL-14, 104407, BioLegend) and CD127 BV421 (100× dilution) (clone A7R34, 135023, BioLegend) (cells from lung only) or CD69 BV421 (100× dilution) (clone H1.2F3, 104527, BioLegend) (cells from LNs only). Cells were recorded on a five-laser FACSymphony (BD Biosciences) and data were analyzed using FlowJo software. First, we selected single cells based on FSC/SSC and living cells based on negativity for LIVE/DEAD. Within this subset, we identified antiviral CTLs as $CD45^+/CD3^+$/CD4-/$CD8^+$/TYQRTRALV in H-2 kB pentamer*cells. In LNs, $T_{CM}$ cells were further gated as $CD44^+/CD62L^+$and $T_{EM}$ cells as $CD44^+/CD62L^-$. In lung parenchyma, $T_{RM}$ cells were further gated as $CD44^+$/$CD62L^-/CD69^+$and $T_{EM}$ cells as $CD44^+/CD62L^-$/CD69-.

CD8+ T Cell Sorting and RNA Extraction.

Lungs and lung-draining mediastinal LNs were isolated from mice one week post-pH1N1 infection and processed to single-cell suspensions as described above. Single cells were stained in FACS buffer with anti-CD16/32, LIVE/DEAD Fixable Aqua, CD45 eFluor450 (500× dilution) (clone 30-Fl1, 48-0451-82, Thermo Fisher Scientific), CD3 PE-Cy7, CD4 FITC (250× dilution) (clone RM4-5, 100510, BioLegend) and CD8 PE (500× dilution) (clone 53-6.7, 12-0081-82, Thermo Fisher Scientific). Samples were run on a three-laser FACSMelody (BD Biosciences) and CD8+ T cells were sorted out (4° C.) of the mixed cell populations and captured in 350 L of RLT+lysis buffer, supplemented with 3-mercaptoethanol (4° C.) (RNeasy Plus Micro Kit, 74034, Qiagen). First, we selected single cells based on FSC/SSC and living cells based on negativity for LIVE/DEAD. We then identified CTLs as $CD45^+/CD3^+$/CD4-/$CD8^+$ cells. RNA was isolated following the manufacturer's instructions (RNeasy Plus Micro Kit, 74034, Qiagen). The concentration, quality and integrity of RNA was addressed using an Agilent 2100 Bioanalyzer (Agilent) and only samples with an RNA integrity number (RIN)≥8, 280/260- and 260/230-values>1.8 were sent for sequencing.

RNA Sequencing, Data Processing, Analysis and Statistical Identification of DEGs.

The VIB Nucleomics Core performed the library preparation and library pooling, two runs of sequencing using an Illumina NextSeq 500 device, processing and analysis of the sequencing data and the statistical identification of DEGs.

For every sample, gene expression levels were first computed. Briefly, the number of reads in the alignments overlapping with gene features were counted for each individual run using the featureCounts R package. This raw count data of both runs was summed, resulting in total merged counts, which were coupled with reference gene annotations. Absent genes, for which all samples had less than 1 counts-per-million, were filtered out. Every sample was corrected for its intrinsic GC-content using full quantile normalization on bins of GC-content. The variation in library size and RNA composition between samples was corrected by full quantile normalization using the EDASeq R package.

For each sample the normalized gene counts were divided by the total number of counts (in millions) and for every gene, these scaled counts were divided by the gene length (in kbp), resulting in the number of fragments per kilobase of gene sequence and per million fragments of library size (FPKM values). Statistical identification of DEGs was done by statistical modelling of the data, specifying the design of the experiment as follows: log(count)=WIV alone (LN)×$\beta_1$+WIV alone (lung)×$\beta_2$+WT IL-1β(LN)×$\beta_3$+WT IL-1β (lung)×$\beta_4$+CD8α ALN-1 (LN)×$\beta_5$+CD8α ALN-1 (lung)×$\beta_6$. The edgeR R package, version 3.20.9, was used to estimate all coefficients β for every gene by fitting a negative binomial generalized linear model (GLM), using offsets instead of normalized counts. These model estimates allowed for computing the contrasts of interest, here being (i) the WT IL-1β effect in lungs and LNs (WIV alone vs. WIV+WT IL-1β) and (ii) the CD8α ALN-1 effect in lungs and LNs (WIV alone vs. CD8α ALN-1). Using edgeR 3.20.9, differential expression (a significant deviation of these contrasts from 0) was tested with a GLM likelihood ratio test. Resulting p-values were corrected for multiple testing with Benjamini-Hochberg to control the FDR. Genes with a FDR<0.05 were selected and considered differentially expressed when the absolute log 2-ratio>1. For every identified DEG, the biological relevance was accounted by checking if the raw counts>50. We conducted an extensive literature research to select for DEGs with known roles during T cell homeostasis, activation, metabolism, exhaustion and memory formation (the search consisted of "gene name" AND "CD8 T cell" OR "influenza").

Statistical Analyses and Data Presentation.

Statistical analyses were performed using the GraphPad Prism 8 software (GraphPad Software). Unless stated otherwise, data are presented as mean±s.e.m. in all experiments. The number of independent biological replicates or the number of individual mice is shown as "n". Normality of the data was accounted by Shapiro-Wilk testing at the $\alpha=0.05$ significance level for every group in the statistical comparison. Normally distributed data sets were compared by unpaired Student's t-testing (two-tailed) for the statistical analysis of differences between two groups or ANOVA (one- or two-way or repeated measurements) with Tukey's or Sidak's multiple comparisons test for the statistical analysis of differences between more than two groups. Non-normally distributed data were compared by unpaired Mann-Whitney U testing (two-tailed) for the statistical analysis of differences between two groups or Kruskall-Wallis testing with Dunn's multiple comparisons test for the statistical analysis of differences between more than two groups.

Log-rank testing was used for the statistical analysis of differences between Kaplan-Meier survival curves. Statistical significance was throughout defined as $p<0.05$.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A vaccine composition, comprising (a) an adjuvant, comprising a chimeric protein or chimeric protein complex, comprising:

(i) a mutant IL-1β, wherein the mutant IL-1β has an amino acid sequence of at least 95% identity to SEQ ID NO: 1, (ii) one or more targeting moieties, said targeting moieties comprising recognition domains which specifically bind to an antigen or receptor of interest; and (iii) a connector between (i) and (ii), the connector being:

(1) an Fc domain, the Fc domain optionally having one or more mutations that reduces or eliminates one or more effector functions of the Fc domain, promotes Fc chain pairing in the Fc domain, and/or stabilizes a hinge region in the Fc domain that connects (i) and (ii) and/or (2) a flexible linker that connects (i) and (ii), wherein the mutant IL-1β is characterized by reduced affinity or activity at the IL-1 receptor, as compared to wild-type IL-1β, which is restorable by attachment to the one or more targeting moieties or upon inclusion of the one or more targeting moieties in the chimeric protein complex; and (b) an antigen which is suitable for inducing an immune response, wherein the antigen is selected from an influenza viral antigen and a 2019-nCoV protein, or an antigenic fragment thereof.

2. The vaccine composition of claim 1, wherein the mutant IL-1β comprises one or more mutations selected from A117G/P118G, R120X, L122A, T125G/L126G, R127G, Q130X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, 1172A, V174A, K208E, K209X, K209A/K210A, K219X, E221X, E221 S/N224A, N224S/K225S, E244K, and N245Q, wherein X is any amino acid, with respect to the amino acid sequence of SEQ ID NO: 1.

3. The vaccine composition of claim 2, wherein the mutant IL-1β comprises Q148G, with respect to the amino acid sequence of SEQ ID NO: 1.

4. The vaccine composition of claim 1, wherein the targeting moiety comprises a recognition domain that recognizes and/or binds an antigen or receptor on an endothelial cell, epithelial cell, mesenchymal cell, stromal cell, extracellular matrix (ECM), immune cell, organ cell, and/or tissue cell.

5. The vaccine composition of claim 4, wherein the targeting moiety comprises a recognition domain that recognizes and/or binds CD8 or CD4.

6. The vaccine composition of claim 1, wherein the targeting moiety comprises a recognition domain that is a full-length antibody or a fragment thereof, a single-domain antibody, a recombinant heavy-chain-only antibody (VHH), a single-chain antibody (scFv), a fully human VH domain, a shark heavy-chain-only antibody (VNAR), a microprotein, a darpin, an anticalin, an adnectin, an aptamer, a Fv, a Fab, a Fab', or a $F(ab')_2$.

7. The vaccine composition of claim 1, further comprising an aluminum gel or salt.

8. The vaccine composition of claim 1, wherein the vaccine further comprises an additional adjuvant selected from oil-in-water emulsion formulations, saponin adjuvants, Freunds Adjuvants, cytokines, toll like receptors ligands, and chitosans.

9. The vaccine composition of claim 1, wherein the connector between (i) and (ii) is a flexible linker.

10. The vaccine composition of claim 1, wherein the vaccine composition is formulated for administration intravenously, to the lung, by inhalation, via aerosol or nebulizer, by liquid nebulization, by dry powder dispersion or by meter-dose administration.

11. The vaccine composition of claim 1, wherein the adjuvant or vaccine composition has (a) low toxicity;

(b) an ability to stimulate a long-lasting immune response against the antigen;

(c) substantial stability;

(d) an ability to elicit a humoral immune response and/or a cell-mediated immunity to the antigen;

(e) a capability of selectively interacting with populations of antigen presenting cells;

(f) an ability to specifically elicit $T_{H1}$ and/or $T_{H2}$ cell-specific immune responses to the antigen; and/or (g) an ability to selectively increase appropriate antibody isotype levels against antigens, the isotype optionally being IgA, when administered to a patient.

12. The vaccine composition of claim 1, wherein the adjuvant or vaccine composition stimulates a $CD8^+$ T cell response to the antigen, when administered to a patient.

13. The vaccine composition of claim 1, wherein the adjuvant or vaccine composition stimulates activation of the IL-1R, when administered to a patient.

14. The vaccine composition of claim 1, wherein the adjuvant or vaccine composition does not substantially cause one or more of fever, neutrophilia and the release of acute phase proteins when administered to a patient.

15. A method for vaccinating a subject against an infectious disease, comprising administering the vaccine composition of claim 1 to the subject, wherein the infectious disease is caused by a virus selected from influenza and SARS-Cov-2.

16. The method of claim 15, wherein the adjuvant and antigen are administered concurrently or wherein the adjuvant complex and antigen are co-formulated.

17. The method of claim 15, wherein the adjuvant and antigen are administered sequentially.

18. The method of claim 15, wherein the adjuvant and antigen are administered in multiple doses.

19. The method of claim 15, wherein the adjuvant is administered in multiple booster doses and the antigen is administered once.

* * * * *

SEQUENCE LISTING

```
<160> NUMBER OF SEQ ID NOS: 571

<210> SEQ ID NO 1
<211> LENGTH: 153
<212> TYPE: PRT
<213> ORGANISM: Artificial Sequence
<220> FEATURE:
<223> OTHER INFORMATION: Synthetic Sequence

<400> SEQUENCE: 1

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125
```

```
Asn Met Pro Val Phe Leu Gly Gly Thr Lys Gly Gly Gln Asp Ile Thr
    130                 135                 140

Asp Phe Thr Met Gln Phe Val Ser Ser
145                 150


<210> SEQ ID NO 2
<211> LENGTH: 5
<212> TYPE: PRT
<213> ORGANISM: Artificial Sequence
<220> FEATURE:
<223> OTHER INFORMATION: Artificial polymer

<400> SEQUENCE: 2

Gly Gly Gly Gly Ser
1               5


<210> SEQ ID NO 3
<211> LENGTH: 10
<212> TYPE: PRT
<213> ORGANISM: Artificial Sequence
<220> FEATURE:
<223> OTHER INFORMATION: Artificial polymer

<400> SEQUENCE: 3

Gly Gly Gly Gly Ser Gly Gly Gly Gly Ser
1               5                   10


<210> SEQ ID NO 4
<211> LENGTH: 15
<212> TYPE: PRT
<213> ORGANISM: Artificial Sequence
<220> FEATURE:
<223> OTHER INFORMATION: Artificial polymer

<400> SEQUENCE: 4

Gly Gly Gly Gly Ser Gly Gly Gly Gly Ser Gly Gly Gly Gly Ser
1               5                   10                  15


<210> SEQ ID NO 5
<211> LENGTH: 20
<212> TYPE: PRT
<213> ORGANISM: Artificial Sequence
<220> FEATURE:
<223> OTHER INFORMATION: Artificial polymer

<400> SEQUENCE: 5

Gly Gly Gly Gly Ser Gly Gly Gly Gly Ser Gly Gly Gly Gly Ser Gly
1               5                   10                  15

Gly Gly Gly Ser
            20


<210> SEQ ID NO 6
<211> LENGTH: 25
<212> TYPE: PRT
<213> ORGANISM: Artificial Sequence
<220> FEATURE:
<223> OTHER INFORMATION: Artificial polymer

<400> SEQUENCE: 6

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 7
```

<211> LENGTH: 30
<212> TYPE: PRT
<213> ORGANISM: Artificial Sequence
<220> FEATURE:
<223> OTHER INFORMATION: Artificial polymer

<400> SEQUENCE: 7

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 8
<211> LENGTH: 35
<212> TYPE: PRT
<213> ORGANISM: Artificial Sequence
<220> FEATURE:
<223> OTHER INFORMATION: Artificial polymer

<400> SEQUENCE: 8

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 9
<211> LENGTH: 40
<212> TYPE: PRT
<213> ORGANISM: Artificial Sequence
<220> FEATURE:
<223> OTHER INFORMATION: Artificial polymer

<400> SEQUENCE: 9

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40
```

<210> SEQ ID NO 10
<211> LENGTH: 16
<212> TYPE: PRT
<213> ORGANISM: Artificial Sequence
<220> FEATURE:
<223> OTHER INFORMATION: Artificial polymer

<400> SEQUENCE: 10

```
Gly Gly Ser Gly Gly Ser Gly Gly Gly Gly Ser Gly Gly Gly Gly Ser
1               5                   10                  15
```

<210> SEQ ID NO 11
<211> LENGTH: 8
<212> TYPE: PRT
<213> ORGANISM: Artificial Sequence
<220> FEATURE:
<223> OTHER INFORMATION: Artificial polymer

<400> SEQUENCE: 11

```
Gly Gly Gly Gly Gly Gly Gly Gly
1               5
```

<210> SEQ ID NO 12
<211> LENGTH: 6
<212> TYPE: PRT
<213> ORGANISM: Artificial Sequence
<220> FEATURE:
<223> OTHER INFORMATION: Artificial polymer

<400> SEQUENCE: 12

Gly Gly Gly Gly Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Artificial polymer

<400> SEQUENCE: 13

Glu Ala Ala Ala Lys
1               5

<210> SEQ ID NO 14
<211> LENGTH: 10
<212> TYPE: PRT
<213> ORGANISM: Artificial Sequence
<220> FEATURE:
<223> OTHER INFORMATION: Artificial polymer

<400> SEQUENCE: 14

Glu Ala Ala Ala Lys Glu Ala Ala Ala Lys
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Artificial polymer

<400> SEQUENCE: 15

Glu Ala Ala Ala Lys Glu Ala Ala Ala Lys Glu Ala Ala Ala Lys
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: Artificial polymer

<400> SEQUENCE: 16

Ala Glu Ala Ala Ala Lys Glu Ala Ala Ala Lys Ala
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Artificial polymer

<400> SEQUENCE: 17

Ala Glu Ala Ala Ala Lys Glu Ala Ala Ala Lys Glu Ala Ala Ala Lys
1               5                   10                  15

Ala

<210> SEQ ID NO 18
<211> LENGTH: 22
<212> TYPE: PRT
<213> ORGANISM: Artificial Sequence
<220> FEATURE:
<223> OTHER INFORMATION: Artificial polymer

<400> SEQUENCE: 18

```
Ala Glu Ala Ala Ala Lys Glu Ala Ala Ala Lys Glu Ala Ala Ala Lys
1               5                   10                  15

Glu Ala Ala Ala Lys Ala
            20
```

<210> SEQ ID NO 19
<211> LENGTH: 27
<212> TYPE: PRT
<213> ORGANISM: Artificial Sequence
<220> FEATURE:
<223> OTHER INFORMATION: Artificial polymer

<400> SEQUENCE: 19

```
Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25
```

<210> SEQ ID NO 20

<400> SEQUENCE: 20

000

<210> SEQ ID NO 21
<211> LENGTH: 46
<212> TYPE: PRT
<213> ORGANISM: Artificial Sequence
<220> FEATURE:
<223> OTHER INFORMATION: Artificial polymer

<400> SEQUENCE: 21

```
Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
        35                  40                  45
```

<210> SEQ ID NO 22
<211> LENGTH: 5
<212> TYPE: PRT
<213> ORGANISM: Artificial Sequence
<220> FEATURE:
<223> OTHER INFORMATION: Artificial polymer

<400> SEQUENCE: 22

```
Pro Ala Pro Ala Pro
1               5
```

<210> SEQ ID NO 23
<211> LENGTH: 18
<212> TYPE: PRT
<213> ORGANISM: Artificial Sequence
<220> FEATURE:
<223> OTHER INFORMATION: Artificial polymer

<400> SEQUENCE: 23

Lys Glu Ser Gly Ser Val Ser Ser Glu Gln Leu Ala Gln Phe Arg Ser
1 5 10 15

Leu Asp

<210> SEQ ID NO 24
<211> LENGTH: 14
<212> TYPE: PRT
<213> ORGANISM: Artificial Sequence
<220> FEATURE:
<223> OTHER INFORMATION: Artificial polymer

<400> SEQUENCE: 24

Glu Gly Lys Ser Ser Gly Ser Gly Ser Glu Ser Lys Ser Thr
1 5 10

<210> SEQ ID NO 25
<211> LENGTH: 12
<212> TYPE: PRT
<213> ORGANISM: Artificial Sequence
<220> FEATURE:
<223> OTHER INFORMATION: Artificial polymer

<400> SEQUENCE: 25

Gly Ser Ala Gly Ser Ala Ala Gly Ser Gly Glu Phe
1 5 10

<210> SEQ ID NO 26
<211> LENGTH: 5
<212> TYPE: PRT
<213> ORGANISM: Artificial Sequence
<220> FEATURE:
<223> OTHER INFORMATION: Artificial polymer

<400> SEQUENCE: 26

Gly Gly Gly Ser Glu
1 5

<210> SEQ ID NO 27
<211> LENGTH: 5
<212> TYPE: PRT
<213> ORGANISM: Artificial Sequence
<220> FEATURE:
<223> OTHER INFORMATION: Artificial polymer

<400> SEQUENCE: 27

Gly Ser Glu Ser Gly
1 5

<210> SEQ ID NO 28
<211> LENGTH: 5
<212> TYPE: PRT
<213> ORGANISM: Artificial Sequence
<220> FEATURE:
<223> OTHER INFORMATION: Artificial polymer

<400> SEQUENCE: 28

Gly Ser Glu Gly Ser
1 5

<210> SEQ ID NO 29
<211> LENGTH: 35
<212> TYPE: PRT
<213> ORGANISM: Artificial Sequence
<220> FEATURE:
<223> OTHER INFORMATION: Artificial polymer

<400> SEQUENCE: 29

Gly Glu Gly Gly Ser Gly Glu Gly Ser Ser Gly Glu Gly Ser Ser Ser
1               5                   10                  15

Glu Gly Gly Gly Ser Glu Gly Gly Gly Ser Glu Gly Gly Gly Ser Glu
            20                  25                  30

Gly Gly Ser
        35

<210> SEQ ID NO 30

<400> SEQUENCE: 30

000

<210> SEQ ID NO 31
<211> LENGTH: 1273
<212> TYPE: PRT
<213> ORGANISM: Artificial Sequence
<220> FEATURE:
<223> OTHER INFORMATION: Artificial polymer

<400> SEQUENCE: 31

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

```
Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685
```

-continued

```
Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
```

```
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270
```

<210> SEQ ID NO 32
<211> LENGTH: 222
<212> TYPE: PRT
<213> ORGANISM: Artificial Sequence
<220> FEATURE:
<223> OTHER INFORMATION: Artificial polymer

<400> SEQUENCE: 32

```
Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125

Leu Thr Arg Pro Leu Leu Glu Ser Glu Leu Val Ile Gly Ala Val Ile
    130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
```

```
            180                 185                 190

Phe Ala Ala Tyr Ser Arg Tyr Arg Ile Gly Asn Tyr Lys Leu Asn Thr
        195                 200                 205

Asp His Ser Ser Ser Ser Asp Asn Ile Ala Leu Leu Val Gln
    210                 215                 220


<210> SEQ ID NO 33
<211> LENGTH: 75
<212> TYPE: PRT
<213> ORGANISM: Artificial Sequence
<220> FEATURE:
<223> OTHER INFORMATION: Artificial polymer

<400> SEQUENCE: 33

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60

Leu Asn Ser Ser Arg Val Pro Asp Leu Leu Val
65                  70                  75


<210> SEQ ID NO 34
<211> LENGTH: 419
<212> TYPE: PRT
<213> ORGANISM: Artificial Sequence
<220> FEATURE:
<223> OTHER INFORMATION: Artificial polymer

<400> SEQUENCE: 34

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190
```

```
Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
                245                 250                 255

Lys Pro Arg Gln Lys Arg Thr Ala Thr Lys Ala Tyr Asn Val Thr Gln
            260                 265                 270

Ala Phe Gly Arg Arg Gly Pro Glu Gln Thr Gln Gly Asn Phe Gly Asp
        275                 280                 285

Gln Glu Leu Ile Arg Gln Gly Thr Asp Tyr Lys His Trp Pro Gln Ile
    290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Lys Ala Asp Glu Thr Gln Ala Leu Pro Gln
    370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala
```

<210> SEQ ID NO 35
<211> LENGTH: 38
<212> TYPE: DNA
<213> ORGANISM: Artificial Sequence
<220> FEATURE:
<223> OTHER INFORMATION: Artificial polymer

<400> SEQUENCE: 35
gaaggcactg catctgggtg gccaggacat ggaacagc 38

<210> SEQ ID NO 36
<211> LENGTH: 38
<212> TYPE: DNA
<213> ORGANISM: Artificial Sequence
<220> FEATURE:
<223> OTHER INFORMATION: Artificial polymer

<400> SEQUENCE: 36
gctgttccat gtcctggcca cccagatgca gtgccttc 38

<210> SEQ ID NO 37
<211> LENGTH: 10
<212> TYPE: PRT
<213> ORGANISM: Artificial Sequence
<220> FEATURE:
<223> OTHER INFORMATION: Artificial polymer

<400> SEQUENCE: 37

Gly Phe Asn Ile Lys Asp Thr Tyr Ile His 1 5 10

<210> SEQ ID NO 38
<211> LENGTH: 17
<212> TYPE: PRT
<213> ORGANISM: Artificial Sequence
<220> FEATURE:
<223> OTHER INFORMATION: Artificial polymer

<400> SEQUENCE: 38

Arg Ile Asp Pro Ala Asn Asp Asn Thr Leu Tyr Ala Ser Lys Phe Gln
1 5 10 15

Gly

<210> SEQ ID NO 39
<211> LENGTH: 17
<212> TYPE: PRT
<213> ORGANISM: Artificial Sequence
<220> FEATURE:
<223> OTHER INFORMATION: Artificial polymer

<400> SEQUENCE: 39

Arg Ile Asp Pro Ala Asn Asp Asn Thr Leu Tyr Ala Arg Lys Phe Gln
1 5 10 15

Gly

<210> SEQ ID NO 40
<211> LENGTH: 11
<212> TYPE: PRT
<213> ORGANISM: Artificial Sequence
<220> FEATURE:
<223> OTHER INFORMATION: Artificial polymer

<400> SEQUENCE: 40

Gly Arg Gly Tyr Gly Tyr Tyr Val Phe Asp His
1 5 10

<210> SEQ ID NO 41
<211> LENGTH: 11
<212> TYPE: PRT
<213> ORGANISM: Artificial Sequence
<220> FEATURE:
<223> OTHER INFORMATION: Artificial polymer

<400> SEQUENCE: 41

Thr Arg Gly Tyr Gly Tyr Tyr Val Phe Asp Thr
1 5 10

<210> SEQ ID NO 42
<211> LENGTH: 5
<212> TYPE: PRT
<213> ORGANISM: Artificial Sequence
<220> FEATURE:
<223> OTHER INFORMATION: Artificial polymer

<400> SEQUENCE: 42

Ser Ile Ser Gln Tyr
1 5

<210> SEQ ID NO 43
<211> LENGTH: 5
<212> TYPE: PRT
<213> ORGANISM: Artificial Sequence
<220> FEATURE:
<223> OTHER INFORMATION: Artificial polymer

<400> SEQUENCE: 43

Ser Ile Ser Lys Tyr
1 5

<210> SEQ ID NO 44
<211> LENGTH: 6
<212> TYPE: PRT
<213> ORGANISM: Artificial Sequence
<220> FEATURE:
<223> OTHER INFORMATION: Artificial polymer

<400> SEQUENCE: 44

Ser Gly Ser Thr Leu Gln
1 5

<210> SEQ ID NO 45
<211> LENGTH: 6
<212> TYPE: PRT
<213> ORGANISM: Artificial Sequence
<220> FEATURE:
<223> OTHER INFORMATION: Artificial polymer

<400> SEQUENCE: 45

His Asn Glu Asn Pro Leu
1 5

<210> SEQ ID NO 46
<211> LENGTH: 6
<212> TYPE: PRT
<213> ORGANISM: Artificial Sequence
<220> FEATURE:
<223> OTHER INFORMATION: Artificial polymer

<400> SEQUENCE: 46

His Asn Glu Phe Pro Val
1 5

<210> SEQ ID NO 47
<211> LENGTH: 6
<212> TYPE: PRT
<213> ORGANISM: Artificial Sequence
<220> FEATURE:
<223> OTHER INFORMATION: Artificial polymer

<400> SEQUENCE: 47

His Asn Glu Phe Pro Pro
1 5

<210> SEQ ID NO 48
<211> LENGTH: 6
<212> TYPE: PRT
<213> ORGANISM: Artificial Sequence
<220> FEATURE:
<223> OTHER INFORMATION: Artificial polymer

<400> SEQUENCE: 48

Val Asn Glu Phe Pro Pro
1 5

<210> SEQ ID NO 49
<211> LENGTH: 6
<212> TYPE: PRT
<213> ORGANISM: Artificial Sequence
<220> FEATURE:
<223> OTHER INFORMATION: Artificial polymer

<400> SEQUENCE: 49

Val Asn Glu Phe Pro Val
1 5

<210> SEQ ID NO 50
<211> LENGTH: 8
<212> TYPE: PRT
<213> ORGANISM: Artificial Sequence
<220> FEATURE:
<223> OTHER INFORMATION: Artificial polymer

<400> SEQUENCE: 50

Gly Phe Ile Phe Ser Asn Tyr Gly
1 5

<210> SEQ ID NO 51
<211> LENGTH: 8
<212> TYPE: PRT
<213> ORGANISM: Artificial Sequence
<220> FEATURE:
<223> OTHER INFORMATION: Artificial polymer

<400> SEQUENCE: 51

Ile Trp Tyr Asp Gly Ser Asn Lys
1 5

<210> SEQ ID NO 52
<211> LENGTH: 16
<212> TYPE: PRT
<213> ORGANISM: Artificial Sequence
<220> FEATURE:
<223> OTHER INFORMATION: Artificial polymer

<400> SEQUENCE: 52

Ala Arg Ser Tyr Asp Met Leu Thr Gly Ser Gly Asp Tyr Tyr Gly Leu
1 5 10 15

<210> SEQ ID NO 53
<211> LENGTH: 6
<212> TYPE: PRT
<213> ORGANISM: Artificial Sequence
<220> FEATURE:
<223> OTHER INFORMATION: Artificial polymer

<400> SEQUENCE: 53

Gln Asp Ile Thr Asn Tyr
1 5

<210> SEQ ID NO 54
<211> LENGTH: 9
<212> TYPE: PRT
<213> ORGANISM: Artificial Sequence
<220> FEATURE:
<223> OTHER INFORMATION: Artificial polymer

<400> SEQUENCE: 54

Gln Gln Tyr Asn Asn Tyr Pro Leu Thr
1 5

<210> SEQ ID NO 55
<211> LENGTH: 11
<212> TYPE: PRT
<213> ORGANISM: Artificial Sequence
<220> FEATURE:
<223> OTHER INFORMATION: Artificial polymer

<400> SEQUENCE: 55

Ser Gly Tyr Thr Gly Thr Asp Tyr Asn Met His
1 5 10

<210> SEQ ID NO 56
<211> LENGTH: 17
<212> TYPE: PRT
<213> ORGANISM: Artificial Sequence
<220> FEATURE:
<223> OTHER INFORMATION: Artificial polymer

<400> SEQUENCE: 56

Tyr Ile Tyr Pro Tyr Thr Gly Gly Thr Gly Tyr Asn Gln Lys Phe Lys
1 5 10 15

Asn

<210> SEQ ID NO 57
<211> LENGTH: 5
<212> TYPE: PRT
<213> ORGANISM: Artificial Sequence
<220> FEATURE:
<223> OTHER INFORMATION: Artificial polymer

<400> SEQUENCE: 57

Asp Phe Gly Met Asn
1 5

<210> SEQ ID NO 58
<211> LENGTH: 11
<212> TYPE: PRT
<213> ORGANISM: Artificial Sequence
<220> FEATURE:
<223> OTHER INFORMATION: Artificial polymer

<400> SEQUENCE: 58

Leu Ile Tyr Tyr Asp Gly Ser Asn Lys Phe Tyr
1 5 10

<210> SEQ ID NO 59
<211> LENGTH: 12
<212> TYPE: PRT
<213> ORGANISM: Artificial Sequence
<220> FEATURE:
<223> OTHER INFORMATION: Artificial polymer

<400> SEQUENCE: 59

Pro His Tyr Asp Gly Tyr Tyr His Phe Phe Asp Ser
1 5 10

<210> SEQ ID NO 60
<211> LENGTH: 15
<212> TYPE: PRT
<213> ORGANISM: Artificial Sequence
<220> FEATURE:
<223> OTHER INFORMATION: Artificial polymer

<400> SEQUENCE: 60

Arg Ala Ser Glu Ser Val Asp Ser Tyr Asp Asn Ser Leu Met His
1 5 10 15

<210> SEQ ID NO 61
<211> LENGTH: 7
<212> TYPE: PRT
<213> ORGANISM: Artificial Sequence
<220> FEATURE:
<223> OTHER INFORMATION: Artificial polymer

<400> SEQUENCE: 61

```
Leu Ala Ser Asn Leu Glu Ser
1               5


<210> SEQ ID NO 62
<211> LENGTH: 9
<212> TYPE: PRT
<213> ORGANISM: Artificial Sequence
<220> FEATURE:
<223> OTHER INFORMATION: Artificial polymer

<400> SEQUENCE: 62

Gln Gln Asn Asn Glu Asp Pro Tyr Thr
1               5


<210> SEQ ID NO 63
<211> LENGTH: 11
<212> TYPE: PRT
<213> ORGANISM: Artificial Sequence
<220> FEATURE:
<223> OTHER INFORMATION: Artificial polymer

<400> SEQUENCE: 63

Lys Gly Ser Gln Asp Ile Asn Asn Tyr Leu Ala
1               5                   10


<210> SEQ ID NO 64
<211> LENGTH: 7
<212> TYPE: PRT
<213> ORGANISM: Artificial Sequence
<220> FEATURE:
<223> OTHER INFORMATION: Artificial polymer

<400> SEQUENCE: 64

Asn Thr Asp Ile Leu His Thr
1               5


<210> SEQ ID NO 65
<211> LENGTH: 8
<212> TYPE: PRT
<213> ORGANISM: Artificial Sequence
<220> FEATURE:
<223> OTHER INFORMATION: Artificial polymer

<400> SEQUENCE: 65

Tyr Gln Tyr Asn Asn Gly Tyr Thr
1               5


<210> SEQ ID NO 66
<211> LENGTH: 7
<212> TYPE: PRT
<213> ORGANISM: Artificial Sequence
<220> FEATURE:
<223> OTHER INFORMATION: Artificial polymer

<400> SEQUENCE: 66

Gly Tyr Thr Phe Thr Ser Tyr
1               5


<210> SEQ ID NO 67
<211> LENGTH: 6
<212> TYPE: PRT
<213> ORGANISM: Artificial Sequence
<220> FEATURE:
<223> OTHER INFORMATION: Artificial polymer

<400> SEQUENCE: 67
```

Asp Pro Ser Asp Asn Tyr
1 5

<210> SEQ ID NO 68
<211> LENGTH: 16
<212> TYPE: PRT
<213> ORGANISM: Artificial Sequence
<220> FEATURE:
<223> OTHER INFORMATION: Artificial polymer

<400> SEQUENCE: 68

Pro Lys Ser Ala Tyr Ala Phe Asp Val Gly Gly Tyr Ala Met Asp Tyr
1 5 10 15

<210> SEQ ID NO 69
<211> LENGTH: 11
<212> TYPE: PRT
<213> ORGANISM: Artificial Sequence
<220> FEATURE:
<223> OTHER INFORMATION: Artificial polymer

<400> SEQUENCE: 69

Arg Thr Ser Glu Asn Ile Asp Ser Tyr Leu Thr
1 5 10

<210> SEQ ID NO 70
<211> LENGTH: 7
<212> TYPE: PRT
<213> ORGANISM: Artificial Sequence
<220> FEATURE:
<223> OTHER INFORMATION: Artificial polymer

<400> SEQUENCE: 70

Ala Ala Thr Leu Leu Ala Asp
1 5

<210> SEQ ID NO 71
<211> LENGTH: 9
<212> TYPE: PRT
<213> ORGANISM: Artificial Sequence
<220> FEATURE:
<223> OTHER INFORMATION: Artificial polymer

<400> SEQUENCE: 71

Gln His Tyr Tyr Ser Thr Pro Trp Thr
1 5

<210> SEQ ID NO 72
<211> LENGTH: 6
<212> TYPE: PRT
<213> ORGANISM: Artificial Sequence
<220> FEATURE:
<223> OTHER INFORMATION: Artificial polymer

<400> SEQUENCE: 72

Gly Phe Asn Ile Lys Asp
1 5

<210> SEQ ID NO 73
<211> LENGTH: 9
<212> TYPE: PRT
<213> ORGANISM: Artificial Sequence
<220> FEATURE:
<223> OTHER INFORMATION: Artificial polymer

<400> SEQUENCE: 73

Arg Ile Asp Pro Ala Asn Asp Asn Thr 1 5

<210> SEQ ID NO 74
<211> LENGTH: 9
<212> TYPE: PRT
<213> ORGANISM: Artificial Sequence
<220> FEATURE:
<223> OTHER INFORMATION: Artificial polymer

<400> SEQUENCE: 74

Gly Tyr Gly Tyr Tyr Val Phe Asp His
1 5

<210> SEQ ID NO 75
<211> LENGTH: 11
<212> TYPE: PRT
<213> ORGANISM: Artificial Sequence
<220> FEATURE:
<223> OTHER INFORMATION: Artificial polymer

<400> SEQUENCE: 75

Arg Thr Ser Arg Ser Ile Ser Gln Tyr Leu Ala
1 5 10

<210> SEQ ID NO 76
<211> LENGTH: 7
<212> TYPE: PRT
<213> ORGANISM: Artificial Sequence
<220> FEATURE:
<223> OTHER INFORMATION: Artificial polymer

<400> SEQUENCE: 76

Ser Gly Ser Thr Leu Gln Ser
1 5

<210> SEQ ID NO 77
<211> LENGTH: 9
<212> TYPE: PRT
<213> ORGANISM: Artificial Sequence
<220> FEATURE:
<223> OTHER INFORMATION: Artificial polymer

<400> SEQUENCE: 77

Gln Gln His Asn Glu Asn Pro Leu Thr
1 5

<210> SEQ ID NO 78
<211> LENGTH: 8
<212> TYPE: PRT
<213> ORGANISM: Artificial Sequence
<220> FEATURE:
<223> OTHER INFORMATION: Artificial polymer

<400> SEQUENCE: 78

Gly Tyr Thr Phe Thr Ala His Ile
1 5

<210> SEQ ID NO 79
<211> LENGTH: 8
<212> TYPE: PRT
<213> ORGANISM: Artificial Sequence
<220> FEATURE:
<223> OTHER INFORMATION: Artificial polymer

<400> SEQUENCE: 79

Ile Lys Pro Gln Tyr Gly Ala Val
1 5

<210> SEQ ID NO 80
<211> LENGTH: 6
<212> TYPE: PRT
<213> ORGANISM: Artificial Sequence
<220> FEATURE:
<223> OTHER INFORMATION: Artificial polymer

<400> SEQUENCE: 80

Gln Gly Val Gly Ser Asp
1               5

<210> SEQ ID NO 81
<211> LENGTH: 5
<212> TYPE: PRT
<213> ORGANISM: Artificial Sequence
<220> FEATURE:
<223> OTHER INFORMATION: Artificial polymer

<400> SEQUENCE: 81

Gln Val Leu Gln Phe
1               5

<210> SEQ ID NO 82
<211> LENGTH: 7
<212> TYPE: PRT
<213> ORGANISM: Artificial Sequence
<220> FEATURE:
<223> OTHER INFORMATION: Artificial polymer

<400> SEQUENCE: 82

Gly Tyr Thr Phe Thr Ser Asn
1               5

<210> SEQ ID NO 83
<211> LENGTH: 6
<212> TYPE: PRT
<213> ORGANISM: Artificial Sequence
<220> FEATURE:
<223> OTHER INFORMATION: Artificial polymer

<400> SEQUENCE: 83

Tyr Pro Arg Ser Gly Asn
1               5

<210> SEQ ID NO 84
<211> LENGTH: 7
<212> TYPE: PRT
<213> ORGANISM: Artificial Sequence
<220> FEATURE:
<223> OTHER INFORMATION: Artificial polymer

<400> SEQUENCE: 84

Arg Val Pro Tyr Phe Asp His
1               5

<210> SEQ ID NO 85
<211> LENGTH: 11
<212> TYPE: PRT
<213> ORGANISM: Artificial Sequence
<220> FEATURE:
<223> OTHER INFORMATION: Artificial polymer

<400> SEQUENCE: 85

Lys Ala Ser Gln Ser Val Gly Asn Asn Val Ala
1               5                   10

<210> SEQ ID NO 86
<211> LENGTH: 7
<212> TYPE: PRT
<213> ORGANISM: Artificial Sequence
<220> FEATURE:
<223> OTHER INFORMATION: Artificial polymer

<400> SEQUENCE: 86

Tyr Ala Ser Asn Arg Tyr Thr
1 5

<210> SEQ ID NO 87
<211> LENGTH: 9
<212> TYPE: PRT
<213> ORGANISM: Artificial Sequence
<220> FEATURE:
<223> OTHER INFORMATION: Artificial polymer

<400> SEQUENCE: 87

Gln Gln His Tyr Ser Ser Pro Phe Thr
1 5

<210> SEQ ID NO 88
<211> LENGTH: 5
<212> TYPE: PRT
<213> ORGANISM: Artificial Sequence
<220> FEATURE:
<223> OTHER INFORMATION: Artificial polymer

<400> SEQUENCE: 88

Gly Tyr Trp Met Tyr
1 5

<210> SEQ ID NO 89
<211> LENGTH: 5
<212> TYPE: PRT
<213> ORGANISM: Artificial Sequence
<220> FEATURE:
<223> OTHER INFORMATION: Artificial polymer

<400> SEQUENCE: 89

Ser Tyr Ser Met Gly
1 5

<210> SEQ ID NO 90
<211> LENGTH: 5
<212> TYPE: PRT
<213> ORGANISM: Artificial Sequence
<220> FEATURE:
<223> OTHER INFORMATION: Artificial polymer

<400> SEQUENCE: 90

Phe Asn Ala Met Gly
1 5

<210> SEQ ID NO 91
<211> LENGTH: 16
<212> TYPE: PRT
<213> ORGANISM: Artificial Sequence
<220> FEATURE:
<223> OTHER INFORMATION: Artificial polymer

<400> SEQUENCE: 91

Ala Ile Ser Pro Gly Gly Gly Ser Thr Tyr Tyr Pro Asp Ser Val Lys
1 5 10 15

<210> SEQ ID NO 92
<211> LENGTH: 16
<212> TYPE: PRT
<213> ORGANISM: Artificial Sequence
<220> FEATURE:
<223> OTHER INFORMATION: Artificial polymer

<400> SEQUENCE: 92

Ala Ile Ser Trp Ser Gly Asp Glu Thr Ser Tyr Ala Asp Ser Val Lys
1 5 10 15

<210> SEQ ID NO 93
<211> LENGTH: 16
<212> TYPE: PRT
<213> ORGANISM: Artificial Sequence
<220> FEATURE:
<223> OTHER INFORMATION: Artificial polymer

<400> SEQUENCE: 93

Thr Ile Ala Arg Ala Gly Ala Thr Lys Tyr Ala Asp Ser Val Lys Gly
1 5 10 15

<210> SEQ ID NO 94
<211> LENGTH: 16
<212> TYPE: PRT
<213> ORGANISM: Artificial Sequence
<220> FEATURE:
<223> OTHER INFORMATION: Artificial polymer

<400> SEQUENCE: 94

Ala Val Arg Trp Ser Ser Thr Gly Ile Tyr Tyr Thr Gln Tyr Ala Asp
1 5 10 15

<210> SEQ ID NO 95
<211> LENGTH: 12
<212> TYPE: PRT
<213> ORGANISM: Artificial Sequence
<220> FEATURE:
<223> OTHER INFORMATION: Artificial polymer

<400> SEQUENCE: 95

Ser Leu Thr Ala Thr His Thr Tyr Glu Tyr Asp Tyr
1 5 10

<210> SEQ ID NO 96
<211> LENGTH: 13
<212> TYPE: PRT
<213> ORGANISM: Artificial Sequence
<220> FEATURE:
<223> OTHER INFORMATION: Artificial polymer

<400> SEQUENCE: 96

Asp Arg Trp Trp Arg Pro Ala Gly Leu Gln Trp Asp Tyr
1 5 10

<210> SEQ ID NO 97
<211> LENGTH: 9
<212> TYPE: PRT
<213> ORGANISM: Artificial Sequence
<220> FEATURE:
<223> OTHER INFORMATION: Artificial polymer

<400> SEQUENCE: 97

Arg Val Phe Asp Leu Pro Asn Asp Tyr
1 5

<210> SEQ ID NO 98

<211> LENGTH: 15
<212> TYPE: PRT
<213> ORGANISM: Artificial Sequence
<220> FEATURE:
<223> OTHER INFORMATION: Artificial polymer

<400> SEQUENCE: 98

Asp Thr Tyr Asn Ser Asn Pro Ala Arg Trp Asp Gly Tyr Asp Phe
1 5 10 15

<210> SEQ ID NO 99
<211> LENGTH: 5
<212> TYPE: PRT
<213> ORGANISM: Artificial Sequence
<220> FEATURE:
<223> OTHER INFORMATION: Artificial polymer

<400> SEQUENCE: 99

Ala Tyr Val Ile Ser
1 5

<210> SEQ ID NO 100
<211> LENGTH: 17
<212> TYPE: PRT
<213> ORGANISM: Artificial Sequence
<220> FEATURE:
<223> OTHER INFORMATION: Artificial polymer

<400> SEQUENCE: 100

Glu Ile Tyr Pro Gly Ser Gly Ser Ser Tyr Tyr Asn Glu Lys Phe Lys
1 5 10 15

Gly

<210> SEQ ID NO 101
<211> LENGTH: 9
<212> TYPE: PRT
<213> ORGANISM: Artificial Sequence
<220> FEATURE:
<223> OTHER INFORMATION: Artificial polymer

<400> SEQUENCE: 101

Ser Gly Asp Gly Ser Lys Phe Val Tyr
1 5

<210> SEQ ID NO 102
<211> LENGTH: 15
<212> TYPE: PRT
<213> ORGANISM: Artificial Sequence
<220> FEATURE:
<223> OTHER INFORMATION: Artificial polymer

<400> SEQUENCE: 102

Lys Ala Ser Gln Ser Val Asp Tyr Cys Gly Asp Ser Tyr Met Asn
1 5 10 15

<210> SEQ ID NO 103
<211> LENGTH: 7
<212> TYPE: PRT
<213> ORGANISM: Artificial Sequence
<220> FEATURE:
<223> OTHER INFORMATION: Artificial polymer

<400> SEQUENCE: 103

Val Ala Ser Asn Leu Glu Ser
1 5

<210> SEQ ID NO 104
<211> LENGTH: 9
<212> TYPE: PRT
<213> ORGANISM: Artificial Sequence
<220> FEATURE:
<223> OTHER INFORMATION: Artificial polymer

<400> SEQUENCE: 104

Gln Gln Ser Leu Gln Asp Pro Pro Thr
1               5

<210> SEQ ID NO 105
<211> LENGTH: 10
<212> TYPE: PRT
<213> ORGANISM: Artificial Sequence
<220> FEATURE:
<223> OTHER INFORMATION: Artificial polymer

<400> SEQUENCE: 105

Gly Tyr Thr Phe Thr Ser Tyr Val Ile His
1               5                   10

<210> SEQ ID NO 106
<211> LENGTH: 16
<212> TYPE: PRT
<213> ORGANISM: Artificial Sequence
<220> FEATURE:
<223> OTHER INFORMATION: Artificial polymer

<400> SEQUENCE: 106

Tyr Ile Asn Pro Tyr Asn Asp Gly Thr Asp Tyr Asp Glu Lys Phe Lys
1               5                   10                  15

<210> SEQ ID NO 107
<211> LENGTH: 13
<212> TYPE: PRT
<213> ORGANISM: Artificial Sequence
<220> FEATURE:
<223> OTHER INFORMATION: Artificial polymer

<400> SEQUENCE: 107

Glu Lys Asp Asn Tyr Ala Thr Gly Ala Trp Phe Ala Tyr
1               5                   10

<210> SEQ ID NO 108
<211> LENGTH: 15
<212> TYPE: PRT
<213> ORGANISM: Artificial Sequence
<220> FEATURE:
<223> OTHER INFORMATION: Artificial polymer

<400> SEQUENCE: 108

Lys Ser Ser Gln Ser Leu Leu Tyr Ser Thr Asn Gln Lys Asn Tyr
1               5                   10                  15

<210> SEQ ID NO 109
<211> LENGTH: 7
<212> TYPE: PRT
<213> ORGANISM: Artificial Sequence
<220> FEATURE:
<223> OTHER INFORMATION: Artificial polymer

<400> SEQUENCE: 109

Trp Ala Ser Thr Arg Glu Ser
1               5

<210> SEQ ID NO 110

<211> LENGTH: 8
<212> TYPE: PRT
<213> ORGANISM: Artificial Sequence
<220> FEATURE:
<223> OTHER INFORMATION: Artificial polymer

<400> SEQUENCE: 110

Gln Gln Tyr Tyr Ser Tyr Arg Thr
1 5

<210> SEQ ID NO 111
<211> LENGTH: 5
<212> TYPE: PRT
<213> ORGANISM: Artificial Sequence
<220> FEATURE:
<223> OTHER INFORMATION: Artificial polymer

<400> SEQUENCE: 111

Ser Tyr Val Ile His
1 5

<210> SEQ ID NO 112
<211> LENGTH: 10
<212> TYPE: PRT
<213> ORGANISM: Artificial Sequence
<220> FEATURE:
<223> OTHER INFORMATION: Artificial polymer

<400> SEQUENCE: 112

Gly Phe Thr Phe Ser Asn Tyr Ala Met Ser
1 5 10

<210> SEQ ID NO 113
<211> LENGTH: 12
<212> TYPE: PRT
<213> ORGANISM: Artificial Sequence
<220> FEATURE:
<223> OTHER INFORMATION: Artificial polymer

<400> SEQUENCE: 113

Ala Ile Ser Asp His Ser Thr Asn Thr Tyr Tyr Pro
1 5 10

<210> SEQ ID NO 114
<211> LENGTH: 13
<212> TYPE: PRT
<213> ORGANISM: Artificial Sequence
<220> FEATURE:
<223> OTHER INFORMATION: Artificial polymer

<400> SEQUENCE: 114

Glu Lys Asp Asn Tyr Ala Thr Gly Ala Trp Phe Ala Tyr
1 5 10

<210> SEQ ID NO 115
<211> LENGTH: 11
<212> TYPE: PRT
<213> ORGANISM: Artificial Sequence
<220> FEATURE:
<223> OTHER INFORMATION: Artificial polymer

<400> SEQUENCE: 115

Ala Arg Lys Tyr Gly Gly Asp Tyr Asp Pro Phe
1 5 10

<210> SEQ ID NO 116
<211> LENGTH: 16

<212> TYPE: PRT
<213> ORGANISM: Artificial Sequence
<220> FEATURE:
<223> OTHER INFORMATION: Artificial polymer

<400> SEQUENCE: 116

Lys Ser Ser Gln Ser Leu Leu Tyr Ser Thr Asn Gln Lys Asn Tyr Leu
1 5 10 15

<210> SEQ ID NO 117
<211> LENGTH: 16
<212> TYPE: PRT
<213> ORGANISM: Artificial Sequence
<220> FEATURE:
<223> OTHER INFORMATION: Artificial polymer

<400> SEQUENCE: 117

Lys Ser Ser Gly Ser Leu Leu Tyr Ser Thr Asn Gln Lys Asn Tyr Leu
1 5 10 15

<210> SEQ ID NO 118
<211> LENGTH: 9
<212> TYPE: PRT
<213> ORGANISM: Artificial Sequence
<220> FEATURE:
<223> OTHER INFORMATION: Artificial polymer

<400> SEQUENCE: 118

Lys Ala Ser Gln Asp Ile Asn Asn Tyr
1 5

<210> SEQ ID NO 119
<211> LENGTH: 7
<212> TYPE: PRT
<213> ORGANISM: Artificial Sequence
<220> FEATURE:
<223> OTHER INFORMATION: Artificial polymer

<400> SEQUENCE: 119

Trp Ala Ser Thr Arg Glu Ser
1 5

<210> SEQ ID NO 120
<211> LENGTH: 11
<212> TYPE: PRT
<213> ORGANISM: Artificial Sequence
<220> FEATURE:
<223> OTHER INFORMATION: Artificial polymer

<400> SEQUENCE: 120

Tyr Thr Ser Thr Leu Gln Pro Gly Val Pro Ser
1 5 10

<210> SEQ ID NO 121
<211> LENGTH: 8
<212> TYPE: PRT
<213> ORGANISM: Artificial Sequence
<220> FEATURE:
<223> OTHER INFORMATION: Artificial polymer

<400> SEQUENCE: 121

Gln Gln Tyr Tyr Ser Tyr Arg Thr
1 5

<210> SEQ ID NO 122
<211> LENGTH: 6
<212> TYPE: PRT

<213> ORGANISM: Artificial Sequence
<220> FEATURE:
<223> OTHER INFORMATION: Artificial polymer

<400> SEQUENCE: 122

Tyr Asp Asn Leu Leu Phe
1               5

<210> SEQ ID NO 123
<211> LENGTH: 5
<212> TYPE: PRT
<213> ORGANISM: Artificial Sequence
<220> FEATURE:
<223> OTHER INFORMATION: Artificial polymer

<400> SEQUENCE: 123

Thr Phe Gly Val His
1               5

<210> SEQ ID NO 124
<211> LENGTH: 5
<212> TYPE: PRT
<213> ORGANISM: Artificial Sequence
<220> FEATURE:
<223> OTHER INFORMATION: Artificial polymer

<400> SEQUENCE: 124

Thr Ala Gly Val His
1               5

<210> SEQ ID NO 125
<211> LENGTH: 5
<212> TYPE: PRT
<213> ORGANISM: Artificial Sequence
<220> FEATURE:
<223> OTHER INFORMATION: Artificial polymer

<400> SEQUENCE: 125

Thr Phe Gly Val Ala
1               5

<210> SEQ ID NO 126
<211> LENGTH: 16
<212> TYPE: PRT
<213> ORGANISM: Artificial Sequence
<220> FEATURE:
<223> OTHER INFORMATION: Artificial polymer

<400> SEQUENCE: 126

Val Ile Trp Arg Ser Gly Ile Thr Asp Tyr Asn Val Pro Phe Met Ser
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Artificial polymer

<400> SEQUENCE: 127

Val Ile Ala Arg Ser Gly Ile Thr Asp Tyr Asn Val Pro Phe Met Ser
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Artificial polymer

<400> SEQUENCE: 128

Val Ile Trp Ala Ser Gly Ile Thr Asp Tyr Asn Val Pro Phe Met Ser
1 5 10 15

<210> SEQ ID NO 129
<211> LENGTH: 9
<212> TYPE: PRT
<213> ORGANISM: Artificial Sequence
<220> FEATURE:
<223> OTHER INFORMATION: Artificial polymer

<400> SEQUENCE: 129

Asn Asp Pro Gly Thr Gly Phe Ala Tyr
1 5

<210> SEQ ID NO 130
<211> LENGTH: 9
<212> TYPE: PRT
<213> ORGANISM: Artificial Sequence
<220> FEATURE:
<223> OTHER INFORMATION: Artificial polymer

<400> SEQUENCE: 130

Asn Asp Pro Gly Thr Gly Ala Ala Tyr
1 5

<210> SEQ ID NO 131
<211> LENGTH: 9
<212> TYPE: PRT
<213> ORGANISM: Artificial Sequence
<220> FEATURE:
<223> OTHER INFORMATION: Artificial polymer

<400> SEQUENCE: 131

Asn Asp Pro Gly Thr Gly Phe Ala Ala
1 5

<210> SEQ ID NO 132
<211> LENGTH: 11
<212> TYPE: PRT
<213> ORGANISM: Artificial Sequence
<220> FEATURE:
<223> OTHER INFORMATION: Artificial polymer

<400> SEQUENCE: 132

Arg Ala Ser Glu Asn Ile Tyr Ser Tyr Leu Ala
1 5 10

<210> SEQ ID NO 133
<211> LENGTH: 11
<212> TYPE: PRT
<213> ORGANISM: Artificial Sequence
<220> FEATURE:
<223> OTHER INFORMATION: Artificial polymer

<400> SEQUENCE: 133

Arg Ala Ser Glu Asn Ile Tyr Ser Ala Leu Ala
1 5 10

<210> SEQ ID NO 134
<211> LENGTH: 7
<212> TYPE: PRT
<213> ORGANISM: Artificial Sequence
<220> FEATURE:

<223> OTHER INFORMATION: Artificial polymer

<400> SEQUENCE: 134

Asp Ala Lys Thr Leu Ala Glu
1 5

<210> SEQ ID NO 135
<211> LENGTH: 9
<212> TYPE: PRT
<213> ORGANISM: Artificial Sequence
<220> FEATURE:
<223> OTHER INFORMATION: Artificial polymer

<400> SEQUENCE: 135

Gln His His Tyr Gly Asn Pro Pro Thr
1 5

<210> SEQ ID NO 136
<211> LENGTH: 9
<212> TYPE: PRT
<213> ORGANISM: Artificial Sequence
<220> FEATURE:
<223> OTHER INFORMATION: Artificial polymer

<400> SEQUENCE: 136

Gln His Ala Tyr Gly Asn Pro Pro Thr
1 5

<210> SEQ ID NO 137
<211> LENGTH: 9
<212> TYPE: PRT
<213> ORGANISM: Artificial Sequence
<220> FEATURE:
<223> OTHER INFORMATION: Artificial polymer

<400> SEQUENCE: 137

Gln His His Ala Gly Asn Pro Pro Thr
1 5

<210> SEQ ID NO 138
<211> LENGTH: 5
<212> TYPE: PRT
<213> ORGANISM: Artificial Sequence
<220> FEATURE:
<223> OTHER INFORMATION: Artificial polymer

<400> SEQUENCE: 138

Asp Tyr Val Ile Asn
1 5

<210> SEQ ID NO 139
<211> LENGTH: 17
<212> TYPE: PRT
<213> ORGANISM: Artificial Sequence
<220> FEATURE:
<223> OTHER INFORMATION: Artificial polymer

<400> SEQUENCE: 139

Glu Ile Tyr Pro Gly Ser Gly Ser Asp Tyr Tyr Asn Glu Asn Leu Lys
1 5 10 15

Asp

<210> SEQ ID NO 140
<211> LENGTH: 12
<212> TYPE: PRT
<213> ORGANISM: Artificial Sequence
<220> FEATURE:
<223> OTHER INFORMATION: Artificial polymer

<400> SEQUENCE: 140

Lys Gly Glu Asn Gly Asn Ser Leu Ala Phe Ala Tyr
1 5 10

<210> SEQ ID NO 141
<211> LENGTH: 12
<212> TYPE: PRT
<213> ORGANISM: Artificial Sequence
<220> FEATURE:
<223> OTHER INFORMATION: Artificial polymer

<400> SEQUENCE: 141

Gln Ser Val Asp Tyr Asp Gly Asp Ser Tyr Met Asn
1 5 10

<210> SEQ ID NO 142
<211> LENGTH: 7
<212> TYPE: PRT
<213> ORGANISM: Artificial Sequence
<220> FEATURE:
<223> OTHER INFORMATION: Artificial polymer

<400> SEQUENCE: 142

Ala Ala Ser Asn Leu Glu Ser
1 5

<210> SEQ ID NO 143
<211> LENGTH: 9
<212> TYPE: PRT
<213> ORGANISM: Artificial Sequence
<220> FEATURE:
<223> OTHER INFORMATION: Artificial polymer

<400> SEQUENCE: 143

Gln Gln Ser Ile Gln Asp Pro Cys Thr
1 5

<210> SEQ ID NO 144
<211> LENGTH: 471
<212> TYPE: PRT
<213> ORGANISM: Artificial Sequence
<220> FEATURE:
<223> OTHER INFORMATION: Artificial polymer

<400> SEQUENCE: 144

Met Glu Trp Ser Gly Val Phe Met Phe Leu Leu Ser Val Thr Ala Gly
1 5 10 15

Val His Ser Gln Val Gln Leu Gln Gln Ser Gly Pro Glu Val Val Lys
20 25 30

Pro Gly Ala Ser Val Lys Met Ser Cys Lys Ala Ser Gly Tyr Thr Phe
35 40 45

Thr Ser Tyr Val Ile His Trp Val Arg Gln Lys Pro Gly Gln Gly Leu
50 55 60

Asp Trp Ile Gly Tyr Ile Asn Pro Tyr Asn Asp Gly Thr Asp Tyr Asp
65 70 75 80

Glu Lys Phe Lys Gly Lys Ala Thr Leu Thr Ser Asp Thr Ser Thr Ser
85 90 95

Thr Ala Tyr Met Glu Leu Ser Ser Leu Arg Ser Glu Asp Thr Ala Val
100 105 110

Tyr Tyr Cys Ala Arg Glu Lys Asp Asn Tyr Ala Thr Gly Ala Trp Phe

```
        115                 120                 125

Ala Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Phe Glu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Ser Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 145
<211> LENGTH: 237
<212> TYPE: PRT
<213> ORGANISM: Artificial Sequence
<220> FEATURE:
<223> OTHER INFORMATION: Artificial polymer

<400> SEQUENCE: 145

Met Glu Trp Ser Gly Val Phe Ile Phe Leu Leu Ser Val Thr Ala Gly
```

```
1               5                   10                  15

Val His Ser Asp Ile Val Met Thr Gln Ser Pro Asp Ser Leu Ala Val
            20                  25                  30

Ser Leu Gly Glu Arg Val Thr Met Asn Cys Lys Ser Ser Gln Ser Leu
        35                  40                  45

Leu Tyr Ser Thr Asn Gln Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Val Gln Ala Glu Asp Val Ala Val Tyr Tyr
            100                 105                 110

Cys Gln Gln Tyr Tyr Tyr Arg Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 146
<211> LENGTH: 122
<212> TYPE: PRT
<213> ORGANISM: Artificial Sequence
<220> FEATURE:
<223> OTHER INFORMATION: Artificial polymer

<400> SEQUENCE: 146

Glu Glu Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asp Cys
            20                  25                  30

Arg Met Tyr Trp Leu Arg Gln Ala Pro Gly Lys Gly Leu Glu Trp Ile
        35                  40                  45

Gly Val Ile Ser Val Lys Ser Glu Asn Tyr Gly Ala Asn Tyr Ala Glu
    50                  55                  60

Ser Val Arg Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Ala Ser Tyr Tyr Arg Tyr Asp Val Gly Ala Phe Ala Tyr
            100                 105                 110

Gly Gln Gly Thr Leu Val Thr Val Ser Ser
        115                 120
```

<210> SEQ ID NO 147
<211> LENGTH: 110
<212> TYPE: PRT
<213> ORGANISM: Artificial Sequence
<220> FEATURE:
<223> OTHER INFORMATION: Artificial polymer

<400> SEQUENCE: 147

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Ile Tyr Trp Tyr Gln Gln Lys Pro Gly Gln Pro Pro
        35                  40                  45

Lys Leu Leu Ile Tyr Leu Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Thr Phe Gly Gln Gly Thr Lys Val Glu Ile Lys
            100                 105                 110

<210> SEQ ID NO 148
<211> LENGTH: 10
<212> TYPE: PRT
<213> ORGANISM: Artificial Sequence
<220> FEATURE:
<223> OTHER INFORMATION: Artificial polymer

<400> SEQUENCE: 148

Gly Phe Thr Phe Asp Asp Tyr Ala Met Ser
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Artificial polymer

<400> SEQUENCE: 149

Gly Phe Thr Phe Asp Asp Tyr Ala Ile Gly
1               5                   10

<210> SEQ ID NO 150
<211> LENGTH: 17
<212> TYPE: PRT
<213> ORGANISM: Artificial Sequence
<220> FEATURE:
<223> OTHER INFORMATION: Artificial polymer

<400> SEQUENCE: 150

Thr Ile Asn Trp Asn Gly Gly Ser Ala Glu Tyr Ala Glu Pro Val Lys
1               5                   10                  15

Gly

<210> SEQ ID NO 151
<211> LENGTH: 17
<212> TYPE: PRT
<213> ORGANISM: Artificial Sequence
<220> FEATURE:
<223> OTHER INFORMATION: Artificial polymer

<400> SEQUENCE: 151

Cys Ile Arg Val Ser Asp Gly Ser Thr Tyr Tyr Ala Asp Pro Val Lys
1 5 10 15

Gly

<210> SEQ ID NO 152
<211> LENGTH: 11
<212> TYPE: PRT
<213> ORGANISM: Artificial Sequence
<220> FEATURE:
<223> OTHER INFORMATION: Artificial polymer

<400> SEQUENCE: 152

Lys Asp Ala Asp Leu Val Trp Tyr Asn Leu Ser
1 5 10

<210> SEQ ID NO 153
<211> LENGTH: 11
<212> TYPE: PRT
<213> ORGANISM: Artificial Sequence
<220> FEATURE:
<223> OTHER INFORMATION: Artificial polymer

<400> SEQUENCE: 153

Lys Asp Ala Asp Leu Val Trp Tyr Asn Leu Arg
1 5 10

<210> SEQ ID NO 154
<211> LENGTH: 24
<212> TYPE: PRT
<213> ORGANISM: Artificial Sequence
<220> FEATURE:
<223> OTHER INFORMATION: Artificial polymer

<400> SEQUENCE: 154

Ala Gly Ser Leu Tyr Thr Cys Val Gln Ser Ile Val Val Val Pro Ala
1 5 10 15

Arg Pro Tyr Tyr Asp Met Asp Tyr
20

<210> SEQ ID NO 155
<211> LENGTH: 132
<212> TYPE: PRT
<213> ORGANISM: Artificial Sequence
<220> FEATURE:
<223> OTHER INFORMATION: Artificial polymer

<400> SEQUENCE: 155

Gln Val Gln Leu Gln Glu Ser Gly Gly Gly Ser Val Gln Pro Gly Gly
1 5 10 15

Ser Leu Arg Leu Ser Cys Ala Ala Ser Gly Phe Thr Phe Asp Asp Tyr
20 25 30

Ala Met Ser Trp Val Arg Gln Val Pro Gly Lys Gly Leu Glu Trp Val
35 40 45

Ser Thr Ile Asn Trp Asn Gly Gly Ser Ala Glu Tyr Ala Glu Pro Val
50 55 60

Lys Gly Arg Phe Thr Ile Ser Arg Asp Asn Ala Lys Asn Thr Val Tyr
65 70 75 80

Leu Gln Met Asn Ser Leu Lys Leu Glu Asp Thr Ala Val Tyr Tyr Cys
85 90 95

Ala Lys Asp Ala Asp Leu Val Trp Tyr Asn Leu Ser Thr Gly Gln Gly
100 105 110

Thr Gln Val Thr Val Ser Ser Ala Ala Ala Tyr Pro Tyr Asp Val Pro
        115                 120                 125

Asp Tyr Gly Ser
    130

<210> SEQ ID NO 156
<211> LENGTH: 132
<212> TYPE: PRT
<213> ORGANISM: Artificial Sequence
<220> FEATURE:
<223> OTHER INFORMATION: Artificial polymer

<400> SEQUENCE: 156

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Val Pro Gly Lys Gly Leu Glu Trp Val
        35                  40                  45

Ser Thr Ile Asn Trp Asn Gly Gly Ser Ala Glu Tyr Ala Glu Pro Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Lys Asp Ala Asp Leu Val Trp Tyr Asn Leu Arg Thr Gly Gln Gly
            100                 105                 110

Thr Gln Val Thr Val Ser Ser Ala Ala Ala Tyr Pro Tyr Asp Val Pro
        115                 120                 125

Asp Tyr Gly Ser
    130

<210> SEQ ID NO 157
<211> LENGTH: 145
<212> TYPE: PRT
<213> ORGANISM: Artificial Sequence
<220> FEATURE:
<223> OTHER INFORMATION: Artificial polymer

<400> SEQUENCE: 157

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Lys Glu Arg Glu Gly Val
        35                  40                  45

Ser Cys Ile Arg Val Ser Asp Gly Ser Thr Tyr Tyr Ala Asp Pro Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Ala Ala Val Tyr Tyr Cys
                85                  90                  95

Ala Ala Gly Ser Leu Tyr Thr Cys Val Gln Ser Ile Val Val Val Pro
            100                 105                 110

Ala Arg Pro Tyr Tyr Asp Met Asp Tyr Trp Gly Lys Gly Thr Gln Val
        115                 120                 125

Thr Val Ser Ser Ala Ala Ala Tyr Pro Tyr Asp Val Pro Asp Tyr Gly 130 135 140

Ser
145

<210> SEQ ID NO 158
<211> LENGTH: 118
<212> TYPE: PRT
<213> ORGANISM: Artificial Sequence
<220> FEATURE:
<223> OTHER INFORMATION: Artificial polymer

<400> SEQUENCE: 158

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Asp Pro Ala Asn Asp Asn Thr Leu Tyr Ala Ser Lys Phe
50 55 60

Gln Gly Arg Ala Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Gly Arg Gly Tyr Gly Tyr Tyr Val Phe Asp His Trp Gly Gln Gly Thr
100 105 110

Leu Val Thr Val Ser Ser
115

<210> SEQ ID NO 159
<211> LENGTH: 118
<212> TYPE: PRT
<213> ORGANISM: Artificial Sequence
<220> FEATURE:
<223> OTHER INFORMATION: Artificial polymer

<400> SEQUENCE: 159

Gln Val Gln Leu Val Gln Ser Gly Ala Glu Val Lys Lys Pro Gly Ala
1 5 10 15

Thr Val Lys Ile Ser Cys Lys Val Ser Gly Phe Asn Ile Lys Asp Thr
20 25 30

Tyr Ile His Trp Val Gln Gln Ala Pro Gly Lys Gly Leu Glu Trp Met
35 40 45

Gly Arg Ile Asp Pro Ala Asn Asp Asn Thr Leu Tyr Ala Ser Lys Phe
50 55 60

Gln Gly Arg Val Thr Ile Thr Ala Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Arg Gly Tyr Gly Tyr Tyr Val Phe Asp His Trp Gly Gln Gly Thr
100 105 110

Leu Val Thr Val Ser Ser
115

<210> SEQ ID NO 160
<211> LENGTH: 107
<212> TYPE: PRT
<213> ORGANISM: Artificial Sequence
<220> FEATURE:

<223> OTHER INFORMATION: Artificial polymer

<400> SEQUENCE: 160

Asp Val Gln Ile Thr Gln Ser Pro Ser Ser Leu Ser Ala Ser Val Gly
1 5 10 15

Asp Arg Val Thr Ile Thr Cys Arg Thr Ser Arg Ser Ile Ser Gln Tyr
20 25 30

Leu Ala Trp Tyr Gln Gln Lys Pro Gly Lys Val Pro Lys Leu Leu Ile
35 40 45

Tyr Ser Gly Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Gln His Asn Glu Asn Pro Leu
85 90 95

Thr Phe Gly Gly Gly Thr Lys Val Glu Ile Lys
100 105

<210> SEQ ID NO 161

<400> SEQUENCE: 161

000

<210> SEQ ID NO 162
<211> LENGTH: 10
<212> TYPE: PRT
<213> ORGANISM: Artificial Sequence
<220> FEATURE:
<223> OTHER INFORMATION: Artificial polymer

<400> SEQUENCE: 162

Gly Arg Ser Phe Ser Ser Tyr Thr Leu Ala
1 5 10

<210> SEQ ID NO 163
<211> LENGTH: 10
<212> TYPE: PRT
<213> ORGANISM: Artificial Sequence
<220> FEATURE:
<223> OTHER INFORMATION: Artificial polymer

<400> SEQUENCE: 163

Gly Arg Thr Phe Ser Ser Tyr Thr Met Gly
1 5 10

<210> SEQ ID NO 164
<211> LENGTH: 10
<212> TYPE: PRT
<213> ORGANISM: Artificial Sequence
<220> FEATURE:
<223> OTHER INFORMATION: Artificial polymer

<400> SEQUENCE: 164

Gly Arg Thr Phe Ser Ser Tyr Ile Met Gly
1 5 10

<210> SEQ ID NO 165
<211> LENGTH: 10
<212> TYPE: PRT
<213> ORGANISM: Artificial Sequence
<220> FEATURE:
<223> OTHER INFORMATION: Artificial polymer

<400> SEQUENCE: 165

Gly Arg Thr Phe Ser Ser Tyr Thr Met Gly
1 5 10

<210> SEQ ID NO 166
<211> LENGTH: 14
<212> TYPE: PRT
<213> ORGANISM: Artificial Sequence
<220> FEATURE:
<223> OTHER INFORMATION: Artificial polymer

<400> SEQUENCE: 166

Gly Arg Thr Ser Gly Arg Thr Phe Ser Ser Tyr Thr Met Gly
1 5 10

<210> SEQ ID NO 167
<211> LENGTH: 10
<212> TYPE: PRT
<213> ORGANISM: Artificial Sequence
<220> FEATURE:
<223> OTHER INFORMATION: Artificial polymer

<400> SEQUENCE: 167

Gly Arg Thr Phe Ser Ser Tyr Ala Met Gly
1 5 10

<210> SEQ ID NO 168
<211> LENGTH: 10
<212> TYPE: PRT
<213> ORGANISM: Artificial Sequence
<220> FEATURE:
<223> OTHER INFORMATION: Artificial polymer

<400> SEQUENCE: 168

Gly Leu Thr Phe Ser Asn Tyr Ile Met Gly
1 5 10

<210> SEQ ID NO 169
<211> LENGTH: 10
<212> TYPE: PRT
<213> ORGANISM: Artificial Sequence
<220> FEATURE:
<223> OTHER INFORMATION: Artificial polymer

<400> SEQUENCE: 169

Gly Arg Thr Phe Ser Ser Tyr Thr Met Gly
1 5 10

<210> SEQ ID NO 170
<211> LENGTH: 10
<212> TYPE: PRT
<213> ORGANISM: Artificial Sequence
<220> FEATURE:
<223> OTHER INFORMATION: Artificial polymer

<400> SEQUENCE: 170

Gly Arg Thr Phe Ser Ser Asp Thr Met Gly
1 5 10

<210> SEQ ID NO 171
<211> LENGTH: 10
<212> TYPE: PRT
<213> ORGANISM: Artificial Sequence
<220> FEATURE:
<223> OTHER INFORMATION: Artificial polymer

<400> SEQUENCE: 171

Gly Leu Thr Phe Ser Asn Tyr Ile Met Gly
1 5 10

<210> SEQ ID NO 172
<211> LENGTH: 10
<212> TYPE: PRT
<213> ORGANISM: Artificial Sequence
<220> FEATURE:
<223> OTHER INFORMATION: Artificial polymer

<400> SEQUENCE: 172

Gly Phe Thr Leu Asp Tyr Tyr Gly Ile Gly
1 5 10

<210> SEQ ID NO 173
<211> LENGTH: 10
<212> TYPE: PRT
<213> ORGANISM: Artificial Sequence
<220> FEATURE:
<223> OTHER INFORMATION: Artificial polymer

<400> SEQUENCE: 173

Gly His Thr Phe Ser Ser Tyr Thr Met Gly
1 5 10

<210> SEQ ID NO 174
<211> LENGTH: 10
<212> TYPE: PRT
<213> ORGANISM: Artificial Sequence
<220> FEATURE:
<223> OTHER INFORMATION: Artificial polymer

<400> SEQUENCE: 174

Gly Arg Thr Phe Ser Ser Tyr Val Ile Gly
1 5 10

<210> SEQ ID NO 175
<211> LENGTH: 10
<212> TYPE: PRT
<213> ORGANISM: Artificial Sequence
<220> FEATURE:
<223> OTHER INFORMATION: Artificial polymer

<400> SEQUENCE: 175

Gly Phe Ala Phe Asp Gly Tyr Ala Ile Gly
1 5 10

<210> SEQ ID NO 176
<211> LENGTH: 10
<212> TYPE: PRT
<213> ORGANISM: Artificial Sequence
<220> FEATURE:
<223> OTHER INFORMATION: Artificial polymer

<400> SEQUENCE: 176

Gly Phe Ala Phe Gly Phe Phe Asp Met Thr
1 5 10

<210> SEQ ID NO 177
<211> LENGTH: 10
<212> TYPE: PRT
<213> ORGANISM: Artificial Sequence
<220> FEATURE:
<223> OTHER INFORMATION: Artificial polymer

<400> SEQUENCE: 177

Gly Arg Thr Phe Ser Asn Tyr Val Ile Gly
1 5 10

<210> SEQ ID NO 178
<211> LENGTH: 10
<212> TYPE: PRT
<213> ORGANISM: Artificial Sequence
<220> FEATURE:
<223> OTHER INFORMATION: Artificial polymer

<400> SEQUENCE: 178

Gly Ser Ile Phe Ser Ile Asn Val Met Gly
1 5 10

<210> SEQ ID NO 179
<211> LENGTH: 10
<212> TYPE: PRT
<213> ORGANISM: Artificial Sequence
<220> FEATURE:
<223> OTHER INFORMATION: Artificial polymer

<400> SEQUENCE: 179

Gly Arg Thr Phe Ser Asn Tyr Asn Val Gly
1 5 10

<210> SEQ ID NO 180
<211> LENGTH: 10
<212> TYPE: PRT
<213> ORGANISM: Artificial Sequence
<220> FEATURE:
<223> OTHER INFORMATION: Artificial polymer

<400> SEQUENCE: 180

Gly His Thr Phe Ser Ser Tyr Thr Met Gly
1 5 10

<210> SEQ ID NO 181
<211> LENGTH: 10
<212> TYPE: PRT
<213> ORGANISM: Artificial Sequence
<220> FEATURE:
<223> OTHER INFORMATION: Artificial polymer

<400> SEQUENCE: 181

Gly Arg Thr Phe Ser Thr Tyr Pro Val Gly
1 5 10

<210> SEQ ID NO 182
<211> LENGTH: 10
<212> TYPE: PRT
<213> ORGANISM: Artificial Sequence
<220> FEATURE:
<223> OTHER INFORMATION: Artificial polymer

<400> SEQUENCE: 182

Gly Arg Thr Phe Ser Asn Tyr Ala Met Gly
1 5 10

<210> SEQ ID NO 183
<211> LENGTH: 10
<212> TYPE: PRT
<213> ORGANISM: Artificial Sequence
<220> FEATURE:
<223> OTHER INFORMATION: Artificial polymer

<400> SEQUENCE: 183

Gly Arg Thr Phe Ser Asp Tyr Arg Met Gly 1 5 10

<210> SEQ ID NO 184
<211> LENGTH: 10
<212> TYPE: PRT
<213> ORGANISM: Artificial Sequence
<220> FEATURE:
<223> OTHER INFORMATION: Artificial polymer

<400> SEQUENCE: 184

Gly Leu Thr Phe Ser Asn Tyr Ile Met Ala
1 5 10

<210> SEQ ID NO 185
<211> LENGTH: 10
<212> TYPE: PRT
<213> ORGANISM: Artificial Sequence
<220> FEATURE:
<223> OTHER INFORMATION: Artificial polymer

<400> SEQUENCE: 185

Gly Arg Thr Phe Ser Asn Ser Val Met Gly
1 5 10

<210> SEQ ID NO 186
<211> LENGTH: 10
<212> TYPE: PRT
<213> ORGANISM: Artificial Sequence
<220> FEATURE:
<223> OTHER INFORMATION: Artificial polymer

<400> SEQUENCE: 186

Gly Arg Thr Phe Ser Ser Tyr Ile Ile Gly
1 5 10

<210> SEQ ID NO 187
<211> LENGTH: 10
<212> TYPE: PRT
<213> ORGANISM: Artificial Sequence
<220> FEATURE:
<223> OTHER INFORMATION: Artificial polymer

<400> SEQUENCE: 187

Gly Arg Thr Phe Ser Ser Tyr Val Met Gly
1 5 10

<210> SEQ ID NO 188
<211> LENGTH: 10
<212> TYPE: PRT
<213> ORGANISM: Artificial Sequence
<220> FEATURE:
<223> OTHER INFORMATION: Artificial polymer

<400> SEQUENCE: 188

Gly Gly Thr Phe Ser Asn Tyr Val Met Gly
1 5 10

<210> SEQ ID NO 189
<211> LENGTH: 10
<212> TYPE: PRT
<213> ORGANISM: Artificial Sequence
<220> FEATURE:
<223> OTHER INFORMATION: Artificial polymer

<400> SEQUENCE: 189

Gly Arg Thr Phe Ser Asn Tyr Gly Ile Gly
1 5 10

<210> SEQ ID NO 190
<211> LENGTH: 10
<212> TYPE: PRT
<213> ORGANISM: Artificial Sequence
<220> FEATURE:
<223> OTHER INFORMATION: Artificial polymer

<400> SEQUENCE: 190

Gly Phe Thr Phe Asp Asp Tyr Ala Ile Ala
1 5 10

<210> SEQ ID NO 191
<211> LENGTH: 10
<212> TYPE: PRT
<213> ORGANISM: Artificial Sequence
<220> FEATURE:
<223> OTHER INFORMATION: Artificial polymer

<400> SEQUENCE: 191

Gly Arg Thr Phe Ser Ser Tyr Thr Val Ala
1 5 10

<210> SEQ ID NO 192
<211> LENGTH: 10
<212> TYPE: PRT
<213> ORGANISM: Artificial Sequence
<220> FEATURE:
<223> OTHER INFORMATION: Artificial polymer

<400> SEQUENCE: 192

Gly Phe Pro Phe Asp Asp Tyr Ala Ile Ala
1 5 10

<210> SEQ ID NO 193
<211> LENGTH: 10
<212> TYPE: PRT
<213> ORGANISM: Artificial Sequence
<220> FEATURE:
<223> OTHER INFORMATION: Artificial polymer

<400> SEQUENCE: 193

Gly Arg Thr Phe Ser Ser Tyr Val Met Gly
1 5 10

<210> SEQ ID NO 194
<211> LENGTH: 10
<212> TYPE: PRT
<213> ORGANISM: Artificial Sequence
<220> FEATURE:
<223> OTHER INFORMATION: Artificial polymer

<400> SEQUENCE: 194

Gly Arg Thr Leu Ser Ser Asn Pro Met Ala
1 5 10

<210> SEQ ID NO 195
<211> LENGTH: 10
<212> TYPE: PRT
<213> ORGANISM: Artificial Sequence
<220> FEATURE:
<223> OTHER INFORMATION: Artificial polymer

<400> SEQUENCE: 195

Gly Phe Thr Phe Asp Asn Tyr Ala Ile Gly
1 5 10

<210> SEQ ID NO 196
<211> LENGTH: 10
<212> TYPE: PRT
<213> ORGANISM: Artificial Sequence
<220> FEATURE:
<223> OTHER INFORMATION: Artificial polymer

<400> SEQUENCE: 196

Gly Arg Ala Phe Ser Ser Tyr Phe Met Gly
1 5 10

<210> SEQ ID NO 197
<211> LENGTH: 10
<212> TYPE: PRT
<213> ORGANISM: Artificial Sequence
<220> FEATURE:
<223> OTHER INFORMATION: Artificial polymer

<400> SEQUENCE: 197

Thr Pro Thr Phe Ser Ser Tyr Asn Met Gly
1 5 10

<210> SEQ ID NO 198
<211> LENGTH: 10
<212> TYPE: PRT
<213> ORGANISM: Artificial Sequence
<220> FEATURE:
<223> OTHER INFORMATION: Artificial polymer

<400> SEQUENCE: 198

Gly Phe Thr Phe Asp Asp Tyr Ala Ile Ala
1 5 10

<210> SEQ ID NO 199
<211> LENGTH: 10
<212> TYPE: PRT
<213> ORGANISM: Artificial Sequence
<220> FEATURE:
<223> OTHER INFORMATION: Artificial polymer

<400> SEQUENCE: 199

Gly Gly Thr Phe Ser Gly Tyr Ile Met Gly
1 5 10

<210> SEQ ID NO 200
<211> LENGTH: 10
<212> TYPE: PRT
<213> ORGANISM: Artificial Sequence
<220> FEATURE:
<223> OTHER INFORMATION: Artificial polymer

<400> SEQUENCE: 200

Gly Arg Ser Phe Ser Ser Tyr Thr Ile Ala
1 5 10

<210> SEQ ID NO 201
<211> LENGTH: 10
<212> TYPE: PRT
<213> ORGANISM: Artificial Sequence
<220> FEATURE:
<223> OTHER INFORMATION: Artificial polymer

<400> SEQUENCE: 201

Gly Phe Ser Ser Asp Asp Tyr Thr Ile Gly
1 5 10

<210> SEQ ID NO 202
<211> LENGTH: 10
<212> TYPE: PRT
<213> ORGANISM: Artificial Sequence
<220> FEATURE:
<223> OTHER INFORMATION: Artificial polymer

<400> SEQUENCE: 202

Gly Phe Thr Phe Asp Asp Tyr Thr Ile Gly
1 5 10

<210> SEQ ID NO 203
<211> LENGTH: 10
<212> TYPE: PRT
<213> ORGANISM: Artificial Sequence
<220> FEATURE:
<223> OTHER INFORMATION: Artificial polymer

<400> SEQUENCE: 203

Gly Phe Ser Ser Asp Asp Tyr Thr Ile Gly
1 5 10

<210> SEQ ID NO 204
<211> LENGTH: 10
<212> TYPE: PRT
<213> ORGANISM: Artificial Sequence
<220> FEATURE:
<223> OTHER INFORMATION: Artificial polymer

<400> SEQUENCE: 204

Gly Phe Thr Phe Asp Gln Tyr Thr Ile Ala
1 5 10

<210> SEQ ID NO 205
<211> LENGTH: 10
<212> TYPE: PRT
<213> ORGANISM: Artificial Sequence
<220> FEATURE:
<223> OTHER INFORMATION: Artificial polymer

<400> SEQUENCE: 205

Gly Arg Thr Phe Ser Ser Tyr Ala Met Ala
1 5 10

<210> SEQ ID NO 206
<211> LENGTH: 10
<212> TYPE: PRT
<213> ORGANISM: Artificial Sequence
<220> FEATURE:
<223> OTHER INFORMATION: Artificial polymer

<400> SEQUENCE: 206

Gly Phe Ala Phe Asp Gly Tyr Ala Ile Gly
1 5 10

<210> SEQ ID NO 207
<211> LENGTH: 10
<212> TYPE: PRT
<213> ORGANISM: Artificial Sequence
<220> FEATURE:
<223> OTHER INFORMATION: Artificial polymer

<400> SEQUENCE: 207

Gly Phe Ser Ser Asp Asp Tyr Thr Ile Ala
1 5 10

<210> SEQ ID NO 208

<211> LENGTH: 10
<212> TYPE: PRT
<213> ORGANISM: Artificial Sequence
<220> FEATURE:
<223> OTHER INFORMATION: Artificial polymer

<400> SEQUENCE: 208

Gly Phe Ser Ser Asp Asp Tyr Thr Ile Gly
1 5 10

<210> SEQ ID NO 209
<211> LENGTH: 10
<212> TYPE: PRT
<213> ORGANISM: Artificial Sequence
<220> FEATURE:
<223> OTHER INFORMATION: Artificial polymer

<400> SEQUENCE: 209

Gly Phe Thr Phe Asp Asp Tyr Thr Ile Gly
1 5 10

<210> SEQ ID NO 210
<211> LENGTH: 10
<212> TYPE: PRT
<213> ORGANISM: Artificial Sequence
<220> FEATURE:
<223> OTHER INFORMATION: Artificial polymer

<400> SEQUENCE: 210

Gly Phe Ser Ser Asp Asp Tyr Thr Ile Gly
1 5 10

<210> SEQ ID NO 211
<211> LENGTH: 10
<212> TYPE: PRT
<213> ORGANISM: Artificial Sequence
<220> FEATURE:
<223> OTHER INFORMATION: Artificial polymer

<400> SEQUENCE: 211

Gly Phe Ser Ser Asp Asp Tyr Thr Ile Gly
1 5 10

<210> SEQ ID NO 212
<211> LENGTH: 10
<212> TYPE: PRT
<213> ORGANISM: Artificial Sequence
<220> FEATURE:
<223> OTHER INFORMATION: Artificial polymer

<400> SEQUENCE: 212

Gly Phe Ser Phe Asp Asp Tyr Ala Ile Ala
1 5 10

<210> SEQ ID NO 213
<211> LENGTH: 10
<212> TYPE: PRT
<213> ORGANISM: Artificial Sequence
<220> FEATURE:
<223> OTHER INFORMATION: Artificial polymer

<400> SEQUENCE: 213

Gly Phe Ser Ser Asp Asp Tyr Thr Ile Gly
1 5 10

<210> SEQ ID NO 214
<211> LENGTH: 10

<212> TYPE: PRT
<213> ORGANISM: Artificial Sequence
<220> FEATURE:
<223> OTHER INFORMATION: Artificial polymer

<400> SEQUENCE: 214

Gly Phe Thr Gly Asn Asp Leu Ala Ile Gly
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Artificial polymer

<400> SEQUENCE: 215

Gly Phe Ser Ser Asp Asp Tyr Thr Ile Ala
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Artificial polymer

<400> SEQUENCE: 216

Glu Gly Thr Leu Ser Ser Tyr Gly Ile Gly
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Artificial polymer

<400> SEQUENCE: 217

Gly Phe Ser Ser Asp Asp Tyr Thr Ile Ala
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Artificial polymer

<400> SEQUENCE: 218

Gly Phe Thr Phe Asp Asp Tyr Ala Ile Ala
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Artificial polymer

<400> SEQUENCE: 219

Gly Leu Ser Ser Asp Asp Tyr Thr Ile Gly
1               5                   10

<210> SEQ ID NO 220
<211> LENGTH: 10
<212> TYPE: PRT

<213> ORGANISM: Artificial Sequence
<220> FEATURE:
<223> OTHER INFORMATION: Artificial polymer

<400> SEQUENCE: 220

Gly Leu Ser Ser Asp Asp Tyr Thr Ile Gly
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Artificial polymer

<400> SEQUENCE: 221

Gly Phe Ser Ser Asp Asp Tyr Thr Ile Gly
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Artificial polymer

<400> SEQUENCE: 222

Gly Phe Ser Phe Asp Asp Tyr Thr Ile Gly
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Artificial polymer

<400> SEQUENCE: 223

Gly Phe Thr Phe Asp Asp Tyr Ala Ile Ala
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Artificial polymer

<400> SEQUENCE: 224

Gly Phe Thr Phe Asp Asp Tyr Ala Ile Gly
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Artificial polymer

<400> SEQUENCE: 225

Gly Phe Thr Phe Gly Asp Tyr Thr Ile Gly
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Artificial polymer

<400> SEQUENCE: 226

Glu Gly Thr Phe Ser Ser Tyr Gly Ile Gly
1 5 10

<210> SEQ ID NO 227
<211> LENGTH: 10
<212> TYPE: PRT
<213> ORGANISM: Artificial Sequence
<220> FEATURE:
<223> OTHER INFORMATION: Artificial polymer

<400> SEQUENCE: 227

Gly Phe Ser Ser Asp Asp Tyr Thr Ile Gly
1 5 10

<210> SEQ ID NO 228
<211> LENGTH: 10
<212> TYPE: PRT
<213> ORGANISM: Artificial Sequence
<220> FEATURE:
<223> OTHER INFORMATION: Artificial polymer

<400> SEQUENCE: 228

Gly Val Ser Ile Gly Asp Tyr Asn Ile Gly
1 5 10

<210> SEQ ID NO 229
<211> LENGTH: 10
<212> TYPE: PRT
<213> ORGANISM: Artificial Sequence
<220> FEATURE:
<223> OTHER INFORMATION: Artificial polymer

<400> SEQUENCE: 229

Gly Phe Thr Phe Asp Asp Tyr Thr Ile Ala
1 5 10

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 10
<212> TYPE: PRT
<213> ORGANISM: Artificial Sequence
<220> FEATURE:
<223> OTHER INFORMATION: Artificial polymer

<400> SEQUENCE: 300

Gly Phe Thr Phe Asp Asp Tyr Thr Ile Ala
1 5 10

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331
<211> LENGTH: 11
<212> TYPE: PRT
<213> ORGANISM: Artificial Sequence
<220> FEATURE:
<223> OTHER INFORMATION: Artificial polymer

<400> SEQUENCE: 331

Ala Ser Ile Thr Trp Gly Gly Gly Asn Thr Tyr
1               5                   10

<210> SEQ ID NO 332
<211> LENGTH: 11
<212> TYPE: PRT
<213> ORGANISM: Artificial Sequence
<220> FEATURE:
<223> OTHER INFORMATION: Artificial polymer

<400> SEQUENCE: 332

Ala Ala Thr Val Trp Thr Gly Ala Gly Thr Val
1               5                   10

<210> SEQ ID NO 333
<211> LENGTH: 11
<212> TYPE: PRT

<213> ORGANISM: Artificial Sequence
<220> FEATURE:
<223> OTHER INFORMATION: Artificial polymer

<400> SEQUENCE: 333

Ala Ala Ile Gly Trp Ser Ala Asp Ile Thr Val
1 5 10

<210> SEQ ID NO 334
<211> LENGTH: 11
<212> TYPE: PRT
<213> ORGANISM: Artificial Sequence
<220> FEATURE:
<223> OTHER INFORMATION: Artificial polymer

<400> SEQUENCE: 334

Ala Phe Ile Asp Trp Ser Gly Gly Gly Thr Tyr
1 5 10

<210> SEQ ID NO 335
<211> LENGTH: 11
<212> TYPE: PRT
<213> ORGANISM: Artificial Sequence
<220> FEATURE:
<223> OTHER INFORMATION: Artificial polymer

<400> SEQUENCE: 335

Ala Thr Ile Thr Trp Gly Gly Gly Ser Thr Tyr
1 5 10

<210> SEQ ID NO 336
<211> LENGTH: 11
<212> TYPE: PRT
<213> ORGANISM: Artificial Sequence
<220> FEATURE:
<223> OTHER INFORMATION: Artificial polymer

<400> SEQUENCE: 336

Ala Ala Ile Ser Trp Ser Gly Gly Pro Thr Val
1 5 10

<210> SEQ ID NO 337
<211> LENGTH: 11
<212> TYPE: PRT
<213> ORGANISM: Artificial Sequence
<220> FEATURE:
<223> OTHER INFORMATION: Artificial polymer

<400> SEQUENCE: 337

Ala Ala Ile Thr Trp Gly Gly Gly Ser Thr Val
1 5 10

<210> SEQ ID NO 338
<211> LENGTH: 11
<212> TYPE: PRT
<213> ORGANISM: Artificial Sequence
<220> FEATURE:
<223> OTHER INFORMATION: Artificial polymer

<400> SEQUENCE: 338

Ala Ala Ile Thr Trp Ser Gly Val Ser Thr Val
1 5 10

<210> SEQ ID NO 339
<211> LENGTH: 11
<212> TYPE: PRT
<213> ORGANISM: Artificial Sequence
<220> FEATURE:
<223> OTHER INFORMATION: Artificial polymer

<400> SEQUENCE: 339

Gly Ala Ile Met Trp Ser Gly Ala Phe Thr His
1 5 10

<210> SEQ ID NO 340
<211> LENGTH: 11
<212> TYPE: PRT
<213> ORGANISM: Artificial Sequence
<220> FEATURE:
<223> OTHER INFORMATION: Artificial polymer

<400> SEQUENCE: 340

Ala Ala Ile Thr Trp Gly Gly Gly Ser Thr Val
1 5 10

<210> SEQ ID NO 341
<211> LENGTH: 11
<212> TYPE: PRT
<213> ORGANISM: Artificial Sequence
<220> FEATURE:
<223> OTHER INFORMATION: Artificial polymer

<400> SEQUENCE: 341

Ser Cys Ile Ser Ser Ser Asp Arg Asn Thr Tyr
1 5 10

<210> SEQ ID NO 342
<211> LENGTH: 11
<212> TYPE: PRT
<213> ORGANISM: Artificial Sequence
<220> FEATURE:
<223> OTHER INFORMATION: Artificial polymer

<400> SEQUENCE: 342

Ala Phe Ile Asp Trp Ser Gly Gly Gly Thr Tyr
1 5 10

<210> SEQ ID NO 343
<211> LENGTH: 11
<212> TYPE: PRT
<213> ORGANISM: Artificial Sequence
<220> FEATURE:
<223> OTHER INFORMATION: Artificial polymer

<400> SEQUENCE: 343

Ala Val Ile Thr Trp Ser Gly Asp Ser Thr Tyr
1 5 10

<210> SEQ ID NO 344
<211> LENGTH: 11
<212> TYPE: PRT
<213> ORGANISM: Artificial Sequence
<220> FEATURE:
<223> OTHER INFORMATION: Artificial polymer

<400> SEQUENCE: 344

Ala Cys Ile Ser Ser Lys Asp Gly Ser Thr Tyr
1 5 10

<210> SEQ ID NO 345
<211> LENGTH: 11
<212> TYPE: PRT
<213> ORGANISM: Artificial Sequence
<220> FEATURE:

<223> OTHER INFORMATION: Artificial polymer

<400> SEQUENCE: 345

Ser Gly Ile Asn Ser Ile Gly Gly Ser Thr Thr
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Artificial polymer

<400> SEQUENCE: 346

Ala Val Val Thr Trp Ser Gly Asp Ser Thr Tyr
1               5                   10

<210> SEQ ID NO 347
<211> LENGTH: 10
<212> TYPE: PRT
<213> ORGANISM: Artificial Sequence
<220> FEATURE:
<223> OTHER INFORMATION: Artificial polymer

<400> SEQUENCE: 347

Ala Lys Ile Thr Asn Phe Gly Ile Thr Ser
1               5                   10

<210> SEQ ID NO 348
<211> LENGTH: 11
<212> TYPE: PRT
<213> ORGANISM: Artificial Sequence
<220> FEATURE:
<223> OTHER INFORMATION: Artificial polymer

<400> SEQUENCE: 348

Ser Phe Ile Ser Trp Ile Ser Asp Ile Thr Tyr
1               5                   10

<210> SEQ ID NO 349
<211> LENGTH: 11
<212> TYPE: PRT
<213> ORGANISM: Artificial Sequence
<220> FEATURE:
<223> OTHER INFORMATION: Artificial polymer

<400> SEQUENCE: 349

Ala Phe Ile Asp Trp Ser Gly Gly Gly Thr Tyr
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Artificial polymer

<400> SEQUENCE: 350

Ala Val Ile Leu Trp Ser Gly Val Ser Thr Tyr
1               5                   10

<210> SEQ ID NO 351
<211> LENGTH: 11
<212> TYPE: PRT
<213> ORGANISM: Artificial Sequence
<220> FEATURE:
<223> OTHER INFORMATION: Artificial polymer

<400> SEQUENCE: 351

Ala Ala Ile Val Trp Ser Gly Gly Ser Thr Tyr
1 5 10

<210> SEQ ID NO 352
<211> LENGTH: 11
<212> TYPE: PRT
<213> ORGANISM: Artificial Sequence
<220> FEATURE:
<223> OTHER INFORMATION: Artificial polymer

<400> SEQUENCE: 352

Ala Ala Ile Ser Ser Ser Gly Tyr His Thr Tyr
1 5 10

<210> SEQ ID NO 353
<211> LENGTH: 11
<212> TYPE: PRT
<213> ORGANISM: Artificial Sequence
<220> FEATURE:
<223> OTHER INFORMATION: Artificial polymer

<400> SEQUENCE: 353

Ser Cys Ile Ser Ser Pro Asp Gly Ser Thr Tyr
1 5 10

<210> SEQ ID NO 354
<211> LENGTH: 11
<212> TYPE: PRT
<213> ORGANISM: Artificial Sequence
<220> FEATURE:
<223> OTHER INFORMATION: Artificial polymer

<400> SEQUENCE: 354

Ala Ala Val Leu Trp Ser Gly Val Ser Thr Ala
1 5 10

<210> SEQ ID NO 355
<211> LENGTH: 11
<212> TYPE: PRT
<213> ORGANISM: Artificial Sequence
<220> FEATURE:
<223> OTHER INFORMATION: Artificial polymer

<400> SEQUENCE: 355

Val Ala Ile Thr Trp Asp Gly Ser Ala Thr Thr
1 5 10

<210> SEQ ID NO 356
<211> LENGTH: 11
<212> TYPE: PRT
<213> ORGANISM: Artificial Sequence
<220> FEATURE:
<223> OTHER INFORMATION: Artificial polymer

<400> SEQUENCE: 356

Ala Ala Ile Gly Trp Asn Gly Gly Ile Thr Tyr
1 5 10

<210> SEQ ID NO 357
<211> LENGTH: 11
<212> TYPE: PRT
<213> ORGANISM: Artificial Sequence
<220> FEATURE:
<223> OTHER INFORMATION: Artificial polymer

<400> SEQUENCE: 357

Gly Phe Ile Thr Trp Ser Gly Ala Ser Thr Tyr
1 5 10

<210> SEQ ID NO 358
<211> LENGTH: 11
<212> TYPE: PRT
<213> ORGANISM: Artificial Sequence
<220> FEATURE:
<223> OTHER INFORMATION: Artificial polymer

<400> SEQUENCE: 358

Ala Gly Ile Asn Trp Ser Gly Glu Ser Ala Asp
1 5 10

<210> SEQ ID NO 359
<211> LENGTH: 11
<212> TYPE: PRT
<213> ORGANISM: Artificial Sequence
<220> FEATURE:
<223> OTHER INFORMATION: Artificial polymer

<400> SEQUENCE: 359

Ser Cys Ile Glu Arg Ser Asp Gly Ser Thr Tyr
1 5 10

<210> SEQ ID NO 360
<211> LENGTH: 11
<212> TYPE: PRT
<213> ORGANISM: Artificial Sequence
<220> FEATURE:
<223> OTHER INFORMATION: Artificial polymer

<400> SEQUENCE: 360

Ser Cys Ile Ser Asn Thr Asp Ser Ser Thr Tyr
1 5 10

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371
<211> LENGTH: 11
<212> TYPE: PRT
<213> ORGANISM: Artificial Sequence
<220> FEATURE:
<223> OTHER INFORMATION: Artificial polymer

<400> SEQUENCE: 371

Ser Cys Ile Ser Asn Thr Asp Ser Ser Thr Tyr
1 5 10

<210> SEQ ID NO 372
<211> LENGTH: 11
<212> TYPE: PRT
<213> ORGANISM: Artificial Sequence
<220> FEATURE:
<223> OTHER INFORMATION: Artificial polymer

<400> SEQUENCE: 372

Ala Gln Ile Ser Trp Ser Ala Gly Ser Ile Tyr
1 5 10

<210> SEQ ID NO 373
<211> LENGTH: 11
<212> TYPE: PRT
<213> ORGANISM: Artificial Sequence
<220> FEATURE:
<223> OTHER INFORMATION: Artificial polymer

<400> SEQUENCE: 373

Ala Gly Met Ser Trp Asn Pro Gly Pro Ala Val
1 5 10

<210> SEQ ID NO 374
<211> LENGTH: 11
<212> TYPE: PRT
<213> ORGANISM: Artificial Sequence
<220> FEATURE:
<223> OTHER INFORMATION: Artificial polymer

<400> SEQUENCE: 374

Ser Cys Ile Ser Arg Ser Asp Gly Ser Thr Tyr
1 5 10

<210> SEQ ID NO 375
<211> LENGTH: 11
<212> TYPE: PRT
<213> ORGANISM: Artificial Sequence
<220> FEATURE:
<223> OTHER INFORMATION: Artificial polymer

<400> SEQUENCE: 375

Ala Asn Ile Gly Trp Thr Gly Asp Met Thr Tyr
1 5 10

<210> SEQ ID NO 376
<211> LENGTH: 11
<212> TYPE: PRT
<213> ORGANISM: Artificial Sequence
<220> FEATURE:
<223> OTHER INFORMATION: Artificial polymer

<400> SEQUENCE: 376

Ala Ala Ile Ile Trp Ser Gly Ser Met Thr Tyr
1 5 10

<210> SEQ ID NO 377
<211> LENGTH: 11
<212> TYPE: PRT
<213> ORGANISM: Artificial Sequence
<220> FEATURE:
<223> OTHER INFORMATION: Artificial polymer

<400> SEQUENCE: 377

Ser Cys Ile Ser Asn Thr Asp Ser Ser Thr Tyr
1 5 10

<210> SEQ ID NO 378
<211> LENGTH: 11
<212> TYPE: PRT
<213> ORGANISM: Artificial Sequence
<220> FEATURE:
<223> OTHER INFORMATION: Artificial polymer

<400> SEQUENCE: 378

Ala Ala Asn Thr Trp Ser Gly Gly Pro Thr Tyr
1 5 10

<210> SEQ ID NO 379
<211> LENGTH: 10
<212> TYPE: PRT
<213> ORGANISM: Artificial Sequence
<220> FEATURE:
<223> OTHER INFORMATION: Artificial polymer

<400> SEQUENCE: 379

Ser Cys Ile Ser Ser Asp Gly Ser Thr Gly
1 5 10

<210> SEQ ID NO 380
<211> LENGTH: 11
<212> TYPE: PRT
<213> ORGANISM: Artificial Sequence
<220> FEATURE:

<223> OTHER INFORMATION: Artificial polymer

<400> SEQUENCE: 380

Ser Cys Tyr Ser Ser Ser Asp Gly Ser Thr Gly
1               5                   10

<210> SEQ ID NO 381
<211> LENGTH: 10
<212> TYPE: PRT
<213> ORGANISM: Artificial Sequence
<220> FEATURE:
<223> OTHER INFORMATION: Artificial polymer

<400> SEQUENCE: 381

Ser Cys Ile Ser Ser Asp Gly Ser Thr Gly
1               5                   10

<210> SEQ ID NO 382
<211> LENGTH: 11
<212> TYPE: PRT
<213> ORGANISM: Artificial Sequence
<220> FEATURE:
<223> OTHER INFORMATION: Artificial polymer

<400> SEQUENCE: 382

Gly Cys Ile Lys Ser Ser Asp Gly Thr Thr Gly
1               5                   10

<210> SEQ ID NO 383
<211> LENGTH: 11
<212> TYPE: PRT
<213> ORGANISM: Artificial Sequence
<220> FEATURE:
<223> OTHER INFORMATION: Artificial polymer

<400> SEQUENCE: 383

Ser Cys Ile Ser Asn Thr Asp Ser Ser Thr Tyr
1               5                   10

<210> SEQ ID NO 384
<211> LENGTH: 11
<212> TYPE: PRT
<213> ORGANISM: Artificial Sequence
<220> FEATURE:
<223> OTHER INFORMATION: Artificial polymer

<400> SEQUENCE: 384

Ala Ala Ile Ala Trp Ser Ala Gly Ser Thr Tyr
1               5                   10

<210> SEQ ID NO 385
<211> LENGTH: 11
<212> TYPE: PRT
<213> ORGANISM: Artificial Sequence
<220> FEATURE:
<223> OTHER INFORMATION: Artificial polymer

<400> SEQUENCE: 385

Ser Cys Ile Ser Ser Lys Glu Gly Ser Thr Tyr
1               5                   10

<210> SEQ ID NO 386
<211> LENGTH: 11
<212> TYPE: PRT
<213> ORGANISM: Artificial Sequence
<220> FEATURE:
<223> OTHER INFORMATION: Artificial polymer

<400> SEQUENCE: 386

Ser Cys Ile Ser Ser Ser Asp Gly Ser Thr Gly
1 5 10

<210> SEQ ID NO 387
<211> LENGTH: 11
<212> TYPE: PRT
<213> ORGANISM: Artificial Sequence
<220> FEATURE:
<223> OTHER INFORMATION: Artificial polymer

<400> SEQUENCE: 387

Ser Cys Tyr Ser Ser Arg Asp Gly Thr Thr Gly
1 5 10

<210> SEQ ID NO 388
<211> LENGTH: 10
<212> TYPE: PRT
<213> ORGANISM: Artificial Sequence
<220> FEATURE:
<223> OTHER INFORMATION: Artificial polymer

<400> SEQUENCE: 388

Ser Cys Ile Ser Ser Asp Gly Ser Thr Gly
1 5 10

<210> SEQ ID NO 389
<211> LENGTH: 11
<212> TYPE: PRT
<213> ORGANISM: Artificial Sequence
<220> FEATURE:
<223> OTHER INFORMATION: Artificial polymer

<400> SEQUENCE: 389

Ser Cys Tyr Ser Ser Ser Asp Gly Ser Thr Gly
1 5 10

<210> SEQ ID NO 390
<211> LENGTH: 11
<212> TYPE: PRT
<213> ORGANISM: Artificial Sequence
<220> FEATURE:
<223> OTHER INFORMATION: Artificial polymer

<400> SEQUENCE: 390

Ser Cys Phe Ser Ser Ser Asp Gly Ser Thr Gly
1 5 10

<210> SEQ ID NO 391
<211> LENGTH: 11
<212> TYPE: PRT
<213> ORGANISM: Artificial Sequence
<220> FEATURE:
<223> OTHER INFORMATION: Artificial polymer

<400> SEQUENCE: 391

Ser Cys Ile Ser Asn Thr Asp Ser Ser Thr Phe
1 5 10

<210> SEQ ID NO 392
<211> LENGTH: 11
<212> TYPE: PRT
<213> ORGANISM: Artificial Sequence
<220> FEATURE:
<223> OTHER INFORMATION: Artificial polymer

<400> SEQUENCE: 392

Ser Cys Tyr Ser Ser Ser Asp Gly Ser Thr Gly
1 5 10

<210> SEQ ID NO 393
<211> LENGTH: 11
<212> TYPE: PRT
<213> ORGANISM: Artificial Sequence
<220> FEATURE:
<223> OTHER INFORMATION: Artificial polymer

<400> SEQUENCE: 393

Ser Cys Ile Ser Asn Thr Asp Ser Ser Thr Tyr
1 5 10

<210> SEQ ID NO 394
<211> LENGTH: 11
<212> TYPE: PRT
<213> ORGANISM: Artificial Sequence
<220> FEATURE:
<223> OTHER INFORMATION: Artificial polymer

<400> SEQUENCE: 394

Ser Cys Ile Ser Ser Ser Asp Gly Ser Thr Gly
1 5 10

<210> SEQ ID NO 395
<211> LENGTH: 11
<212> TYPE: PRT
<213> ORGANISM: Artificial Sequence
<220> FEATURE:
<223> OTHER INFORMATION: Artificial polymer

<400> SEQUENCE: 395

Gly Gly Ile Asn Trp Ser Gly Asp Ser Thr Asp
1 5 10

<210> SEQ ID NO 396
<211> LENGTH: 11
<212> TYPE: PRT
<213> ORGANISM: Artificial Sequence
<220> FEATURE:
<223> OTHER INFORMATION: Artificial polymer

<400> SEQUENCE: 396

Ser Cys Phe Ser Ser Ser Asp Gly Ser Ala Gly
1 5 10

<210> SEQ ID NO 397
<211> LENGTH: 11
<212> TYPE: PRT
<213> ORGANISM: Artificial Sequence
<220> FEATURE:
<223> OTHER INFORMATION: Artificial polymer

<400> SEQUENCE: 397

Ser Cys Ile Ser Asn Thr Asp Ser Ser Thr Tyr
1 5 10

<210> SEQ ID NO 398
<211> LENGTH: 11
<212> TYPE: PRT
<213> ORGANISM: Artificial Sequence
<220> FEATURE:
<223> OTHER INFORMATION: Artificial polymer

<400> SEQUENCE: 398

Ser Cys Phe Ser Thr Arg Asp Gly Asn Ala Gly
1 5 10

<210> SEQ ID NO 399
<211> LENGTH: 11
<212> TYPE: PRT
<213> ORGANISM: Artificial Sequence
<220> FEATURE:
<223> OTHER INFORMATION: Artificial polymer

<400> SEQUENCE: 399

Ser Cys Phe Ser Ser Arg Asp Gly Ser Thr Gly
1 5 10

<210> SEQ ID NO 400
<211> LENGTH: 11
<212> TYPE: PRT
<213> ORGANISM: Artificial Sequence
<220> FEATURE:
<223> OTHER INFORMATION: Artificial polymer

<400> SEQUENCE: 400

Ser Cys Phe Ser Ser Arg Asp Gly Ser Thr Gly
1 5 10

<210> SEQ ID NO 401
<211> LENGTH: 10
<212> TYPE: PRT
<213> ORGANISM: Artificial Sequence
<220> FEATURE:
<223> OTHER INFORMATION: Artificial polymer

<400> SEQUENCE: 401

Ser Cys Ile Ser Ser Asp Gly Ser Thr Gly
1 5 10

<210> SEQ ID NO 402
<211> LENGTH: 11
<212> TYPE: PRT
<213> ORGANISM: Artificial Sequence
<220> FEATURE:
<223> OTHER INFORMATION: Artificial polymer

<400> SEQUENCE: 402

Ser Cys Ile Ser Asn Thr Asp Ser Ser Thr Tyr
1 5 10

<210> SEQ ID NO 403
<211> LENGTH: 11
<212> TYPE: PRT
<213> ORGANISM: Artificial Sequence
<220> FEATURE:
<223> OTHER INFORMATION: Artificial polymer

<400> SEQUENCE: 403

Ser Cys Ile Ser Ser Pro Asp Gly Ser Thr Tyr
1 5 10

<210> SEQ ID NO 404
<211> LENGTH: 11
<212> TYPE: PRT
<213> ORGANISM: Artificial Sequence
<220> FEATURE:
<223> OTHER INFORMATION: Artificial polymer

<400> SEQUENCE: 404

Ser Cys Tyr Ser Ser Ser Asp Gly Asn Thr Gly
1 5 10

<210> SEQ ID NO 405
<211> LENGTH: 11
<212> TYPE: PRT
<213> ORGANISM: Artificial Sequence
<220> FEATURE:
<223> OTHER INFORMATION: Artificial polymer

<400> SEQUENCE: 405

Gly Gly Ile Asn Trp Ser Gly Asp Ser Thr Asp
1 5 10

<210> SEQ ID NO 406
<211> LENGTH: 11
<212> TYPE: PRT
<213> ORGANISM: Artificial Sequence
<220> FEATURE:
<223> OTHER INFORMATION: Artificial polymer

<400> SEQUENCE: 406

Ser Cys Phe Ser Ser Ser Asp Gly Ser Thr Gly
1 5 10

<210> SEQ ID NO 407
<211> LENGTH: 11
<212> TYPE: PRT
<213> ORGANISM: Artificial Sequence
<220> FEATURE:
<223> OTHER INFORMATION: Artificial polymer

<400> SEQUENCE: 407

Ser Cys Ile Ser Ser Gly Asp Gly Thr Thr Tyr
1 5 10

<210> SEQ ID NO 408
<211> LENGTH: 10
<212> TYPE: PRT
<213> ORGANISM: Artificial Sequence
<220> FEATURE:
<223> OTHER INFORMATION: Artificial polymer

<400> SEQUENCE: 408

Ser Cys Ile Ser Ser Asp Gly Ser Thr Gly
1 5 10

<210> SEQ ID NO 409
<211> LENGTH: 10
<212> TYPE: PRT
<213> ORGANISM: Artificial Sequence
<220> FEATURE:
<223> OTHER INFORMATION: Artificial polymer

<400> SEQUENCE: 409

Ser Cys Ile Ser Ser Asp Gly Ser Thr Gly
1 5 10

<210> SEQ ID NO 410
<211> LENGTH: 11
<212> TYPE: PRT
<213> ORGANISM: Artificial Sequence
<220> FEATURE:
<223> OTHER INFORMATION: Artificial polymer

<400> SEQUENCE: 410

Ser Ser Ile Ser Arg Ser Asp Gly Ser Thr Tyr 1 5 10

<210> SEQ ID NO 411
<211> LENGTH: 19
<212> TYPE: PRT
<213> ORGANISM: Artificial Sequence
<220> FEATURE:
<223> OTHER INFORMATION: Artificial polymer

<400> SEQUENCE: 411

Ala Lys Gly Leu Arg Asn Ser Asp Trp Asp Leu Arg Arg Gly Tyr Glu
1 5 10 15

Tyr Asp Tyr

<210> SEQ ID NO 412
<211> LENGTH: 25
<212> TYPE: PRT
<213> ORGANISM: Artificial Sequence
<220> FEATURE:
<223> OTHER INFORMATION: Artificial polymer

<400> SEQUENCE: 412

Ala Asp Gln Ala Ser Val Pro Pro Pro Tyr Gly Ser Glu Arg Tyr Asp
1 5 10 15

Ile Ala Ser Pro Ser Glu Tyr Asp Tyr
20 25

<210> SEQ ID NO 413
<211> LENGTH: 21
<212> TYPE: PRT
<213> ORGANISM: Artificial Sequence
<220> FEATURE:
<223> OTHER INFORMATION: Artificial polymer

<400> SEQUENCE: 413

Ala Asn Ser Arg Ala Tyr Tyr Ser Ser Ser Tyr Asp Leu Gly Arg Leu
1 5 10 15

Ala Ser Tyr Asp Tyr
20

<210> SEQ ID NO 414
<211> LENGTH: 16
<212> TYPE: PRT
<213> ORGANISM: Artificial Sequence
<220> FEATURE:
<223> OTHER INFORMATION: Artificial polymer

<400> SEQUENCE: 414

Ala Ala Gln Arg Leu Gly Ser Val Thr Asp Tyr Thr Lys Tyr Asp Tyr
1 5 10 15

<210> SEQ ID NO 415
<211> LENGTH: 21
<212> TYPE: PRT
<213> ORGANISM: Artificial Sequence
<220> FEATURE:
<223> OTHER INFORMATION: Artificial polymer

<400> SEQUENCE: 415

Ala Ser Val Lys Val Val Ala Gly Ser Gly Ile Asp Ile Ser Gly Ser
1 5 10 15

Arg Asn Tyr Asp Tyr
20

<210> SEQ ID NO 416
<211> LENGTH: 21
<212> TYPE: PRT
<213> ORGANISM: Artificial Sequence
<220> FEATURE:
<223> OTHER INFORMATION: Artificial polymer

<400> SEQUENCE: 416

Ala Lys Arg Leu Asp Tyr Ser Ala Thr Asp Lys Gly Val Asp Leu Ser
1               5                   10                  15

Asp Glu Tyr Asp Tyr
            20

<210> SEQ ID NO 417
<211> LENGTH: 19
<212> TYPE: PRT
<213> ORGANISM: Artificial Sequence
<220> FEATURE:
<223> OTHER INFORMATION: Artificial polymer

<400> SEQUENCE: 417

Ala Ala Gly Gly Ser Gly Arg Leu Arg Asp Leu Lys Val Gly Gln Asn
1               5                   10                  15

Tyr Asp Tyr

<210> SEQ ID NO 418
<211> LENGTH: 23
<212> TYPE: PRT
<213> ORGANISM: Artificial Sequence
<220> FEATURE:
<223> OTHER INFORMATION: Artificial polymer

<400> SEQUENCE: 418

Ala Asp Ser Pro Pro Arg Thr Tyr Ser Ser Gly Ser Val Asn Leu Glu
1               5                   10                  15

Asp Gly Ser Glu Tyr Asp Tyr
            20

<210> SEQ ID NO 419
<211> LENGTH: 21
<212> TYPE: PRT
<213> ORGANISM: Artificial Sequence
<220> FEATURE:
<223> OTHER INFORMATION: Artificial polymer

<400> SEQUENCE: 419

Val Ile Pro Gly Arg Gly Ser Ala Leu Pro Ile Asp Val Gly Lys Ser
1               5                   10                  15

Asp Glu Tyr Glu Tyr
            20

<210> SEQ ID NO 420
<211> LENGTH: 19
<212> TYPE: PRT
<213> ORGANISM: Artificial Sequence
<220> FEATURE:
<223> OTHER INFORMATION: Artificial polymer

<400> SEQUENCE: 420

Ala Ala Gly Ala Ser Gly Arg Leu Arg Asp Leu Lys Val Gly Gln Asn
1               5                   10                  15

Tyr Asp Tyr

<210> SEQ ID NO 421

<211> LENGTH: 23
<212> TYPE: PRT
<213> ORGANISM: Artificial Sequence
<220> FEATURE:
<223> OTHER INFORMATION: Artificial polymer

<400> SEQUENCE: 421

Ala Asp Gly Asn Val Trp Ser Pro Pro Ile Cys Gly Ser Ala Gly Pro
1               5                   10                  15

Pro Pro Gly Gly Met Asp Tyr
            20

<210> SEQ ID NO 422
<211> LENGTH: 16
<212> TYPE: PRT
<213> ORGANISM: Artificial Sequence
<220> FEATURE:
<223> OTHER INFORMATION: Artificial polymer

<400> SEQUENCE: 422

Ala Ala Gln Arg Leu Gly Ser Val Thr Asp Tyr Thr Lys Tyr Asp Tyr
1               5                   10                  15

<210> SEQ ID NO 423
<211> LENGTH: 22
<212> TYPE: PRT
<213> ORGANISM: Artificial Sequence
<220> FEATURE:
<223> OTHER INFORMATION: Artificial polymer

<400> SEQUENCE: 423

Ala Ile Pro Pro Arg Ala Tyr Ser Gly Gly Ser Tyr Ser Leu Lys Asp
1               5                   10                  15

Gln Ser Lys Tyr Glu Tyr
            20

<210> SEQ ID NO 424
<211> LENGTH: 23
<212> TYPE: PRT
<213> ORGANISM: Artificial Sequence
<220> FEATURE:
<223> OTHER INFORMATION: Artificial polymer

<400> SEQUENCE: 424

Ala Asp Gly Asn Val Trp Ser Pro Pro Ile Cys Ser Ser Ala Gly Pro
1               5                   10                  15

Pro Pro Gly Gly Met Asp Tyr
            20

<210> SEQ ID NO 425
<211> LENGTH: 9
<212> TYPE: PRT
<213> ORGANISM: Artificial Sequence
<220> FEATURE:
<223> OTHER INFORMATION: Artificial polymer

<400> SEQUENCE: 425

Lys Ser Arg Ser Ser Tyr Ser Asn Asn
1               5

<210> SEQ ID NO 426
<211> LENGTH: 22
<212> TYPE: PRT
<213> ORGANISM: Artificial Sequence
<220> FEATURE:
<223> OTHER INFORMATION: Artificial polymer

<400> SEQUENCE: 426

Ala Met Pro Pro Arg Ala Tyr Thr Gly Arg Ser Val Ser Leu Lys Asp
1 5 10 15

Gln Ser Lys Tyr Glu Tyr
20

<210> SEQ ID NO 427
<211> LENGTH: 13
<212> TYPE: PRT
<213> ORGANISM: Artificial Sequence
<220> FEATURE:
<223> OTHER INFORMATION: Artificial polymer

<400> SEQUENCE: 427

Leu Asp Thr Thr Gly Trp Gly Pro Pro Pro Tyr Gln Tyr
1 5 10

<210> SEQ ID NO 428
<211> LENGTH: 22
<212> TYPE: PRT
<213> ORGANISM: Artificial Sequence
<220> FEATURE:
<223> OTHER INFORMATION: Artificial polymer

<400> SEQUENCE: 428

Ala His Pro Pro Asp Pro Ser Arg Gly Gly Glu Trp Arg Leu Gln Thr
1 5 10 15

Pro Ser Glu Tyr Asp Tyr
20

<210> SEQ ID NO 429
<211> LENGTH: 16
<212> TYPE: PRT
<213> ORGANISM: Artificial Sequence
<220> FEATURE:
<223> OTHER INFORMATION: Artificial polymer

<400> SEQUENCE: 429

Ala Ala Gln Arg Leu Gly Ser Val Thr Asp Tyr Thr Lys Tyr Asp Tyr
1 5 10 15

<210> SEQ ID NO 430
<211> LENGTH: 24
<212> TYPE: PRT
<213> ORGANISM: Artificial Sequence
<220> FEATURE:
<223> OTHER INFORMATION: Artificial polymer

<400> SEQUENCE: 430

Val Pro Arg Ser His Phe Thr Thr Ala Gln Asp Met Gly Gln Asp Met
1 5 10 15

Gly Ala Pro Ser Trp Tyr Glu Tyr
20

<210> SEQ ID NO 431
<211> LENGTH: 22
<212> TYPE: PRT
<213> ORGANISM: Artificial Sequence
<220> FEATURE:
<223> OTHER INFORMATION: Artificial polymer

<400> SEQUENCE: 431

Ala Val Leu Ile Arg Tyr Tyr Ser Gly Gly Tyr Gln Gly Leu Ser Asp
1 5 10 15

Ala Asn Glu Tyr Asp Tyr
20

<210> SEQ ID NO 432
<211> LENGTH: 17
<212> TYPE: PRT
<213> ORGANISM: Artificial Sequence
<220> FEATURE:
<223> OTHER INFORMATION: Artificial polymer

<400> SEQUENCE: 432

Val Val Lys Tyr Leu Ser Gly Ser Tyr Ser Tyr Ala Gly Gln Tyr Asn
1 5 10 15

Phe

<210> SEQ ID NO 433
<211> LENGTH: 23
<212> TYPE: PRT
<213> ORGANISM: Artificial Sequence
<220> FEATURE:
<223> OTHER INFORMATION: Artificial polymer

<400> SEQUENCE: 433

Ala Asp Phe Asn Val Trp Ser Pro Pro Ile Cys Gly Ser Val Gly Pro
1 5 10 15

Pro Pro Gly Gly Met Asp Tyr
20

<210> SEQ ID NO 434
<211> LENGTH: 21
<212> TYPE: PRT
<213> ORGANISM: Artificial Sequence
<220> FEATURE:
<223> OTHER INFORMATION: Artificial polymer

<400> SEQUENCE: 434

Ala His Glu Ser Thr Tyr Tyr Ser Gly Thr Tyr Tyr Leu Thr Asp Pro
1 5 10 15

Arg Arg Tyr Val Tyr
20

<210> SEQ ID NO 435
<211> LENGTH: 19
<212> TYPE: PRT
<213> ORGANISM: Artificial Sequence
<220> FEATURE:
<223> OTHER INFORMATION: Artificial polymer

<400> SEQUENCE: 435

Ala Val Pro Ala Arg Gly Leu Thr Met Asp Leu Glu Asn Ser Asp Ile
1 5 10 15

Tyr Asp His

<210> SEQ ID NO 436
<211> LENGTH: 22
<212> TYPE: PRT
<213> ORGANISM: Artificial Sequence
<220> FEATURE:
<223> OTHER INFORMATION: Artificial polymer

<400> SEQUENCE: 436

Ala Ala Thr Leu Gln Val Thr Gly Ser Tyr Tyr Leu Asp Leu Ser Thr
1 5 10 15

Val Asp Ile Tyr Asp Asn
20

<210> SEQ ID NO 437
<211> LENGTH: 20
<212> TYPE: PRT
<213> ORGANISM: Artificial Sequence
<220> FEATURE:
<223> OTHER INFORMATION: Artificial polymer

<400> SEQUENCE: 437

Ala Thr Leu Phe Arg Ser Asn Gly Pro Lys Asp Leu Ser Ser Gly Tyr
1 5 10 15

Glu Tyr Asp Tyr
20

<210> SEQ ID NO 438
<211> LENGTH: 13
<212> TYPE: PRT
<213> ORGANISM: Artificial Sequence
<220> FEATURE:
<223> OTHER INFORMATION: Artificial polymer

<400> SEQUENCE: 438

Ala Gly Glu Ser Gly Val Trp Val Gly Gly Leu Asp Tyr
1 5 10

<210> SEQ ID NO 439
<211> LENGTH: 22
<212> TYPE: PRT
<213> ORGANISM: Artificial Sequence
<220> FEATURE:
<223> OTHER INFORMATION: Artificial polymer

<400> SEQUENCE: 439

Val Gly Ser Ala Asn Ser Gly Glu Phe Arg Phe Gly Trp Val Leu Lys
1 5 10 15

Pro Asp Leu Tyr Asn Tyr
20

<210> SEQ ID NO 440
<211> LENGTH: 23
<212> TYPE: PRT
<213> ORGANISM: Artificial Sequence
<220> FEATURE:
<223> OTHER INFORMATION: Artificial polymer

<400> SEQUENCE: 440

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 441
<211> LENGTH: 23
<212> TYPE: PRT
<213> ORGANISM: Artificial Sequence
<220> FEATURE:
<223> OTHER INFORMATION: Artificial polymer

<400> SEQUENCE: 441

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 442
<211> LENGTH: 20
<212> TYPE: PRT
<213> ORGANISM: Artificial Sequence
<220> FEATURE:
<223> OTHER INFORMATION: Artificial polymer

<400> SEQUENCE: 442

Glu Arg Gly Tyr Ala Tyr Cys Ser Asp Asp Gly Cys Gln Arg Thr Gln
1 5 10 15

Asp Tyr Asp Tyr
20

<210> SEQ ID NO 443
<211> LENGTH: 21
<212> TYPE: PRT
<213> ORGANISM: Artificial Sequence
<220> FEATURE:
<223> OTHER INFORMATION: Artificial polymer

<400> SEQUENCE: 443

Gly Ala Ala Arg Ala Trp Trp Ser Gly Ser Tyr Asp Tyr Thr Arg Met
1 5 10 15

Asn Asn Tyr Asp Tyr
20

<210> SEQ ID NO 444
<211> LENGTH: 23
<212> TYPE: PRT
<213> ORGANISM: Artificial Sequence
<220> FEATURE:
<223> OTHER INFORMATION: Artificial polymer

<400> SEQUENCE: 444

Ala Glu Thr Ser Ala Asp Ser Gly Glu Phe Arg Phe Gly Trp Val Leu
1 5 10 15

Lys Pro Ser Leu Tyr Asp Tyr
20

<210> SEQ ID NO 445
<211> LENGTH: 21
<212> TYPE: PRT
<213> ORGANISM: Artificial Sequence
<220> FEATURE:
<223> OTHER INFORMATION: Artificial polymer

<400> SEQUENCE: 445

Ala Ala Gly Ser Ala Tyr Ser Gly Ser Tyr Trp Asn Ile Thr Met Ala
1 5 10 15

Ala Asn Tyr Asp Tyr
20

<210> SEQ ID NO 446
<211> LENGTH: 18
<212> TYPE: PRT
<213> ORGANISM: Artificial Sequence
<220> FEATURE:
<223> OTHER INFORMATION: Artificial polymer

<400> SEQUENCE: 446

Ala Gln Arg Ile Phe Gly Ala Gln Pro Met Asp Leu Ser Gly Asp Tyr
1 5 10 15

Glu Tyr

<210> SEQ ID NO 447
<211> LENGTH: 23
<212> TYPE: PRT
<213> ORGANISM: Artificial Sequence
<220> FEATURE:
<223> OTHER INFORMATION: Artificial polymer

<400> SEQUENCE: 447

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 448
<211> LENGTH: 18
<212> TYPE: PRT
<213> ORGANISM: Artificial Sequence
<220> FEATURE:
<223> OTHER INFORMATION: Artificial polymer

<400> SEQUENCE: 448

Ala Arg Asp Tyr Arg Gly Ile Lys Asp Leu Asp Leu Lys Gly Asp Tyr
1 5 10 15

Asp Tyr

<210> SEQ ID NO 449
<211> LENGTH: 25
<212> TYPE: PRT
<213> ORGANISM: Artificial Sequence
<220> FEATURE:
<223> OTHER INFORMATION: Artificial polymer

<400> SEQUENCE: 449

Ala Asp Phe Asn Val Trp Ser Pro Pro Ile Cys Gly Ser Ile Trp Tyr
1 5 10 15

Gly Pro Pro Pro Arg Gly Met Asp Tyr
20 25

<210> SEQ ID NO 450
<211> LENGTH: 25
<212> TYPE: PRT
<213> ORGANISM: Artificial Sequence
<220> FEATURE:
<223> OTHER INFORMATION: Artificial polymer

<400> SEQUENCE: 450

Ala Asp Ser Asn Val Trp Ser Pro Pro Ile Cys Gly Ser Arg Trp Tyr
1 5 10 15

Gly Pro Pro Pro Gly Gly Met Ala Tyr
20 25

<210> SEQ ID NO 451
<211> LENGTH: 25
<212> TYPE: PRT
<213> ORGANISM: Artificial Sequence
<220> FEATURE:
<223> OTHER INFORMATION: Artificial polymer

<400> SEQUENCE: 451

Ala Asp Phe Asn Val Trp Ser Pro Pro Ile Cys Gly Ser Asn Trp Tyr
1 5 10 15

Gly Pro Pro Pro Gly Gly Met Asp Tyr
20 25

<210> SEQ ID NO 452
<211> LENGTH: 25
<212> TYPE: PRT
<213> ORGANISM: Artificial Sequence
<220> FEATURE:
<223> OTHER INFORMATION: Artificial polymer

<400> SEQUENCE: 452

Ala Asp Phe Asn Val Trp Ser Pro Pro Ile Cys Gly Ser Ile Trp Tyr
1 5 10 15

Gly Pro Pro Pro Gly Gly Met Asp Tyr
20 25

<210> SEQ ID NO 453
<211> LENGTH: 23
<212> TYPE: PRT
<213> ORGANISM: Artificial Sequence
<220> FEATURE:
<223> OTHER INFORMATION: Artificial polymer

<400> SEQUENCE: 453

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 454
<211> LENGTH: 17
<212> TYPE: PRT
<213> ORGANISM: Artificial Sequence
<220> FEATURE:
<223> OTHER INFORMATION: Artificial polymer

<400> SEQUENCE: 454

Ala Arg Ile Ile Thr Val Ala Thr Met Arg Leu Asp Ser Asp Tyr Asp
1 5 10 15

Tyr

<210> SEQ ID NO 455
<211> LENGTH: 23
<212> TYPE: PRT
<213> ORGANISM: Artificial Sequence
<220> FEATURE:
<223> OTHER INFORMATION: Artificial polymer

<400> SEQUENCE: 455

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 456
<211> LENGTH: 25
<212> TYPE: PRT
<213> ORGANISM: Artificial Sequence
<220> FEATURE:
<223> OTHER INFORMATION: Artificial polymer

<400> SEQUENCE: 456

Ala Asp Ser Asn Val Trp Ser Pro Pro Ile Cys Gly Arg Thr Trp Tyr
1 5 10 15

Gly Pro Pro Pro Gly Gly Met Asp Tyr
20 25

<210> SEQ ID NO 457
<211> LENGTH: 25
<212> TYPE: PRT
<213> ORGANISM: Artificial Sequence
<220> FEATURE:
<223> OTHER INFORMATION: Artificial polymer

<400> SEQUENCE: 457

Ala Asp Phe Asn Val Trp Ser Pro Pro Ile Cys Gly Ser Ile Trp Tyr
1               5                   10                  15

Gly Pro Pro Pro Gly Gly Met Ala Tyr
            20                  25

<210> SEQ ID NO 458
<211> LENGTH: 25
<212> TYPE: PRT
<213> ORGANISM: Artificial Sequence
<220> FEATURE:
<223> OTHER INFORMATION: Artificial polymer

<400> SEQUENCE: 458

Ala Asp Phe Asn Val Trp Ser Pro Pro Ile Cys Gly Ser Asn Trp Tyr
1               5                   10                  15

Gly Pro Pro Pro Gly Gly Met Asp Tyr
            20                  25

<210> SEQ ID NO 459
<211> LENGTH: 25
<212> TYPE: PRT
<213> ORGANISM: Artificial Sequence
<220> FEATURE:
<223> OTHER INFORMATION: Artificial polymer

<400> SEQUENCE: 459

Ala Asp Phe Asn Val Trp Ser Pro Pro Ile Cys Gly Ser Ser Trp Tyr
1               5                   10                  15

Gly Pro Pro Pro Gly Gly Met Asp Tyr
            20                  25

<210> SEQ ID NO 460
<211> LENGTH: 25
<212> TYPE: PRT
<213> ORGANISM: Artificial Sequence
<220> FEATURE:
<223> OTHER INFORMATION: Artificial polymer

<400> SEQUENCE: 460

Ala Asp Phe Asn Val Trp Ser Pro Pro Ile Cys Gly Ser Arg Trp Tyr
1               5                   10                  15

Gly Pro Pro Pro Gly Gly Met Glu Tyr
            20                  25

<210> SEQ ID NO 461
<211> LENGTH: 23
<212> TYPE: PRT
<213> ORGANISM: Artificial Sequence
<220> FEATURE:
<223> OTHER INFORMATION: Artificial polymer

<400> SEQUENCE: 461

Ala Asp Gly Asn Val Trp Ser Pro Pro Ile Cys Gly Ser Ala Gly Pro
1               5                   10                  15

Pro Pro Gly Gly Met Asp Tyr

20

<210> SEQ ID NO 462
<211> LENGTH: 25
<212> TYPE: PRT
<213> ORGANISM: Artificial Sequence
<220> FEATURE:
<223> OTHER INFORMATION: Artificial polymer

<400> SEQUENCE: 462

Ala Asp Phe Asn Val Trp Ser Pro Pro Ile Cys Gly Ser Arg Trp Tyr
1 5 10 15

Gly Pro Pro Pro Gly Gly Met Ala Tyr
20 25

<210> SEQ ID NO 463
<211> LENGTH: 23
<212> TYPE: PRT
<213> ORGANISM: Artificial Sequence
<220> FEATURE:
<223> OTHER INFORMATION: Artificial polymer

<400> SEQUENCE: 463

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 464
<211> LENGTH: 25
<212> TYPE: PRT
<213> ORGANISM: Artificial Sequence
<220> FEATURE:
<223> OTHER INFORMATION: Artificial polymer

<400> SEQUENCE: 464

Ala Asp Ser Asn Val Trp Ser Pro Pro Ile Cys Gly Lys Thr Trp Tyr
1 5 10 15

Gly Pro Pro Pro Gly Gly Met Asp Tyr
20 25

<210> SEQ ID NO 465
<211> LENGTH: 13
<212> TYPE: PRT
<213> ORGANISM: Artificial Sequence
<220> FEATURE:
<223> OTHER INFORMATION: Artificial polymer

<400> SEQUENCE: 465

Ala Gly Glu Ser Gly Val Trp Val Gly Gly Leu Asp Tyr
1 5 10

<210> SEQ ID NO 466
<211> LENGTH: 25
<212> TYPE: PRT
<213> ORGANISM: Artificial Sequence
<220> FEATURE:
<223> OTHER INFORMATION: Artificial polymer

<400> SEQUENCE: 466

Ala Asp Ser Asn Val Trp Ser Pro Pro Ile Cys Gly Ser Thr Trp Tyr
1 5 10 15

Gly Pro Pro Pro Gly Gly Met Ala Tyr
20 25

<210> SEQ ID NO 467
<211> LENGTH: 23
<212> TYPE: PRT
<213> ORGANISM: Artificial Sequence
<220> FEATURE:
<223> OTHER INFORMATION: Artificial polymer

<400> SEQUENCE: 467

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 468
<211> LENGTH: 25
<212> TYPE: PRT
<213> ORGANISM: Artificial Sequence
<220> FEATURE:
<223> OTHER INFORMATION: Artificial polymer

<400> SEQUENCE: 468

Ala Asp Phe Asn Val Trp Ser Pro Pro Ile Cys Gly Ser Arg Trp Tyr
1 5 10 15

Gly Pro Pro Pro Gly Gly Met Asp Tyr
20 25

<210> SEQ ID NO 469
<211> LENGTH: 25
<212> TYPE: PRT
<213> ORGANISM: Artificial Sequence
<220> FEATURE:
<223> OTHER INFORMATION: Artificial polymer

<400> SEQUENCE: 469

Ala Asp Phe Asn Val Trp Ser Pro Pro Ile Cys Gly Ser Arg Trp Tyr
1 5 10 15

Gly Pro Pro Pro Gly Gly Met Asp Tyr
20 25

<210> SEQ ID NO 470
<211> LENGTH: 25
<212> TYPE: PRT
<213> ORGANISM: Artificial Sequence
<220> FEATURE:
<223> OTHER INFORMATION: Artificial polymer

<400> SEQUENCE: 470

Ala Asp Phe Asn Val Trp Ser Pro Pro Ile Cys Gly Ser Arg Trp Tyr
1 5 10 15

Gly Pro Pro Pro Gly Gly Met Asp Tyr
20 25

<210> SEQ ID NO 471
<211> LENGTH: 25
<212> TYPE: PRT
<213> ORGANISM: Artificial Sequence
<220> FEATURE:
<223> OTHER INFORMATION: Artificial polymer

<400> SEQUENCE: 471

Ala Asp Phe Asn Val Trp Ser Pro Pro Ile Cys Gly Ser Ile Trp Tyr
1 5 10 15

Gly Pro Pro Pro Gly Gly Met Asp Tyr
20 25

<210> SEQ ID NO 472
<211> LENGTH: 23
<212> TYPE: PRT
<213> ORGANISM: Artificial Sequence
<220> FEATURE:
<223> OTHER INFORMATION: Artificial polymer

<400> SEQUENCE: 472

Ala Asp Gly Asn Val Trp Ser Pro Pro Ile Cys Gly Ser Ala Gly Pro
1 5 10 15

Pro Pro Gly Gly Met Asp Tyr
20

<210> SEQ ID NO 473
<211> LENGTH: 23
<212> TYPE: PRT
<213> ORGANISM: Artificial Sequence
<220> FEATURE:
<223> OTHER INFORMATION: Artificial polymer

<400> SEQUENCE: 473

Ala Asp Phe Asn Val Trp Ser Pro Pro Ile Cys Gly Ser Val Gly Pro
1 5 10 15

Pro Pro Gly Gly Met Asp Tyr
20

<210> SEQ ID NO 474
<211> LENGTH: 25
<212> TYPE: PRT
<213> ORGANISM: Artificial Sequence
<220> FEATURE:
<223> OTHER INFORMATION: Artificial polymer

<400> SEQUENCE: 474

Ala Asp Phe Asn Val Trp Ser Pro Pro Ile Cys Gly Ser Ser Trp Tyr
1 5 10 15

Gly Pro Pro Pro Gly Gly Met Ala Tyr
20 25

<210> SEQ ID NO 475
<211> LENGTH: 13
<212> TYPE: PRT
<213> ORGANISM: Artificial Sequence
<220> FEATURE:
<223> OTHER INFORMATION: Artificial polymer

<400> SEQUENCE: 475

Ala Gly Glu Ser Gly Val Trp Val Gly Gly Leu Asp Tyr
1 5 10

<210> SEQ ID NO 476
<211> LENGTH: 25
<212> TYPE: PRT
<213> ORGANISM: Artificial Sequence
<220> FEATURE:
<223> OTHER INFORMATION: Artificial polymer

<400> SEQUENCE: 476

Ala Asp Phe Asn Val Trp Ser Pro Pro Ile Cys Gly Ser Ser Trp Tyr
1 5 10 15

Gly Pro Pro Pro Gly Gly Met Glu Tyr
20 25

<210> SEQ ID NO 477
<211> LENGTH: 23
<212> TYPE: PRT
<213> ORGANISM: Artificial Sequence
<220> FEATURE:
<223> OTHER INFORMATION: Artificial polymer

<400> SEQUENCE: 477

```
Ala Asp Gly Asn Val Trp Ser Pro Pro Ile Cys Gly Ser Ala Gly Pro
1               5                   10                  15

Pro Pro Gly Gly Met Asp Tyr
            20
```

<210> SEQ ID NO 478
<211> LENGTH: 25
<212> TYPE: PRT
<213> ORGANISM: Artificial Sequence
<220> FEATURE:
<223> OTHER INFORMATION: Artificial polymer

<400> SEQUENCE: 478

```
Ala Asp Phe Asn Val Trp Ser Pro Pro Ile Cys Ser Ser Asn Trp Tyr
1               5                   10                  15

Gly Pro Pro Pro Arg Gly Met Asp Tyr
            20                  25
```

<210> SEQ ID NO 479
<211> LENGTH: 25
<212> TYPE: PRT
<213> ORGANISM: Artificial Sequence
<220> FEATURE:
<223> OTHER INFORMATION: Artificial polymer

<400> SEQUENCE: 479

```
Ala Asp Phe Asn Val Trp Ser Pro Pro Ile Cys Gly Ser Ile Trp Tyr
1               5                   10                  15

Gly Pro Pro Pro Arg Gly Met Asp Tyr
            20                  25
```

<210> SEQ ID NO 480
<211> LENGTH: 146
<212> TYPE: PRT
<213> ORGANISM: Artificial Sequence
<220> FEATURE:
<223> OTHER INFORMATION: Artificial polymer

<400> SEQUENCE: 480

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ser Phe Ser Ser Tyr
            20                  25                  30

Thr Leu Ala Trp Phe Arg Gln Ala Pro Gly Lys Glu Arg Glu Phe Val
        35                  40                  45

Ala Ser Ile Thr Trp Gly Gly Gly Asn Thr Tyr Tyr Pro Asp Ser Val
    50                  55                  60

Lys Gly Arg Phe Thr Ile Ser Arg Asp Asp Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Lys Gly Leu Arg Asn Ser Asp Trp Asp Leu Arg Arg Gly Tyr
            100                 105                 110

Glu Tyr Asp Tyr Trp Gly Gln Gly Thr Gln Val Thr Val Ser Ser Ala
```

```
        115                 120                 125

Ala Ala Tyr Pro Tyr Asp Val Pro Asp Tyr Gly Ser His His His His
    130                 135                 140

His His
145


<210> SEQ ID NO 481
<211> LENGTH: 152
<212> TYPE: PRT
<213> ORGANISM: Artificial Sequence
<220> FEATURE:
<223> OTHER INFORMATION: Artificial polymer

<400> SEQUENCE: 481

Gln Val Gln Leu Gln Glu Ser Gly Gly Gly Leu Val Gln Asp Gly Gly
1               5                   10                  15

Ser Leu Arg Leu Ser Cys Ala Phe Ser Gly Arg Thr Phe Ser Ser Tyr
            20                  25                  30

Thr Met Gly Trp Phe Arg Gln Gly Pro Gly Lys Glu Arg Glu Phe Val
        35                  40                  45

Ala Ala Thr Val Trp Thr Gly Ala Gly Thr Val Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Gln Ala Ser Val Pro Pro Pro Tyr Gly Ser Glu Arg Tyr
            100                 105                 110

Asp Ile Ala Ser Pro Ser Glu Tyr Asp Tyr Trp Gly Gln Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 482
<211> LENGTH: 148
<212> TYPE: PRT
<213> ORGANISM: Artificial Sequence
<220> FEATURE:
<223> OTHER INFORMATION: Artificial polymer

<400> SEQUENCE: 482

Gln Val Gln Leu Gln Glu Ser Gly Gly Gly Leu Val Gln Ala Gly Ala
1               5                   10                  15

Ser Leu Arg Leu Ser Cys Ala Ala Ser Gly Arg Thr Phe Ser Ser Tyr
            20                  25                  30

Ile Met Gly Trp Phe Arg Gln Ala Pro Gly Lys Glu Arg Glu Phe Val
        35                  40                  45

Ala Ala Ile Gly Trp Ser Ala Asp Ile Thr Val Tyr Ala Asp Ser Val
    50                  55                  60

Lys Gly Arg Phe Thr Ile Ser Arg Asp Asn Ala Glu Asn Met Val Tyr
65                  70                  75                  80

Leu Gln Met Asn Ser Leu Asn Pro Glu Asp Thr Ala Val Tyr Tyr Cys
                85                  90                  95

Ala Ala Asn Ser Arg Ala Tyr Tyr Ser Ser Ser Tyr Asp Leu Gly Arg
            100                 105                 110
```

Leu Ala Ser Tyr Asp Tyr Trp Gly Gln Gly Thr Gln Val Thr Val Ser
115 120 125

Ser Ala Ala Ala Tyr Pro Tyr Asp Val Pro Asp Tyr Gly Ser His His
130 135 140

His His His His
145

<210> SEQ ID NO 483
<211> LENGTH: 143
<212> TYPE: PRT
<213> ORGANISM: Artificial Sequence
<220> FEATURE:
<223> OTHER INFORMATION: Artificial polymer

<400> SEQUENCE: 483

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Ser Tyr
20 25 30

Thr Met Gly Trp Phe Arg Gln Ala Pro Gly Lys Glu Arg Glu Phe Val
35 40 45

Ala Phe Ile Asp Trp Ser Gly Gly Gly Thr Tyr Tyr Asp Asp Ser Val
50 55 60

Lys Gly Arg Phe Thr Ile Ser Arg Asp Asn Ala Glu Asn Thr Val Tyr
65 70 75 80

Leu Gln Met Asn Asn Leu Glu Pro Glu Asp Thr Ala Val Tyr Tyr Cys
85 90 95

Ala Ala Ala Gln Arg Leu Gly Ser Val Thr Asp Tyr Thr Lys Tyr Asp
100 105 110

Tyr Trp Gly Gln Gly Thr Gln Val Thr Val Ser Ser Ala Ala Ala Tyr
115 120 125

Pro Tyr Asp Val Pro Asp Tyr Gly Ser His His His His His His
130 135 140

<210> SEQ ID NO 484
<211> LENGTH: 152
<212> TYPE: PRT
<213> ORGANISM: Artificial Sequence
<220> FEATURE:
<223> OTHER INFORMATION: Artificial polymer

<400> SEQUENCE: 484

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Ser Gly Arg Thr
20 25 30

Phe Ser Ser Tyr Thr Met Gly Trp Phe Arg Gln Ala Pro Gly Lys Glu
35 40 45

Arg Glu Phe Val Ala Thr Ile Thr Trp Gly Gly Gly Ser Thr Tyr Tyr
50 55 60

Ala Asp Ser Val Lys Gly Arg Phe Thr Ile Ser Arg Asp Asn Ala Asn
65 70 75 80

Asn Thr Val Tyr Leu Gln Met Asn Ser Leu Lys Pro Glu Asp Thr Ala
85 90 95

Val Tyr Tyr Cys Ala Ala Ser Val Lys Val Val Ala Gly Ser Gly Ile
100 105 110

Asp Ile Ser Gly Ser Arg Asn Tyr Asp Tyr Trp Gly Gln Gly Thr Gln
115 120 125

```
Val Thr Val Ser Ser Ala Ala Ala Tyr Pro Tyr Asp Val Pro Asp Tyr
    130                 135                 140

Gly Ser His His His His His His
145                 150


<210> SEQ ID NO 485
<211> LENGTH: 148
<212> TYPE: PRT
<213> ORGANISM: Artificial Sequence
<220> FEATURE:
<223> OTHER INFORMATION: Artificial polymer

<400> SEQUENCE: 485

Gln Val Gln Leu Gln Glu Ser Gly Gly Gly Leu Val Gln Pro Gly Gly
1               5                   10                  15

Ser Leu Arg Leu Ser Cys Leu Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Pro Thr Val Tyr Ala Asp His Val
    50                  55                  60

Lys Gly Arg Phe Thr Ile Ser Arg Asp Asn Ala Lys Asn Thr Val Tyr
65                  70                  75                  80

Leu Gln Val Asn Ser Leu Lys Pro Glu Asp Thr Ala Asp Tyr Tyr Cys
                85                  90                  95

Ala Ala Lys Arg Leu Asp Tyr Ser Ala Thr Asp Lys Gly Val Asp Leu
            100                 105                 110

Ser Asp Glu Tyr Asp Tyr Trp Gly Gln Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145


<210> SEQ ID NO 486
<211> LENGTH: 146
<212> TYPE: PRT
<213> ORGANISM: Artificial Sequence
<220> FEATURE:
<223> OTHER INFORMATION: Artificial polymer

<400> SEQUENCE: 486

Gln Val Gln Leu Gln Glu Ser Gly Gly Gly Leu Val Gln Ala Gly Asp
1               5                   10                  15

Ser Leu Arg Leu Ser Cys Ala Ala Ser Gly Leu Thr Phe Ser Asn Tyr
            20                  25                  30

Ile Met Gly Trp Phe Arg Gln Ala Pro Gly Lys Glu Arg Glu Phe Val
        35                  40                  45

Ala Ala Ile Thr Trp Gly Gly Gly Ser Thr Val Tyr Ala Asp Ser Val
    50                  55                  60

Glu Gly Arg Phe Thr Ile Ser Arg Asp Gly Thr Lys Asn Thr Val Ser
65                  70                  75                  80

Leu Gln Met Asn Ser Leu Leu Pro Glu Asp Thr Ala Val Tyr Tyr Cys
                85                  90                  95

Ala Ala Ala Gly Gly Ser Gly Arg Leu Arg Asp Leu Lys Val Gly Gln
            100                 105                 110

Asn Tyr Asp Tyr Trp Gly Gln Gly Thr Gln Val Thr Val Ser Ser Ala
```

```
        115                 120                 125

Ala Ala Tyr Pro Tyr Asp Val Pro Asp Tyr Gly Ser His His His His
    130                 135                 140

His His
145


<210> SEQ ID NO 487
<211> LENGTH: 150
<212> TYPE: PRT
<213> ORGANISM: Artificial Sequence
<220> FEATURE:
<223> OTHER INFORMATION: Artificial polymer

<400> SEQUENCE: 487

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Thr Met Gly Trp Phe Arg Gln Ala Pro Gly Arg Glu Arg Glu Phe Val
        35                  40                  45

Ala Ala Ile Thr Trp Ser Gly Val Ser Thr Val Tyr Thr Asp Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Ser Pro Pro Arg Thr Tyr Ser Ser Gly Ser Val Asn Leu
            100                 105                 110

Glu Asp Gly Ser Glu Tyr Asp Tyr Trp Gly Gln Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 488
<211> LENGTH: 148
<212> TYPE: PRT
<213> ORGANISM: Artificial Sequence
<220> FEATURE:
<223> OTHER INFORMATION: Artificial polymer

<400> SEQUENCE: 488

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Asp
            20                  25                  30

Thr Met Gly Trp Phe Arg Gln Ala Pro Gly Lys Glu Arg Glu Phe Val
        35                  40                  45

Gly Ala Ile Met Trp Ser Gly Ala Phe Thr His Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ala Leu Lys Pro Glu Asp Thr Ala Val Tyr Tyr Cys
                85                  90                  95

Ala Val Ile Pro Gly Arg Gly Ser Ala Leu Pro Ile Asp Val Gly Lys
            100                 105                 110
```

Ser Asp Glu Tyr Glu Tyr Trp Gly Gln Gly Thr Gln Val Thr Val Ser
115 120 125

Ser Ala Ala Ala Tyr Pro Tyr Asp Val Pro Asp Tyr Gly Ser His His
130 135 140

His His His His
145

<210> SEQ ID NO 489
<211> LENGTH: 146
<212> TYPE: PRT
<213> ORGANISM: Artificial Sequence
<220> FEATURE:
<223> OTHER INFORMATION: Artificial polymer

<400> SEQUENCE: 489

Gln Val Gln Leu Gln Glu Ser Gly Gly Gly Leu Val Gln Ala Gly Asp
1 5 10 15

Ser Leu Arg Leu Ser Cys Ala Ala Ser Gly Leu Thr Phe Ser Asn Tyr
20 25 30

Ile Met Gly Trp Phe Arg Gln Ala Pro Gly Lys Glu Arg Glu Phe Val
35 40 45

Ala Ala Ile Thr Trp Gly Gly Gly Ser Thr Val Tyr Ala Asp Ser Val
50 55 60

Glu Gly Arg Phe Thr Ile Ser Arg Asp Gly Thr Lys Asn Thr Val Ser
65 70 75 80

Leu Gln Met Asn Ser Leu Gln Pro Glu Asp Thr Ala Val Tyr Tyr Cys
85 90 95

Ala Ala Ala Gly Ala Ser Gly Arg Leu Arg Asp Leu Lys Val Gly Gln
100 105 110

Asn Tyr Asp Tyr Trp Gly Gln Gly Thr Gln Val Thr Val Ser Ser Ala
115 120 125

Ala Ala Tyr Pro Tyr Asp Val Pro Asp Tyr Gly Ser His His His His
130 135 140

His His
145

<210> SEQ ID NO 490
<211> LENGTH: 150
<212> TYPE: PRT
<213> ORGANISM: Artificial Sequence
<220> FEATURE:
<223> OTHER INFORMATION: Artificial polymer

<400> SEQUENCE: 490

Gln Val Gln Leu Gln Glu Ser Gly Gly Gly Leu Val Gln Ala Gly Gly
1 5 10 15

Ser Leu Arg Leu Ser Cys Ala Gly Ser Gly Phe Thr Leu Asp Tyr Tyr
20 25 30

Gly Ile Gly Trp Phe Arg Gln Ala Pro Gly Lys Glu Arg Glu Gly Val
35 40 45

Ser Cys Ile Ser Ser Ser Asp Arg Asn Thr Tyr Tyr Ala Asp Ser Val
50 55 60

Lys Gly Arg Phe Thr Ile Ser Gly Asp Asn Ala Lys Asn Thr Val Tyr
65 70 75 80

Leu Gln Met Asn Asn Leu Lys Pro Glu Asp Thr Ala Val Tyr Tyr Cys
85 90 95

Ala Ala Asp Gly Asn Val Trp Ser Pro Pro Ile Cys Gly Ser Ala Gly
100 105 110

```
Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 491
<211> LENGTH: 143
<212> TYPE: PRT
<213> ORGANISM: Artificial Sequence
<220> FEATURE:
<223> OTHER INFORMATION: Artificial polymer

<400> SEQUENCE: 491

Gln Val Gln Leu Gln Glu Ser Gly Gly Gly Leu Val Gln Ala Gly Gly
1               5                   10                  15

Ser Leu Arg Leu Ser Cys Val Ala Ser Gly His Thr Phe Ser Ser Tyr
            20                  25                  30

Thr Met Gly Trp Phe Arg Gln Ala Pro Gly Lys Glu Arg Glu Phe Val
        35                  40                  45

Ala Phe Ile Asp Trp Ser Gly Gly Gly Thr Tyr Tyr Ala Asn Ser Val
    50                  55                  60

Lys Gly Arg Phe Thr Ile Ser Arg Asp Asn Ala Glu Asn Thr Val Tyr
65                  70                  75                  80

Leu Gln Met Asn Asn Leu Lys Pro Glu Asp Thr Ala Val Tyr Tyr Cys
                85                  90                  95

Ala Ala Ala Gln Arg Leu Gly Ser Val Thr Asp Tyr Thr Lys Tyr Asp
            100                 105                 110

Tyr Trp Gly Gln Gly Thr Gln Val Thr Val Ser Ser Ala Ala Ala Tyr
        115                 120                 125

Pro Tyr Asp Val Pro Asp Tyr Gly Ser His His His His His His
    130                 135                 140


<210> SEQ ID NO 492
<211> LENGTH: 149
<212> TYPE: PRT
<213> ORGANISM: Artificial Sequence
<220> FEATURE:
<223> OTHER INFORMATION: Artificial polymer

<400> SEQUENCE: 492

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Ile Gly Trp Phe Arg Gln Ala Pro Gly Lys Glu Arg Glu Phe Val
        35                  40                  45

Ala Val Ile Thr Trp Ser Gly Asp Ser Thr Tyr Ser Ser Asp Ser Leu
    50                  55                  60

Lys Gly Arg Phe Thr Ile Ser Arg Asp Asn Ala Lys Asn Thr Val Tyr
65                  70                  75                  80

Leu Gln Met Asn Ala Leu Asn Pro Glu Asp Thr Ala Val Tyr Tyr Cys
                85                  90                  95

Ala Ala Ile Pro Pro Arg Ala Tyr Ser Gly Gly Ser Tyr Ser Leu Lys
            100                 105                 110

Asp Gln Ser Lys Tyr Glu Tyr Trp Gly Gln Gly Thr Gln Val Thr Val
```

115 120 125

Ser Ser Ala Ala Ala Tyr Pro Tyr Asp Val Pro Asp Tyr Gly Ser His
130 135 140

His His His His His
145

<210> SEQ ID NO 493
<211> LENGTH: 149
<212> TYPE: PRT
<213> ORGANISM: Artificial Sequence
<220> FEATURE:
<223> OTHER INFORMATION: Artificial polymer

<400> SEQUENCE: 493

Gln Val Gln Leu Gln Glu Ser Gly Gly Gly Leu Val Gln Ala Glu Gly
1 5 10 15

Ser Leu Lys Leu Ser Cys Ile Ser Gly Phe Ala Phe Asp Gly Tyr Ala
20 25 30

Ile Gly Trp Phe Arg Gln Ala Pro Gly Lys Glu Arg Glu Gly Val Ala
35 40 45

Cys Ile Ser Ser Lys Asp Gly Ser Thr Tyr Tyr Ala Asp Ser Val Lys
50 55 60

Gly Arg Phe Thr Met Ser Val Asp Lys Thr Lys Asn Thr Val Tyr Leu
65 70 75 80

Gln Met Ser Ser Leu Lys Pro Glu Asp Thr Ala Val Tyr Tyr Cys Ala
85 90 95

Ala Asp Gly Asn Val Trp Ser Pro Pro Ile Cys Ser Ser Ala Gly Pro
100 105 110

Pro Pro Gly Gly Met Asp Tyr Trp Gly Lys Gly Thr Gln Val Thr Val
115 120 125

Ser Ser Ala Ala Ala Tyr Pro Tyr Asp Val Pro Asp Tyr Gly Ser His
130 135 140

His His His His His
145

<210> SEQ ID NO 494
<211> LENGTH: 139
<212> TYPE: PRT
<213> ORGANISM: Artificial Sequence
<220> FEATURE:
<223> OTHER INFORMATION: Artificial polymer

<400> SEQUENCE: 494

Gln Val Gln Leu Gln Glu Ser Gly Gly Gly Leu Val Gln Pro Gly Gly
1 5 10 15

Ser Leu Thr Leu Ser Cys Ala Ala Ser Gly Phe Ala Phe Gly Phe Phe
20 25 30

Asp Met Thr Trp Val Arg Gln Ala Pro Gly Lys Gly Leu Glu Trp Val
35 40 45

Ser Gly Ile Asn Ser Ile Gly Gly Ser Thr Thr Tyr Ala Asp Ser Val
50 55 60

Lys Gly Arg Phe Thr Ile Ser Arg Asp Asn Ala Lys Asn Glu Leu Tyr
65 70 75 80

Leu Gln Met Asn Ser Leu Lys Pro Asp Asp Thr Ala Val Tyr Tyr Cys
85 90 95

Ala Lys Ser Arg Ser Ser Tyr Ser Asn Asn Trp Arg Pro Pro Gly Gln
100 105 110

```
Gly Thr Gln Val Thr Val Ser Ser Ala Ala Ala Tyr Pro Tyr Asp Val
        115                 120                 125

Pro Asp Tyr Gly Ser His His His His His His
    130                 135


<210> SEQ ID NO 495
<211> LENGTH: 149
<212> TYPE: PRT
<213> ORGANISM: Artificial Sequence
<220> FEATURE:
<223> OTHER INFORMATION: Artificial polymer

<400> SEQUENCE: 495

Gln Val Gln Leu Gln Glu Ser Gly Gly Gly Leu Val Gln Ala Arg Gly
1               5                   10                  15

Ser Leu Thr Leu Ser Cys Ala Ala Ser Gly Arg Thr Phe Ser Asn Tyr
            20                  25                  30

Val Ile Gly Trp Phe Arg Gln Ala Pro Gly Glu Glu Arg Glu Phe Val
        35                  40                  45

Ala Val Val Thr Trp Ser Gly Asp Ser Thr Tyr Ser Ser Asp Ser Leu
    50                  55                  60

Lys Gly Arg Phe Thr Ile Ser Arg Asp Asn Ala Lys Asn Thr Val Tyr
65                  70                  75                  80

Leu Gln Met Asn Asn Leu Asn Pro Glu Asp Thr Ala Val Tyr Tyr Cys
                85                  90                  95

Ala Ala Met Pro Pro Arg Ala Tyr Thr Gly Arg Ser Val Ser Leu Lys
            100                 105                 110

Asp Gln Ser Lys Tyr Glu Tyr Trp Gly Gln Gly Thr Gln Val Thr Val
        115                 120                 125

Ser Ser Ala Ala Ala Tyr Pro Tyr Asp Val Pro Asp Tyr Gly Ser His
    130                 135                 140

His His His His His
145


<210> SEQ ID NO 496
<211> LENGTH: 139
<212> TYPE: PRT
<213> ORGANISM: Artificial Sequence
<220> FEATURE:
<223> OTHER INFORMATION: Artificial polymer

<400> SEQUENCE: 496

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Val Met Gly Trp Tyr Arg Gln Thr Pro Gly Lys Glu Arg Glu Leu Val
        35                  40                  45

Ala Lys Ile Thr Asn Phe Gly Ile Thr Ser Tyr Ala Asp Ser Ala Gln
    50                  55                  60

Gly Arg Phe Thr Ile Ser Arg Gly Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Asp Thr Thr Gly Trp Gly Pro Pro Pro Tyr Gln Tyr Trp Gly Gln
            100                 105                 110

Gly Thr Gln Val Thr Val Ser Ser Ala Ala Ala Tyr Pro Tyr Asp Val
        115                 120                 125
```

Pro Asp Tyr Gly Ser His His His His His His
130 135

<210> SEQ ID NO 497
<211> LENGTH: 149
<212> TYPE: PRT
<213> ORGANISM: Artificial Sequence
<220> FEATURE:
<223> OTHER INFORMATION: Artificial polymer

<400> SEQUENCE: 497

Gln Val Gln Leu Gln Glu Ser Gly Gly Gly Leu Val Gln Ala Gly Ala
1 5 10 15

Ser Leu Arg Leu Ser Cys Ala Ala Ser Gly Arg Thr Phe Ser Asn Tyr
20 25 30

Asn Val Gly Trp Phe Arg Gln Ala Pro Gly Lys Glu Arg Glu Phe Val
35 40 45

Ser Phe Ile Ser Trp Ile Ser Asp Ile Thr Tyr Tyr Ser Asp Ser Val
50 55 60

Lys Gly Arg Phe Ile Ile Ser Arg Asp Asn Ala Lys Asn Met Val Tyr
65 70 75 80

Leu Gln Met Asn Ser Leu Lys Pro Glu Asp Thr Ala Val Tyr Tyr Cys
85 90 95

Ala Ala His Pro Pro Asp Pro Ser Arg Gly Gly Glu Trp Arg Leu Gln
100 105 110

Thr Pro Ser Glu Tyr Asp Tyr Trp Gly Gln Gly Thr Gln Val Thr Val
115 120 125

Ser Ser Ala Ala Ala Tyr Pro Tyr Asp Val Pro Asp Tyr Gly Ser His
130 135 140

His His His His His
145

<210> SEQ ID NO 498
<211> LENGTH: 143
<212> TYPE: PRT
<213> ORGANISM: Artificial Sequence
<220> FEATURE:
<223> OTHER INFORMATION: Artificial polymer

<400> SEQUENCE: 498

Gln Val Gln Leu Gln Glu Ser Gly Gly Gly Leu Val Gln Ala Gly Gly
1 5 10 15

Ser Leu Arg Leu Ser Cys Ala Ala Ser Gly His Thr Phe Ser Ser Tyr
20 25 30

Thr Met Gly Trp Phe Arg Gln Ala Pro Gly Lys Glu Arg Glu Phe Val
35 40 45

Ala Phe Ile Asp Trp Ser Gly Gly Gly Thr Tyr Tyr Ala Asp Ser Val
50 55 60

Lys Gly Arg Phe Thr Ile Ser Arg Asp Asn Ala Glu Asn Thr Val Tyr
65 70 75 80

Leu Gln Met Asn Asn Leu Lys Pro Glu Asp Thr Ala Val Tyr Tyr Cys
85 90 95

Ala Ala Ala Gln Arg Leu Gly Ser Val Thr Asp Tyr Thr Lys Tyr Asp
100 105 110

Tyr Trp Gly Gln Gly Thr Gln Val Thr Val Ser Ser Ala Ala Ala Tyr
115 120 125

Pro Tyr Asp Val Pro Asp Tyr Gly Ser His His His His His His 130 135 140

<210> SEQ ID NO 499
<211> LENGTH: 151
<212> TYPE: PRT
<213> ORGANISM: Artificial Sequence
<220> FEATURE:
<223> OTHER INFORMATION: Artificial polymer

<400> SEQUENCE: 499

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Thr Tyr
20 25 30

Pro Val Gly Trp Phe Arg Gln Ala Pro Gly Lys Glu Arg Glu Phe Val
35 40 45

Ala Val Ile Leu Trp Ser Gly Val Ser Thr Tyr Tyr Ala Asp Ser Val
50 55 60

Lys Gly Arg Phe Thr Ile Ser Arg Asp Asn Ala Gln Asn Thr Val Tyr
65 70 75 80

Leu Gln Met Asp Ser Leu Lys Pro Glu Asp Thr Ala Val Tyr Tyr Cys
85 90 95

Ala Val Pro Arg Ser His Phe Thr Thr Ala Gln Asp Met Gly Gln Asp
100 105 110

Met Gly Ala Pro Ser Trp Tyr Glu Tyr Trp Gly Gln Gly Thr Gln Val
115 120 125

Thr Val Ser Ser Ala Ala Ala Tyr Pro Tyr Asp Val Pro Asp Tyr Gly
130 135 140

Ser His His His His His His
145 150

<210> SEQ ID NO 500
<211> LENGTH: 149
<212> TYPE: PRT
<213> ORGANISM: Artificial Sequence
<220> FEATURE:
<223> OTHER INFORMATION: Artificial polymer

<400> SEQUENCE: 500

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Asn Tyr
20 25 30

Ala Met Gly Trp Phe Arg Gln Ala Pro Gly Lys Glu Arg Glu Phe Val
35 40 45

Ala Ala Ile Val Trp Ser Gly Gly Ser Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Val Leu Ile Arg Tyr Tyr Ser Gly Gly Tyr Gln Gly Leu Ser
100 105 110

Asp Ala Asn Glu Tyr Asp Tyr Trp Gly Gln Gly Thr Gln Val Thr Val
115 120 125

Ser Ser Ala Ala Ala Tyr Pro Tyr Asp Val Pro Asp Tyr Gly Ser His
130 135 140

His His His His His
145

<210> SEQ ID NO 501
<211> LENGTH: 144
<212> TYPE: PRT
<213> ORGANISM: Artificial Sequence
<220> FEATURE:
<223> OTHER INFORMATION: Artificial polymer

<400> SEQUENCE: 501

Gln Val Gln Leu Gln Glu Ser Gly Gly Gly Leu Val Gln Ala Gly Ala
1 5 10 15

Ser Leu Arg Leu Ser Cys Ser Ala Ser Gly Arg Thr Phe Ser Asp Tyr
20 25 30

Arg Met Gly Trp Phe Arg Gln Ala Pro Gly Lys Glu Arg Glu Trp Val
35 40 45

Ala Ala Ile Ser Ser Ser Gly Tyr His Thr Tyr Tyr Ala Asp Ser Val
50 55 60

Lys Gly Arg Phe Thr Ile Ser Arg Asp Asn Ala Lys Asn Thr Gly Tyr
65 70 75 80

Leu Gln Met Ser Ser Leu Lys Pro Glu Asp Thr Ala Val Tyr Tyr Cys
85 90 95

Ala Val Val Lys Tyr Leu Ser Gly Ser Tyr Ser Tyr Ala Gly Gln Tyr
100 105 110

Asn Phe Trp Gly Gln Gly Thr Gln Val Thr Val Ser Ser Ala Ala Ala
115 120 125

Tyr Pro Tyr Asp Val Pro Asp Tyr Gly Ser His His His His His His
130 135 140

<210> SEQ ID NO 502
<211> LENGTH: 150
<212> TYPE: PRT
<213> ORGANISM: Artificial Sequence
<220> FEATURE:
<223> OTHER INFORMATION: Artificial polymer

<400> SEQUENCE: 502

Gln Val Gln Leu Gln Glu Ser Gly Gly Gly Leu Val Gln Ala Gly Asp
1 5 10 15

Ser Leu Lys Leu Ser Cys Ala Ala Ser Gly Leu Thr Phe Ser Asn Tyr
20 25 30

Ile Met Ala Trp Phe Arg Gln Ala Pro Gly Lys Glu Arg Glu Gly Val
35 40 45

Ser Cys Ile Ser Ser Pro Asp Gly Ser Thr Tyr Tyr Ala Asp Ser Val
50 55 60

Lys Gly Arg Phe Thr Ile Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asp Phe Asn Val Trp Ser Pro Pro Ile Cys Gly Ser Val Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 503
<211> LENGTH: 148
<212> TYPE: PRT
<213> ORGANISM: Artificial Sequence
<220> FEATURE:
<223> OTHER INFORMATION: Artificial polymer

<400> SEQUENCE: 503

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Ser
            20                  25                  30

Val Met Gly Trp Phe Arg Gln Pro Pro Gly Lys Glu Arg Glu Phe Val
        35                  40                  45

Ala Ala Val Leu Trp Ser Gly Val Ser Thr Ala Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Asp Asp Thr Ala Val Tyr Tyr Cys
                85                  90                  95

Ala Ala His Glu Ser Thr Tyr Tyr Ser Gly Thr Tyr Tyr Leu Thr Asp
            100                 105                 110

Pro Arg Arg Tyr Val Tyr Trp Gly Gln Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145
```

<210> SEQ ID NO 504
<211> LENGTH: 145
<212> TYPE: PRT
<213> ORGANISM: Artificial Sequence
<220> FEATURE:
<223> OTHER INFORMATION: Artificial polymer

<400> SEQUENCE: 504

```
Gln Val Gln Leu Gln Glu Ser Gly Gly Gly Leu Val Gln Ala Gly Gly
1               5                   10                  15

Ser Leu Arg Leu Ser Cys Val Gly Asp Gly Arg Thr Phe Ser Ser Tyr
            20                  25                  30

Ile Ile Gly Trp Phe Arg Gln Ala Pro Gly Asn Glu Arg Glu Phe Val
        35                  40                  45

Val Ala Ile Thr Trp Asp Gly Ser Ala Thr Thr Tyr Ala Asp Ser Val
    50                  55                  60

Lys Gly Arg Phe Thr Val Ser Arg Asp Ser Ala Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ala Val Pro Ala Arg Gly Leu Thr Met Asp Leu Glu Asn Ser Asp
            100                 105                 110

Ile Tyr Asp His Trp Gly Arg Gly Thr Gln Val Thr Val Ser Ser Ala
        115                 120                 125

Ala Ala Tyr Pro Tyr Asp Val Pro Asp Tyr Gly Ser His His His His
    130                 135                 140

His
```

145

<210> SEQ ID NO 505
<211> LENGTH: 149
<212> TYPE: PRT
<213> ORGANISM: Artificial Sequence
<220> FEATURE:
<223> OTHER INFORMATION: Artificial polymer

<400> SEQUENCE: 505

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Ser Tyr
20 25 30

Val Met Gly Trp Phe Arg Gln Ala Leu Gly Lys Glu Arg Glu Phe Val
35 40 45

Ala Ala Ile Gly Trp Asn Gly Gly Ile Thr Tyr Tyr Ala Asp Ser Val
50 55 60

Lys Gly Arg Phe Ala Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Ala Thr Leu Gln Val Thr Gly Ser Tyr Tyr Leu Asp Leu Ser
100 105 110

Thr Val Asp Ile Tyr Asp Asn Trp Gly Gln Gly Thr Gln Val Thr Val
115 120 125

Ser Ser Ala Ala Ala Tyr Pro Tyr Asp Val Pro Asp Tyr Gly Ser His
130 135 140

His His His His His
145

<210> SEQ ID NO 506
<211> LENGTH: 147
<212> TYPE: PRT
<213> ORGANISM: Artificial Sequence
<220> FEATURE:
<223> OTHER INFORMATION: Artificial polymer

<400> SEQUENCE: 506

Gln Val Gln Leu Gln Glu Ser Gly Gly Gly Leu Val Gln Ala Gly Gly
1 5 10 15

Ser Leu Arg Leu Ser Cys Ala Ala Ser Gly Gly Thr Phe Ser Asn Tyr
20 25 30

Val Met Gly Trp Phe Arg Gln Ala Pro Gly Lys Glu Arg Glu Phe Val
35 40 45

Gly Phe Ile Thr Trp Ser Gly Ala Ser Thr Tyr Tyr Ala Asp Ser Val
50 55 60

Lys Gly Arg Phe Thr Ile Ser Arg Asp Asn Ala Glu Asn Thr Val Tyr
65 70 75 80

Leu Gln Met Asn Ser Leu Lys Pro Glu Asp Thr Ala Val Tyr Tyr Cys
85 90 95

Ala Ala Thr Leu Phe Arg Ser Asn Gly Pro Lys Asp Leu Ser Ser Gly
100 105 110

Tyr Glu Tyr Asp Tyr Trp Gly Gln Gly Thr Gln Val Thr Val Ser Ser
115 120 125

Ala Ala Ala Tyr Pro Tyr Asp Val Pro Asp Tyr Gly Ser His His His
130 135 140

His His His
145

<210> SEQ ID NO 507
<211> LENGTH: 140
<212> TYPE: PRT
<213> ORGANISM: Artificial Sequence
<220> FEATURE:
<223> OTHER INFORMATION: Artificial polymer
<220> FEATURE:
<221> NAME/KEY: misc_feature
<222> LOCATION: (112)..(112)
<223> OTHER INFORMATION: Xaa can be any naturally occurring amino acid

<400> SEQUENCE: 507

Gln Val Gln Leu Gln Glu Ser Gly Gly Gly Leu Val Gln Ala Gly Asp
1 5 10 15

Ser Leu Arg Leu Thr Cys Thr Ala Ser Gly Arg Thr Phe Ser Asn Tyr
20 25 30

Gly Ile Gly Trp Phe Arg Gln Ala Pro Gly Lys Glu Arg Glu Phe Val
35 40 45

Ala Gly Ile Asn Trp Ser Gly Glu Ser Ala Asp Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Gly Glu Ser Gly Val Trp Val Gly Gly Leu Asp Tyr Trp Xaa
100 105 110

Gln Gly Thr Gln Val Thr Val Ser Ser Ala Ala Ala Tyr Pro Tyr Asp
115 120 125

Val Pro Asp Tyr Gly Ser His His His His His His
130 135 140

<210> SEQ ID NO 508
<211> LENGTH: 149
<212> TYPE: PRT
<213> ORGANISM: Artificial Sequence
<220> FEATURE:
<223> OTHER INFORMATION: Artificial polymer

<400> SEQUENCE: 508

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Thr Phe Asp Asp Tyr
20 25 30

Ala Ile Ala Trp Phe Arg Gln Ala Pro Gly Lys Glu Arg Glu Gly Val
35 40 45

Ser Cys Ile Glu Arg Ser Asp Gly Ser Thr Tyr Tyr Ala Asp Ser Val
50 55 60

Lys Gly Arg Phe Thr Ile Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Val Gly Ser Ala Asn Ser Gly Glu Phe Arg Phe Gly Trp Val Leu
100 105 110

Lys Pro Asp Leu Tyr Asn Tyr Trp Gly Gln Gly Thr Gln Val Thr Val
115 120 125

Ser Ser Ala Ala Ala Tyr Pro Tyr Asp Val Pro Asp Tyr Gly Ser His

```
    130                 135                 140

His His His His His
145


<210> SEQ ID NO 509
<211> LENGTH: 150
<212> TYPE: PRT
<213> ORGANISM: Artificial Sequence
<220> FEATURE:
<223> OTHER INFORMATION: Artificial polymer

<400> SEQUENCE: 509

Gln Val Gln Leu Gln Glu Ser Gly Gly Gly Leu Val Gln Ala Gly Gly
1               5                   10                  15

Ser Leu Arg Leu Ser Cys Thr Ala Ser Gly Arg Thr Phe Ser Ser Tyr
            20                  25                  30

Thr Val Ala Trp Phe Arg Gln Ser Pro Gly Lys Glu Arg Glu Gly Ile
        35                  40                  45

Ser Cys Ile Ser Asn Thr Asp Ser Ser Thr Tyr Tyr Ala Asp Ser Val
    50                  55                  60

Lys Gly Arg Phe Thr Ile Ser Ser Asp Asn Ala Lys Ser Thr Val His
65                  70                  75                  80

Leu Gln Met Ser Ser Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 510
<211> LENGTH: 150
<212> TYPE: PRT
<213> ORGANISM: Artificial Sequence
<220> FEATURE:
<223> OTHER INFORMATION: Artificial polymer

<400> SEQUENCE: 510

Gln Val Gln Leu Gln Glu Ser Gly Gly Gly Leu Val Gln Pro Gly Gly
1               5                   10                  15

Ser Leu Arg Leu Ser Cys Ala Thr Phe Gly Phe Pro Phe Asp Asp Tyr
            20                  25                  30

Ala Ile Ala Trp Phe Arg Gln Ala Pro Gly Lys Glu Arg Glu Gly Val
        35                  40                  45

Ser Cys Ile Ser Asn Thr Asp Ser Ser Thr Tyr Tyr Ala Asp Ser Val
    50                  55                  60

Lys Gly Arg Phe Thr Ile Ser Ser Asp Asn Ala Lys Asn Thr Val His
65                  70                  75                  80

Leu Gln Met Ser Ser Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125
```

```
Val Ser Ser Ala Ala Ala Tyr Pro Tyr Asp Val Pro Asp Tyr Gly Ser
    130                 135                 140

His His His His His His
145                 150


<210> SEQ ID NO 511
<211> LENGTH: 147
<212> TYPE: PRT
<213> ORGANISM: Artificial Sequence
<220> FEATURE:
<223> OTHER INFORMATION: Artificial polymer

<400> SEQUENCE: 511

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Val Met Gly Trp Phe Arg Gln Ala Pro Gly Lys Glu Arg Glu Phe Val
        35                  40                  45

Ala Gln Ile Ser Trp Ser Ala Gly Ser Ile Tyr Tyr Ala Asp Ser Val
    50                  55                  60

Lys Gly Arg Phe Thr Ile Ser Asn Asp Asn Ala Lys Arg Thr Val Tyr
65                  70                  75                  80

Leu Gln Met Asn Ser Leu Lys Pro Glu Asp Thr Ala Val Tyr Tyr Cys
                85                  90                  95

Ala Glu Arg Gly Tyr Ala Tyr Cys Ser Asp Asp Gly Cys Gln Arg Thr
            100                 105                 110

Gln Asp Tyr Asp Tyr Trp Gly Gln Gly Thr Gln Val Thr Val Ser Ser
        115                 120                 125

Ala Ala Ala Tyr Pro Tyr Asp Val Pro Asp Tyr Gly Ser His His His
    130                 135                 140

His His His
145


<210> SEQ ID NO 512
<211> LENGTH: 148
<212> TYPE: PRT
<213> ORGANISM: Artificial Sequence
<220> FEATURE:
<223> OTHER INFORMATION: Artificial polymer

<400> SEQUENCE: 512

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Leu Ser Ser Asn
            20                  25                  30

Pro Met Ala Trp Phe Arg Gln Ala Ala Gly Lys Glu Arg Glu Phe Val
        35                  40                  45

Ala Gly Met Ser Trp Asn Pro Gly Pro Ala Val Tyr Ala Asp Ser Val
    50                  55                  60

Lys Gly Arg Phe Thr Ile Ser Arg Asp Ser Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Gly Ala Ala Arg Ala Trp Trp Ser Gly Ser Tyr Asp Tyr Thr Arg
            100                 105                 110

Met Asn Asn Tyr Asp Tyr Trp Gly Pro Gly Thr Gln Val Thr Val Ser
        115                 120                 125
```

Ser Ala Ala Ala Tyr Pro Tyr Asp Val Pro Asp Tyr Gly Ser His His
130 135 140

His His His His
145

<210> SEQ ID NO 513
<211> LENGTH: 150
<212> TYPE: PRT
<213> ORGANISM: Artificial Sequence
<220> FEATURE:
<223> OTHER INFORMATION: Artificial polymer

<400> SEQUENCE: 513

Gln Val Gln Leu Gln Glu Ser Gly Gly Gly Leu Val Gln Ala Gly Gly
1 5 10 15

Ser Leu Arg Leu Ser Cys Ala Val Ser Gly Phe Thr Phe Asp Asn Tyr
20 25 30

Ala Ile Gly Trp Phe Arg Gln Ala Pro Gly Lys Glu Arg Glu Gly Val
35 40 45

Ser Cys Ile Ser Arg Ser Asp Gly Ser Thr Tyr Tyr Ala Asp Ser Val
50 55 60

Arg Gly Arg Phe Thr Ile Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Glu Thr Ser Ala Asp Ser Gly Glu Phe Arg Phe Gly Trp Val
100 105 110

Leu Lys Pro Ser Leu Tyr Asp Tyr Trp Gly Gln Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 514
<211> LENGTH: 131
<212> TYPE: PRT
<213> ORGANISM: Artificial Sequence
<220> FEATURE:
<223> OTHER INFORMATION: Artificial polymer

<400> SEQUENCE: 514

Gln Val Gln Leu Gln Glu Ser Gly Gly Gly Leu Val Gln Ala Gly Gly
1 5 10 15

Ser Leu Arg Leu Ser Cys Ala Val Ser Gly Phe Thr Phe Asp Asn Tyr
20 25 30

Ala Ile Gly Trp Phe Arg Gln Ala Pro Gly Lys Glu Arg Glu Gly Val
35 40 45

Ser Ser Ile Ser Arg Ser Asp Gly Ser Thr Tyr Tyr Ala Asp Ser Val
50 55 60

Arg Gly Arg Phe Thr Ile Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Glu Thr Ser Ala Asp Ser Gly Glu Phe Arg Phe Gly Trp Val
100 105 110

Leu Lys Pro Ser Leu Tyr Asp Tyr Trp Gly Gln Gly Thr Gln Val Thr

```
        115                 120                 125

Val Ser Ser
    130


<210> SEQ ID NO 515
<211> LENGTH: 148
<212> TYPE: PRT
<213> ORGANISM: Artificial Sequence
<220> FEATURE:
<223> OTHER INFORMATION: Artificial polymer

<400> SEQUENCE: 515

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ala Phe Ser Ser Tyr
            20                  25                  30

Phe Met Gly Trp Phe Arg Gln Thr Pro Gly Lys Glu Arg Glu Phe Val
        35                  40                  45

Ala Asn Ile Gly Trp Thr Gly Asp Met Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Gly Ser Ala Tyr Ser Gly Ser Tyr Trp Asn Ile Thr Met
            100                 105                 110

Ala Ala Asn Tyr Asp Tyr Trp Gly Gln Gly Thr Gln Val Thr Val Ser
        115                 120                 125

Ser Ala Ala Ala Tyr Pro Tyr Asp Val Pro Asp Tyr Gly Ser His His
    130                 135                 140

His His His His
145


<210> SEQ ID NO 516
<211> LENGTH: 145
<212> TYPE: PRT
<213> ORGANISM: Artificial Sequence
<220> FEATURE:
<223> OTHER INFORMATION: Artificial polymer

<400> SEQUENCE: 516

Gln Val Gln Leu Gln Glu Ser Gly Gly Gly Leu Val Gln Ala Gly Gly
1               5                   10                  15

Ser Leu Arg Leu Ser Cys Ala Ala Ser Thr Pro Thr Phe Ser Ser Tyr
            20                  25                  30

Asn Met Gly Trp Phe Arg Gln Ala Pro Gly Lys Glu Arg Glu Phe Val
        35                  40                  45

Ala Ala Ile Ile Trp Ser Gly Ser Met Thr Tyr Tyr Ala Asp Ser Met
    50                  55                  60

Lys Gly Arg Phe Thr Val Ser Ile Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gln Arg Ile Phe Gly Ala Gln Pro Met Asp Leu Ser Gly Asp
            100                 105                 110

Tyr Glu Tyr Trp Gly Gln Gly Thr Gln Val Thr Val Ser Ser Ala Ala
        115                 120                 125
```

Ala Tyr Pro Tyr Asp Val Pro Asp Tyr Gly Ser His His His His His
    130                 135                 140

His
145

<210> SEQ ID NO 517
<211> LENGTH: 150
<212> TYPE: PRT
<213> ORGANISM: Artificial Sequence
<220> FEATURE:
<223> OTHER INFORMATION: Artificial polymer

<400> SEQUENCE: 517

Gln Val Gln Leu Gln Glu Ser Gly Gly Gly Leu Val Gln Ala Gly Gly
1               5                   10                  15

Ser Leu Arg Leu Ser Cys Ala Thr Phe Gly Phe Thr Phe Asp Asp Tyr
            20                  25                  30

Ala Ile Ala Trp Phe Arg Gln Ala Pro Gly Lys Glu Arg Glu Gly Ile
        35                  40                  45

Ser Cys Ile Ser Asn Thr Asp Ser Ser Thr Tyr Tyr Ala Asp Ser Val
    50                  55                  60

Lys Gly Arg Phe Thr Ile Ser Ser Asp Ser Ala Lys Asn Thr Val His
65                  70                  75                  80

Leu Gln Met Ser Ser Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150

<210> SEQ ID NO 518
<211> LENGTH: 145
<212> TYPE: PRT
<213> ORGANISM: Artificial Sequence
<220> FEATURE:
<223> OTHER INFORMATION: Artificial polymer

<400> SEQUENCE: 518

Gln Val Gln Leu Gln Glu Ser Gly Gly Gly Leu Val Gln Ala Gly Gly
1               5                   10                  15

Ser Leu Arg Leu Ser Cys Lys Ala Ser Gly Gly Thr Phe Ser Gly Tyr
            20                  25                  30

Ile Met Gly Trp Phe Arg Gln Ala Pro Gly Lys Glu Arg Glu Phe Val
        35                  40                  45

Ala Ala Asn Thr Trp Ser Gly Gly Pro Thr Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Thr Leu Lys Pro Glu Asp Thr Ala Val Tyr Gln Cys
                85                  90                  95

Ala Ala Arg Asp Tyr Arg Gly Ile Lys Asp Leu Asp Leu Lys Gly Asp
            100                 105                 110

Tyr Asp Tyr Trp Gly Gln Gly Thr Gln Val Thr Val Ser Ser Ala Ala
        115                 120                 125

Ala Tyr Pro Tyr Asp Val Pro Asp Tyr Gly Ser His His His His His
130 135 140

His
145

<210> SEQ ID NO 519
<211> LENGTH: 151
<212> TYPE: PRT
<213> ORGANISM: Artificial Sequence
<220> FEATURE:
<223> OTHER INFORMATION: Artificial polymer

<400> SEQUENCE: 519

Gln Val Gln Leu Gln Glu Ser Gly Gly Gly Leu Val Gln Ala Gly Asp
1 5 10 15

Ser Leu Lys Leu Ser Cys Ala Thr Ser Gly Arg Ser Phe Ser Ser Tyr
20 25 30

Thr Ile Ala Trp Phe Arg Gln Ala Pro Gly Lys Glu Arg Glu Gly Ile
35 40 45

Ser Cys Ile Ser Ser Asp Gly Ser Thr Gly Tyr Ala Asp Ser Val Arg
50 55 60

Gly Arg Phe Thr Ile Ser Ser Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Ala Asp Phe Asn Val Trp Ser Pro Pro Ile Cys Gly Ser Ile Trp Tyr
100 105 110

Gly Pro Pro Pro Arg Gly Met Asp Tyr Trp Gly Lys Gly Thr Gln Val
115 120 125

Thr Val Ser Ser Ala Ala Ala Tyr Pro Tyr Asp Val Pro Asp Tyr Gly
130 135 140

Ser His His His His His His
145 150

<210> SEQ ID NO 520
<211> LENGTH: 152
<212> TYPE: PRT
<213> ORGANISM: Artificial Sequence
<220> FEATURE:
<223> OTHER INFORMATION: Artificial polymer

<400> SEQUENCE: 520

Gln Val Gln Leu Gln Glu Ser Gly Gly Gly Leu Val Gln Ala Gly Gly
1 5 10 15

Tyr Leu Arg Leu Ser Cys Ala Ala Ser Gly Phe Ser Ser Asp Asp Tyr
20 25 30

Thr Ile Gly Trp Phe Arg Gln Ala Pro Gly Lys Glu Arg Glu Gly Ile
35 40 45

Ser Cys Tyr Ser Ser Ser Asp Gly Ser Thr Gly Phe Ala Asp Ser Val
50 55 60

Lys Gly Arg Phe Thr Ile Ser Ser Asp Asn Ala Lys Asn Thr Val Tyr
65 70 75 80

Leu Gln Met Asn Asn Leu Arg Pro Glu Asp Thr Ala Val Tyr Tyr Cys
85 90 95

Ala Ala Asp Ser Asn Val Trp Ser Pro Pro Ile Cys Gly Ser Arg Trp
100 105 110

Tyr Gly Pro Pro Pro Gly Gly Met Ala Tyr Trp Gly Lys Gly Thr Gln 115 120 125

Val Thr Val Ser Ser Ala Ala Ala Tyr Pro Tyr Asp Val Pro Asp Tyr
130 135 140

Gly Ser His His His His His His
145 150

<210> SEQ ID NO 521
<211> LENGTH: 151
<212> TYPE: PRT
<213> ORGANISM: Artificial Sequence
<220> FEATURE:
<223> OTHER INFORMATION: Artificial polymer

<400> SEQUENCE: 521

Gln Val Gln Leu Gln Glu Ser Gly Gly Gly Leu Ala Gln Val Gly Gly
1 5 10 15

Ser Leu Arg Leu Ser Cys Thr Ala Ser Gly Phe Thr Phe Asp Asp Tyr
20 25 30

Thr Ile Gly Trp Phe Arg Gln Ala Pro Gly Lys Glu Arg Glu Gly Ile
35 40 45

Ser Cys Ile Ser Ser Asp Gly Ser Thr Gly Tyr Ala Asp Ser Val Lys
50 55 60

Gly Arg Phe Thr Ile Ser Ser Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Ala Asp Phe Asn Val Trp Ser Pro Pro Ile Cys Gly Ser Asn Trp Tyr
100 105 110

Gly Pro Pro Pro Gly Gly Met Asp Tyr Trp Gly Lys Gly Thr Gln Val
115 120 125

Thr Val Ser Ser Ala Ala Ala Tyr Pro Tyr Asp Val Pro Asp Tyr Gly
130 135 140

Ser His His His His His His
145 150

<210> SEQ ID NO 522
<211> LENGTH: 152
<212> TYPE: PRT
<213> ORGANISM: Artificial Sequence
<220> FEATURE:
<223> OTHER INFORMATION: Artificial polymer

<400> SEQUENCE: 522

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ser Ser Asp Asp Tyr
20 25 30

Thr Ile Gly Trp Phe Arg Gln Ala Pro Gly Lys Glu Arg Glu Gly Ile
35 40 45

Gly Cys Ile Lys Ser Ser Asp Gly Thr Thr Gly Tyr Ala Asp Ser Val
50 55 60

Lys Gly Arg Phe Thr Ile Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asp Phe Asn Val Trp Ser Pro Pro Ile Cys Gly Ser Ile Trp
100 105 110

```
Tyr Gly Pro Pro Pro Gly Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 523
<211> LENGTH: 150
<212> TYPE: PRT
<213> ORGANISM: Artificial Sequence
<220> FEATURE:
<223> OTHER INFORMATION: Artificial polymer

<400> SEQUENCE: 523

Gln Val Gln Leu Gln Glu Ser Gly Gly Gly Leu Ala Gln Ala Gly Gly
1               5                   10                  15

Ser Leu Arg Leu Ser Cys Ala Ala Ser Gly Phe Thr Phe Asp Gln Tyr
            20                  25                  30

Thr Ile Ala Trp Phe Arg Gln Ala Pro Gly Lys Glu Arg Glu Gly Val
        35                  40                  45

Ser Cys Ile Ser Asn Thr Asp Ser Ser Thr Tyr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 524
<211> LENGTH: 144
<212> TYPE: PRT
<213> ORGANISM: Artificial Sequence
<220> FEATURE:
<223> OTHER INFORMATION: Artificial polymer

<400> SEQUENCE: 524

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Ala Trp Phe Arg Gln Ala Pro Gly Lys Glu Arg Glu Phe Val
        35                  40                  45

Ala Ala Ile Ala Trp Ser Ala Gly Ser Thr Tyr Tyr Ala Asp Ser Val
    50                  55                  60

Lys Gly Arg Phe Ala Ile Ser Arg Asp Asn Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ile Ile Thr Val Ala Thr Met Arg Leu Asp Ser Asp Tyr
            100                 105                 110
```

Asp Tyr Trp Gly Gln Gly Thr Gln Val Thr Val Ser Ser Ala Ala Ala
115 120 125

Tyr Pro Tyr Asp Val Pro Asp Tyr Gly Ser His His His His His His
130 135 140

<210> SEQ ID NO 525
<211> LENGTH: 150
<212> TYPE: PRT
<213> ORGANISM: Artificial Sequence
<220> FEATURE:
<223> OTHER INFORMATION: Artificial polymer

<400> SEQUENCE: 525

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ala Phe Asp Gly Tyr
20 25 30

Ala Ile Gly Trp Phe Arg Gln Ala Pro Gly Lys Glu Arg Glu Gly Val
35 40 45

Ser Cys Ile Ser Ser Lys Glu Gly Ser Thr Tyr Tyr Ala Asp Ser Val
50 55 60

Lys Gly Arg Phe Thr Ile Ser Ser Asp Asn Ala Lys Asn Thr Val Tyr
65 70 75 80

Leu Gln Met Ser Ser Leu Lys Pro Glu Asp Thr Ala Val Tyr Tyr Cys
85 90 95

Ala Ala Asp Gly Asn Val Trp Ser Pro Pro Ile Cys Gly Ser Ala Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 526
<211> LENGTH: 152
<212> TYPE: PRT
<213> ORGANISM: Artificial Sequence
<220> FEATURE:
<223> OTHER INFORMATION: Artificial polymer

<400> SEQUENCE: 526

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ser Ser Asp Asp Tyr
20 25 30

Thr Ile Ala Trp Phe Arg Arg Ala Pro Gly Lys Glu Arg Glu Gly Ile
35 40 45

Ser Cys Ile Ser Ser Ser Asp Gly Ser Thr Gly Tyr Ala Asp Ser Val
50 55 60

Lys Gly Arg Phe Thr Ile Thr Ser Asp Ser Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asp Ser Asn Val Trp Ser Pro Pro Ile Cys Gly Arg Thr Trp
100 105 110

Tyr Gly Pro Pro Pro Gly Gly Met Asp Tyr Trp Gly Lys Gly Thr Gln

```
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 527
<211> LENGTH: 152
<212> TYPE: PRT
<213> ORGANISM: Artificial Sequence
<220> FEATURE:
<223> OTHER INFORMATION: Artificial polymer

<400> SEQUENCE: 527

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Ile
        35                  40                  45

Ser Cys Tyr Ser Ser Arg Asp Gly Thr Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Ile Trp
            100                 105                 110

Tyr Gly Pro Pro Pro Gly Gly Met Ala Tyr Trp Gly Gln Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 528
<211> LENGTH: 151
<212> TYPE: PRT
<213> ORGANISM: Artificial Sequence
<220> FEATURE:
<223> OTHER INFORMATION: Artificial polymer

<400> SEQUENCE: 528

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Thr Ile Gly Trp Phe Arg Gln Ala Pro Gly Lys Glu Arg Glu Gly Ile
        35                  40                  45

Ser Cys Ile Ser Ser Asp Gly Ser Thr Gly Tyr Ala Asp Ser Val Lys
    50                  55                  60

Gly Arg Phe Thr Ile Ser Ser Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Phe Asn Val Trp Ser Pro Pro Ile Cys Gly Ser Asn Trp Tyr
            100                 105                 110
```

```
Gly Pro Pro Pro Gly Gly Met Asp Tyr Trp Gly Lys Gly Thr Gln Val
        115                 120                 125

Thr Val Ser Ser Ala Ala Ala Tyr Pro Tyr Asp Val Pro Asp Tyr Gly
    130                 135                 140

Ser His His His His His His
145                 150


<210> SEQ ID NO 529
<211> LENGTH: 152
<212> TYPE: PRT
<213> ORGANISM: Artificial Sequence
<220> FEATURE:
<223> OTHER INFORMATION: Artificial polymer

<400> SEQUENCE: 529

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Ile
        35                  40                  45

Ser Cys Tyr Ser Ser Ser Asp Gly Ser Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Ser Trp
            100                 105                 110

Tyr Gly Pro Pro Pro Gly Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 530
<211> LENGTH: 152
<212> TYPE: PRT
<213> ORGANISM: Artificial Sequence
<220> FEATURE:
<223> OTHER INFORMATION: Artificial polymer

<400> SEQUENCE: 530

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Ile
        35                  40                  45

Ser Cys Phe Ser Ser Ser Asp Gly Ser Thr Gly Phe Ala Asp Ser Val
    50                  55                  60

Lys Gly Arg Phe Thr Ile Ser Ser Asp Asn Ala Thr Asn Thr Val Tyr
65                  70                  75                  80

Leu Glu Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Arg Trp
            100                 105                 110
```

Tyr Gly Pro Pro Pro Gly Gly Met Glu Tyr Trp Gly Lys Gly Thr Gln
115 120 125

Val Thr Val Ser Ser Ala Ala Ala Tyr Pro Tyr Asp Val Pro Asp Tyr
130 135 140

Gly Ser His His His His His His
145 150

<210> SEQ ID NO 531
<211> LENGTH: 150
<212> TYPE: PRT
<213> ORGANISM: Artificial Sequence
<220> FEATURE:
<223> OTHER INFORMATION: Artificial polymer

<400> SEQUENCE: 531

Gln Val Gln Leu Gln Glu Ser Gly Gly Gly Leu Val Gln Ala Gly Gly
1 5 10 15

Ser Leu Arg Leu Ser Cys Ala Thr Phe Gly Phe Ser Phe Asp Asp Tyr
20 25 30

Ala Ile Ala Trp Phe Arg Gln Ala Pro Gly Lys Glu Arg Glu Gly Ile
35 40 45

Ser Cys Ile Ser Asn Thr Asp Ser Ser Thr Phe Tyr Ala Asp Ser Val
50 55 60

Lys Gly Arg Phe Thr Ile Ser Ser Asp Asn Ala Lys Asn Thr Val His
65 70 75 80

Leu Gln Met Ser Ser Leu Lys Pro Glu Asp Thr Ala Val Tyr Tyr Cys
85 90 95

Ala Ala Asp Gly Asn Val Trp Ser Pro Pro Ile Cys Gly Ser Ala Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 532
<211> LENGTH: 152
<212> TYPE: PRT
<213> ORGANISM: Artificial Sequence
<220> FEATURE:
<223> OTHER INFORMATION: Artificial polymer

<400> SEQUENCE: 532

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ser Ser Asp Asp Tyr
20 25 30

Thr Ile Gly Trp Phe Arg Gln Ala Pro Gly Lys Glu Arg Glu Gly Ile
35 40 45

Ser Cys Tyr Ser Ser Ser Asp Gly Ser Thr Gly Phe Ala Asp Ser Val
50 55 60

Lys Gly Arg Phe Thr Ile Ser Ser Asp Asn Ala Lys Asn Thr Val Tyr
65 70 75 80

Leu Gln Met Asn Ser Leu Arg Pro Glu Asp Thr Ala Val Tyr Tyr Cys
85 90 95

Ala Ala Asp Phe Asn Val Trp Ser Pro Pro Ile Cys Gly Ser Arg Trp

```
            100                 105                 110

Tyr Gly Pro Pro Pro Gly Gly Met Ala Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 533
<211> LENGTH: 151
<212> TYPE: PRT
<213> ORGANISM: Artificial Sequence
<220> FEATURE:
<223> OTHER INFORMATION: Artificial polymer

<400> SEQUENCE: 533

Gln Val Gln Leu Gln Glu Ser Gly Gly Gly Leu Val Gln Val Gly Gly
1               5                   10                  15

Ser Leu Arg Leu Ser Cys Thr Ile Ser Gly Phe Thr Gly Asn Asp Leu
            20                  25                  30

Ala Ile Gly Trp Phe Arg Gln Ala Pro Gly Lys Asp Gln Arg Glu Gly
        35                  40                  45

Ile Ser Cys Ile Ser Asn Thr Asp Ser Ser Thr Tyr Tyr Ala Asp Ser
    50                  55                  60

Val Lys Gly Arg Phe Thr Ile Ser Ser Asp Asn Ala Lys Asn Thr Val
65                  70                  75                  80

His Leu Gln Met Ser Ser Leu Lys Pro Glu Asp Thr Ala Val Tyr Tyr
                85                  90                  95

Cys Ala Ala Asp Gly Asn Val Trp Ser Pro Pro Ile Cys Gly Ser Ala
            100                 105                 110

Gly Pro Pro Pro Gly Gly Met Asp Tyr Trp Gly Lys Gly Thr Gln Val
        115                 120                 125

Thr Val Ser Ser Ala Ala Ala Tyr Pro Tyr Asp Val Pro Asp Tyr Gly
    130                 135                 140

Ser His His His His His His
145                 150


<210> SEQ ID NO 534
<211> LENGTH: 152
<212> TYPE: PRT
<213> ORGANISM: Artificial Sequence
<220> FEATURE:
<223> OTHER INFORMATION: Artificial polymer

<400> SEQUENCE: 534

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Ala Trp Phe Arg Arg Ala Pro Gly Lys Glu Arg Glu Gly Ile
        35                  40                  45

Ser Cys Ile Ser Ser Ser Asp Gly Ser Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Thr Ser Leu Lys Pro Glu Asp Thr Ala Val Tyr Tyr Cys
                85                  90                  95
```

Ala Ala Asp Ser Asn Val Trp Ser Pro Pro Ile Cys Gly Lys Thr Trp
100 105 110

Tyr Gly Pro Pro Pro Gly Gly Met Asp Tyr Trp Gly Lys Gly Thr Gln
115 120 125

Val Thr Val Ser Ser Ala Ala Ala Tyr Pro Tyr Asp Val Pro Asp Tyr
130 135 140

Gly Ser His His His His His His
145 150

<210> SEQ ID NO 535
<211> LENGTH: 140
<212> TYPE: PRT
<213> ORGANISM: Artificial Sequence
<220> FEATURE:
<223> OTHER INFORMATION: Artificial polymer

<400> SEQUENCE: 535

Gln Val Gln Leu Gln Glu Ser Gly Gly Gly Leu Val Gln Ala Gly Asp
1 5 10 15

Ser Leu Arg Leu Ser Cys Ala Gly Ser Glu Gly Thr Leu Ser Ser Tyr
20 25 30

Gly Ile Gly Trp Phe Arg Gln Ala Pro Gly Lys Glu Arg Glu Phe Val
35 40 45

Gly Gly Ile Asn Trp Ser Gly Asp Ser Thr Asp Tyr Ala Asp Ser Val
50 55 60

Lys Gly Arg Phe Thr Ile Ser Arg Asp Ser Ala Lys Asn Thr Val Tyr
65 70 75 80

Leu Gln Met Asn Ser Leu Lys Pro Glu Asp Thr Ala Val Tyr Tyr Cys
85 90 95

Ala Ala Gly Glu Ser Gly Val Trp Val Gly Gly Leu Asp Tyr Trp Gly
100 105 110

Gln Gly Thr Gln Val Thr Val Ser Ser Ala Ala Ala Tyr Pro Tyr Asp
115 120 125

Val Pro Asp Tyr Gly Ser His His His His His His
130 135 140

<210> SEQ ID NO 536
<211> LENGTH: 152
<212> TYPE: PRT
<213> ORGANISM: Artificial Sequence
<220> FEATURE:
<223> OTHER INFORMATION: Artificial polymer

<400> SEQUENCE: 536

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ser Ser Asp Asp Tyr
20 25 30

Thr Ile Ala Trp Phe Arg Arg Ala Pro Gly Lys Glu Arg Glu Gly Ile
35 40 45

Ser Cys Phe Ser Ser Ser Asp Gly Ser Ala Gly Tyr Ala Asp Ser Val
50 55 60

Lys Gly Arg Phe Thr Val Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asp Ser Asn Val Trp Ser Pro Pro Ile Cys Gly Ser Thr Trp
100 105 110

Tyr Gly Pro Pro Pro Gly Gly Met Ala Tyr Trp Gly Lys Gly Thr Gln
115 120 125

Val Thr Val Ser Ser Ala Ala Ala Tyr Pro Tyr Asp Val Pro Asp Tyr
130 135 140

Gly Ser His His His His His His
145 150

<210> SEQ ID NO 537
<211> LENGTH: 150
<212> TYPE: PRT
<213> ORGANISM: Artificial Sequence
<220> FEATURE:
<223> OTHER INFORMATION: Artificial polymer

<400> SEQUENCE: 537

Gln Val Gln Leu Gln Glu Ser Gly Gly Gly Leu Val Gln Ala Gly Gly
1 5 10 15

Ser Leu Arg Leu Ser Cys Ala Thr Ser Gly Phe Thr Phe Asp Asp Tyr
20 25 30

Ala Ile Ala Trp Phe Arg Gln Ala Pro Gly Lys Glu Arg Glu Gly Val
35 40 45

Ser Cys Ile Ser Asn Thr Asp Ser Ser Thr Tyr Tyr Ala Asp Ser Val
50 55 60

Lys Gly Arg Phe Thr Ile Ser Ser Asp Asn Ala Lys Asn Thr Val Tyr
65 70 75 80

Leu Gln Met Ser Ser Leu Lys Pro Glu Asp Thr Ala Val Tyr Tyr Cys
85 90 95

Ala Ala Asp Gly Asn Val Trp Ser Pro Pro Ile Cys Gly Ser Ala Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 538
<211> LENGTH: 152
<212> TYPE: PRT
<213> ORGANISM: Artificial Sequence
<220> FEATURE:
<223> OTHER INFORMATION: Artificial polymer

<400> SEQUENCE: 538

Gln Val Gln Leu Gln Glu Ser Gly Gly Gly Leu Val Gln Ala Gly Gly
1 5 10 15

Ser Leu Arg Leu Ser Cys Glu Val Ser Gly Leu Ser Ser Asp Asp Tyr
20 25 30

Thr Ile Gly Trp Phe Arg Gln Ala Pro Gly Lys Glu Arg Glu Gly Phe
35 40 45

Ser Cys Phe Ser Thr Arg Asp Gly Asn Ala Gly Tyr Ala Asp Ser Val
50 55 60

Lys Gly Arg Phe Thr Ile Ser Ser Asp Asn Ala Lys Asn Thr Val Tyr
65 70 75 80

Leu Gln Met Asn Asn Leu Lys Pro Glu Asp Thr Ala Val Tyr Tyr Cys
85 90 95

Ala Ala Asp Phe Asn Val Trp Ser Pro Pro Ile Cys Gly Ser Arg Trp

```
            100                 105                 110

Tyr Gly Pro Pro Pro Gly Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 539
<211> LENGTH: 152
<212> TYPE: PRT
<213> ORGANISM: Artificial Sequence
<220> FEATURE:
<223> OTHER INFORMATION: Artificial polymer

<400> SEQUENCE: 539

Gln Val Gln Leu Gln Glu Ser Gly Gly Gly Leu Val Gln Ala Gly Gly
1               5                   10                  15

Ser Leu Arg Leu Ser Cys Glu Val Ser Gly Leu Ser Ser Asp Asp Tyr
            20                  25                  30

Thr Ile Gly Trp Phe Arg Gln Ala Pro Gly Lys Lys Arg Glu Gly Phe
        35                  40                  45

Ser Cys Phe Ser Ser Arg Asp Gly Ser Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Arg Trp
            100                 105                 110

Tyr Gly Pro Pro Pro Gly Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 540
<211> LENGTH: 152
<212> TYPE: PRT
<213> ORGANISM: Artificial Sequence
<220> FEATURE:
<223> OTHER INFORMATION: Artificial polymer

<400> SEQUENCE: 540

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Phe
        35                  40                  45

Ser Cys Phe Ser Ser Arg Asp Gly Ser Thr Gly Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95
```

Ala Ala Asp Phe Asn Val Trp Ser Pro Pro Ile Cys Gly Ser Arg Trp
100 105 110

Tyr Gly Pro Pro Pro Gly Gly Met Asp Tyr Trp Gly Lys Gly Thr Gln
115 120 125

Val Thr Val Ser Ser Ala Ala Ala Tyr Pro Tyr Asp Val Pro Asp Tyr
130 135 140

Gly Ser His His His His His His
145 150

<210> SEQ ID NO 541
<211> LENGTH: 151
<212> TYPE: PRT
<213> ORGANISM: Artificial Sequence
<220> FEATURE:
<223> OTHER INFORMATION: Artificial polymer

<400> SEQUENCE: 541

Gln Val Gln Leu Gln Glu Ser Gly Gly Gly Leu Val Gln Ala Gly Gly
1 5 10 15

Ser Leu Arg Leu Ser Cys Ala Ala Ser Gly Phe Ser Phe Asp Asp Tyr
20 25 30

Thr Ile Gly Trp Phe Arg Gln Val Pro Gly Lys Glu Arg Glu Gly Ile
35 40 45

Ser Cys Ile Ser Ser Asp Gly Ser Thr Gly Tyr Ala Asp Ser Val Lys
50 55 60

Gly Arg Phe Thr Ile Ser Ser Asp Asn Ala Lys Asn Thr Val Tyr Leu
65 70 75 80

Gln Ile Asn Ser Leu Lys Pro Glu Asp Thr Ala Val Tyr Tyr Cys Ala
85 90 95

Ala Asp Phe Asn Val Trp Ser Pro Pro Ile Cys Gly Ser Ile Trp Tyr
100 105 110

Gly Pro Pro Pro Gly Gly Met Asp Tyr Trp Gly Lys Gly Thr Gln Val
115 120 125

Thr Val Ser Ser Ala Ala Ala Tyr Pro Tyr Asp Val Pro Asp Tyr Gly
130 135 140

Ser His His His His His His
145 150

<210> SEQ ID NO 542
<211> LENGTH: 150
<212> TYPE: PRT
<213> ORGANISM: Artificial Sequence
<220> FEATURE:
<223> OTHER INFORMATION: Artificial polymer

<400> SEQUENCE: 542

Gln Val Gln Leu Gln Glu Ser Gly Gly Gly Leu Val Gln Ala Gly Gly
1 5 10 15

Ser Leu Arg Leu Ser Cys Ala Thr Phe Gly Phe Thr Phe Asp Asp Tyr
20 25 30

Ala Ile Ala Trp Phe Arg Gln Ala Pro Gly Lys Glu Arg Glu Gly Ile
35 40 45

Ser Cys Ile Ser Asn Thr Asp Ser Ser Thr Tyr Tyr Ala Asp Ser Val
50 55 60

Lys Gly Arg Phe Thr Ile Ser Ser Asp Asn Ala Lys Asn Thr Val His
65 70 75 80

Leu Gln Met Ser Ser Leu Lys Pro Glu Asp Thr Ala Val Tyr Tyr Cys
85 90 95

Ala Ala Asp Gly Asn Val Trp Ser Pro Pro Ile Cys Gly Ser Ala Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 543
<211> LENGTH: 150
<212> TYPE: PRT
<213> ORGANISM: Artificial Sequence
<220> FEATURE:
<223> OTHER INFORMATION: Artificial polymer
<220> FEATURE:
<221> NAME/KEY: misc_feature
<222> LOCATION: (19)..(19)
<223> OTHER INFORMATION: Xaa can be any naturally occurring amino acid

<400> SEQUENCE: 543

Gln Val Gln Leu Gln Glu Ser Gly Gly Gly Leu Val Gln Ala Gly Gly
1 5 10 15

Ser Leu Xaa Leu Ser Cys Ala Ala Ser Gly Phe Thr Phe Asp Asp Tyr
20 25 30

Ala Ile Gly Trp Phe Arg Gln Ala Pro Gly Lys Glu Arg Glu Gly Val
35 40 45

Ser Cys Ile Ser Ser Pro Asp Gly Ser Thr Tyr Tyr Ala Asp Ser Val
50 55 60

Lys Gly Arg Phe Thr Ile Ser Ser Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asp Phe Asn Val Trp Ser Pro Pro Ile Cys Gly Ser Val Gly
100 105 110

Pro Pro Pro Gly Gly Met Asp Tyr Trp Gly Lys Gly Thr Gln Val Thr
115 120 125

Val Ser Ser Ala Ala Ala Tyr Pro Tyr Asp Val Pro Asp Tyr Gly Ser
130 135 140

His His His His His His
145 150

<210> SEQ ID NO 544
<211> LENGTH: 152
<212> TYPE: PRT
<213> ORGANISM: Artificial Sequence
<220> FEATURE:
<223> OTHER INFORMATION: Artificial polymer

<400> SEQUENCE: 544

Gln Val Gln Leu Gln Glu Ser Gly Gly Gly Leu Val Gln Ala Gly Ala
1 5 10 15

Ser Leu Arg Leu Ser Cys Lys Ala Ser Gly Phe Thr Phe Gly Asp Tyr
20 25 30

Thr Ile Gly Trp Phe Arg Gln Ala Pro Gly Lys Glu Arg Glu Gly Ile
35 40 45

Ser Cys Tyr Ser Ser Ser Asp Gly Asn Thr Gly Tyr Ala Asp Ser Val
50 55 60

```
Lys Gly Arg Phe Thr Ile Ser Ser Asp Asn Ala Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Phe Asn Val Trp Ser Pro Pro Ile Cys Gly Ser Ser Trp
            100                 105                 110

Tyr Gly Pro Pro Pro Gly Gly Met Ala Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150
```

```
<210> SEQ ID NO 545
<211> LENGTH: 140
<212> TYPE: PRT
<213> ORGANISM: Artificial Sequence
<220> FEATURE:
<223> OTHER INFORMATION: Artificial polymer

<400> SEQUENCE: 545

Gln Val Gln Leu Gln Glu Ser Gly Gly Gly Leu Val Gln Ala Gly Asp
1               5                   10                  15

Ser Leu Arg Leu Ser Cys Ala Gly Ser Glu Gly Thr Phe Ser Ser Tyr
            20                  25                  30

Gly Ile Gly Trp Phe Arg Gln Ala Pro Gly Lys Glu Arg Glu Phe Val
        35                  40                  45

Gly Gly Ile Asn Trp Ser Gly Asp Ser Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Glu Ser Gly Val Trp Val Gly Gly Leu Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

```
<210> SEQ ID NO 546
<211> LENGTH: 152
<212> TYPE: PRT
<213> ORGANISM: Artificial Sequence
<220> FEATURE:
<223> OTHER INFORMATION: Artificial polymer

<400> SEQUENCE: 546

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Ser Asp Asp Tyr
            20                  25                  30

Thr Ile Gly Trp Phe Arg Gln Ala Pro Gly Lys Glu Arg Glu Gly Ile
        35                  40                  45

Ser Cys Phe Ser Ser Ser Asp Gly Ser Thr Gly Phe Ala Asp Ser Val
    50                  55                  60

Lys Gly Arg Phe Thr Ile Ser Ser Asp Asn Ala Thr Asn Thr Val Tyr
65                  70                  75                  80
```

```
Leu Gln Met Asn Ser Leu Lys Pro Glu Asp Thr Ala Val Tyr Tyr Cys
                85                  90                  95

Ala Ala Asp Phe Asn Val Trp Ser Pro Pro Ile Cys Gly Ser Ser Trp
            100                 105                 110

Tyr Gly Pro Pro Pro Gly Gly Met Glu Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 547
<211> LENGTH: 150
<212> TYPE: PRT
<213> ORGANISM: Artificial Sequence
<220> FEATURE:
<223> OTHER INFORMATION: Artificial polymer

<400> SEQUENCE: 547

Gln Val Gln Leu Gln Glu Ser Gly Gly Gly Leu Val Gln Ala Gly Asp
1               5                   10                  15

Ser Leu Arg Leu Ser Cys Thr Ala Ser Gly Val Ser Ile Gly Asp Tyr
            20                  25                  30

Asn Ile Gly Trp Phe Arg Gln Ala Pro Gly Lys Glu Arg Glu Gly Val
        35                  40                  45

Ser Cys Ile Ser Ser Gly Asp Gly Thr Thr Tyr Tyr Thr Asp Ser Val
    50                  55                  60

Lys Gly Arg Phe Thr Ile Ser Thr Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Gly Asn Val Trp Ser Pro Pro Ile Cys Gly Ser Ala Gly
            100                 105                 110

Pro Pro Pro Gly Gly Met Asp Tyr Trp Gly Lys Gly Thr Gln Val Thr
        115                 120                 125

Val Ser Ser Ala Ala Ala Tyr Pro Tyr Asp Val Pro Asp Tyr Gly Ser
    130                 135                 140

His His His His His His
145                 150


<210> SEQ ID NO 548
<211> LENGTH: 152
<212> TYPE: PRT
<213> ORGANISM: Artificial Sequence
<220> FEATURE:
<223> OTHER INFORMATION: Artificial polymer

<400> SEQUENCE: 548

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Thr Ile Ala Trp Phe Arg Gln Ala Pro Gly Gly Lys Glu Arg Glu Gly
        35                  40                  45

Ile Ser Cys Ile Ser Ser Asp Gly Ser Thr Gly Tyr Ala Asp Ser Val
    50                  55                  60

Lys Gly Arg Phe Thr Ile Ser Ser Asp Asn Ala Lys Asn Met Val Tyr
```

```
65                  70                  75                  80

Leu Gln Met Asn Ser Leu Lys Pro Glu Asp Thr Ala Leu Tyr Tyr Cys
                85                  90                  95

Ala Ala Asp Phe Asn Val Trp Ser Pro Pro Ile Cys Ser Ser Asn Trp
            100                 105                 110

Tyr Gly Pro Pro Pro Arg Gly Met Asp Tyr Trp Gly Lys Gly Thr Gln
        115                 120                 125

Val Thr Val Ser Ser Ala Ala Ala Tyr Pro Tyr Asp Val Pro Asp Tyr
    130                 135                 140

Gly Ser His His His His His His
145                 150


<210> SEQ ID NO 549
<211> LENGTH: 151
<212> TYPE: PRT
<213> ORGANISM: Artificial Sequence
<220> FEATURE:
<223> OTHER INFORMATION: Artificial polymer

<400> SEQUENCE: 549

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Thr Ile Ala Trp Phe Arg Gln Ala Pro Gly Lys Glu Arg Glu Gly Ile
        35                  40                  45

Ser Cys Ile Ser Ser Asp Gly Ser Thr Gly Tyr Ala Asp Ser Val Arg
    50                  55                  60

Gly Arg Phe Thr Ile Ser Ser Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Asp Phe Asn Val Trp Ser Pro Pro Ile Cys Gly Ser Ile Trp Tyr
            100                 105                 110

Gly Pro Pro Pro Arg Gly Met Asp Tyr Trp Gly Lys Gly Thr Gln Val
        115                 120                 125

Thr Val Ser Ser Ala Ala Ala Tyr Pro Tyr Asp Val Pro Asp Tyr Gly
    130                 135                 140

Ser His His His His His His
145                 150


<210> SEQ ID NO 550
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 550

His His His His His His
1               5


<210> SEQ ID NO 551
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 551
```

Tyr Pro Tyr Asp Val Pro Asp Tyr Gly Ser
1 5 10

<210> SEQ ID NO 552
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 552

Ala Ala Ala Tyr Pro Tyr Asp Val Pro Asp Tyr Gly Ser His His His
1 5 10 15

His His His

<210> SEQ ID NO 553
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 553

Gly Ala Ser
1

<210> SEQ ID NO 554
<211> LENGTH: 2
<212> TYPE: PRT
<213> ORGANISM: Artificial Sequence
<220> FEATURE:
<223> OTHER INFORMATION: Synthetic Sequence

<400> SEQUENCE: 554

Ala Arg
1

<210> SEQ ID NO 555
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 555

Val Met Gly
1

<210> SEQ ID NO 556
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 556

Gly Gly Ser
1

<210> SEQ ID NO 557
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 557

Gly Gly Ser Gly Gly Ser
1               5

<210> SEQ ID NO 558
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 558

Gly Gly Ser Gly Gly Ser Gly Gly Ser
1               5

<210> SEQ ID NO 559
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 559

Gly Gly Ser Gly Gly Ser Gly Gly Ser Gly Gly Ser
1               5                   10

<210> SEQ ID NO 560
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 560

Gly Gly Ser Gly Gly Ser Gly Gly Ser Gly Gly Ser Gly Gly Ser
1               5                   10                  15

<210> SEQ ID NO 561
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 561

Gly Gly Ser Gly Gly Ser Gly Gly Ser Gly Gly Ser Gly Gly Ser Gly
1               5                   10                  15

Gly Ser

<210> SEQ ID NO 562
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 562

Gly Gly Ser Gly Gly Ser Gly Gly Ser Gly Gly Ser Gly Gly Ser Gly
1               5                   10                  15

Gly Ser Gly Gly Ser
            20

<210> SEQ ID NO 563
<211> LENGTH: 24
<212> TYPE: PRT

<213> ORGANISM: Artificial Sequence
<220> FEATURE:
<223> OTHER INFORMATION: Synthetic Sequence

<400> SEQUENCE: 563

Gly Gly Ser Gly Gly Ser Gly Gly Ser Gly Gly Ser Gly Gly Ser Gly
1 5 10 15

Gly Ser Gly Gly Ser Gly Gly Ser
20

<210> SEQ ID NO 564
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 564

Gly Gly Gly Ser
1

<210> SEQ ID NO 565
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 565

Gly Gly Gly Ser Gly Gly Gly Ser
1 5

<210> SEQ ID NO 566
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 566

Gly Gly Gly Ser Gly Gly Gly Ser Gly Gly Gly Ser
1 5 10

<210> SEQ ID NO 567
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 567

Gly Gly Gly Ser Gly Gly Gly Ser Gly Gly Gly Ser Gly Gly Gly Ser
1 5 10 15

<210> SEQ ID NO 568
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 568

Gly Gly Gly Ser Gly Gly Gly Ser Gly Gly Gly Ser Gly Gly Gly Ser
1 5 10 15

Gly Gly Gly Ser
20

-continued

```
<210> SEQ ID NO 569
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 569

Gly Gly Gly Ser Gly Gly Gly Ser Gly Gly Gly Ser Gly Gly Gly Ser
1               5                   10                  15

Gly Gly Gly Ser Gly Gly Gly Ser
            20


<210> SEQ ID NO 570
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 570

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser
            20                  25


<210> SEQ ID NO 571
<211> LENGTH: 32
<212> TYPE: PRT
<213> ORGANISM: Artificial Sequence
<220> FEATURE:
<223> OTHER INFORMATION: Synthetic Sequence

<400> SEQUENCE: 571

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30
```